(12) United States Patent
Nittoli

(10) Patent No.: US 12,419,963 B2
(45) Date of Patent: Sep. 23, 2025

(54) DIELS-ALDER CONJUGATION METHODS

(71) Applicant: Regeneron Pharmaceuticals, Inc., Tarrytown, NY (US)

(72) Inventor: Thomas Nittoli, Orangeburg, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

(21) Appl. No.: 18/196,863

(22) Filed: May 12, 2023

(65) Prior Publication Data
US 2024/0207412 A1 Jun. 27, 2024

Related U.S. Application Data

(63) Continuation of application No. 17/232,854, filed on Apr. 16, 2021, now Pat. No. 11,701,427.

(60) Provisional application No. 63/010,903, filed on Apr. 16, 2020.

(51) Int. Cl.
| | |
|---|---|
| *A61K 47/68* | (2017.01) |
| *A61K 31/395* | (2006.01) |
| *A61K 31/5383* | (2006.01) |
| *A61K 31/5517* | (2006.01) |
| *A61K 38/07* | (2006.01) |
| *A61K 38/17* | (2006.01) |
| *A61K 47/54* | (2017.01) |
| *A61K 47/55* | (2017.01) |
| *A61K 47/65* | (2017.01) |
| *A61K 49/00* | (2006.01) |
| *A61K 51/10* | (2006.01) |
| *A61P 31/04* | (2006.01) |
| *A61P 35/00* | (2006.01) |

(52) U.S. Cl.
CPC ........ *A61K 47/6803* (2017.08); *A61K 31/395* (2013.01); *A61K 31/5383* (2013.01); *A61K 31/5517* (2013.01); *A61K 38/07* (2013.01); *A61K 38/1729* (2013.01); *A61K 47/542* (2017.08); *A61K 47/545* (2017.08); *A61K 47/55* (2017.08); *A61K 47/65* (2017.08); *A61K 47/68031* (2023.08); *A61K 47/68035* (2023.08); *A61K 47/6849* (2017.08); *A61K 49/0052* (2013.01); *A61K 49/0058* (2013.01); *A61K 51/1093* (2013.01); *A61P 31/04* (2018.01); *A61P 35/00* (2018.01)

(58) Field of Classification Search
CPC .................................................. A61K 47/545
USPC ...................................................... 424/181.1
See application file for complete search history.

(56) References Cited

U.S. PATENT DOCUMENTS 9,717,803 B2  8/2017  Bregeon et al.

FOREIGN PATENT DOCUMENTS

| JP | 2017-519045 A | 7/2017 |
| JP | 2019-503979 A | 2/2019 |
| WO | 2018/218004 A1 | 11/2018 |

OTHER PUBLICATIONS

International Search Report—Written Opinion dated Jul. 27, 2021 from corresponding Application No. PCT/US21/27707.
Andre H. St. Amant et al. "Tuning the Diels-Alder Reaction for Bioconjugation to Maleimide Drug-Linkers", Bioconjugate Chemistry, vol. 29, No. 7, Jun. 22, 2018, pp. 2406-2414.
Oller-Salvia et al., "Rapid and Efficient Generation of Stable Antibody-Drug Conjugates via an Encoded Cyclopropene and an Inverse-Electron-Demand Diels-Alder Reaction," Angewandte Chemie International Edition 57(11):2831-2834 (2018).
Amant et al., "A Diene-Containing Noncanonical Amino Acid Enables Dual Functionality in Proteins: Rapid Diels-Alder Reaction with Maleimide or Proximity-Based Dimerization," Angewandte Chemie International Edition 58(25):8489-8493 (2019).

*Primary Examiner* — Taofiq A Solola
(74) *Attorney, Agent, or Firm* — Troutman Pepper Locke LLP

(57) ABSTRACT

Described herein are protein-payload conjugates and compositions thereof that are useful, for example, for target-specific delivery of therapeutic and/or imaging agent moieties. In certain embodiments, provided are specific and efficient methods for producing protein-payload constructs (e.g., antibody-drug conjugates) utilizing a combination of transglutaminase and Diels-Alder techniques. Antibody-drug conjugates and compositions which comprise glutaminyl-modified antibodies, Diels-Alder adducts, and reactive payloads and are provided.

16 Claims, No Drawings
Specification includes a Sequence Listing.

SEQUENCE LISTING

```
Sequence total quantity: 466
SEQ ID NO: 1                moltype = DNA   length = 363
FEATURE                     Location/Qualifiers
misc_feature                1..363
                            note = Synthetic
source                      1..363
                            mol_type = other DNA
                            organism = synthetic construct
SEQUENCE: 1
caggtccaat tggtacagtc tgggggctgag gtgaagaagc ctggggcctc agtgaaggtg   60
tcctgcaagg tttccggata caccctcact gaattatcca tacactgggt gcgccaggtt  120
cctggaaaag gacttgagtg gatgggaggt tttgatcctg aagagggtga aacaatcttc  180
gcacaggagt tccgggacag agtcaccttg accgaggaca catctccaga cacagcctac  240
atggagttga gcagcctgaa atctgaggac gcggccgtat attactgtac aaccccccga  300
tattgtaata atggtatatg ttatgactac tggggccagg gaaccctggt caccgtctct  360
tca                                                                363

SEQ ID NO: 2                moltype = AA    length = 121
FEATURE                     Location/Qualifiers
REGION                      1..121
                            note = Synthetic
source                      1..121
                            mol_type = protein
                            organism = synthetic construct
SEQUENCE: 2
QVQLVQSGAE VKKPGASVKV SCKVSGYTLT ELSIHWVRQV PGKGLEWMGG FDPEEGETIF   60
AQEFRDRVTL TEDTSPDTAY MELSSLKSED AAVYYCTTPR YCNNGICYDY WGQGTLVTVS  120
S                                                                  121

SEQ ID NO: 3                moltype = DNA   length = 24
FEATURE                     Location/Qualifiers
misc_feature                1..24
                            note = Synthetic
source                      1..24
                            mol_type = other DNA
                            organism = synthetic construct
SEQUENCE: 3
ggatacaccc tcactgaatt atcc                                          24

SEQ ID NO: 4                moltype = AA    length = 8
FEATURE                     Location/Qualifiers
REGION                      1..8
                            note = Synthetic
source                      1..8
                            mol_type = protein
                            organism = synthetic construct
SEQUENCE: 4
GYTLTELS                                                            8

SEQ ID NO: 5                moltype = DNA   length = 24
FEATURE                     Location/Qualifiers
misc_feature                1..24
                            note = Synthetic
source                      1..24
                            mol_type = other DNA
                            organism = synthetic construct
SEQUENCE: 5
tttgatcctg aagagggtga aaca                                          24

SEQ ID NO: 6                moltype = AA    length = 8
FEATURE                     Location/Qualifiers
REGION                      1..8
                            note = Synthetic
source                      1..8
                            mol_type = protein
                            organism = synthetic construct
SEQUENCE: 6
FDPEEGET                                                            8

SEQ ID NO: 7                moltype = DNA   length = 42
FEATURE                     Location/Qualifiers
misc_feature                1..42
                            note = Synthetic
source                      1..42
                            mol_type = other DNA
                            organism = synthetic construct
SEQUENCE: 7
acaaccccccc gatattgtaa taatggtata tgttatgact ac                     42
```

| SEQ ID NO: 8 | moltype = AA   length = 14 |
|---|---|
| FEATURE | Location/Qualifiers |
| REGION | 1..14 |
| | note = Synthetic |
| source | 1..14 |
| | mol_type = protein |
| | organism = synthetic construct |

SEQUENCE: 8
TTPRYCNNGI CYDY                                                           14

| SEQ ID NO: 9 | moltype = DNA   length = 327 |
|---|---|
| FEATURE | Location/Qualifiers |
| misc_feature | 1..327 |
| | note = Synthetic |
| source | 1..327 |
| | mol_type = other DNA |
| | organism = synthetic construct |

SEQUENCE: 9
```
gacatccaga tgacccagtc gccttcctcc ctgtctgcat ctgtgggaga cagagtcacc   60
atcacttgcc gggcaagtca gagcattagc aactatttaa attggtatca gcagaaacca  120
gggaaagccc ctaagctcct gatctatact gcatccagtt tgcaaagtgg ggtcccatca  180
aggttcagtg gcagtggatc tgggacagat ttcactctca ccatcagcag tcttcaaact  240
gaagattttg caacttacta ttgtcaacag agttacagta attttccgat caccttcggc  300
caagggacac gactggagat taaacga                                     327
```

| SEQ ID NO: 10 | moltype = AA   length = 109 |
|---|---|
| FEATURE | Location/Qualifiers |
| REGION | 1..109 |
| | note = Synthetic |
| source | 1..109 |
| | mol_type = protein |
| | organism = synthetic construct |

SEQUENCE: 10
DIQMTQSPSS LSASVGDRVT ITCRASQSIS NYLNWYQQKP GKAPKLLIYT ASSLQSGVPS   60
RFSGSGSGTD FTLTISSLQT EDFATYYCQQ SYSNFPITFG QGTRLEIKR             109

| SEQ ID NO: 11 | moltype = DNA   length = 18 |
|---|---|
| FEATURE | Location/Qualifiers |
| misc_feature | 1..18 |
| | note = Synthetic |
| source | 1..18 |
| | mol_type = other DNA |
| | organism = synthetic construct |

SEQUENCE: 11
cagagcatta gcaactat                                                       18

| SEQ ID NO: 12 | moltype = AA   length = 6 |
|---|---|
| FEATURE | Location/Qualifiers |
| REGION | 1..6 |
| | note = Synthetic |
| source | 1..6 |
| | mol_type = protein |
| | organism = synthetic construct |

SEQUENCE: 12
QSISNY                                                                     6

| SEQ ID NO: 13 | moltype =     length = |
|---|---|
SEQUENCE: 13
000

| SEQ ID NO: 14 | moltype =     length = |
|---|---|
SEQUENCE: 14
000

| SEQ ID NO: 15 | moltype = DNA   length = 30 |
|---|---|
| FEATURE | Location/Qualifiers |
| misc_feature | 1..30 |
| | note = Synthetic |
| source | 1..30 |
| | mol_type = other DNA |
| | organism = synthetic construct |

SEQUENCE: 15
caacagagtt acagtaattt tccgatcacc                                          30

| SEQ ID NO: 16 | moltype = AA   length = 10 |
|---|---|
| FEATURE | Location/Qualifiers |
| REGION | 1..10 |
| | note = Synthetic |

```
source                         1..10
                               mol_type = protein
                               organism = synthetic construct
SEQUENCE: 16
QQSYSNFPIT                                                                    10

SEQ ID NO: 17                  moltype = DNA   length = 360
FEATURE                        Location/Qualifiers
misc_feature                   1..360
                               note = Synthetic
source                         1..360
                               mol_type = other DNA
                               organism = synthetic construct
SEQUENCE: 17
gtgcagctgg tggagtctgg gggaggcttg gtccagcctg gagggtccct gagactctcc          60
tgtgcagcct ctggattcac cttcagtgac cactacatgg actgggtccg tcaggctcct         120
gggaaggggc tggagtgggt tggccgaacc agaaacaaag ctaatagtca caccacagaa         180
tacgccgcgt ctgtgagtgg cagattcacc atctccaaga tgattcaaa gaactcattg          240
tatctgcaaa tgaacagcct gaaaaccgag gacacggccg tgtattattg cactagagcc         300
ggtataattg gaaccctctt tgactactgg ggccagggaa ccctggtcac cgtctcctca         360

SEQ ID NO: 18                  moltype = AA   length = 120
FEATURE                        Location/Qualifiers
REGION                         1..120
                               note = Synthetic
source                         1..120
                               mol_type = protein
                               organism = synthetic construct
SEQUENCE: 18
VQLVESGGGL VQPGGSLRLS CAASGFTFSD HYMDWVRQAP GKGLEWVGRT RNKANSHTTE           60
YAASVSGRFT ISRDDSKNSL YLQMNSLKTE DTAVYYCTRA GIIGTLFDYW GQGTLVTVSS          120

SEQ ID NO: 19                  moltype = DNA   length = 24
FEATURE                        Location/Qualifiers
misc_feature                   1..24
                               note = Synthetic
source                         1..24
                               mol_type = other DNA
                               organism = synthetic construct
SEQUENCE: 19
ggattcacct tcagtgacca ctac                                                   24

SEQ ID NO: 20                  moltype = AA   length = 8
FEATURE                        Location/Qualifiers
REGION                         1..8
                               note = Synthetic
source                         1..8
                               mol_type = protein
                               organism = synthetic construct
SEQUENCE: 20
GFTFSDHY                                                                      8

SEQ ID NO: 21                  moltype = DNA   length = 30
FEATURE                        Location/Qualifiers
misc_feature                   1..30
                               note = Synthetic
source                         1..30
                               mol_type = other DNA
                               organism = synthetic construct
SEQUENCE: 21
accagaaaca aagctaatag tcacaccaca                                             30

SEQ ID NO: 22                  moltype = AA   length = 10
FEATURE                        Location/Qualifiers
REGION                         1..10
                               note = Synthetic
source                         1..10
                               mol_type = protein
                               organism = synthetic construct
SEQUENCE: 22
TRNKANSHTT                                                                   10

SEQ ID NO: 23                  moltype = DNA   length = 36
FEATURE                        Location/Qualifiers
misc_feature                   1..36
                               note = Synthetic
source                         1..36
                               mol_type = other DNA
                               organism = synthetic construct
```

```
SEQUENCE: 23
actagagccg gtataattgg aaccctcttt gactac                              36

SEQ ID NO: 24            moltype = AA  length = 12
FEATURE                  Location/Qualifiers
REGION                   1..12
                         note = Synthetic
source                   1..12
                         mol_type = protein
                         organism = synthetic construct
SEQUENCE: 24
TRAGIIGTLF DY                                                        12

SEQ ID NO: 25            moltype = DNA  length = 327
FEATURE                  Location/Qualifiers
misc_feature             1..327
                         note = Synthetic
source                   1..327
                         mol_type = other DNA
                         organism = synthetic construct
SEQUENCE: 25
gacatccaga tgacccagtc tccatcctcc ctgtctgcat ctgtaggaga cagagtcacc    60
atcacttgcc gggcaagtca gagcattagc agctatttaa attggtatca gcagaaacca  120
gggaaagccc ctaagctcct gatctatgct gcatccagtt tgcaaagtgg ggtcccgtca  180
aggttcagtg gcagtggatc tgggacagat ttcactctca ccatcagcag tctgcaacct  240
gaagattttg caacttacta ctgtcaacag agttacagta cccctccgat caccttcggc  300
caagggacac gactggagat taaacga                                      327

SEQ ID NO: 26            moltype = AA  length = 109
FEATURE                  Location/Qualifiers
REGION                   1..109
                         note = Synthetic
source                   1..109
                         mol_type = protein
                         organism = synthetic construct
SEQUENCE: 26
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPPITFG QGTRLEIKR              109

SEQ ID NO: 27            moltype = DNA  length = 18
FEATURE                  Location/Qualifiers
misc_feature             1..18
                         note = Synthetic
source                   1..18
                         mol_type = other DNA
                         organism = synthetic construct
SEQUENCE: 27
cagagcatta gcagctat                                                  18

SEQ ID NO: 28            moltype = AA  length = 6
FEATURE                  Location/Qualifiers
REGION                   1..6
                         note = Synthetic
source                   1..6
                         mol_type = protein
                         organism = synthetic construct
SEQUENCE: 28
QSISSY                                                                6

SEQ ID NO: 29            moltype =   length =
SEQUENCE: 29
000

SEQ ID NO: 30            moltype =   length =
SEQUENCE: 30
000

SEQ ID NO: 31            moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 31
caacagagtt acagtacccc tccgatcacc                                     30

SEQ ID NO: 32            moltype = AA  length = 10
FEATURE                  Location/Qualifiers
```

```
REGION                         1..10
                               note = Synthetic
source                         1..10
                               mol_type = protein
                               organism = synthetic construct
SEQUENCE: 32
QQSYSTPPIT                                                              10

SEQ ID NO: 33                  moltype = DNA  length = 363
FEATURE                        Location/Qualifiers
misc_feature                   1..363
                               note = Synthetic
source                         1..363
                               mol_type = other DNA
                               organism = synthetic construct
SEQUENCE: 33
gaggtgcagc tggtggagtc tgggggaggc ttggtccagc ctggagggtc cctgagactc         60
tcctgtgcag cctctggatt cacccttcagt gaccactata tggactgggt ccgccaggct       120
ccagggaagg ggctggaatg ggttggccgt actcgaaaca aagctaatag tcacaccaca        180
gaatacaccg cgtctgtgac aggcagattc accatctcaa gagatgattc aagaaactca        240
ctatatctgc aaatgaacag cctgaaaacc gaggacacgg ccgtatatta ctgtgttaga        300
gccggtataa ttggaaccct cttttgactat tggggccagg gaaccctggt caccgtctcc       360
tca                                                                     363

SEQ ID NO: 34                  moltype = AA  length = 121
FEATURE                        Location/Qualifiers
REGION                         1..121
                               note = Synthetic
source                         1..121
                               mol_type = protein
                               organism = synthetic construct
SEQUENCE: 34
EVQLVESGGG LVQPGGSLRL SCAASGFTFS DHYMDWVRQA PGKGLEWVGR TRNKANSHTT         60
EYTASVTGRF TISRDDSRNS LYLQMNSLKT EDTAVYYCVR AGIIGTLFDY WGQGTLVTVS        120
S                                                                       121

SEQ ID NO: 35                  moltype = DNA  length = 24
FEATURE                        Location/Qualifiers
misc_feature                   1..24
                               note = Synthetic
source                         1..24
                               mol_type = other DNA
                               organism = synthetic construct
SEQUENCE: 35
ggattcacct tcagtgacca ctat                                               24

SEQ ID NO: 36                  moltype = AA  length = 8
FEATURE                        Location/Qualifiers
REGION                         1..8
                               note = Synthetic
source                         1..8
                               mol_type = protein
                               organism = synthetic construct
SEQUENCE: 36
GFTFSDHY                                                                 8

SEQ ID NO: 37                  moltype = DNA  length = 30
FEATURE                        Location/Qualifiers
misc_feature                   1..30
                               note = Synthetic
source                         1..30
                               mol_type = other DNA
                               organism = synthetic construct
SEQUENCE: 37
actcgaaaca aagctaatag tcacaccaca                                         30

SEQ ID NO: 38                  moltype = AA  length = 10
FEATURE                        Location/Qualifiers
REGION                         1..10
                               note = Synthetic
source                         1..10
                               mol_type = protein
                               organism = synthetic construct
SEQUENCE: 38
TRNKANSHTT                                                               10

SEQ ID NO: 39                  moltype = DNA  length = 36
FEATURE                        Location/Qualifiers
misc_feature                   1..36
```

```
                        note = Synthetic
source                  1..36
                        mol_type = other DNA
                        organism = synthetic construct
SEQUENCE: 39
gttagagccg gtataattgg aaccctcttt gactat                            36

SEQ ID NO: 40           moltype = AA  length = 12
FEATURE                 Location/Qualifiers
REGION                  1..12
                        note = Synthetic
source                  1..12
                        mol_type = protein
                        organism = synthetic construct
SEQUENCE: 40
VRAGIIGTLF DY                                                     12

SEQ ID NO: 41           moltype = DNA  length = 327
FEATURE                 Location/Qualifiers
misc_feature            1..327
                        note = Synthetic
source                  1..327
                        mol_type = other DNA
                        organism = synthetic construct
SEQUENCE: 41
gacatccaga tgacccagtt tccatcctcc ctgtctgcat ctgtaggaga cagagtcacc  60
atcacttgcc gggcaagtca gagcattagc agctttttaa attggtttca gcagaaacca 120
gggaaagccc ctaagttcct gatctatgct gcatccagtt tgcaaagtgg ggtcccatca 180
aggttcagtg gcagtgggtc tgggacagat ttcactctca ccatcagcag tctacaacct 240
gaagattttg caacttacta ctgtcaacag agttacagtt cccctccgat caccttcggc 300
caagggacac gactggagat taaacga                                    327

SEQ ID NO: 42           moltype = AA  length = 109
FEATURE                 Location/Qualifiers
REGION                  1..109
                        note = Synthetic
source                  1..109
                        mol_type = protein
                        organism = synthetic construct
SEQUENCE: 42
DIQMTQFPSS LSASVGDRVT ITCRASQSIS SFLNWFQQKP GKAPKFLIYA ASSLQSGVPS  60
RFSGSGSGTD FTLTISSLQP EDFATYYCQQ SYSSPPITFG QGTRLEIKR            109

SEQ ID NO: 43           moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 43
cagagcatta gcagcttt                                               18

SEQ ID NO: 44           moltype = AA  length = 6
FEATURE                 Location/Qualifiers
REGION                  1..6
                        note = Synthetic
source                  1..6
                        mol_type = protein
                        organism = synthetic construct
SEQUENCE: 44
QSISSF                                                             6

SEQ ID NO: 45           moltype =  length =
SEQUENCE: 45
000

SEQ ID NO: 46           moltype =  length =
SEQUENCE: 46
000

SEQ ID NO: 47           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 47
```

```
caacagagtt acagttcccc tccgatcacc                                       30

SEQ ID NO: 48           moltype = AA   length = 10
FEATURE                 Location/Qualifiers
REGION                  1..10
                        note = Synthetic
source                  1..10
                        mol_type = protein
                        organism = synthetic construct
SEQUENCE: 48
QQSYSSPPIT                                                             10

SEQ ID NO: 49           moltype = DNA  length = 357
FEATURE                 Location/Qualifiers
misc_feature            1..357
                        note = Synthetic
source                  1..357
                        mol_type = other DNA
                        organism = synthetic construct
SEQUENCE: 49
caggtgcagc tgcaggagtc gggcccagga ctggtgaagc cttcggagac cctgtccctc      60
acctgcactg tcactggtgg ctccatcagt aggaactact ggagttggat ccggcagccc     120
ccagggaagg gactgaatg gattggatat atctattaca gtgggagtat cgactacaat      180
ccctccctca agagtcgagt caccatatca gtagacacgt ccaagaacca gttctccctg     240
aagctgagtt ctatgaccgc tgcggacacg gccgtatact actgtgcgag agatcggtgg     300
aactggaaat acggtatgga cgtctggggc caagggacca cggtcatcgt ctcgtca        357

SEQ ID NO: 50           moltype = AA   length = 119
FEATURE                 Location/Qualifiers
REGION                  1..119
                        note = Synthetic
source                  1..119
                        mol_type = protein
                        organism = synthetic construct
SEQUENCE: 50
QVQLQESGPG LVKPSETLSL TCTVTGGSIS RNYWSWIRQP PGKGLEWIGY IYYSGSIDYN      60
PSLKSRVTIS VDTSKNQFSL KLSSMTAADT AVYYCARDRW NWKYGMDVWG QGTTVIVSS      119

SEQ ID NO: 51           moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 51
ggtggctcca tcagtaggaa ctac                                             24

SEQ ID NO: 52           moltype = AA   length = 8
FEATURE                 Location/Qualifiers
REGION                  1..8
                        note = Synthetic
source                  1..8
                        mol_type = protein
                        organism = synthetic construct
SEQUENCE: 52
GGSISRNY                                                                8

SEQ ID NO: 53           moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 53
atctattaca gtgggagtat c                                                21

SEQ ID NO: 54           moltype = AA   length = 7
FEATURE                 Location/Qualifiers
REGION                  1..7
                        note = Synthetic
source                  1..7
                        mol_type = protein
                        organism = synthetic construct
SEQUENCE: 54
IYYSGSI                                                                 7

SEQ ID NO: 55           moltype = DNA  length = 39
```

```
FEATURE                 Location/Qualifiers
misc_feature            1..39
                        note = Synthetic
source                  1..39
                        mol_type = other DNA
                        organism = synthetic construct
SEQUENCE: 55
gcgagagatc ggtggaactg gaaatacggt atggacgtc                              39

SEQ ID NO: 56           moltype = AA   length = 13
FEATURE                 Location/Qualifiers
REGION                  1..13
                        note = Synthetic
source                  1..13
                        mol_type = protein
                        organism = synthetic construct
SEQUENCE: 56
ARDRWNWKYG MDV                                                          13

SEQ ID NO: 57           moltype = DNA   length = 327
FEATURE                 Location/Qualifiers
misc_feature            1..327
                        note = Synthetic
source                  1..327
                        mol_type = other DNA
                        organism = synthetic construct
SEQUENCE: 57
gaaattgtgt tgacgcagtc tccaggcacc ctgtctttgt ctccagggga aagagccacc       60
ctctcctgca gggccagtca gactgttaga aacaactact tagcctggta ccaccagaaa      120
cctggccagg ctcccaggct cctcatctat ggtgcatcca gcagggccac tggcatccca      180
gacaggttca gtggcagtgg gtctgggaca gacttcactc tcaccatcag cagactggag      240
cctgaagatt ttacagtgta ttactgtcac cagtatggta actcaccttg gacgttcggc      300
caagggacca aatggaaat caaacga                                           327

SEQ ID NO: 58           moltype = AA   length = 109
FEATURE                 Location/Qualifiers
REGION                  1..109
                        note = Synthetic
source                  1..109
                        mol_type = protein
                        organism = synthetic construct
SEQUENCE: 58
EIVLTQSPGT LSLSPGERAT LSCRASQTVR NNYLAWYHQK PGQAPRLLIY GASSRATGIP       60
DRFSGSGSGT DFTLTISRLE PEDFTVYYCH QYGNSPWTFG QGTKMEIKR                  109

SEQ ID NO: 59           moltype = DNA   length = 21
FEATURE                 Location/Qualifiers
misc_feature            1..21
                        note = Synthetic
source                  1..21
                        mol_type = other DNA
                        organism = synthetic construct
SEQUENCE: 59
cagactgtta gaaacaacta c                                                 21

SEQ ID NO: 60           moltype = AA   length = 7
FEATURE                 Location/Qualifiers
REGION                  1..7
                        note = Synthetic
source                  1..7
                        mol_type = protein
                        organism = synthetic construct
SEQUENCE: 60
QTVRNNY                                                                  7

SEQ ID NO: 61           moltype =   length =
SEQUENCE: 61
000

SEQ ID NO: 62           moltype =   length =
SEQUENCE: 62
000

SEQ ID NO: 63           moltype = DNA   length = 27
FEATURE                 Location/Qualifiers
misc_feature            1..27
                        note = Synthetic
source                  1..27
                        mol_type = other DNA
```

```
                        organism = synthetic construct
SEQUENCE: 63
caccagtatg gtaactcacc ttggacg                                                    27

SEQ ID NO: 64           moltype = AA   length = 9
FEATURE                 Location/Qualifiers
REGION                  1..9
                        note = Synthetic
source                  1..9
                        mol_type = protein
                        organism = synthetic construct
SEQUENCE: 64
HQYGNSPWT                                                                         9

SEQ ID NO: 65           moltype = DNA  length = 363
FEATURE                 Location/Qualifiers
misc_feature            1..363
                        note = Synthetic
source                  1..363
                        mol_type = other DNA
                        organism = synthetic construct
SEQUENCE: 65
gaggtgcagc tggtggagtc tgggggaggc ttggtccagc ctggagggtc cctgagactc                60
tcctgtgcag cctctggatt caccttcagt gaccactaca tggactgggt ccgccaggct               120
cctgggaagg ggctggagtg ggttggccga actagaaaca aagctaatag ttacaccaca               180
gaatacgccg cgtctgtgag tggcagattc accatctcaa gagatgattc aaagaactca               240
ttatatctgc aaatgaacag cctgaaaacc gaggacacgg ccgtgtatta ttgcactaga               300
gccggtataa ttggaaccct ctttgactac tggggccagg gaaccctggt caccgtctcc               360
tca                                                                             363

SEQ ID NO: 66           moltype = AA   length = 121
FEATURE                 Location/Qualifiers
REGION                  1..121
                        note = Synthetic
source                  1..121
                        mol_type = protein
                        organism = synthetic construct
SEQUENCE: 66
EVQLVESGGG LVQPGGSLRL SCAASGFTFS DHYMDWVRQA PGKGLEWVGR TRNKANSYTT                60
EYAASVSGRF TISRDDSKNS LYLQMNSLKT EDTAVYYCTR AGIIGTLFDY WGQGTLVTVS               120
S                                                                               121

SEQ ID NO: 67           moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 67
ggattcacct tcagtgacca ctac                                                       24

SEQ ID NO: 68           moltype = AA   length = 8
FEATURE                 Location/Qualifiers
REGION                  1..8
                        note = Synthetic
source                  1..8
                        mol_type = protein
                        organism = synthetic construct
SEQUENCE: 68
GFTFSDHY                                                                          8

SEQ ID NO: 69           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 69
actagaaaca aagctaatag ttacaccaca                                                 30

SEQ ID NO: 70           moltype = AA   length = 10
FEATURE                 Location/Qualifiers
REGION                  1..10
                        note = Synthetic
source                  1..10
                        mol_type = protein
                        organism = synthetic construct
```

```
SEQUENCE: 70
TRNKANSYTT                                                                      10

SEQ ID NO: 71           moltype = DNA   length = 36
FEATURE                 Location/Qualifiers
misc_feature            1..36
                        note = Synthetic
source                  1..36
                        mol_type = other DNA
                        organism = synthetic construct
SEQUENCE: 71
actagagccg gtataattgg aaccctcttt gactac                                          36

SEQ ID NO: 72           moltype = AA    length = 12
FEATURE                 Location/Qualifiers
REGION                  1..12
                        note = Synthetic
source                  1..12
                        mol_type = protein
                        organism = synthetic construct
SEQUENCE: 72
TRAGIIGTLF DY                                                                    12

SEQ ID NO: 73           moltype = DNA   length = 327
FEATURE                 Location/Qualifiers
misc_feature            1..327
                        note = Synthetic
source                  1..327
                        mol_type = other DNA
                        organism = synthetic construct
SEQUENCE: 73
gacatccaga tgacccagtc tccatcctcc ctgtctgcat ctgtaggaga cagagtcacc                60
atcacttgcc gggcaagtca gatcattggt agatatttaa attggtttca gcagaaacca              120
gggaaagtcc ctaagctcct gatctatgct gcatccagtt tgcaacgtgg ggtcccatca              180
aggttcagtg gcagtggatc tgggacagat ttcactctca ccatcagcag tctgcaacct              240
gaagattttg caacttacta ctgtcaacag agttacaata cccctccgat caccttcggc              300
caagggacac gactggagat taaacga                                                  327

SEQ ID NO: 74           moltype = AA    length = 109
FEATURE                 Location/Qualifiers
REGION                  1..109
                        note = Synthetic
source                  1..109
                        mol_type = protein
                        organism = synthetic construct
SEQUENCE: 74
DIQMTQSPSS LSASVGDRVT ITCRASQIIG RYLNWFQQKP GKVPKLLIYA ASSLQRGVPS                60
RFSGSGSGTD FTLTISSLQP EDFATYYCQQ SYNTPPITFG QGTRLEIKR                           109

SEQ ID NO: 75           moltype = DNA   length = 18
FEATURE                 Location/Qualifiers
misc_feature            1..18
                        note = Synthetic
source                  1..18
                        mol_type = other DNA
                        organism = synthetic construct
SEQUENCE: 75
cagatcattg gtagatat                                                              18

SEQ ID NO: 76           moltype = AA    length = 6
FEATURE                 Location/Qualifiers
REGION                  1..6
                        note = Synthetic
source                  1..6
                        mol_type = protein
                        organism = synthetic construct
SEQUENCE: 76
QIIGRY                                                                            6

SEQ ID NO: 77           moltype =       length =
SEQUENCE: 77
000

SEQ ID NO: 78           moltype =       length =
SEQUENCE: 78
000

SEQ ID NO: 79           moltype = DNA   length = 30
FEATURE                 Location/Qualifiers
```

```
misc_feature            1..30
                        note = Synthetic
source                  1..30
                        mol_type = other DNA
                        organism = synthetic construct
SEQUENCE: 79
caacagagtt acaatacccc tccgatcacc                                        30

SEQ ID NO: 80           moltype = AA   length = 10
FEATURE                 Location/Qualifiers
REGION                  1..10
                        note = Synthetic
source                  1..10
                        mol_type = protein
                        organism = synthetic construct
SEQUENCE: 80
QQSYNTPPIT                                                              10

SEQ ID NO: 81           moltype = DNA   length = 363
FEATURE                 Location/Qualifiers
misc_feature            1..363
                        note = Synthetic
source                  1..363
                        mol_type = other DNA
                        organism = synthetic construct
SEQUENCE: 81
caggtccagc tggtgcagtc tggggctgag gtgagggagc ctggggcctc agtgaagctc        60
tcctgcaagg tttccggata caccctcact gaattatcca tccactgggt gcgacaggct       120
cctggaaaag gacttgagtg gatgggaggt tttgatcctg aagagggtga acagtctac        180
gcacagaagt tccggggcag agtcaccctg accgaggaca taagtccaga cacgcctac        240
atggagctga gcagcctgac ctctgaggac acggccgtat attattgtgc aaccccccgc       300
tattgtaata atggtatatg ttatgactac tggggccagg gaaccctaat caccgtctcc       360
tca                                                                    363

SEQ ID NO: 82           moltype = AA   length = 121
FEATURE                 Location/Qualifiers
REGION                  1..121
                        note = Synthetic
source                  1..121
                        mol_type = protein
                        organism = synthetic construct
SEQUENCE: 82
QVQLVQSGAE VREPGASVKL SCKVSGYTLT ELSIHWVRQA PGKGLEWMGG FDPEEGETVY        60
AQKFRGRVTL TEDISPDTAY MELSSLTSED TAVYYCATPR YCNNGICYDY WGQGTLITVS       120
S                                                                      121

SEQ ID NO: 83           moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 83
ggatacaccc tcactgaatt atcc                                              24

SEQ ID NO: 84           moltype = AA   length = 8
FEATURE                 Location/Qualifiers
REGION                  1..8
                        note = Synthetic
source                  1..8
                        mol_type = protein
                        organism = synthetic construct
SEQUENCE: 84
GYTLTELS                                                                 8

SEQ ID NO: 85           moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 85
tttgatcctg aagagggtga aaca                                              24

SEQ ID NO: 86           moltype = AA   length = 8
FEATURE                 Location/Qualifiers
REGION                  1..8
```

```
                        note = Synthetic
source                  1..8
                        mol_type = protein
                        organism = synthetic construct
SEQUENCE: 86
FDPEEGET                                                                 8

SEQ ID NO: 87           moltype = DNA   length = 42
FEATURE                 Location/Qualifiers
misc_feature            1..42
                        note = Synthetic
source                  1..42
                        mol_type = other DNA
                        organism = synthetic construct
SEQUENCE: 87
gcaaccccc gctattgtaa taatggtata tgttatgact ac                           42

SEQ ID NO: 88           moltype = AA   length = 14
FEATURE                 Location/Qualifiers
REGION                  1..14
                        note = Synthetic
source                  1..14
                        mol_type = protein
                        organism = synthetic construct
SEQUENCE: 88
ATPRYCNNGI CYDY                                                         14

SEQ ID NO: 89           moltype = DNA   length = 324
FEATURE                 Location/Qualifiers
misc_feature            1..324
                        note = Synthetic
source                  1..324
                        mol_type = other DNA
                        organism = synthetic construct
SEQUENCE: 89
gacatccaga tgacccagtc tccatcctcc ctgtctgcat ctgtaggaga cagagtcacc        60
atcacttgcc gggcaagtca gagcattagc agctatttaa attggtatca gcagaaacca      120
gggaaagccc ctaagctcct gatctatgct gcatccagtt tgcaaagtgg ggtcccgtca      180
aggttcagtg gcagtggatc tgggacagat ttcactctca ccatcagcag tctgcaacct      240
gaagattttg caacttacta ctgtcaacag agttacagta ccccctccgat caccttcggc     300
caagggacac gactggagat taaa                                             324

SEQ ID NO: 90           moltype = AA   length = 108
FEATURE                 Location/Qualifiers
REGION                  1..108
                        note = Synthetic
source                  1..108
                        mol_type = protein
                        organism = synthetic construct
SEQUENCE: 90
DIQMTQSPSS LSASVGDRVT ITCRASQSIS SYLNWYQQKP GKAPKLLIYA ASSLQSGVPS       60
RFSGSGSGTD FTLTISSLQP EDFATYYCQQ SYSTPPITFG QGTRLEIK                   108

SEQ ID NO: 91           moltype = DNA   length = 18
FEATURE                 Location/Qualifiers
misc_feature            1..18
                        note = Synthetic
source                  1..18
                        mol_type = other DNA
                        organism = synthetic construct
SEQUENCE: 91
cagagcatta gcagctat                                                     18

SEQ ID NO: 92           moltype = AA   length = 6
FEATURE                 Location/Qualifiers
REGION                  1..6
                        note = Synthetic
source                  1..6
                        mol_type = protein
                        organism = synthetic construct
SEQUENCE: 92
QSISSY                                                                   6

SEQ ID NO: 93           moltype =   length =
SEQUENCE: 93
000

SEQ ID NO: 94           moltype =   length =
SEQUENCE: 94
```

```
000

SEQ ID NO: 95           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 95
caacagagtt acagtacccc tccgatcacc                                           30

SEQ ID NO: 96           moltype = AA  length = 10
FEATURE                 Location/Qualifiers
REGION                  1..10
                        note = Synthetic
source                  1..10
                        mol_type = protein
                        organism = synthetic construct
SEQUENCE: 96
QQSYSTPPIT                                                                 10

SEQ ID NO: 97           moltype = DNA  length = 363
FEATURE                 Location/Qualifiers
misc_feature            1..363
                        note = Synthetic
source                  1..363
                        mol_type = other DNA
                        organism = synthetic construct
SEQUENCE: 97
gaggtgcagc tgttggagtc tgggggaggc ttggtacagc ctggggggtc cctgagactc          60
tcctgtgcag cctctggatt cacctttagt aattatgcca tgacctgggt ccgccaggct         120
ccagggacgg ggctggagtg ggtctcagct attagtggtc gtggtagtaa cacatactac         180
acagactccg tgaagggccg gttcaccatc tccagagaca attccaagaa catgctgtat         240
ctgcaaatga acagcctgag agccgaggac acggcctcat attactgtgc gaaagatcgt         300
tttactacag tggggaactg gttcgacccc tggggccagg gaaccctggt caccgtctcc         360
tca                                                                      363

SEQ ID NO: 98           moltype = AA  length = 121
FEATURE                 Location/Qualifiers
REGION                  1..121
                        note = Synthetic
source                  1..121
                        mol_type = protein
                        organism = synthetic construct
SEQUENCE: 98
EVQLLESGGG LVQPGGSLRL SCAASGFTFS NYAMTWVRQA PGTGLEWVSA ISGRGSNTYY           60
TDSVKGRFTI SRDNSKNMLY LQMNSLRAED TASYYCAKDR FTTVGNWFDP WGQGTLVTVS          120
S                                                                        121

SEQ ID NO: 99           moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 99
ggattcacct ttagtaatta tgcc                                                 24

SEQ ID NO: 100          moltype = AA  length = 8
FEATURE                 Location/Qualifiers
REGION                  1..8
                        note = Synthetic
source                  1..8
                        mol_type = protein
                        organism = synthetic construct
SEQUENCE: 100
GFTFSNYA                                                                    8

SEQ ID NO: 101          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 101
attagtggtc gtggtagtaa caca                                                 24
```

```
SEQ ID NO: 102          moltype = AA   length = 8
FEATURE                 Location/Qualifiers
REGION                  1..8
                        note = Synthetic
source                  1..8
                        mol_type = protein
                        organism = synthetic construct
SEQUENCE: 102
ISGRGSNT                                                                 8

SEQ ID NO: 103          moltype = DNA  length = 42
FEATURE                 Location/Qualifiers
misc_feature            1..42
                        note = Synthetic
source                  1..42
                        mol_type = other DNA
                        organism = synthetic construct
SEQUENCE: 103
gcgaaagatc gttttactac agtggggaac tggttcgacc cc                           42

SEQ ID NO: 104          moltype = AA   length = 14
FEATURE                 Location/Qualifiers
REGION                  1..14
                        note = Synthetic
source                  1..14
                        mol_type = protein
                        organism = synthetic construct
SEQUENCE: 104
AKDRFTTVGN WFDP                                                          14

SEQ ID NO: 105          moltype = DNA  length = 327
FEATURE                 Location/Qualifiers
misc_feature            1..327
                        note = Synthetic
source                  1..327
                        mol_type = other DNA
                        organism = synthetic construct
SEQUENCE: 105
gacatccaga tgacccagtc tccatcctcc ctgtctgcat ctgtaggaga cagagtcacc        60
atcacttgcc gggcaagtca gagtattagc agctatttaa attggtatca gcagaaacca       120
gggaaagccc ctaagctcct gatctatgct gcgtccagtt tgcaaaatgg ggtcccatca       180
aggttcagtg gcagtggatc tgggacagat ttcactctca ccatcagcag tctgcagcct       240
gaagattttg caacttacta ctgtcaacag agttacagta gtcttccgat caccttcggc       300
caagggacac gactggatat taaacga                                           327

SEQ ID NO: 106          moltype = AA   length = 109
FEATURE                 Location/Qualifiers
REGION                  1..109
                        note = Synthetic
source                  1..109
                        mol_type = protein
                        organism = synthetic construct
SEQUENCE: 106
DIQMTQSPSS LSASVGDRVT ITCRASQSIS SYLNWYQQKP GKAPKLLIYA ASSLQNGVPS        60
RFSGSGSGTD FTLTISSLQP EDFATYYCQQ SYSSLPITFG QGTRLDIKR                   109

SEQ ID NO: 107          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 107
cagagtatta gcagctat                                                      18

SEQ ID NO: 108          moltype = AA   length = 6
FEATURE                 Location/Qualifiers
REGION                  1..6
                        note = Synthetic
source                  1..6
                        mol_type = protein
                        organism = synthetic construct
SEQUENCE: 108
QSISSY                                                                   6

SEQ ID NO: 109          moltype =    length =
SEQUENCE: 109
```

```
000

SEQ ID NO: 110          moltype =    length =
SEQUENCE: 110
000

SEQ ID NO: 111          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 111
caacagagtt acagtagtct tccgatcacc                                    30

SEQ ID NO: 112          moltype = AA   length = 10
FEATURE                 Location/Qualifiers
REGION                  1..10
                        note = Synthetic
source                  1..10
                        mol_type = protein
                        organism = synthetic construct
SEQUENCE: 112
QQSYSSLPIT                                                          10

SEQ ID NO: 113          moltype = DNA   length = 357
FEATURE                 Location/Qualifiers
misc_feature            1..357
                        note = Synthetic
source                  1..357
                        mol_type = other DNA
                        organism = synthetic construct
SEQUENCE: 113
caggtgcagc tgcaggagtc gggcccagga ctggtgaagc cttcggagac cctgtccctc   60
acctgcactg tcactggtgg ctccatcagt aggaactact ggagttggat ccggcagccc  120
ccagggaagg gactggaatg gattggatat atctattaca gtgggagtat caactacaat  180
ccctccctca agagtcgagt caccatatca gtggacatgt ctaagaacca gttctcccta  240
aagctgaatt ctgtgaccgc tgcggacacg gccgtgtact actgtgcgag agatcgatgg  300
aactggaaat acggtatgga cgtctggggc caagggacca cggtcatcgt ctcgtca     357

SEQ ID NO: 114          moltype = AA   length = 119
FEATURE                 Location/Qualifiers
REGION                  1..119
                        note = Synthetic
source                  1..119
                        mol_type = protein
                        organism = synthetic construct
SEQUENCE: 114
QVQLQESGPG LVKPSETLSL TCTVTGGSIS RNYWSWIRQP PGKGLEWIGY IYYSGSINYN   60
PSLKSRVTIS VDMSKNQFSL KLNSVTAADT AVYYCARDRW NWKYGMDVWG QGTTVIVSS   119

SEQ ID NO: 115          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 115
ggtggctcca tcagtaggaa ctac                                          24

SEQ ID NO: 116          moltype = AA   length = 8
FEATURE                 Location/Qualifiers
REGION                  1..8
                        note = Synthetic
source                  1..8
                        mol_type = protein
                        organism = synthetic construct
SEQUENCE: 116
GGSISRNY                                                             8

SEQ ID NO: 117          moltype = DNA   length = 21
FEATURE                 Location/Qualifiers
misc_feature            1..21
                        note = Synthetic
source                  1..21
                        mol_type = other DNA
                        organism = synthetic construct
```

```
SEQUENCE: 117
atctattaca gtgggagtat c                                              21

SEQ ID NO: 118          moltype = AA  length = 7
FEATURE                 Location/Qualifiers
REGION                  1..7
                        note = Synthetic
source                  1..7
                        mol_type = protein
                        organism = synthetic construct
SEQUENCE: 118
IYYSGSI                                                              7

SEQ ID NO: 119          moltype = DNA  length = 39
FEATURE                 Location/Qualifiers
misc_feature            1..39
                        note = Synthetic
source                  1..39
                        mol_type = other DNA
                        organism = synthetic construct
SEQUENCE: 119
gcgagagatc gatggaactg gaaatacggt atggacgtc                           39

SEQ ID NO: 120          moltype = AA  length = 13
FEATURE                 Location/Qualifiers
REGION                  1..13
                        note = Synthetic
source                  1..13
                        mol_type = protein
                        organism = synthetic construct
SEQUENCE: 120
ARDRWNWKYG MDV                                                       13

SEQ ID NO: 121          moltype = DNA  length = 327
FEATURE                 Location/Qualifiers
misc_feature            1..327
                        note = Synthetic
source                  1..327
                        mol_type = other DNA
                        organism = synthetic construct
SEQUENCE: 121
gaaattgtgt tgacgcagtc tccaggcacc ctgtctttgt ctccagggga aagagccacc    60
ctctcctgca gggccagtca gactgttaga aacagctact tagcctggta ccaccagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gttcatattg gacgttcggc   300
caagggacca aaatggaaat caaacga                                       327

SEQ ID NO: 122          moltype = AA  length = 109
FEATURE                 Location/Qualifiers
REGION                  1..109
                        note = Synthetic
source                  1..109
                        mol_type = protein
                        organism = synthetic construct
SEQUENCE: 122
EIVLTQSPGT LSLSPGERAT LSCRASQTVR NSYLAWYHQK PGQAPRLLIY GASSRATGIP    60
DRFSGSGSGT DFTLTISRLE PEDFAVYYCQ QYGSSYWTFG QGTKMEIKR               109

SEQ ID NO: 123          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 123
cagactgtta gaaacagcta c                                              21

SEQ ID NO: 124          moltype = AA  length = 7
FEATURE                 Location/Qualifiers
REGION                  1..7
                        note = Synthetic
source                  1..7
                        mol_type = protein
                        organism = synthetic construct
SEQUENCE: 124
QTVRNSY                                                              7
```

-continued

```
SEQ ID NO: 125          moltype =    length =
SEQUENCE: 125
000

SEQ ID NO: 126          moltype =    length =
SEQUENCE: 126
000

SEQ ID NO: 127          moltype = DNA   length = 27
FEATURE                 Location/Qualifiers
misc_feature            1..27
                        note = Synthetic
source                  1..27
                        mol_type = other DNA
                        organism = synthetic construct
SEQUENCE: 127
cagcagtatg gtagttcata ttggacg                                        27

SEQ ID NO: 128          moltype = AA   length = 9
FEATURE                 Location/Qualifiers
REGION                  1..9
                        note = Synthetic
source                  1..9
                        mol_type = protein
                        organism = synthetic construct
SEQUENCE: 128
QQYGSSYWT                                                            9

SEQ ID NO: 129          moltype = DNA   length = 363
FEATURE                 Location/Qualifiers
misc_feature            1..363
                        note = Synthetic
source                  1..363
                        mol_type = other DNA
                        organism = synthetic construct
SEQUENCE: 129
caggtccagc tggtgcagtc tggggctgag gtgaagaagc ctggggcctc agtgaaggtc    60
tcctgcaagg tttccggata caccctcact gaattatcca tacactgggt gcgacaggct   120
cctggaaaag gacttgagtg gatgggaggt tttgatcctg aagatggtga acaatctac   180
gcacagaagt tccggggcag agtcaccatg accgaggaca tatctccaga cacagcctac   240
atggagctga gcagcctgag atctgaagac acggccgtat attactgtgc aaccccccgc   300
tattgtaata atggtatatg ttatgactat tggggccagg gaaccctggt caccgtctcc   360
tca                                                                 363

SEQ ID NO: 130          moltype = AA   length = 121
FEATURE                 Location/Qualifiers
REGION                  1..121
                        note = Synthetic
source                  1..121
                        mol_type = protein
                        organism = synthetic construct
SEQUENCE: 130
QVQLVQSGSE VKKPGASVKV SCKVSGYTLT ELSIHWVRQA PGKGLEWMGG FDPEDGETIY    60
AQKFRGRVTM TEDISPDTAY MELSSLRSED TAVYYCATPR YCNNGICYDY WGQGTLVTVS   120
S                                                                   121

SEQ ID NO: 131          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 131
ggatacaccc tcactgaatt atcc                                           24

SEQ ID NO: 132          moltype = AA   length = 8
FEATURE                 Location/Qualifiers
REGION                  1..8
                        note = Synthetic
source                  1..8
                        mol_type = protein
                        organism = synthetic construct
SEQUENCE: 132
GYTLTELS                                                             8

SEQ ID NO: 133          moltype = DNA   length = 24
FEATURE                 Location/Qualifiers
misc_feature            1..24
```

```
                            note = Synthetic
source                      1..24
                            mol_type = other DNA
                            organism = synthetic construct
SEQUENCE: 133
tttgatcctg aagatggtga aaca                                              24

SEQ ID NO: 134              moltype = AA  length = 8
FEATURE                     Location/Qualifiers
REGION                      1..8
                            note = Synthetic
source                      1..8
                            mol_type = protein
                            organism = synthetic construct
SEQUENCE: 134
FDPEDGET                                                                8

SEQ ID NO: 135              moltype = DNA  length = 42
FEATURE                     Location/Qualifiers
misc_feature                1..42
                            note = Synthetic
source                      1..42
                            mol_type = other DNA
                            organism = synthetic construct
SEQUENCE: 135
gcaaccccc gctattgtaa taatggtata tgttatgact at                           42

SEQ ID NO: 136              moltype = AA  length = 14
FEATURE                     Location/Qualifiers
REGION                      1..14
                            note = Synthetic
source                      1..14
                            mol_type = protein
                            organism = synthetic construct
SEQUENCE: 136
ATPRYCNNGI CYDY                                                         14

SEQ ID NO: 137              moltype = DNA  length = 327
FEATURE                     Location/Qualifiers
misc_feature                1..327
                            note = Synthetic
source                      1..327
                            mol_type = other DNA
                            organism = synthetic construct
SEQUENCE: 137
gacatccaga tgacccagtc tccatcctcc ctgtctgcat ctataggaga cagagtcacc        60
atcacttgcc gggcaagtca gagcattagc agctatttaa attggtatca gcagaaacca       120
gggaaagccc ctatgctcct gatctatgct gcatccagtt tgcaaagtgg ggtcccatca       180
aggttcagtg gcagtggatc tgggacagat ttcactctca ccatcagcag tctgcaaact       240
gaagattttg caacttacta ctgtcaacag agttacagta cccctccgat caccttcggc       300
caagggacac gactggagat taaacga                                          327

SEQ ID NO: 138              moltype = AA  length = 109
FEATURE                     Location/Qualifiers
REGION                      1..109
                            note = Synthetic
source                      1..109
                            mol_type = protein
                            organism = synthetic construct
SEQUENCE: 138
DIQMTQSPSS LSASIGDRVT ITCRASQSIS SYLNWYQQKP GKAPMLLIYA ASSLQSGVPS        60
RFSGSGSGTD FTLTISSLQT EDFATYYCQQ SYSTPPITFG QGTRLEIKR                   109

SEQ ID NO: 139              moltype = DNA  length = 18
FEATURE                     Location/Qualifiers
misc_feature                1..18
                            note = Synthetic
source                      1..18
                            mol_type = other DNA
                            organism = synthetic construct
SEQUENCE: 139
cagagcatta gcagctat                                                     18

SEQ ID NO: 140              moltype = AA  length = 6
FEATURE                     Location/Qualifiers
REGION                      1..6
                            note = Synthetic
source                      1..6
                            mol_type = protein
```

```
                        organism = synthetic construct
SEQUENCE: 140
QSISSY                                                                  6

SEQ ID NO: 141          moltype =    length =
SEQUENCE: 141
000

SEQ ID NO: 142          moltype =    length =
SEQUENCE: 142
000

SEQ ID NO: 143          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 143
caacagagtt acagtaccccc tccgatcacc                                       30

SEQ ID NO: 144          moltype = AA   length = 10
FEATURE                 Location/Qualifiers
REGION                  1..10
                        note = Synthetic
source                  1..10
                        mol_type = protein
                        organism = synthetic construct
SEQUENCE: 144
QQSYSTPPIT                                                              10

SEQ ID NO: 145          moltype = DNA  length = 345
FEATURE                 Location/Qualifiers
misc_feature            1..345
                        note = Synthetic
source                  1..345
                        mol_type = other DNA
                        organism = synthetic construct
SEQUENCE: 145
caggtgcagc tggtggagtc tgggggaggc ttggtcaagc ctggagggtc cctgagactc        60
tcctgtgcag cctctggatt cattttagt gactactaca tgagctggat ccgccaggct       120
ccagggaagg ggctggagtg ggtttcatac attagtagta gtggtactac catatatgga      180
gactctgtga agggccgatt caccatgtcc agggacaacg ccaagaactc actgtatctg      240
caaatgaaca gcctgagagc cgaggacacg gccgtgtatt actgtgcgag gaactacgct      300
ctctttgact actggggcca gggaaccctg gtcaccgtct cctca                      345

SEQ ID NO: 146          moltype = AA   length = 115
FEATURE                 Location/Qualifiers
REGION                  1..115
                        note = Synthetic
source                  1..115
                        mol_type = protein
                        organism = synthetic construct
SEQUENCE: 146
QVQLVESGGG LVKPGGSLRL SCAASGFIFS DYYMSWIRQA PGKGLEWVSY ISSSGTTIYG        60
DSVKGRFTMS RDNAKNSLYL QMNSLRAEDT AVYYCARNYA LFDYWGQGTL VTVSS           115

SEQ ID NO: 147          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 147
ggattcattt ttagtgacta ctac                                              24

SEQ ID NO: 148          moltype = AA   length = 8
FEATURE                 Location/Qualifiers
REGION                  1..8
                        note = Synthetic
source                  1..8
                        mol_type = protein
                        organism = synthetic construct
SEQUENCE: 148
GFIFSDYY                                                                8

SEQ ID NO: 149          moltype = DNA  length = 24
```

| FEATURE | Location/Qualifiers |
|---|---|
| misc_feature | 1..24 |
| | note = Synthetic |
| source | 1..24 |
| | mol_type = other DNA |
| | organism = synthetic construct |

SEQUENCE: 149
attagtagta gtggtactac cata                                                  24

| SEQ ID NO: 150 | moltype = AA   length = 8 |
|---|---|
| FEATURE | Location/Qualifiers |
| REGION | 1..8 |
| | note = Synthetic |
| source | 1..8 |
| | mol_type = protein |
| | organism = synthetic construct |

SEQUENCE: 150
ISSSGTTI                                                                    8

| SEQ ID NO: 151 | moltype = DNA   length = 27 |
|---|---|
| FEATURE | Location/Qualifiers |
| misc_feature | 1..27 |
| | note = Synthetic |
| source | 1..27 |
| | mol_type = other DNA |
| | organism = synthetic construct |

SEQUENCE: 151
gcgaggaact acgctctctt tgactac                                               27

| SEQ ID NO: 152 | moltype = AA   length = 9 |
|---|---|
| FEATURE | Location/Qualifiers |
| REGION | 1..9 |
| | note = Synthetic |
| source | 1..9 |
| | mol_type = protein |
| | organism = synthetic construct |

SEQUENCE: 152
ARNYALFDY                                                                   9

| SEQ ID NO: 153 | moltype = DNA   length = 324 |
|---|---|
| FEATURE | Location/Qualifiers |
| misc_feature | 1..324 |
| | note = Synthetic |
| source | 1..324 |
| | mol_type = other DNA |
| | organism = synthetic construct |

SEQUENCE: 153
gacatccaga tgacccagtc tccatcctcc ctgtctgcat ctgtaggaga cagagtcacc    60
atcacttgcc aggcgagtca ggacattagc aaatatttaa attggtatca gcagaaacca   120
gggaaagccc ctaagctcct gatctactat acatccaatt tggaaacagg ggtcccatca   180
aggttcagtg gaagtggatc tgggacagat tttactttca ccatcagcag cctgcagcct   240
gaagatattg caacatatta ctgtcaccag tctgattatc tcccattcac tttcggccct   300
gggaccaaag tggatatcaa acga                                          324

| SEQ ID NO: 154 | moltype = AA   length = 108 |
|---|---|
| FEATURE | Location/Qualifiers |
| REGION | 1..108 |
| | note = Synthetic |
| source | 1..108 |
| | mol_type = protein |
| | organism = synthetic construct |

SEQUENCE: 154
DIQMTQSPSS LSASVGDRVT ITCQASQDIS KYLNWYQQKP GKAPKLLIYY TSNLETGVPS    60
RFSGSGSGTD FTFTISSLQP EDIATYYCHQ SDYLPFTFGP GTKVDIKR                108

| SEQ ID NO: 155 | moltype = DNA   length = 18 |
|---|---|
| FEATURE | Location/Qualifiers |
| misc_feature | 1..18 |
| | note = Synthetic |
| source | 1..18 |
| | mol_type = other DNA |
| | organism = synthetic construct |

SEQUENCE: 155
caggacatta gcaaatat                                                         18

| SEQ ID NO: 156 | moltype = AA   length = 6 |
|---|---|
| FEATURE | Location/Qualifiers |
| REGION | 1..6 |
| | note = Synthetic |

```
source                  1..6
                        mol_type = protein
                        organism = synthetic construct
SEQUENCE: 156
QDISKY                                                              6

SEQ ID NO: 157          moltype =    length =
SEQUENCE: 157
000

SEQ ID NO: 158          moltype =    length =
SEQUENCE: 158
000

SEQ ID NO: 159          moltype = DNA   length = 27
FEATURE                 Location/Qualifiers
misc_feature            1..27
                        note = Synthetic
source                  1..27
                        mol_type = other DNA
                        organism = synthetic construct
SEQUENCE: 159
caccagtctg attatctccc attcact                                       27

SEQ ID NO: 160          moltype = AA   length = 9
FEATURE                 Location/Qualifiers
REGION                  1..9
                        note = Synthetic
source                  1..9
                        mol_type = protein
                        organism = synthetic construct
SEQUENCE: 160
HQSDYLPFT                                                           9

SEQ ID NO: 161          moltype = DNA   length = 363
FEATURE                 Location/Qualifiers
misc_feature            1..363
                        note = Synthetic
source                  1..363
                        mol_type = other DNA
                        organism = synthetic construct
SEQUENCE: 161
cagctgcagc tgcaggagtc gggcccagga ctggtgaagc cttcggagac cctgtccctc   60
acctgcactg tctctggtgg ctccatcagc cgtattagtt actactgggg ctggatccgc  120
cagcccccag gaaggggct ggagtggatt gggagtatct atgatagtgg gagtacctac   180
tacaacccgt ccctcaagag tcgagtcacc atatccatag acacgtccaa gaaccagttc  240
tccctgaagc tgagctctgt gaccgccgca gacacggctg tgtattactg tgtgagatat  300
agcagttcgt ccgccttcgc ttttgactac tggggccagg gaaccctggt caccgtctcc  360
tca                                                                363

SEQ ID NO: 162          moltype = AA   length = 121
FEATURE                 Location/Qualifiers
REGION                  1..121
                        note = Synthetic
source                  1..121
                        mol_type = protein
                        organism = synthetic construct
SEQUENCE: 162
QLQLQESGPG LVKPSETLSL TCTVSGGSIS RISYYWGWIR QPPGKGLEWI GSIYDSGSTY   60
YNPSLKSRVT ISIDTSKNQF SLKLSSVTAA DTAVYYCVRY SSSSAFAFDY WGQGTLVTVS  120
S                                                                  121

SEQ ID NO: 163          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 163
ggtggctcca tcagccgtat tagttactac                                    30

SEQ ID NO: 164          moltype = AA   length = 10
FEATURE                 Location/Qualifiers
REGION                  1..10
                        note = Synthetic
source                  1..10
                        mol_type = protein
                        organism = synthetic construct
```

```
SEQUENCE: 164
GGSISRISYY                                                              10

SEQ ID NO: 165          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 165
atctatgata gtgggagtac c                                                 21

SEQ ID NO: 166          moltype = AA  length = 7
FEATURE                 Location/Qualifiers
REGION                  1..7
                        note = Synthetic
source                  1..7
                        mol_type = protein
                        organism = synthetic construct
SEQUENCE: 166
IYDSGST                                                                 7

SEQ ID NO: 167          moltype = DNA  length = 39
FEATURE                 Location/Qualifiers
misc_feature            1..39
                        note = Synthetic
source                  1..39
                        mol_type = other DNA
                        organism = synthetic construct
SEQUENCE: 167
gtgagatata gcagttcgtc cgccttcgct tttgactac                              39

SEQ ID NO: 168          moltype = AA  length = 13
FEATURE                 Location/Qualifiers
REGION                  1..13
                        note = Synthetic
source                  1..13
                        mol_type = protein
                        organism = synthetic construct
SEQUENCE: 168
VRYSSSSAFA FDY                                                          13

SEQ ID NO: 169          moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 169
gacatccaga tgacccagtc tccatcttcc gtgtctgcat ctgtaggaga cagagtcacc       60
atcacttgtc gggcgagtca gggtattagc agttggttag cctggtatca gcagaaacca     120
gggaaagccc ctaagctcct gatctatgct gcatccagtt tgcaaagtgg ggtcccatca     180
aggttcagcg gcagtggatc tgggacagat ttcactctca ccatcagcag cctgcagcct     240
gaagattttg caacttacta ttgtcaacag gctaacagtt tcccattcac tttcggccct     300
gggaccaaag tggatatcaa acga                                            324

SEQ ID NO: 170          moltype = AA  length = 108
FEATURE                 Location/Qualifiers
REGION                  1..108
                        note = Synthetic
source                  1..108
                        mol_type = protein
                        organism = synthetic construct
SEQUENCE: 170
DIQMTQSPSS VSASVGDRVT ITCRASQGIS SWLAWYQQKP GKAPKLLIYA ASSLQSGVPS       60
RFSGSGSGTD FTLTISSLQP EDFATYYCQQ ANSFPFTFGP GTKVDIKR                  108

SEQ ID NO: 171          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 171
cagggtatta gcagttgg                                                     18
```

```
SEQ ID NO: 172            moltype = AA   length = 6
FEATURE                   Location/Qualifiers
REGION                    1..6
                          note = Synthetic
source                    1..6
                          mol_type = protein
                          organism = synthetic construct
SEQUENCE: 172
QGISSW                                                                    6

SEQ ID NO: 173            moltype =    length =
SEQUENCE: 173
000

SEQ ID NO: 174            moltype =    length =
SEQUENCE: 174
000

SEQ ID NO: 175            moltype = DNA   length = 27
FEATURE                   Location/Qualifiers
misc_feature              1..27
                          note = Synthetic
source                    1..27
                          mol_type = other DNA
                          organism = synthetic construct
SEQUENCE: 175
caacaggcta acagtttccc attcact                                             27

SEQ ID NO: 176            moltype = AA   length = 9
FEATURE                   Location/Qualifiers
REGION                    1..9
                          note = Synthetic
source                    1..9
                          mol_type = protein
                          organism = synthetic construct
SEQUENCE: 176
QQANSFPFT                                                                 9

SEQ ID NO: 177            moltype = DNA   length = 360
FEATURE                   Location/Qualifiers
misc_feature              1..360
                          note = Synthetic
source                    1..360
                          mol_type = other DNA
                          organism = synthetic construct
SEQUENCE: 177
cagctgcagc tgcaggagtc gggcccagga ctggtgaagc cttcggagac cctgtccctc         60
acctgcactg tctctggtgg ctccatcagc agtagtactt actactgggg ctggatccgc         120
cagcccccag ggaaggggct ggagtggatt gggagtttct attatagtgg gagcacctac         180
tacaacccgt ccctcaagag tcgagtcacc atatccgtag acacgtccaa gaaccagttc         240
tccctgaagc tgagctctgt gaccgccgca gacacggctg tttatttctg tgcgagaggg         300
gggctcctgg ggagaccttt tgttatctgg ggccaaggga caatggtcac cgtctcttca         360

SEQ ID NO: 178            moltype = AA   length = 120
FEATURE                   Location/Qualifiers
REGION                    1..120
                          note = Synthetic
source                    1..120
                          mol_type = protein
                          organism = synthetic construct
SEQUENCE: 178
QLQLQESGPG LVKPSETLSL TCTVSGGSIS SSTYYWGWIR QPPGKGLEWI GSFYYSGSTY         60
YNPSLKSRVT ISVGTSKNQF SLKLSSVTAA DTAVYFCARG GLLGRPFVIW GQGTMVTVSS         120

SEQ ID NO: 179            moltype = DNA   length = 30
FEATURE                   Location/Qualifiers
misc_feature              1..30
                          note = Synthetic
source                    1..30
                          mol_type = other DNA
                          organism = synthetic construct
SEQUENCE: 179
ggtggctcca tcagcagtag tacttactac                                          30

SEQ ID NO: 180            moltype = AA   length = 10
FEATURE                   Location/Qualifiers
REGION                    1..10
                          note = Synthetic
source                    1..10
```

```
                         mol_type = protein
                         organism = synthetic construct
SEQUENCE: 180
GGSISSSTYY                                                      10

SEQ ID NO: 181           moltype = DNA  length = 21
FEATURE                  Location/Qualifiers
misc_feature             1..21
                         note = Synthetic
source                   1..21
                         mol_type = other DNA
                         organism = synthetic construct
SEQUENCE: 181
ttctattata gtgggagcac c                                         21

SEQ ID NO: 182           moltype = AA  length = 7
FEATURE                  Location/Qualifiers
REGION                   1..7
                         note = Synthetic
source                   1..7
                         mol_type = protein
                         organism = synthetic construct
SEQUENCE: 182
FYYSGST                                                         7

SEQ ID NO: 183           moltype = DNA  length = 36
FEATURE                  Location/Qualifiers
misc_feature             1..36
                         note = Synthetic
source                   1..36
                         mol_type = other DNA
                         organism = synthetic construct
SEQUENCE: 183
gcgagagggg ggctcctggg gagacctttt gttatc                         36

SEQ ID NO: 184           moltype = AA  length = 12
FEATURE                  Location/Qualifiers
REGION                   1..12
                         note = Synthetic
source                   1..12
                         mol_type = protein
                         organism = synthetic construct
SEQUENCE: 184
ARGGLLGRPF VI                                                   12

SEQ ID NO: 185           moltype = DNA  length = 324
FEATURE                  Location/Qualifiers
misc_feature             1..324
                         note = Synthetic
source                   1..324
                         mol_type = other DNA
                         organism = synthetic construct
SEQUENCE: 185
gacatccaga tgacccagtc tccatcctcc ctgtctgcat ctgtaggaga cagagtcacc  60
atcacttgcc gggcaagtca gggcattaga aatgatttag gctggtatca gcagaaacca  120
gggaaagccc ctaagcgcct gatctatgct gcatccagtt tgcaaagtgg ggtcccatca  180
aggttcagcg gcagtggatc tgggacagaa ttcactctca caatcagcag cctgcagcct  240
gaagattttg caacttatta ctgtctacag cataatagtt acccgctcac tttcggcgga  300
gggaccaagg tggagatcaa acga                                      324

SEQ ID NO: 186           moltype = AA  length = 108
FEATURE                  Location/Qualifiers
REGION                   1..108
                         note = Synthetic
source                   1..108
                         mol_type = protein
                         organism = synthetic construct
SEQUENCE: 186
DIQMTQSPSS LSASVGDRVT ITCRASQGIR NDLGWYQQKP GKAPKRLIYA ASSLQSGVPS  60
RFSGSGSGTE FTLTISSLQP EDFATYYCLQ HNSYPLTFGG GTKVEIKR            108

SEQ ID NO: 187           moltype = DNA  length = 18
FEATURE                  Location/Qualifiers
misc_feature             1..18
                         note = Synthetic
source                   1..18
                         mol_type = other DNA
                         organism = synthetic construct
SEQUENCE: 187
```

```
cagggcatta gaaatgat                                                       18

SEQ ID NO: 188          moltype = AA   length = 6
FEATURE                 Location/Qualifiers
REGION                  1..6
                        note = Synthetic
source                  1..6
                        mol_type = protein
                        organism = synthetic construct
SEQUENCE: 188
QGIRND                                                                    6

SEQ ID NO: 189          moltype =    length =
SEQUENCE: 189
000

SEQ ID NO: 190          moltype =    length =
SEQUENCE: 190
000

SEQ ID NO: 191          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 191
ctacagcata atagttaccc gctcact                                             27

SEQ ID NO: 192          moltype = AA   length = 9
FEATURE                 Location/Qualifiers
REGION                  1..9
                        note = Synthetic
source                  1..9
                        mol_type = protein
                        organism = synthetic construct
SEQUENCE: 192
LQHNSYPLT                                                                 9

SEQ ID NO: 193          moltype = DNA  length = 366
FEATURE                 Location/Qualifiers
misc_feature            1..366
                        note = Synthetic
source                  1..366
                        mol_type = other DNA
                        organism = synthetic construct
SEQUENCE: 193
gaggtgcagc tggtggagtc tagggggaggc ttggtacagc ctgggggggtc cctgagactc        60
tcctgtgcag cctctggatt cactttttagc agctatgcca tgagctgggt ccgccaggct       120
ccagggaagg ggctggagtg ggtctcagct attagtggta gtggtggtag cacattctac       180
gcagactccg tgaagggccg gttcaccatc tccagagaca attccaagaa cacggtatat       240
ctgcaaatga acagcctgag agccgaggac acggccgtat attactgtgc gaaagccctc       300
gtattgcgat ttttggagtg gttaggggac tactggggcc agggaaccct ggtcaccgtc       360
tcctca                                                                  366

SEQ ID NO: 194          moltype = AA   length = 122
FEATURE                 Location/Qualifiers
REGION                  1..122
                        note = Synthetic
source                  1..122
                        mol_type = protein
                        organism = synthetic construct
SEQUENCE: 194
EVQLVESRGG LVQPGGSLRL SCAASGFTFS SYAMSWVRQA PGKGLEWVSA ISGSGGSTFY          60
ADSVKGRFTI SRDNSKNTVY LQMNSLRAED TAVYYCAKAL VLRFLEWLGD YWGQGTLVTV        120
SS                                                                      122

SEQ ID NO: 195          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 195
ggattcactt ttagcagcta tgcc                                                24

SEQ ID NO: 196          moltype = AA   length = 8
```

```
FEATURE                 Location/Qualifiers
REGION                  1..8
                        note = Synthetic
source                  1..8
                        mol_type = protein
                        organism = synthetic construct
SEQUENCE: 196
GFTFSSYA                                                              8

SEQ ID NO: 197          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 197
attagtggta gtggtggtag caca                                            24

SEQ ID NO: 198          moltype = AA  length = 8
FEATURE                 Location/Qualifiers
REGION                  1..8
                        note = Synthetic
source                  1..8
                        mol_type = protein
                        organism = synthetic construct
SEQUENCE: 198
ISGSGGST                                                              8

SEQ ID NO: 199          moltype = DNA  length = 45
FEATURE                 Location/Qualifiers
misc_feature            1..45
                        note = Synthetic
source                  1..45
                        mol_type = other DNA
                        organism = synthetic construct
SEQUENCE: 199
gcgaaagccc tcgtattgcg atttttggag tggttagggg actac                     45

SEQ ID NO: 200          moltype = AA  length = 15
FEATURE                 Location/Qualifiers
REGION                  1..15
                        note = Synthetic
source                  1..15
                        mol_type = protein
                        organism = synthetic construct
SEQUENCE: 200
AKALVLRFLE WLGDY                                                      15

SEQ ID NO: 201          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 201
gacatccaga tgacccagtc tccttccacc ctgtctgcat ctgtaggaga cagagtcacc     60
atcacttgtc gggccagtca gagtattagt agctggttgg cctggtttca gcagaaacca    120
gggaaagccc ctaagcttct gatctataag gcgtctagtt tagaaagtgg ggtcccatca    180
aggttcagcg gcagtggatc tgggacagaa ttcactctca ccatcagcag cctgcagcct    240
gatgattttg caacttatta ctgtcaacag tataaaagtt attggacgtt cggccaaggg    300
accaaggtgg aaatcaaacg a                                              321

SEQ ID NO: 202          moltype = AA  length = 107
FEATURE                 Location/Qualifiers
REGION                  1..107
                        note = Synthetic
source                  1..107
                        mol_type = protein
                        organism = synthetic construct
SEQUENCE: 202
DIQMTQSPST LSASVGDRVT ITCRASQSIS SWLAWFQQKP GKAPKLLIYK ASSLESGVPS     60
RFSGSGSGTE FTLTISSLQP DDFATYYCQQ YKSYWTFGQG TKVEIKR                  107

SEQ ID NO: 203          moltype = DNA  length = 18
FEATURE                 Location/Qualifiers
misc_feature            1..18
                        note = Synthetic
```

```
source              1..18
                    mol_type = other DNA
                    organism = synthetic construct
SEQUENCE: 203
cagagtatta gtagctgg                                                   18

SEQ ID NO: 204      moltype = AA  length = 6
FEATURE             Location/Qualifiers
REGION              1..6
                    note = Synthetic
source              1..6
                    mol_type = protein
                    organism = synthetic construct
SEQUENCE: 204
QSISSW                                                                 6

SEQ ID NO: 205      moltype =    length =
SEQUENCE: 205
000

SEQ ID NO: 206      moltype =    length =
SEQUENCE: 206
000

SEQ ID NO: 207      moltype = DNA  length = 24
FEATURE             Location/Qualifiers
misc_feature        1..24
                    note = Synthetic
source              1..24
                    mol_type = other DNA
                    organism = synthetic construct
SEQUENCE: 207
caacagtata aaagttattg gacg                                            24

SEQ ID NO: 208      moltype = AA  length = 8
FEATURE             Location/Qualifiers
REGION              1..8
                    note = Synthetic
source              1..8
                    mol_type = protein
                    organism = synthetic construct
SEQUENCE: 208
QQYKSYWT                                                               8

SEQ ID NO: 209      moltype = DNA  length = 372
FEATURE             Location/Qualifiers
misc_feature        1..372
                    note = Synthetic
source              1..372
                    mol_type = other DNA
                    organism = synthetic construct
SEQUENCE: 209
gaggtgcagc tggtggagtc tgggggaggc ctggtacagc ctgggggggtc cctgagactc     60
tcctgtgcag cctctggatt cacctttagc agctatgcca tgagctgggt ccgccaggct    120
ccagggaagg ggctggagtg ggtctcaagt attagtggta gtggtgatag cacattctac    180
acagactccg tgaagggccg gttcaccatc tccagagaca tttccaagaa cacgctgtat    240
ctgcaaatga acagcctgag agccgaggac acggccgtat attactgtgc gaaagatcgt    300
cttctatggt tcggggactt aatatccccc tttcactact ggggccaggg aaccctggtc    360
accgtctcct ca                                                        372

SEQ ID NO: 210      moltype = AA  length = 124
FEATURE             Location/Qualifiers
REGION              1..124
                    note = Synthetic
source              1..124
                    mol_type = protein
                    organism = synthetic construct
SEQUENCE: 210
EVQLVESGGG LVQPGGSLRL SCAASGFTFS SYAMSWVRQA PGKGLEWVSS ISGSGDSTFY     60
TDSVKGRFTI SRDISKNTLY LQMNSLRAED TAVYYCAKDR LLWFGDLISP FHYWGQGTLV    120
TVSS                                                                 124

SEQ ID NO: 211      moltype = DNA  length = 24
FEATURE             Location/Qualifiers
misc_feature        1..24
                    note = Synthetic
source              1..24
                    mol_type = other DNA
                    organism = synthetic construct
```

```
SEQUENCE: 211
ggattcacct ttagcagcta tgcc                                           24

SEQ ID NO: 212              moltype = AA  length = 8
FEATURE                     Location/Qualifiers
REGION                      1..8
                            note = Synthetic
source                      1..8
                            mol_type = protein
                            organism = synthetic construct
SEQUENCE: 212
GFTFSSYA                                                              8

SEQ ID NO: 213              moltype = DNA  length = 24
FEATURE                     Location/Qualifiers
misc_feature                1..24
                            note = Synthetic
source                      1..24
                            mol_type = other DNA
                            organism = synthetic construct
SEQUENCE: 213
attagtggta gtggtgatag caca                                           24

SEQ ID NO: 214              moltype = AA  length = 8
FEATURE                     Location/Qualifiers
REGION                      1..8
                            note = Synthetic
source                      1..8
                            mol_type = protein
                            organism = synthetic construct
SEQUENCE: 214
ISGSGDST                                                              8

SEQ ID NO: 215              moltype = DNA  length = 51
FEATURE                     Location/Qualifiers
misc_feature                1..51
                            note = Synthetic
source                      1..51
                            mol_type = other DNA
                            organism = synthetic construct
SEQUENCE: 215
gcgaaagatc gtcttctatg gttcggggac ttaatatccc cctttcacta c             51

SEQ ID NO: 216              moltype = AA  length = 17
FEATURE                     Location/Qualifiers
REGION                      1..17
                            note = Synthetic
source                      1..17
                            mol_type = protein
                            organism = synthetic construct
SEQUENCE: 216
AKDRLLWFGD LISPFHY                                                   17

SEQ ID NO: 217              moltype = DNA  length = 327
FEATURE                     Location/Qualifiers
misc_feature                1..327
                            note = Synthetic
source                      1..327
                            mol_type = other DNA
                            organism = synthetic construct
SEQUENCE: 217
gaaattgtgt tgacgcagtc tccaggcacc ctgtctttgt ctccagggga aagagccacc    60
ctctcctgca gggccagtca gagtgttagc aacatctact tagcctggta ccagcagaaa   120
cctgcccagg ctcccaggct cctcatctat ggtgcatcca gcagggccac tggcatccca   180
gacaggttta gtgtcagtgg gtctgggaca gacttcactc tcaccatcag cagactggag   240
cctgaagatt ttgcagtgta ttactgtcag cagtatggta gctcacctcg gacgttcggc   300
caagggacca aggtggaaat caaacga                                       327

SEQ ID NO: 218              moltype = AA  length = 109
FEATURE                     Location/Qualifiers
REGION                      1..109
                            note = Synthetic
source                      1..109
                            mol_type = protein
                            organism = synthetic construct
SEQUENCE: 218
EIVLTQSPGT LSLSPGERAT LSCRASQSVS NIYLAWYQQK PAQAPRLLIY GASSRATGIP    60
DRFSVSGSGT DFTLTISRLE PEDFAVYYCQ QYGSSPRTFG QGTKVEIKR               109
```

```
SEQ ID NO: 219          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 219
cagagtgtta gcaacatcta c                                             21

SEQ ID NO: 220          moltype = AA  length = 7
FEATURE                 Location/Qualifiers
REGION                  1..7
                        note = Synthetic
source                  1..7
                        mol_type = protein
                        organism = synthetic construct
SEQUENCE: 220
QSVSNIY                                                             7

SEQ ID NO: 221          moltype =     length =
SEQUENCE: 221
000

SEQ ID NO: 222          moltype =     length =
SEQUENCE: 222
000

SEQ ID NO: 223          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 223
cagcagtatg gtagctcacc tcggacg                                       27

SEQ ID NO: 224          moltype = AA  length = 9
FEATURE                 Location/Qualifiers
REGION                  1..9
                        note = Synthetic
source                  1..9
                        mol_type = protein
                        organism = synthetic construct
SEQUENCE: 224
QQYGSSPRT                                                           9

SEQ ID NO: 225          moltype = DNA  length = 366
FEATURE                 Location/Qualifiers
misc_feature            1..366
                        note = Synthetic
source                  1..366
                        mol_type = other DNA
                        organism = synthetic construct
SEQUENCE: 225
gaggtgcagc tggtggagtc tgggggaggc ttggtacagc ctggggggtc cctgagactc   60
tcctgtacag cctctggatt cacctttagc agctatgcca tgagttgggt ccgccaggct  120
ccagggaagg ggctggaatg ggtctcagct attagtggga ctggtagtag tacatacttc  180
acagactccg tgaagggccg gttcgccatc tccagagaca attccaagaa cacgctgtat  240
ctgcaaatga acagcctgag agccgaggac acggccgtat attactgtgc gaaagatgga  300
gagtggctct ctacggtgac cctttttgac tactgggccc agggaaccct ggtcaccgtc  360
tcctca                                                             366

SEQ ID NO: 226          moltype = AA  length = 122
FEATURE                 Location/Qualifiers
REGION                  1..122
                        note = Synthetic
source                  1..122
                        mol_type = protein
                        organism = synthetic construct
SEQUENCE: 226
EVQLVESGGG LVQPGGSLRL SCTASGFTFS SYAMSWVRQA PGKGLEWVSA ISGTGSSTYF   60
TDSVKGRFAI SRDNSKNTLY LQMNSLRAED TAVYYCAKDG EWLSTVTLFD YWGQGTLVTV  120
SS                                                                 122

SEQ ID NO: 227          moltype = DNA  length = 24
FEATURE                 Location/Qualifiers
misc_feature            1..24
```

```
                        note = Synthetic
source                  1..24
                        mol_type = other DNA
                        organism = synthetic construct
SEQUENCE: 227
ggattcacct ttagcagcta tgcc                                              24

SEQ ID NO: 228          moltype = AA  length = 8
FEATURE                 Location/Qualifiers
REGION                  1..8
                        note = Synthetic
source                  1..8
                        mol_type = protein
                        organism = synthetic construct
SEQUENCE: 228
GFTFSSYA                                                                 8

SEQ ID NO: 229          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 229
attagtggga ctggtagtag taca                                              24

SEQ ID NO: 230          moltype = AA  length = 8
FEATURE                 Location/Qualifiers
REGION                  1..8
                        note = Synthetic
source                  1..8
                        mol_type = protein
                        organism = synthetic construct
SEQUENCE: 230
ISGTGSST                                                                 8

SEQ ID NO: 231          moltype = DNA  length = 45
FEATURE                 Location/Qualifiers
misc_feature            1..45
                        note = Synthetic
source                  1..45
                        mol_type = other DNA
                        organism = synthetic construct
SEQUENCE: 231
gcgaaagatg gagagtggct ctctacggtg acccttttg actac                        45

SEQ ID NO: 232          moltype = AA  length = 15
FEATURE                 Location/Qualifiers
REGION                  1..15
                        note = Synthetic
source                  1..15
                        mol_type = protein
                        organism = synthetic construct
SEQUENCE: 232
AKDGEWLSTV TLFDY                                                        15

SEQ ID NO: 233          moltype = DNA  length = 330
FEATURE                 Location/Qualifiers
misc_feature            1..330
                        note = Synthetic
source                  1..330
                        mol_type = other DNA
                        organism = synthetic construct
SEQUENCE: 233
gaaattgtga tgacgcagtc tccagccacc ctgtctgtgt ctccagggga aagagccacc        60
ctctcctgca gggccagtca gagtgttagc agcaacttag cctggtacca gcagaaacct       120
ggccaggctc ccaggctcct catctatggt gcatccacca gggccactgg tatcccagcc       180
aggttcagtg gcagtgggtc tgggacagat ttcactctca ccatcagcag cctgcagtct       240
gaagattttg cactttatta ctgtcagcag tatttatct ggcctccgca tcccactttc        300
ggccctggga ccaaagtgga tatcaaacga                                        330

SEQ ID NO: 234          moltype = AA  length = 110
FEATURE                 Location/Qualifiers
REGION                  1..110
                        note = Synthetic
source                  1..110
                        mol_type = protein
                        organism = synthetic construct
```

```
SEQUENCE: 234
EIVMTQSPAT LSVSPGERAT LSCRASQSVS SNLAWYQQKP GQAPRLLIYG ASTRATGIPA    60
RFSGSGSGTD FTLTISSLQS EDFALYYCQQ YFIWPPHPTF GPGTKVDIKR              110

SEQ ID NO: 235           moltype = DNA  length = 18
FEATURE                  Location/Qualifiers
misc_feature             1..18
                         note = Synthetic
source                   1..18
                         mol_type = other DNA
                         organism = synthetic construct
SEQUENCE: 235
cagagtgtta gcagcaac                                                 18

SEQ ID NO: 236           moltype = AA  length = 6
FEATURE                  Location/Qualifiers
REGION                   1..6
                         note = Synthetic
source                   1..6
                         mol_type = protein
                         organism = synthetic construct
SEQUENCE: 236
QSVSSN                                                              6

SEQ ID NO: 237           moltype =   length =
SEQUENCE: 237
000

SEQ ID NO: 238           moltype =   length =
SEQUENCE: 238
000

SEQ ID NO: 239           moltype = DNA  length = 33
FEATURE                  Location/Qualifiers
misc_feature             1..33
                         note = Synthetic
source                   1..33
                         mol_type = other DNA
                         organism = synthetic construct
SEQUENCE: 239
cagcagtatt ttatctggcc tccgcatccc act                                33

SEQ ID NO: 240           moltype = AA  length = 11
FEATURE                  Location/Qualifiers
REGION                   1..11
                         note = Synthetic
source                   1..11
                         mol_type = protein
                         organism = synthetic construct
SEQUENCE: 240
QQYFIWPPHP T                                                        11

SEQ ID NO: 241           moltype = DNA  length = 363
FEATURE                  Location/Qualifiers
misc_feature             1..363
                         note = Synthetic
source                   1..363
                         mol_type = other DNA
                         organism = synthetic construct
SEQUENCE: 241
caggtgcagc tggtggagtc tgggggagcc gtggtccagc ctggggaggtc cctgagactc   60
tcctgtgcag cctctggatt caccttcagt tactatggca tgcactgggt ccgccaggct  120
ccaggcaagg ggctggagtg ggtggcagtt atatcatatg atggaagtaa aaaatactat  180
gcagactccg tgaagggccg attcaccatc tccagagaca attccaagaa cacgctgtat  240
ctgcaaatga acagcctgag agctgaggac acggctgtgt attactgtgc gaaagatctg  300
acagtagact ctactacgg tatggacgtc tggggccaag ggaccacggt caccgtctcc  360
tca                                                                363

SEQ ID NO: 242           moltype = AA  length = 121
FEATURE                  Location/Qualifiers
REGION                   1..121
                         note = Synthetic
source                   1..121
                         mol_type = protein
                         organism = synthetic construct
SEQUENCE: 242
QVQLVESGGA VVQPGRSLRL SCAASGFTFS YYGMHWVRQA PGKGLEWVAV ISYDGSKKYY    60
ADSVKGRFTI SRDNSKNTLY LQMNSLRAED TAVYYCAKDL TVDFYYGMDV WGQGTTVTVS  120
S                                                                  121
```

| | | |
|---|---|---|
| SEQ ID NO: 243 | moltype = DNA length = 24 | |
| FEATURE | Location/Qualifiers | |
| misc_feature | 1..24 | |
| | note = Synthetic | |
| source | 1..24 | |
| | mol_type = other DNA | |
| | organism = synthetic construct | |
| SEQUENCE: 243 | | |
| ggattcacct tcagttacta tggc | | 24 |
| | | |
| SEQ ID NO: 244 | moltype = AA length = 8 | |
| FEATURE | Location/Qualifiers | |
| REGION | 1..8 | |
| | note = Synthetic | |
| source | 1..8 | |
| | mol_type = protein | |
| | organism = synthetic construct | |
| SEQUENCE: 244 | | |
| GFTFSYYG | | 8 |
| | | |
| SEQ ID NO: 245 | moltype = DNA length = 24 | |
| FEATURE | Location/Qualifiers | |
| misc_feature | 1..24 | |
| | note = Synthetic | |
| source | 1..24 | |
| | mol_type = other DNA | |
| | organism = synthetic construct | |
| SEQUENCE: 245 | | |
| atatcatatg atggaagtaa aaaa | | 24 |
| | | |
| SEQ ID NO: 246 | moltype = AA length = 8 | |
| FEATURE | Location/Qualifiers | |
| REGION | 1..8 | |
| | note = Synthetic | |
| source | 1..8 | |
| | mol_type = protein | |
| | organism = synthetic construct | |
| SEQUENCE: 246 | | |
| ISYDGSKK | | 8 |
| | | |
| SEQ ID NO: 247 | moltype = DNA length = 42 | |
| FEATURE | Location/Qualifiers | |
| misc_feature | 1..42 | |
| | note = Synthetic | |
| source | 1..42 | |
| | mol_type = other DNA | |
| | organism = synthetic construct | |
| SEQUENCE: 247 | | |
| gcgaaagatc tgacagtaga cttctactac ggtatggacg tc | | 42 |
| | | |
| SEQ ID NO: 248 | moltype = AA length = 14 | |
| FEATURE | Location/Qualifiers | |
| REGION | 1..14 | |
| | note = Synthetic | |
| source | 1..14 | |
| | mol_type = protein | |
| | organism = synthetic construct | |
| SEQUENCE: 248 | | |
| AKDLTVDFYY GMDV | | 14 |
| | | |
| SEQ ID NO: 249 | moltype = DNA length = 324 | |
| FEATURE | Location/Qualifiers | |
| misc_feature | 1..324 | |
| | note = Synthetic | |
| source | 1..324 | |
| | mol_type = other DNA | |
| | organism = synthetic construct | |
| SEQUENCE: 249 | | |
| gacatccaga tgacccagtc tccatcttcc gtgtctgcat ctgtaggaga cagagtcacc | | 60 |
| atcacttgtc gggcgagtca gggtattagc agctggttag cctggtatca gcagaaacca | | 120 |
| gggaaagccc ctaagctcct gatctatgct acatccagtt tgcaaagtgg ggccccatca | | 180 |
| aggttcagcg gcagtggatc tgggacagat ttcactctca ccatcagcag cctgcagcct | | 240 |
| gaagattttg caacttactt ttgtcaacag gctaacagtt tcccatacac ttttggccag | | 300 |
| gggaccaagc tggagatcaa acga | | 324 |
| | | |
| SEQ ID NO: 250 | moltype = AA length = 108 | |
| FEATURE | Location/Qualifiers | |
| REGION | 1..108 | |

```
                           note = Synthetic
source                     1..108
                           mol_type = protein
                           organism = synthetic construct
SEQUENCE: 250
DIQMTQSPSS VSASVGDRVT ITCRASQGIS SWLAWYQQKP GKAPKLLIYA TSSLQSGAPS    60
RFSGSGSGTD FTLTISSLQP EDFATYFCQQ ANSFPYTFGQ GTKLEIKR                108

SEQ ID NO: 251             moltype = DNA  length = 18
FEATURE                    Location/Qualifiers
misc_feature               1..18
                           note = Synthetic
source                     1..18
                           mol_type = other DNA
                           organism = synthetic construct
SEQUENCE: 251
cagggtatta gcagctgg                                                  18

SEQ ID NO: 252             moltype = AA  length = 6
FEATURE                    Location/Qualifiers
REGION                     1..6
                           note = Synthetic
source                     1..6
                           mol_type = protein
                           organism = synthetic construct
SEQUENCE: 252
QGISSW                                                                6

SEQ ID NO: 253             moltype =   length =
SEQUENCE: 253
000

SEQ ID NO: 254             moltype =   length =
SEQUENCE: 254
000

SEQ ID NO: 255             moltype = DNA  length = 27
FEATURE                    Location/Qualifiers
misc_feature               1..27
                           note = Synthetic
source                     1..27
                           mol_type = other DNA
                           organism = synthetic construct
SEQUENCE: 255
caacaggcta acagtttccc atacact                                        27

SEQ ID NO: 256             moltype = AA  length = 9
FEATURE                    Location/Qualifiers
REGION                     1..9
                           note = Synthetic
source                     1..9
                           mol_type = protein
                           organism = synthetic construct
SEQUENCE: 256
QQANSFPYT                                                             9

SEQ ID NO: 257             moltype = DNA  length = 342
FEATURE                    Location/Qualifiers
misc_feature               1..342
                           note = Synthetic
source                     1..342
                           mol_type = other DNA
                           organism = synthetic construct
SEQUENCE: 257
caggtgcagc tgcaggagtc gggcccagga ctggtgaagc cttcggagac cctgtccctc    60
acctgcactg tctctgatgg ctccatcagt agttactact ggagctggat ccggcagccc   120
ccagggaggg gactggagtg gattgggttt atctattaca gtgggagcac cagctacaac   180
ccctccctca agagtcgagt caccatttca gtagacacgt ccatgagcca gttctccctg   240
aagctgaggt ctgtgaccgc cgcagacacg gccgtgtatt actgtgcgcg tgggagcccc   300
tttgactact ggggcccggg aaccctggtc accgtctcct ca                      342

SEQ ID NO: 258             moltype = AA  length = 114
FEATURE                    Location/Qualifiers
REGION                     1..114
                           note = Synthetic
source                     1..114
                           mol_type = protein
                           organism = synthetic construct
SEQUENCE: 258
```

```
QVQLQESGPG LVKPSETLSL TCTVSDGSIS SYYWSWIRQP PGRGLEWIGF IYYSGSTSYN   60
PSLKSRVTIS VDTSMSQFSL KLRSVTAADT AVYYCARGSP FDYWGPGTLV TVSS        114

SEQ ID NO: 259          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 259
gatggctcca tcagtagtta ctac                                         24

SEQ ID NO: 260          moltype = AA   length = 8
FEATURE                 Location/Qualifiers
REGION                  1..8
                        note = Synthetic
source                  1..8
                        mol_type = protein
                        organism = synthetic construct
SEQUENCE: 260
DGSISSYY                                                            8

SEQ ID NO: 261          moltype = DNA   length = 21
FEATURE                 Location/Qualifiers
misc_feature            1..21
                        note = Synthetic
source                  1..21
                        mol_type = other DNA
                        organism = synthetic construct
SEQUENCE: 261
atctattaca gtgggagcac c                                            21

SEQ ID NO: 262          moltype = AA   length = 7
FEATURE                 Location/Qualifiers
REGION                  1..7
                        note = Synthetic
source                  1..7
                        mol_type = protein
                        organism = synthetic construct
SEQUENCE: 262
IYYSGST                                                             7

SEQ ID NO: 263          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 263
gcgcgtggga gccctttga ctac                                          24

SEQ ID NO: 264          moltype = AA   length = 8
FEATURE                 Location/Qualifiers
REGION                  1..8
                        note = Synthetic
source                  1..8
                        mol_type = protein
                        organism = synthetic construct
SEQUENCE: 264
ARGSPFDY                                                            8

SEQ ID NO: 265          moltype = DNA   length = 327
FEATURE                 Location/Qualifiers
misc_feature            1..327
                        note = Synthetic
source                  1..327
                        mol_type = other DNA
                        organism = synthetic construct
SEQUENCE: 265
gaaattgtgt tgacgcagtc tccaggcacc ctgtctttgt ctccagggga aagagccacc   60
ctctcctgca gggccagtca gagtgttagc agcagctact tagcctggta ccagcaaaga  120
cctggccagg ctcccagcct cctcatctct ggtgcatcct ggagggccac tggcatccca  180
gacaggttca gtggcagtgg gtctgggaca gacttcactc tcaccatcag aagactggag  240
cctgaagatt ttgcaatgta ttactgtcag cagtatggta gttcacctcc cactttcggc  300
ggagggacca aggtggagat caaacga                                      327

SEQ ID NO: 266          moltype = AA   length = 109
```

| | | |
|---|---|---|
| FEATURE | Location/Qualifiers | |
| REGION | 1..109 | |
| | note = Synthetic | |
| source | 1..109 | |
| | mol_type = protein | |
| | organism = synthetic construct | |
| SEQUENCE: 266 | | |
| EIVLTQSPGT LSLSPGERAT LSCRASQSVS SSYLAWYQQR PGQAPSLLIS GASRRATGIP | | 60 |
| DRFSGSGSGT DFTLTIRRLE PEDFAMYYCQ QYGSSPPTFG GGTKVEIKR | | 109 |
| | | |
| SEQ ID NO: 267 | moltype = DNA  length = 21 | |
| FEATURE | Location/Qualifiers | |
| misc_feature | 1..21 | |
| | note = Synthetic | |
| source | 1..21 | |
| | mol_type = other DNA | |
| | organism = synthetic construct | |
| SEQUENCE: 267 | | |
| cagagtgtta gcagcagcta c | | 21 |
| | | |
| SEQ ID NO: 268 | moltype = AA  length = 7 | |
| FEATURE | Location/Qualifiers | |
| REGION | 1..7 | |
| | note = Synthetic | |
| source | 1..7 | |
| | mol_type = protein | |
| | organism = synthetic construct | |
| SEQUENCE: 268 | | |
| QSVSSSY | | 7 |
| | | |
| SEQ ID NO: 269 | moltype =   length = | |
| SEQUENCE: 269 | | |
| 000 | | |
| | | |
| SEQ ID NO: 270 | moltype =   length = | |
| SEQUENCE: 270 | | |
| 000 | | |
| | | |
| SEQ ID NO: 271 | moltype = DNA  length = 27 | |
| FEATURE | Location/Qualifiers | |
| misc_feature | 1..27 | |
| | note = Synthetic | |
| source | 1..27 | |
| | mol_type = other DNA | |
| | organism = synthetic construct | |
| SEQUENCE: 271 | | |
| cagcagtatg gtagttcacc tcccact | | 27 |
| | | |
| SEQ ID NO: 272 | moltype = AA  length = 9 | |
| FEATURE | Location/Qualifiers | |
| REGION | 1..9 | |
| | note = Synthetic | |
| source | 1..9 | |
| | mol_type = protein | |
| | organism = synthetic construct | |
| SEQUENCE: 272 | | |
| QQYGSSPPT | | 9 |
| | | |
| SEQ ID NO: 273 | moltype = DNA  length = 363 | |
| FEATURE | Location/Qualifiers | |
| misc_feature | 1..363 | |
| | note = Synthetic | |
| source | 1..363 | |
| | mol_type = other DNA | |
| | organism = synthetic construct | |
| SEQUENCE: 273 | | |
| gaggtgcagc tggtggagtc tgggggaggc ttggtccagc ctggggggtc cctgagactc | | 60 |
| tcctgtgcag cctctggatt cacgttcagt aactatgcta tgcactgggt ccgccaggct | | 120 |
| ccagggaagg gactggaata tgtttcagct attagtagta atggggtag tacatattat | | 180 |
| gcagactctg tgaagggcag aatcaccatc tccagagaca attccaagaa cacgctgtat | | 240 |
| cttcaaatgg gcagcctgag agctgaggat atggctgtgt attactgtgc gagagggcga | | 300 |
| ccgtactact actacttcgg tatggacgtc tggggccaag ggaccacggt caccgtctcc | | 360 |
| tca | | 363 |
| | | |
| SEQ ID NO: 274 | moltype = AA  length = 121 | |
| FEATURE | Location/Qualifiers | |
| REGION | 1..121 | |
| | note = Synthetic | |
| source | 1..121 | |

```
                         mol_type = protein
                         organism = synthetic construct
SEQUENCE: 274
EVQLVESGGG LVQPGGSLRL SCAASGFTFS NYAMHWVRQA PGKGLEYVSA ISSNGGSTYY      60
ADSVKGRITI SRDNSKNTLY LQMGSLRAED MAVYYCARGR PYYYYFGMDV WGQGTTVTVS     120
S                                                                    121

SEQ ID NO: 275          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 275
ggattcacgt tcagtaacta tgct                                            24

SEQ ID NO: 276          moltype = AA   length = 8
FEATURE                 Location/Qualifiers
REGION                  1..8
                        note = Synthetic
source                  1..8
                        mol_type = protein
                        organism = synthetic construct
SEQUENCE: 276
GFTFSNYA                                                              8

SEQ ID NO: 277          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 277
attagtagta atgggggtag taca                                            24

SEQ ID NO: 278          moltype = AA   length = 8
FEATURE                 Location/Qualifiers
REGION                  1..8
                        note = Synthetic
source                  1..8
                        mol_type = protein
                        organism = synthetic construct
SEQUENCE: 278
ISSNGGST                                                              8

SEQ ID NO: 279          moltype = DNA   length = 42
FEATURE                 Location/Qualifiers
misc_feature            1..42
                        note = Synthetic
source                  1..42
                        mol_type = other DNA
                        organism = synthetic construct
SEQUENCE: 279
gcgagagggc gaccgtacta ctactacttc ggtatggacg tc                        42

SEQ ID NO: 280          moltype = AA   length = 14
FEATURE                 Location/Qualifiers
REGION                  1..14
                        note = Synthetic
source                  1..14
                        mol_type = protein
                        organism = synthetic construct
SEQUENCE: 280
ARGRPYYYYF GMDV                                                       14

SEQ ID NO: 281          moltype = DNA   length = 339
FEATURE                 Location/Qualifiers
misc_feature            1..339
                        note = Synthetic
source                  1..339
                        mol_type = other DNA
                        organism = synthetic construct
SEQUENCE: 281
gatattgtga tgactcagac tccagtctcc tcacctgtca cccttggaca gccggcctcc     60
atctcctgca ggtctagtca aagcctcgta cacagtgatg gaaacaccta cttgagttgg    120
tttcagcaga ggccgggcca gcctccaaga ctcctaattt ataagatttc taaccggttc    180
tctggggtcc cagacagatt cagtggcagt ggggcaggga cagatttcac actgaaaatc    240
```

```
agcagggtgg aagctgagga tgtcggggtt tattactgca tgcaagctac acaatttcct    300
ctcaatttcg gcggagggac caaggtggag atcaaacga                           339

SEQ ID NO: 282          moltype = AA  length = 113
FEATURE                 Location/Qualifiers
REGION                  1..113
                        note = Synthetic
source                  1..113
                        mol_type = protein
                        organism = synthetic construct
SEQUENCE: 282
DIVMTQTPVS SPVTLGQPAS ISCRSSQSLV HSDGNTYLSW FQQRPGQPPR LLIYKISNRF    60
SGVPDRFSGS GAGTDFTLKI SRVEAEDVGV YYCMQATQFP LNFGGGTKVE IKR           113

SEQ ID NO: 283          moltype = DNA  length = 33
FEATURE                 Location/Qualifiers
misc_feature            1..33
                        note = Synthetic
source                  1..33
                        mol_type = other DNA
                        organism = synthetic construct
SEQUENCE: 283
caaagcctcg tacacagtga tggaaacacc tac                                 33

SEQ ID NO: 284          moltype = AA  length = 11
FEATURE                 Location/Qualifiers
REGION                  1..11
                        note = Synthetic
source                  1..11
                        mol_type = protein
                        organism = synthetic construct
SEQUENCE: 284
QSLVHSDGNT Y                                                         11

SEQ ID NO: 285          moltype =     length =
SEQUENCE: 285
000

SEQ ID NO: 286          moltype =     length =
SEQUENCE: 286
000

SEQ ID NO: 287          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 287
atgcaagcta cacaatttcc tctcaat                                        27

SEQ ID NO: 288          moltype = AA  length = 9
FEATURE                 Location/Qualifiers
REGION                  1..9
                        note = Synthetic
source                  1..9
                        mol_type = protein
                        organism = synthetic construct
SEQUENCE: 288
MQATQFPLN                                                            9

SEQ ID NO: 289          moltype = DNA  length = 366
FEATURE                 Location/Qualifiers
misc_feature            1..366
                        note = Synthetic
source                  1..366
                        mol_type = other DNA
                        organism = synthetic construct
SEQUENCE: 289
gaggtgcagc tggtggagtc tgggggaggc ttggtacagc ctgggggtc cctgagactc     60
tcctgtgcag cctctggatt cacctttagg acctatgcca tgacctgggt ccgccaggct   120
ccagggaagg ggctagactg ggtctcagct attactggtg atggtggtaa tacatactac   180
gcagactccg tgaagggccg gttcaccatt tccagagaca attccaagaa cacgctgtat   240
ctgcaaatga acagcctgag agccgaggac acggccatct attactgtgc gaaagatcag   300
agattcagct ttgctctata ctactttgac tactggggcc agggaaccct ggtcactgtc   360
tcctca                                                              366

SEQ ID NO: 290          moltype = AA  length = 122
```

| | | |
|---|---|---|
| FEATURE | Location/Qualifiers | |
| REGION | 1..122 | |
| | note = Synthetic | |
| source | 1..122 | |
| | mol_type = protein | |
| | organism = synthetic construct | |
| SEQUENCE: 290 | | |

```
EVQLVESGGG LVQPGGSLRL SCAASGFTFR TYAMTWVRQA PGKGLDWVSA ITGDGGNTYY    60
ADSVKGRFTI SRDNSKNTLY LQMNSLRAED TAIYYCAKDQ RFSFALYYFD YWGQGTLVTV   120
SS                                                                 122
```

| | | |
|---|---|---|
| SEQ ID NO: 291 | moltype = DNA length = 24 | |
| FEATURE | Location/Qualifiers | |
| misc_feature | 1..24 | |
| | note = Synthetic | |
| source | 1..24 | |
| | mol_type = other DNA | |
| | organism = synthetic construct | |
| SEQUENCE: 291 | | |

```
ggattcacct ttaggaccta tgcc                                          24
```

| | | |
|---|---|---|
| SEQ ID NO: 292 | moltype = AA length = 8 | |
| FEATURE | Location/Qualifiers | |
| REGION | 1..8 | |
| | note = Synthetic | |
| source | 1..8 | |
| | mol_type = protein | |
| | organism = synthetic construct | |
| SEQUENCE: 292 | | |

```
GFTFRTYA                                                             8
```

| | | |
|---|---|---|
| SEQ ID NO: 293 | moltype = DNA length = 24 | |
| FEATURE | Location/Qualifiers | |
| misc_feature | 1..24 | |
| | note = Synthetic | |
| source | 1..24 | |
| | mol_type = other DNA | |
| | organism = synthetic construct | |
| SEQUENCE: 293 | | |

```
attactggtg atggtggtaa taca                                          24
```

| | | |
|---|---|---|
| SEQ ID NO: 294 | moltype = AA length = 8 | |
| FEATURE | Location/Qualifiers | |
| REGION | 1..8 | |
| | note = Synthetic | |
| source | 1..8 | |
| | mol_type = protein | |
| | organism = synthetic construct | |
| SEQUENCE: 294 | | |

```
ITGDGGNT                                                             8
```

| | | |
|---|---|---|
| SEQ ID NO: 295 | moltype = DNA length = 45 | |
| FEATURE | Location/Qualifiers | |
| misc_feature | 1..45 | |
| | note = Synthetic | |
| source | 1..45 | |
| | mol_type = other DNA | |
| | organism = synthetic construct | |
| SEQUENCE: 295 | | |

```
gcgaaagatc agagattcag ctttgctcta tactactttg actac                   45
```

| | | |
|---|---|---|
| SEQ ID NO: 296 | moltype = AA length = 15 | |
| FEATURE | Location/Qualifiers | |
| REGION | 1..15 | |
| | note = Synthetic | |
| source | 1..15 | |
| | mol_type = protein | |
| | organism = synthetic construct | |
| SEQUENCE: 296 | | |

```
AKDQRFSFAL YYFDY                                                    15
```

| | | |
|---|---|---|
| SEQ ID NO: 297 | moltype = DNA length = 324 | |
| FEATURE | Location/Qualifiers | |
| misc_feature | 1..324 | |
| | note = Synthetic | |
| source | 1..324 | |
| | mol_type = other DNA | |
| | organism = synthetic construct | |
| SEQUENCE: 297 | | |

```
gacatccaga tgacccagtc tccatcttcc gtgtctgcat ctgtaggaga cagagtcacc    60
atcacttgtc gggcgagtca gggtattagc agctggttag cctggtatca gcagaaacca   120
gggaacgccc ctaagctcct gatctatgct gcattcagtt tgcaaagtgg ggtcccgtca   180
aggttcagcg gcagtggatc tgggacagat ttcactctca ccatcagcag cctgcagcct   240
gaagattttg caacttacta ttgtcaacag gctaacaatt tcccgtggac gttcggccaa   300
gggaccaagg tggaaatcaa acga                                           324
```

SEQ ID NO: 298           moltype = AA   length = 108
FEATURE                  Location/Qualifiers
REGION                   1..108
                         note = Synthetic
source                   1..108
                         mol_type = protein
                         organism = synthetic construct
SEQUENCE: 298
DIQMTQSPSS VSASVGDRVT ITCRASQGIS SWLAWYQQKP GNAPKLLIYA AFSLQSGVPS    60
RFSGSGSGTD FTLTISSLQP EDFATYYCQQ ANNFPWTFGQ GTKVEIKR                108

SEQ ID NO: 299           moltype = DNA   length = 18
FEATURE                  Location/Qualifiers
misc_feature             1..18
                         note = Synthetic
source                   1..18
                         mol_type = other DNA
                         organism = synthetic construct
SEQUENCE: 299
cagggtatta gcagctgg                                                   18

SEQ ID NO: 300           moltype = AA   length = 6
FEATURE                  Location/Qualifiers
REGION                   1..6
                         note = Synthetic
source                   1..6
                         mol_type = protein
                         organism = synthetic construct
SEQUENCE: 300
QGISSW                                                                 6

SEQ ID NO: 301           moltype =    length =
SEQUENCE: 301
000

SEQ ID NO: 302           moltype =    length =
SEQUENCE: 302
000

SEQ ID NO: 303           moltype = DNA   length = 27
FEATURE                  Location/Qualifiers
misc_feature             1..27
                         note = Synthetic
source                   1..27
                         mol_type = other DNA
                         organism = synthetic construct
SEQUENCE: 303
caacaggcta acaatttccc gtggacg                                         27

SEQ ID NO: 304           moltype = AA   length = 9
FEATURE                  Location/Qualifiers
REGION                   1..9
                         note = Synthetic
source                   1..9
                         mol_type = protein
                         organism = synthetic construct
SEQUENCE: 304
QQANNFPWT                                                              9

SEQ ID NO: 305           moltype = DNA   length = 354
FEATURE                  Location/Qualifiers
misc_feature             1..354
                         note = Synthetic
source                   1..354
                         mol_type = other DNA
                         organism = synthetic construct
SEQUENCE: 305
```
```
caggtgcagc tggtggagtc tgggggaggc gtggtccagc ctggggggtc cctgagactc    60
tcctgtgcag cctctggatt cacccttcagt aactatgaca tgcactgggt ccgccaggct   120
ccaggcaagg ggctggagtg gatggcagtt atatcatatg atggaattaa taaatattat   180
gcagactccg tgaagggccg attcaccatc tccagagaca attccaagaa cacgctgtat   240
ctgcaaatga acagcctgag agctgaggac acggctgtgt attactgtgc gaaaggtact   300
```

```
tactcctggt acttcgatct ctggggccgt ggcaccctgg tcactgtctc ctca          354
```

SEQ ID NO: 306            moltype = AA   length = 118
FEATURE                   Location/Qualifiers
REGION                    1..118
                          note = Synthetic
source                    1..118
                          mol_type = protein
                          organism = synthetic construct
SEQUENCE: 306
QVQLVESGGG VVQPGRSLRL SCAASGFTFS NYDMHWVRQA PGKGLEWMAV ISYDGINKYY    60
ADSVKGRFTI SRDNSKNTLY LQMNSLRAED TAVYYCAKGT YSWYFDLWGR GTLVTVSS     118

SEQ ID NO: 307            moltype = DNA   length = 24
FEATURE                   Location/Qualifiers
misc_feature              1..24
                          note = Synthetic
source                    1..24
                          mol_type = other DNA
                          organism = synthetic construct
SEQUENCE: 307
ggattcacct tcagtaacta tgac                                           24

SEQ ID NO: 308            moltype = AA   length = 8
FEATURE                   Location/Qualifiers
REGION                    1..8
                          note = Synthetic
source                    1..8
                          mol_type = protein
                          organism = synthetic construct
SEQUENCE: 308
GFTFSNYD                                                             8

SEQ ID NO: 309            moltype = DNA   length = 24
FEATURE                   Location/Qualifiers
misc_feature              1..24
                          note = Synthetic
source                    1..24
                          mol_type = other DNA
                          organism = synthetic construct
SEQUENCE: 309
atatcatatg atggaattaa taaa                                           24

SEQ ID NO: 310            moltype = AA   length = 8
FEATURE                   Location/Qualifiers
REGION                    1..8
                          note = Synthetic
source                    1..8
                          mol_type = protein
                          organism = synthetic construct
SEQUENCE: 310
ISYDGINK                                                             8

SEQ ID NO: 311            moltype = DNA   length = 33
FEATURE                   Location/Qualifiers
misc_feature              1..33
                          note = Synthetic
source                    1..33
                          mol_type = other DNA
                          organism = synthetic construct
SEQUENCE: 311
gcgaaaggta cttactcctg gtacttcgat ctc                                 33

SEQ ID NO: 312            moltype = AA   length = 11
FEATURE                   Location/Qualifiers
REGION                    1..11
                          note = Synthetic
source                    1..11
                          mol_type = protein
                          organism = synthetic construct
SEQUENCE: 312
AKGTYSWYFD L                                                         11

SEQ ID NO: 313            moltype = DNA   length = 324
FEATURE                   Location/Qualifiers
misc_feature              1..324
                          note = Synthetic
source                    1..324
                          mol_type = other DNA

```
                        organism = synthetic construct
SEQUENCE: 313
gacatccaga tgacccagtc tccttccacc ctgtctacat ctgtaggaga cagagtcacc    60
atcacttgcc gggccagtca gactattagt agctggttgg cctggtatca gcagaaacca   120
gggaaaagcc ctaagctcct gatctataag gcgtctcgtt tagaaagtgg ggtcccatca   180
aggttcagcg gcagtggatc tgggacagaa ttcactctca ccatcagcag cctgcagcct   240
gatgattttg caacttatta ctgccaacag tataatagtt attcgtggac gttcggccaa   300
gggaccaagg tggaaatcaa acga                                          324

SEQ ID NO: 314          moltype = AA  length = 108
FEATURE                 Location/Qualifiers
REGION                  1..108
                        note = Synthetic
source                  1..108
                        mol_type = protein
                        organism = synthetic construct
SEQUENCE: 314
DIQMTQSPST LSTSVGDRVT ITCRASQTIS SWLAWYQQKP GKAPKLLIYK ASRLESGVPS    60
RFSGSGSGTE FTLTISSLQP DDFATYYCQQ YNSYSWTFGQ GTKVEIKR                108

SEQ ID NO: 315          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 315
cagactatta gtagctgg                                                  18

SEQ ID NO: 316          moltype = AA  length = 6
FEATURE                 Location/Qualifiers
REGION                  1..6
                        note = Synthetic
source                  1..6
                        mol_type = protein
                        organism = synthetic construct
SEQUENCE: 316
QTISSW                                                                6

SEQ ID NO: 317          moltype =     length =
SEQUENCE: 317
000

SEQ ID NO: 318          moltype =     length =
SEQUENCE: 318
000

SEQ ID NO: 319          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 319
caacagtata atagttattc gtggacg                                        27

SEQ ID NO: 320          moltype = AA  length = 9
FEATURE                 Location/Qualifiers
REGION                  1..9
                        note = Synthetic
source                  1..9
                        mol_type = protein
                        organism = synthetic construct
SEQUENCE: 320
QQYNSYSWT                                                             9

SEQ ID NO: 321          moltype = DNA  length = 366
FEATURE                 Location/Qualifiers
misc_feature            1..366
                        note = Synthetic
source                  1..366
                        mol_type = other DNA
                        organism = synthetic construct
SEQUENCE: 321
gaagtgcagc tggtggagtc tgggggaggc ttggtacagc ctgcaggtc cctgagactc     60
tcctgtgcag cctctggatt caccttttgat gcttatgcca tgcactgggt ccggcaagct  120
ccagggaagg gcctggagtg ggtctcaggt attagttgga atagtggtag cataggctat   180
```

-continued

```
gcggactctg tgaagggccg attcaccatt tccagagaca acgccaagaa ctccctgtat    240
ctgcaaatga acagtctgag agaagaggac acggccttgt attactgtgc aaaagataaa    300
attttggaac tttactacta cggtatggac gtctggggcc aagggaccac ggtcaccgtc    360
tcctca                                                                366

SEQ ID NO: 322          moltype = AA   length = 122
FEATURE                 Location/Qualifiers
REGION                  1..122
                        note = Synthetic
source                  1..122
                        mol_type = protein
                        organism = synthetic construct
SEQUENCE: 322
EVQLVESGGG LVQPGRSLRL SCAASGFTFD AYAMHWVRQA PGKGLEWVSG ISWNSGSIGY     60
ADSVKGRFTI SRDNAKNSLY LQMNSLREED TALYYCAKDK ILELYYYGMD VWGQGTTVTV    120
SS                                                                   122

SEQ ID NO: 323          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 323
ggattcacct ttgatgctta tgcc                                            24

SEQ ID NO: 324          moltype = AA   length = 8
FEATURE                 Location/Qualifiers
REGION                  1..8
                        note = Synthetic
source                  1..8
                        mol_type = protein
                        organism = synthetic construct
SEQUENCE: 324
GFTFDAYA                                                              8

SEQ ID NO: 325          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 325
attagttgga atagtggtag cata                                            24

SEQ ID NO: 326          moltype = AA   length = 8
FEATURE                 Location/Qualifiers
REGION                  1..8
                        note = Synthetic
source                  1..8
                        mol_type = protein
                        organism = synthetic construct
SEQUENCE: 326
ISWNSGSI                                                              8

SEQ ID NO: 327          moltype = DNA   length = 45
FEATURE                 Location/Qualifiers
misc_feature            1..45
                        note = Synthetic
source                  1..45
                        mol_type = other DNA
                        organism = synthetic construct
SEQUENCE: 327
gcaaaagata aaattttgga actttactac tacggtatgg acgtc                     45

SEQ ID NO: 328          moltype = AA   length = 15
FEATURE                 Location/Qualifiers
REGION                  1..15
                        note = Synthetic
source                  1..15
                        mol_type = protein
                        organism = synthetic construct
SEQUENCE: 328
AKDKILELYY YGMDV                                                      15

SEQ ID NO: 329          moltype = DNA   length = 369
FEATURE                 Location/Qualifiers
```

```
misc_feature          1..369
                      note = Synthetic
source                1..369
                      mol_type = other DNA
                      organism = synthetic construct
SEQUENCE: 329
gaggtgcagc tggtggagtc tgggggagac ttggtacagc ctgggggttc cctgagactc    60
tcctgttcag cctctggatt cacctttaac atctatgcca tgagctgggt ccgccaggct   120
ccagggaagg ggctggagtg ggtctcaggt attagtggta gtggtggtag cacatactac   180
gcagactccg tgaagggccg gttcaccatc tccagagaca attcaaagaa cacgctgtat   240
ttccaaatga atagcctgag agtcgaggac acggccgtat attactgtgc gaaaaaaata   300
agcagctcgt cctactacta ctacgctatg gacgtctggg gccaagggac cacggtcacc   360
gtctcctca                                                           369

SEQ ID NO: 330         moltype = AA  length = 123
FEATURE                Location/Qualifiers
REGION                 1..123
                       note = Synthetic
source                 1..123
                       mol_type = protein
                       organism = synthetic construct
SEQUENCE: 330
EVQLVESGGD LVQPGGSLRL SCSASGFTFN IYAMSWVRQA PGKGLEWVSG ISGSGGSTYY     60
ADSVKGRFTI SRDNSKNTLY FQMNSLRVED TAVYYCAKKI SSSSYYYYAM DVWGQGTTVT    120
VSS                                                                  123

SEQ ID NO: 331         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 331
ggattcacct ttaacatcta tgcc                                            24

SEQ ID NO: 332         moltype = AA  length = 8
FEATURE                Location/Qualifiers
REGION                 1..8
                       note = Synthetic
source                 1..8
                       mol_type = protein
                       organism = synthetic construct
SEQUENCE: 332
GFTFNIYA                                                               8

SEQ ID NO: 333         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 333
attagtggta gtggtggtag caca                                            24

SEQ ID NO: 334         moltype = AA  length = 8
FEATURE                Location/Qualifiers
REGION                 1..8
                       note = Synthetic
source                 1..8
                       mol_type = protein
                       organism = synthetic construct
SEQUENCE: 334
ISGSGGST                                                               8

SEQ ID NO: 335         moltype = DNA  length = 48
FEATURE                Location/Qualifiers
misc_feature           1..48
                       note = Synthetic
source                 1..48
                       mol_type = other DNA
                       organism = synthetic construct
SEQUENCE: 335
gcgaaaaaaa taagcagctc gtcctactac tactacgcta tggacgtc                  48

SEQ ID NO: 336         moltype = AA  length = 16
FEATURE                Location/Qualifiers
REGION                 1..16
```

```
                        note = Synthetic
source                  1..16
                        mol_type = protein
                        organism = synthetic construct
SEQUENCE: 336
AKKISSSSYY YYAMDV                                                       16

SEQ ID NO: 337          moltype = DNA  length = 355
FEATURE                 Location/Qualifiers
misc_feature            1..355
                        note = Synthetic
source                  1..355
                        mol_type = other DNA
                        organism = synthetic construct
SEQUENCE: 337
caggtgcagc tggtgcagtc tggggctgag gtgaagaagc ctgggtcctc ggtgaaggtc        60
tcctgcaagg cttctggagg caccttcagc agatatgata tcagctgggt gcgacaggcc       120
cctggacaag gacttgagtg gatgggaggg atcatcccta tctttggtac atcaaactac       180
gcacagaagt tccagggcag agtcacgatt accacggacg aatccacgag tacagtctac       240
atggagctga gcagtctgag atctgaagac acggccgtgt attattgtgc gagaggaggt       300
cgatatggct ggttcgaccc ctggggccag ggaaccctgg tcaccgtctc ctcag            355

SEQ ID NO: 338          moltype = AA  length = 118
FEATURE                 Location/Qualifiers
REGION                  1..118
                        note = Synthetic
source                  1..118
                        mol_type = protein
                        organism = synthetic construct
SEQUENCE: 338
QVQLVQSGAE VKKPGSSVKV SCKASGGTFS RYDISWVRQA PGQGLEWMGG IIPIFGTSNY        60
AQKFQGRVTI TTDESTSTVY MELSSLRSED TAVYYCARGG RYGWFDPWGQ GTLVTVSS         118

SEQ ID NO: 339          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 339
ggaggcacct tcagcagata tgat                                              24

SEQ ID NO: 340          moltype = AA  length = 8
FEATURE                 Location/Qualifiers
REGION                  1..8
                        note = Synthetic
source                  1..8
                        mol_type = protein
                        organism = synthetic construct
SEQUENCE: 340
GGTFSRYD                                                                 8

SEQ ID NO: 341          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 341
atcatcccta tctttggtac atca                                              24

SEQ ID NO: 342          moltype = AA  length = 8
FEATURE                 Location/Qualifiers
REGION                  1..8
                        note = Synthetic
source                  1..8
                        mol_type = protein
                        organism = synthetic construct
SEQUENCE: 342
IIPIFGTS                                                                 8

SEQ ID NO: 343          moltype = DNA  length = 33
FEATURE                 Location/Qualifiers
misc_feature            1..33
                        note = Synthetic
source                  1..33
                        mol_type = other DNA
```

```
                         organism = synthetic construct
SEQUENCE: 343
gcgagaggag gtcgatatgg ctggttcgac ccc                                33

SEQ ID NO: 344           moltype = AA   length = 11
FEATURE                  Location/Qualifiers
REGION                   1..11
                         note = Synthetic
source                   1..11
                         mol_type = protein
                         organism = synthetic construct
SEQUENCE: 344
ARGGRYGWFD P                                                        11

SEQ ID NO: 345           moltype = DNA   length = 375
FEATURE                  Location/Qualifiers
misc_feature             1..375
                         note = Synthetic
source                   1..375
                         mol_type = other DNA
                         organism = synthetic construct
SEQUENCE: 345
gaggtgcagc tggtggagtc tgggggaggc ttggtacagc ctggggggtc cctgagactc    60
tcctgtgcag cctctggatt cacctttagc agctttgcca tgagctgggt ccgccaggct   120
ccagggaagg aactggagtg ggtctcatct attagtggtc gtggtggtag cacatactac   180
gcagactccg tgaggggccg gttcaccatc tccagagaca attccaagat cacgctgtat   240
ctgcaaatga acagcctgag agccgaggac acggccgtat attactgtgc gaaagatatt   300
gtcttccggt ataccagctc ggcctactgg tacttcgatc tctggggccg tggcaccctg   360
gtcaccgtct cctca                                                   375

SEQ ID NO: 346           moltype = AA   length = 125
FEATURE                  Location/Qualifiers
REGION                   1..125
                         note = Synthetic
source                   1..125
                         mol_type = protein
                         organism = synthetic construct
SEQUENCE: 346
EVQLVESGGG LVQPGGSLRL SCAASGFTFS SFAMSWVRQA PGKELEWVSS ISGRGGSTYY    60
ADSVRGRFTI SRDNSKITLY LQMNSLRAED TAVYYCAKDI VFRYTSSAYW YFDLWGRGTL   120
VTVSS                                                              125

SEQ ID NO: 347           moltype = DNA   length = 24
FEATURE                  Location/Qualifiers
misc_feature             1..24
                         note = Synthetic
source                   1..24
                         mol_type = other DNA
                         organism = synthetic construct
SEQUENCE: 347
ggattcacct ttagcagctt tgcc                                          24

SEQ ID NO: 348           moltype = AA   length = 8
FEATURE                  Location/Qualifiers
REGION                   1..8
                         note = Synthetic
source                   1..8
                         mol_type = protein
                         organism = synthetic construct
SEQUENCE: 348
GFTFSSFA                                                             8

SEQ ID NO: 349           moltype = DNA   length = 24
FEATURE                  Location/Qualifiers
misc_feature             1..24
                         note = Synthetic
source                   1..24
                         mol_type = other DNA
                         organism = synthetic construct
SEQUENCE: 349
attagtggtc gtggtggtag caca                                          24

SEQ ID NO: 350           moltype = AA   length = 8
FEATURE                  Location/Qualifiers
REGION                   1..8
                         note = Synthetic
source                   1..8
                         mol_type = protein
                         organism = synthetic construct
```

```
SEQUENCE: 350
ISGRGGST                                                                    8

SEQ ID NO: 351          moltype = DNA  length = 54
FEATURE                 Location/Qualifiers
misc_feature            1..54
                        note = Synthetic
source                  1..54
                        mol_type = other DNA
                        organism = synthetic construct
SEQUENCE: 351
gcgaaagata ttgtcttccg gtataccagc tcggcctact ggtacttcga tctc                54

SEQ ID NO: 352          moltype = AA   length = 18
FEATURE                 Location/Qualifiers
REGION                  1..18
                        note = Synthetic
source                  1..18
                        mol_type = protein
                        organism = synthetic construct
SEQUENCE: 352
AKDIVFRYTS SAYWYFDL                                                        18

SEQ ID NO: 353          moltype = DNA  length = 375
FEATURE                 Location/Qualifiers
misc_feature            1..375
                        note = Synthetic
source                  1..375
                        mol_type = other DNA
                        organism = synthetic construct
SEQUENCE: 353
gaggtgcagc tggtggagtc tgggggaggc ttggtacagc ctggggggtc cctgagactc          60
tcctgtgcag cctctggatt cacctttagc agctatggca tgaactgggt ccgccaggct         120
ccagggaagg ggctggagtg ggtctcagtt attagtggta gtggtggtag cacatactac         180
gcagactccg tgaaggggcg gttcaccatc tccagagaca attccaagaa cacgctgtat         240
ctgcaaatga acagcctgag agccgaggac acggccgtat attactgtgc gaaagatcgt         300
tggacgtatt actatgatag tagtggttcc ccctttgact actggggcca gggaaccctg         360
gtcaccgtct cctca                                                          375

SEQ ID NO: 354          moltype = AA   length = 125
FEATURE                 Location/Qualifiers
REGION                  1..125
                        note = Synthetic
source                  1..125
                        mol_type = protein
                        organism = synthetic construct
SEQUENCE: 354
EVQLVESGGG LVQPGGSLRL SCAASGFTFS SYGMNWVRQA PGKGLEWVSV ISGSGGSTYY          60
ADSVKGRFTI SRDNSKNTLY LQMNSLRAED TAVYYCAKDR WTYYYDSSGS PFDYWGQGTL         120
VTVSS                                                                     125

SEQ ID NO: 355          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 355
ggattcacct ttagcagcta tggc                                                 24

SEQ ID NO: 356          moltype = AA   length = 8
FEATURE                 Location/Qualifiers
REGION                  1..8
                        note = Synthetic
source                  1..8
                        mol_type = protein
                        organism = synthetic construct
SEQUENCE: 356
GFTFSSYG                                                                    8

SEQ ID NO: 357          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 357
```

```
attagtggta gtggtggtag caca                                              24

SEQ ID NO: 358          moltype = AA  length = 8
FEATURE                 Location/Qualifiers
REGION                  1..8
                        note = Synthetic
source                  1..8
                        mol_type = protein
                        organism = synthetic construct
SEQUENCE: 358
ISGSGGST                                                                8

SEQ ID NO: 359          moltype = DNA  length = 54
FEATURE                 Location/Qualifiers
misc_feature            1..54
                        note = Synthetic
source                  1..54
                        mol_type = other DNA
                        organism = synthetic construct
SEQUENCE: 359
gcgaaagatc gttggacgta ttactatgat agtagtggtt cccccttgga ctac             54

SEQ ID NO: 360          moltype = AA  length = 18
FEATURE                 Location/Qualifiers
REGION                  1..18
                        note = Synthetic
source                  1..18
                        mol_type = protein
                        organism = synthetic construct
SEQUENCE: 360
AKDRWTYYYD SSGSPFDY                                                     18

SEQ ID NO: 361          moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 361
gaaattgtgt tgacgcagtc tccaggcacc ctgtctttgt ctccagggga aagagccacc       60
ctctcctgca gggccagtca gagtgttagc agcagctact tagcctggta ccagcagaaa      120
cctggccagg ctcccaggct cctcatctat ggtgcatcca gcagggccac tggcatccca      180
gacaggttca gtggcagtgg gtctgggaca gacttcactc tcaccatcag cagactggag      240
cctgaagatt ttgcagtgta ttactgtcag cagtatggta gctcaccttg gacgttcggc      300
caagggacca aggtggaaat caaa                                             324

SEQ ID NO: 362          moltype = AA  length = 108
FEATURE                 Location/Qualifiers
REGION                  1..108
                        note = Synthetic
source                  1..108
                        mol_type = protein
                        organism = synthetic construct
SEQUENCE: 362
EIVLTQSPGT LSLSPGERAT LSCRASQSVS SSYLAWYQQK PGQAPRLLIY GASSRATGIP       60
DRFSGSGSGT DFTLTISRLE PEDFAVYYCQ QYGSSPWTFG QGTKVEIK                   108

SEQ ID NO: 363          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 363
cagagtgtta gcagcagcta c                                                 21

SEQ ID NO: 364          moltype = AA  length = 7
FEATURE                 Location/Qualifiers
REGION                  1..7
                        note = Synthetic
source                  1..7
                        mol_type = protein
                        organism = synthetic construct
SEQUENCE: 364
QSVSSSY                                                                 7

SEQ ID NO: 365          moltype =    length =
```

```
SEQUENCE: 365
000

SEQ ID NO: 366          moltype =    length =
SEQUENCE: 366
000

SEQ ID NO: 367          moltype = DNA   length = 27
FEATURE                 Location/Qualifiers
misc_feature            1..27
                        note = Synthetic
source                  1..27
                        mol_type = other DNA
                        organism = synthetic construct
SEQUENCE: 367
cagcagtatg gtagctcacc ttggacg                                         27

SEQ ID NO: 368          moltype = AA    length = 9
FEATURE                 Location/Qualifiers
REGION                  1..9
                        note = Synthetic
source                  1..9
                        mol_type = protein
                        organism = synthetic construct
SEQUENCE: 368
QQYGSSPWT                                                              9

SEQ ID NO: 369          moltype = DNA   length = 363
FEATURE                 Location/Qualifiers
misc_feature            1..363
                        note = Synthetic
source                  1..363
                        mol_type = other DNA
                        organism = synthetic construct
SEQUENCE: 369
gaggtgcagc tggtggagtc tgggggaggc tttgtacagc ctggggggtc cctgagactc     60
tcctgtgcag cctctggatt cacttttagc agttatgcca tgagttgggt ccgccaggct    120
ccaggtaagg ggctggagtg ggtctcagct attagtggta ctggtagtaa cacatactac    180
gcagactccg tgaagggccg gttcaccatc tccagagaca attccaagaa cacgctgtat    240
ctgcaaatga acagcctgag agccgaggac acggccgttt actactgtgc gaaagatcgc    300
gtgactacag taacctacta ctttgactac tggggccagg gaaccctggt caccgtctcc    360
tca                                                                  363

SEQ ID NO: 370          moltype = AA    length = 121
FEATURE                 Location/Qualifiers
REGION                  1..121
                        note = Synthetic
source                  1..121
                        mol_type = protein
                        organism = synthetic construct
SEQUENCE: 370
EVQLVESGGG FVQPGGSLRL SCAASGFTFS SYAMSWVRQA PGKGLEWVSA ISGTGSNTYY     60
ADSVKGRFTI SRDNSKNTLY LQMNSLRAED TAVYYCAKDR VTTVTYYFDY WGQGTLVTVS    120
S                                                                    121

SEQ ID NO: 371          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 371
ggattcactt ttagcagtta tgcc                                            24

SEQ ID NO: 372          moltype = AA    length = 8
FEATURE                 Location/Qualifiers
REGION                  1..8
                        note = Synthetic
source                  1..8
                        mol_type = protein
                        organism = synthetic construct
SEQUENCE: 372
GFTFSSYA                                                               8

SEQ ID NO: 373          moltype = DNA   length = 24
FEATURE                 Location/Qualifiers
misc_feature            1..24
                        note = Synthetic
```

```
source                   1..24
                         mol_type = other DNA
                         organism = synthetic construct
SEQUENCE: 373
attagtggta ctggtagtaa caca                                              24

SEQ ID NO: 374           moltype = AA  length = 8
FEATURE                  Location/Qualifiers
REGION                   1..8
                         note = Synthetic
source                   1..8
                         mol_type = protein
                         organism = synthetic construct
SEQUENCE: 374
ISGTGSNT                                                                8

SEQ ID NO: 375           moltype = DNA  length = 42
FEATURE                  Location/Qualifiers
misc_feature             1..42
                         note = Synthetic
source                   1..42
                         mol_type = other DNA
                         organism = synthetic construct
SEQUENCE: 375
gcgaaagatc gcgtgactac agtaacctac tactttgact ac                          42

SEQ ID NO: 376           moltype = AA  length = 14
FEATURE                  Location/Qualifiers
REGION                   1..14
                         note = Synthetic
source                   1..14
                         mol_type = protein
                         organism = synthetic construct
SEQUENCE: 376
AKDRVTTVTY YFDY                                                         14

SEQ ID NO: 377           moltype = DNA  length = 372
FEATURE                  Location/Qualifiers
misc_feature             1..372
                         note = Synthetic
source                   1..372
                         mol_type = other DNA
                         organism = synthetic construct
SEQUENCE: 377
gaggtgcagc tggtggagtc tgggggaggc ttggtacagc ctgggggtc cctgagactc         60
tcctgtgcag cctctggttt caccttagc agctatgcca tgaactgggt ccgccaggct        120
ccagggaagg gactggagtg ggtctcagct attagtggta gtggtgatag cacatactac       180
gcagactccg tgaagggccg gttcaccatc tccagagaca attccaggac acgctgtct        240
ctgcaattga acagcctgag agccgaggac acggccgtat attactgtgc gaaagatcga       300
ctactatggt tcggggaatt aggatcccca tttcactact ggggccaggg aaccctggtc       360
accgtctcct ca                                                          372

SEQ ID NO: 378           moltype = AA  length = 124
FEATURE                  Location/Qualifiers
REGION                   1..124
                         note = Synthetic
source                   1..124
                         mol_type = protein
                         organism = synthetic construct
SEQUENCE: 378
EVQLVESGGG LVQPGGSLRL SCAASGFTFS SYAMNWVRQA PGKGLEWVSA ISGSGDSTYY        60
ADSVKGRFTI SRDNSRTTLS LQLNSLRAED TAVYYCAKDR LLWFGELGSP FHYWGQGTLV       120
TVSS                                                                   124

SEQ ID NO: 379           moltype = DNA  length = 24
FEATURE                  Location/Qualifiers
misc_feature             1..24
                         note = Synthetic
source                   1..24
                         mol_type = other DNA
                         organism = synthetic construct
SEQUENCE: 379
ggtttcacct ttagcagcta tgcc                                              24

SEQ ID NO: 380           moltype = AA  length = 8
FEATURE                  Location/Qualifiers
REGION                   1..8
                         note = Synthetic
source                   1..8
```

```
                        mol_type = protein
                        organism = synthetic construct
SEQUENCE: 380
GFTFSSYA                                                                    8

SEQ ID NO: 381          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 381
attagtggta gtggtgatag caca                                                 24

SEQ ID NO: 382          moltype = AA  length = 8
FEATURE                 Location/Qualifiers
REGION                  1..8
                        note = Synthetic
source                  1..8
                        mol_type = protein
                        organism = synthetic construct
SEQUENCE: 382
ISGSGDST                                                                    8

SEQ ID NO: 383          moltype = DNA  length = 51
FEATURE                 Location/Qualifiers
misc_feature            1..51
                        note = Synthetic
source                  1..51
                        mol_type = other DNA
                        organism = synthetic construct
SEQUENCE: 383
gcgaaagatc gactactatg gttcggggaa ttaggatccc catttcacta c                   51

SEQ ID NO: 384          moltype = AA  length = 17
FEATURE                 Location/Qualifiers
REGION                  1..17
                        note = Synthetic
source                  1..17
                        mol_type = protein
                        organism = synthetic construct
SEQUENCE: 384
AKDRLLWFGE LGSPFHY                                                         17

SEQ ID NO: 385          moltype = DNA  length = 363
FEATURE                 Location/Qualifiers
misc_feature            1..363
                        note = Synthetic
source                  1..363
                        mol_type = other DNA
                        organism = synthetic construct
SEQUENCE: 385
gaggtgcagc tggtggagtc tgggggaggc ttgaacagc ctggggggtc cctgagactc           60
tcctgtgcag cctctggatt caccttagc agctatgcca tgagctgggt ccgccaggct          120
ccagggaagg ggctggagtg ggtctcagtc attagtggta gtggtggtta cacaaactac         180
gcagactccg tgaagggccg gttcaccatc tccagagaca attccaagaa cacgctgtat         240
ctgcaaatga accgcctgag agccgaggac tcggccgttt attactgtgc gaggcataat         300
tggaactacg actattacgg tatggacgtc tggggccagg gaccacggt caccgtctcc          360
tca                                                                       363

SEQ ID NO: 386          moltype = AA  length = 121
FEATURE                 Location/Qualifiers
REGION                  1..121
                        note = Synthetic
source                  1..121
                        mol_type = protein
                        organism = synthetic construct
SEQUENCE: 386
EVQLVESGGG LEQPGGSLRL SCAASGFTFS SYAMSWVRQA PGKGLEWVSV ISGSGGYTNY           60
ADSVKGRFTI SRDNSKNTLY LQMNRLRAED SAVYYCARHN WNYDYYGMDV WGQGTTVTVS         120
S                                                                         121

SEQ ID NO: 387          moltype = DNA  length = 24
FEATURE                 Location/Qualifiers
misc_feature            1..24
                        note = Synthetic
source                  1..24
                        mol_type = other DNA
```

```
                        organism = synthetic construct
SEQUENCE: 387
ggattcacct ttagcagcta tgcc                                             24

SEQ ID NO: 388          moltype = AA   length = 8
FEATURE                 Location/Qualifiers
REGION                  1..8
                        note = Synthetic
source                  1..8
                        mol_type = protein
                        organism = synthetic construct
SEQUENCE: 388
GFTFSSYA                                                                8

SEQ ID NO: 389          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 389
attagtggta gtggtggtta caca                                             24

SEQ ID NO: 390          moltype = AA   length = 8
FEATURE                 Location/Qualifiers
REGION                  1..8
                        note = Synthetic
source                  1..8
                        mol_type = protein
                        organism = synthetic construct
SEQUENCE: 390
ISGSGGYT                                                                8

SEQ ID NO: 391          moltype = DNA   length = 42
FEATURE                 Location/Qualifiers
misc_feature            1..42
                        note = Synthetic
source                  1..42
                        mol_type = other DNA
                        organism = synthetic construct
SEQUENCE: 391
gcgaggcata attggaacta cgactattac ggtatggacg tc                         42

SEQ ID NO: 392          moltype = AA   length = 14
FEATURE                 Location/Qualifiers
REGION                  1..14
                        note = Synthetic
source                  1..14
                        mol_type = protein
                        organism = synthetic construct
SEQUENCE: 392
ARHNWNYDYY GMDV                                                        14

SEQ ID NO: 393          moltype = DNA   length = 360
FEATURE                 Location/Qualifiers
misc_feature            1..360
                        note = Synthetic
source                  1..360
                        mol_type = other DNA
                        organism = synthetic construct
SEQUENCE: 393
caggtgcagc tggtggagtc tgggggaggc gtggtccagt ctggaggtc cctgagactc       60
tcctgtgcag ccgctggatt caccttcagt aattatggca tgcactgggt ccgccaggct     120
ccaggcaagg ggctgagtg gtggcactt atgtcatttg atggaagtga taaatactat       180
gcagactccg tgaagggccg attcaccatc tccagagaca attccaagaa cacgttgtat     240
ctgcaaatga acagcctgag agctgaggac acggctctgt attactgtgc gaaaggatac    300
gatttttgga gtggttattg ggactactgg ggccagggaa ccctggtcac cgtctcctca    360

SEQ ID NO: 394          moltype = AA   length = 120
FEATURE                 Location/Qualifiers
REGION                  1..120
                        note = Synthetic
source                  1..120
                        mol_type = protein
                        organism = synthetic construct
SEQUENCE: 394
QVQLVESGGG VVQSGRSLRL SCAAAGFTFS NYGMHWVRQA PGKGLEWVAL MSFDGSDKYY      60
ADSVKGRFTI SRDNSKNTLY LQMNSLRAED TALYYCAKGY DFWSGYWDYW GQGTLVTVSS    120
```

```
SEQ ID NO: 395          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 395
ggattcacct tcagtaatta tggc                                              24

SEQ ID NO: 396          moltype = AA  length = 8
FEATURE                 Location/Qualifiers
REGION                  1..8
                        note = Synthetic
source                  1..8
                        mol_type = protein
                        organism = synthetic construct
SEQUENCE: 396
GFTFSNYG                                                                 8

SEQ ID NO: 397          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 397
atgtcatttg atggaagtga taaa                                              24

SEQ ID NO: 398          moltype = AA  length = 8
FEATURE                 Location/Qualifiers
REGION                  1..8
                        note = Synthetic
source                  1..8
                        mol_type = protein
                        organism = synthetic construct
SEQUENCE: 398
MSFDGSDK                                                                 8

SEQ ID NO: 399          moltype = DNA  length = 39
FEATURE                 Location/Qualifiers
misc_feature            1..39
                        note = Synthetic
source                  1..39
                        mol_type = other DNA
                        organism = synthetic construct
SEQUENCE: 399
gcgaaaggat acgattttg gagtggttat tgggactac                               39

SEQ ID NO: 400          moltype = AA  length = 13
FEATURE                 Location/Qualifiers
REGION                  1..13
                        note = Synthetic
source                  1..13
                        mol_type = protein
                        organism = synthetic construct
SEQUENCE: 400
AKGYDFWSGY WDY                                                          13

SEQ ID NO: 401          moltype = DNA  length = 351
FEATURE                 Location/Qualifiers
misc_feature            1..351
                        note = Synthetic
source                  1..351
                        mol_type = other DNA
                        organism = synthetic construct
SEQUENCE: 401
gaggtgcagc tggtggagtc tgggggaggc ttggtacaac ctgggggtc cctgagactc         60
tcctgtgcag cctctggatt cacctttagc acctatgcca tgagctgggt ccgccaggct       120
ccagggaagg ggcttgagtg ggtctcaact attagtggtc gttctgatat tacatacttc       180
gcagactccg tgaagggccg gtttaccgtc tccagagaca attccaagac cacgctatat       240
ctccaaatga acagtctgag agccgaggac acggccgtat attactgtgc gacagatgac       300
gacctgcccc ttgactactg gggccaggga accctggtca ccgtctcctc a                351

SEQ ID NO: 402          moltype = AA  length = 117
FEATURE                 Location/Qualifiers
REGION                  1..117
```

|   |   |
|---|---|
|   | note = Synthetic |
| source | 1..117 |
|   | mol_type = protein |
|   | organism = synthetic construct |

SEQUENCE: 402
EVQLVESGGG LVQPGGSLRL SCAASGFTFS TYAMSWVRQA PGKGLEWVST ISGRSDITYF  60
ADSVKGRFTV SRDNSKTTLY LQMNSLRAED TAVYYCATDD DLPLDYWGQG TLVTVSS    117

|   |   |
|---|---|
| SEQ ID NO: 403 | moltype = DNA  length = 24 |
| FEATURE | Location/Qualifiers |
| misc_feature | 1..24 |
|   | note = Synthetic |
| source | 1..24 |
|   | mol_type = other DNA |
|   | organism = synthetic construct |

SEQUENCE: 403
ggattcacct ttagcaccta tgcc                                        24

|   |   |
|---|---|
| SEQ ID NO: 404 | moltype = AA  length = 8 |
| FEATURE | Location/Qualifiers |
| REGION | 1..8 |
|   | note = Synthetic |
| source | 1..8 |
|   | mol_type = protein |
|   | organism = synthetic construct |

SEQUENCE: 404
GFTFSTYA                                                          8

|   |   |
|---|---|
| SEQ ID NO: 405 | moltype = DNA  length = 24 |
| FEATURE | Location/Qualifiers |
| misc_feature | 1..24 |
|   | note = Synthetic |
| source | 1..24 |
|   | mol_type = other DNA |
|   | organism = synthetic construct |

SEQUENCE: 405
attagtggtc gttctgatat taca                                        24

|   |   |
|---|---|
| SEQ ID NO: 406 | moltype = AA  length = 8 |
| FEATURE | Location/Qualifiers |
| REGION | 1..8 |
|   | note = Synthetic |
| source | 1..8 |
|   | mol_type = protein |
|   | organism = synthetic construct |

SEQUENCE: 406
ISGRSDIT                                                          8

|   |   |
|---|---|
| SEQ ID NO: 407 | moltype = DNA  length = 30 |
| FEATURE | Location/Qualifiers |
| misc_feature | 1..30 |
|   | note = Synthetic |
| source | 1..30 |
|   | mol_type = other DNA |
|   | organism = synthetic construct |

SEQUENCE: 407
gcgacagatg acgacctgcc ccttgactac                                  30

|   |   |
|---|---|
| SEQ ID NO: 408 | moltype = AA  length = 10 |
| FEATURE | Location/Qualifiers |
| REGION | 1..10 |
|   | note = Synthetic |
| source | 1..10 |
|   | mol_type = protein |
|   | organism = synthetic construct |

SEQUENCE: 408
ATDDDLPLDY                                                        10

|   |   |
|---|---|
| SEQ ID NO: 409 | moltype = DNA  length = 354 |
| FEATURE | Location/Qualifiers |
| misc_feature | 1..354 |
|   | note = Synthetic |
| source | 1..354 |
|   | mol_type = other DNA |
|   | organism = synthetic construct |

SEQUENCE: 409
caggtgcagc tggtgcagtc tgggactgag gtgaagaagc ctgggtcctc ggtgaaggtc  60
tcctgcaagg cttctggagg caccttcagc agatatactt tcagctgggt gcgacaggcc  120
cctggacaag ggcttgagtg gatgggaggg atcatcccta tctttggtac aacaaactac  180

```
gcacagaagt tccagggcag agtcacgatt accacggacg aatccacgag cacagtctac    240
atggagctga gcagcctgag atctgaggac acgccgtgt attattgtac cagaggaggt     300
cgatatggct ggttcgaccc ctggggccag ggaaccctgg tcaccgtctc ctca          354
```

```
SEQ ID NO: 410              moltype = AA  length = 118
FEATURE                     Location/Qualifiers
REGION                      1..118
                            note = Synthetic
source                      1..118
                            mol_type = protein
                            organism = synthetic construct
SEQUENCE: 410
QVQLVQSGTE VKKPGSSVKV SCKASGGTFS RYTFSWVRQA PGQGLEWMGG IIPIFGTTNY     60
AQKFQGRVTI TTDESTSTVY MELSSLRSED TAVYYCTRGG RYGWFDPWGQ GTLVTVSS     118

SEQ ID NO: 411              moltype = DNA  length = 24
FEATURE                     Location/Qualifiers
misc_feature                1..24
                            note = Synthetic
source                      1..24
                            mol_type = other DNA
                            organism = synthetic construct
SEQUENCE: 411
ggaggcacct tcagcagata tact                                            24

SEQ ID NO: 412              moltype = AA  length = 8
FEATURE                     Location/Qualifiers
REGION                      1..8
                            note = Synthetic
source                      1..8
                            mol_type = protein
                            organism = synthetic construct
SEQUENCE: 412
GGTFSRYT                                                               8

SEQ ID NO: 413              moltype = DNA  length = 24
FEATURE                     Location/Qualifiers
misc_feature                1..24
                            note = Synthetic
source                      1..24
                            mol_type = other DNA
                            organism = synthetic construct
SEQUENCE: 413
atcatcccta tctttggtac aaca                                            24

SEQ ID NO: 414              moltype = AA  length = 8
FEATURE                     Location/Qualifiers
REGION                      1..8
                            note = Synthetic
source                      1..8
                            mol_type = protein
                            organism = synthetic construct
SEQUENCE: 414
IIPIFGTT                                                               8

SEQ ID NO: 415              moltype = DNA  length = 33
FEATURE                     Location/Qualifiers
misc_feature                1..33
                            note = Synthetic
source                      1..33
                            mol_type = other DNA
                            organism = synthetic construct
SEQUENCE: 415
accagaggag gtcgatatgg ctggttcgac ccc                                  33

SEQ ID NO: 416              moltype = AA  length = 11
FEATURE                     Location/Qualifiers
REGION                      1..11
                            note = Synthetic
source                      1..11
                            mol_type = protein
                            organism = synthetic construct
SEQUENCE: 416
TRGGRYGWFD P                                                          11

SEQ ID NO: 417              moltype = AA  length = 403
FEATURE                     Location/Qualifiers
REGION                      1..403
                            note = misc_feature - His-myc tagged human MSR1 antibody
```

|  | (extracellular domain) |  |
|---|---|---|
| source | 1..403 |  |
|  | mol_type = protein |  |
|  | organism = Homo sapiens |  |

SEQUENCE: 417
```
HHHHHHEQKL ISEEDLGGEQ KLISEEDLKW ETKNCSVSST NANDITQSLT GKGNDSEEEM   60
RFQEVFMEHM SNMEKRIQHI LDMEANLMDT EHFQNFSMTT DQRFNDILLQ LSTLFSSVQG  120
HGNAIDEISK SLISLNTTLL DLQLNIENLN GKIQENTFKQ QEEISKLEER VYNVSAEIMA  180
MKEEQVHLEQ EIKGEVKVLN NITNDLRLKD WEHSQTLRNI TLIQGPPGPP GEKGDRGPTG  240
ESGPRGFPGP IGPPGLKGDR GAIGFPGSRG LPGYAGRPGN SGPKGQKGEK GSGNTLTPFT  300
KVRLVGGSGP HEGRVEILHS GQWGTICDDR WEVRVGQVVC RSLGYPGVQA VHKAAHFGQG  360
TGPIWLNEVF CFGRESSIEE CKIRQWGTRA CSHSEDAGVT CTL                   403
```

| SEQ ID NO: 418 | moltype = AA  length = 403 |
|---|---|
| FEATURE | Location/Qualifiers |
| REGION | 1..403 |
|  | note = misc_feature - His-myc tagged monkey MSR1 antibody |
|  | (extracellular domain) |
| source | 1..403 |
|  | mol_type = protein |
|  | organism = Macaca fascicularis |

SEQUENCE: 418
```
HHHHHHEQKL ISEEDLGGEQ KLISEEDLKW ETKNCSIGST NADDITQSLT GKGNDSEAET   60
RFQEVFMEHM SNMEKRIQHI SDMEANLIDA EHFQNFSMTT DQRFNDILLQ LSTLFSSVQG  120
HGNTIDEISK SLISLNTTLL DLQLNIEKLN GKIQEKTFKQ QEEISKLEEH VYNVSAEIMA  180
MKEEQVHLEQ EIKGEVKVLN NITNDLRLKD WEHSQTLRNI TLIQGPPGPP GEKGDRGPTG  240
ESGPRGFPGP VGPPGLKGDR GAIGFPGSRG LPGYAGRPGN SGPKGQKGEK GSGNTLTSFK  300
KVRLVGGSGP HEGRVEILHS GQWGTICDDR WEVRVGQVIC RSLGYPGVQA VHKAAHFGQG  360
TGPIWLNEVY CFGRESSIEE CKIRQWGTRT CSHSEDAGVT CTL                   403
```

| SEQ ID NO: 419 | moltype = DNA  length = 360 |
|---|---|
| FEATURE | Location/Qualifiers |
| misc_feature | 1..360 |
|  | note = Synthetic |
| source | 1..360 |
|  | mol_type = other DNA |
|  | organism = synthetic construct |

SEQUENCE: 419
```
gaggtgcagc tggtggagtc tgggggaggc ctggtcaagc cggggggggtc cctgagactc   60
tcctgtgcag cctctggatt cacttcagt agatatagta tgaactgggt ccgccaggct  120
ccagggaagg ggctggagtg ggtctcatcc attagcagta gcagtagtta catatactac  180
ggagacacag tgaagggccg attcaccatc tccagagaca cgccaagaa gtcactgtat  240
ctgcaaatga acagcctgag agccgaggac acggctgtct attactgtgt gagagatcga  300
ggacagctcg tcctctactt tgactactgg ggccaggga ccctggtcac cgtctcctca  360
```

| SEQ ID NO: 420 | moltype = AA  length = 120 |
|---|---|
| FEATURE | Location/Qualifiers |
| REGION | 1..120 |
|  | note = Synthetic |
| source | 1..120 |
|  | mol_type = protein |
|  | organism = synthetic construct |

SEQUENCE: 420
```
EVQLVESGGG LVKPGGSLRL SCAASGFTFS RYSMNWVRQA PGKGLEWVSS ISSSSYIYY   60
GDTVKGRFTI SRDNAKKSLY LQMNSLRAED TAVYYCVRDR GQLVLYFDYW GQGTLVTVSS  120
```

| SEQ ID NO: 421 | moltype = DNA  length = 24 |
|---|---|
| FEATURE | Location/Qualifiers |
| misc_feature | 1..24 |
|  | note = Synthetic |
| source | 1..24 |
|  | mol_type = other DNA |
|  | organism = synthetic construct |

SEQUENCE: 421
```
ggattcactt tcagtagata tagt                                          24
```

| SEQ ID NO: 422 | moltype = AA  length = 8 |
|---|---|
| FEATURE | Location/Qualifiers |
| REGION | 1..8 |
|  | note = Synthetic |
| source | 1..8 |
|  | mol_type = protein |
|  | organism = synthetic construct |

SEQUENCE: 422
```
GFTFSRYS                                                             8
```

| SEQ ID NO: 423 | moltype = DNA  length = 24 |
|---|---|
| FEATURE | Location/Qualifiers |
| misc_feature | 1..24 |

```
                        note = Synthetic
source                  1..24
                        mol_type = other DNA
                        organism = synthetic construct
SEQUENCE: 423
attagcagta gcagtagtta cata                                              24

SEQ ID NO: 424          moltype = AA  length = 8
FEATURE                 Location/Qualifiers
REGION                  1..8
                        note = Synthetic
source                  1..8
                        mol_type = protein
                        organism = synthetic construct
SEQUENCE: 424
ISSSSSYI                                                                 8

SEQ ID NO: 425          moltype = DNA  length = 39
FEATURE                 Location/Qualifiers
misc_feature            1..39
                        note = Synthetic
source                  1..39
                        mol_type = other DNA
                        organism = synthetic construct
SEQUENCE: 425
gtgagagatc gaggacagct cgtcctctac tttgactac                              39

SEQ ID NO: 426          moltype = AA  length = 13
FEATURE                 Location/Qualifiers
REGION                  1..13
                        note = Synthetic
source                  1..13
                        mol_type = protein
                        organism = synthetic construct
SEQUENCE: 426
VRDRGQLVLY FDY                                                          13

SEQ ID NO: 427          moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 427
gacatccaga tgacccagtc tccagcctcc ctgtctacat ctataagaga cagagtcacc        60
atcacttgcc gggcaagtct gagcattagc agcttttaa attggtttca gcagagacca       120
gggaaagccc ctaaactcct gatctatgtt gcatccaatt tgcaaagtgg ggtcccatca       180
agattcagtg acagtggatc tgggacagat ttcactctca ccatcagcag tctgcaacct       240
gaagattttg caacttacta ctgtcaacag aattacagta ccccctccgat caccttcggc      300
caagggacac gactggagat taaa                                             324

SEQ ID NO: 428          moltype = AA  length = 108
FEATURE                 Location/Qualifiers
REGION                  1..108
                        note = Synthetic
source                  1..108
                        mol_type = protein
                        organism = synthetic construct
SEQUENCE: 428
DIQMTQSPAS LSTSIRDRVT ITCRASLSIS SFLNWFQQRP GKAPKLLIYV ASNLQSGVPS        60
RFSDSGSGTD FTLTISSLQP EDFATYYCQQ NYSTPPITFG QGTRLEIK                   108

SEQ ID NO: 429          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 429
ctgagcatta gcagcttt                                                     18

SEQ ID NO: 430          moltype = AA  length = 6
FEATURE                 Location/Qualifiers
REGION                  1..6
                        note = Synthetic
source                  1..6
                        mol_type = protein
```

-continued

```
                        organism = synthetic construct
SEQUENCE: 430
LSISSF                                                                  6

SEQ ID NO: 431          moltype =    length =
SEQUENCE: 431
000

SEQ ID NO: 432          moltype =    length =
SEQUENCE: 432
000

SEQ ID NO: 433          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 433
caacagaatt acagtacccc tccgatcacc                                       30

SEQ ID NO: 434          moltype = AA   length = 10
FEATURE                 Location/Qualifiers
REGION                  1..10
                        note = Synthetic
source                  1..10
                        mol_type = protein
                        organism = synthetic construct
SEQUENCE: 434
QQNYSTPPIT                                                             10

SEQ ID NO: 435          moltype = DNA   length = 369
FEATURE                 Location/Qualifiers
misc_feature            1..369
                        note = Synthetic
source                  1..369
                        mol_type = other DNA
                        organism = synthetic construct
SEQUENCE: 435
caggtgcagc tggtggagtc tgggggaggc gtggtccagc ctggggaggtc cctgagactc      60
tcctgtgcgg gctctggatt caccttcagt agctatggct tgcactgggt ccgccaggct     120
ccaggcaagg ggctggagtg ggtggcagtt atatcatatg atggaagtaa taaatattat     180
gcagactccg tgaagggccg attcaccatc tccagagaca attccaagaa cacgctgtat     240
ctgcaaatga gcagcctgag agctgaggac acggctgtgt attactgtgc gaaagatcga     300
cttgtacgat attctgactg gccattcttt gactattggg gccagggaac cctggtcacc     360
gtctcctca                                                             369

SEQ ID NO: 436          moltype = AA   length = 123
FEATURE                 Location/Qualifiers
REGION                  1..123
                        note = Synthetic
source                  1..123
                        mol_type = protein
                        organism = synthetic construct
SEQUENCE: 436
QVQLVESGGG VVQPGRSLRL SCAGSGFTFS SYGLHWVRQA PGKGLEWVAV ISYDGSNKYY      60
ADSVKGRFTI SRDNSKNTLY LQMSSLRAED TAVYYCAKDR LVRYSDWPFF DYWGQGTLVT    120
VSS                                                                  123

SEQ ID NO: 437          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 437
ggattcacct tcagtagcta tggc                                             24

SEQ ID NO: 438          moltype = AA   length = 8
FEATURE                 Location/Qualifiers
REGION                  1..8
                        note = Synthetic
source                  1..8
                        mol_type = protein
                        organism = synthetic construct
SEQUENCE: 438
GFTFSSYG                                                                8
```

```
SEQ ID NO: 439          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 439
atatcatatg atggaagtaa taaa                                            24

SEQ ID NO: 440          moltype = AA  length = 8
FEATURE                 Location/Qualifiers
REGION                  1..8
                        note = Synthetic
source                  1..8
                        mol_type = protein
                        organism = synthetic construct
SEQUENCE: 440
ISYDGSNK                                                              8

SEQ ID NO: 441          moltype = DNA  length = 48
FEATURE                 Location/Qualifiers
misc_feature            1..48
                        note = Synthetic
source                  1..48
                        mol_type = other DNA
                        organism = synthetic construct
SEQUENCE: 441
gcgaaagatc gacttgtacg atattctgac tggccattct ttgactat                  48

SEQ ID NO: 442          moltype = AA  length = 16
FEATURE                 Location/Qualifiers
REGION                  1..16
                        note = Synthetic
source                  1..16
                        mol_type = protein
                        organism = synthetic construct
SEQUENCE: 442
AKDRLVRYSD WPFFDY                                                     16

SEQ ID NO: 443          moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 443
gacatccaga tgacccagtc tccatcctcc ctgtctgcat ctgtaggaga cagagtcacc     60
atcacttgcc gggcaagtca aaacattacc agctatttga attgctatca gcagaaacca    120
gggaaagccc ctaaactcct gatctatgct gcatccagtt tgyaaagtgg ggtcccatca    180
aggttcagtg gcagtggatc tgggacagat ttcactctca ccatcagcag tctgcaacct    240
gaagattttg caacttacta ctgtcaacag agtttcagta gtcctccgat caccttcggc    300
caagggacac gactggagat taca                                           324

SEQ ID NO: 444          moltype = AA  length = 108
FEATURE                 Location/Qualifiers
REGION                  1..108
                        note = Synthetic
VARIANT                 55
                        note = misc_feature - Xaa can be any naturally occurring
                         amino acid
source                  1..108
                        mol_type = protein
                        organism = synthetic construct
SEQUENCE: 444
DIQMTQSPSS LSASVGDRVT ITCRASQNIT SYLNCYQQKP GKAPKLLIYA ASSLXSGVPS     60
RFSGSGSGTD FTLTISSLQP EDFATYYCQQ SFSSPPITFG QGTRLEIT                 108

SEQ ID NO: 445          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 445
caaaacatta ccagctat                                                   18
```

```
SEQ ID NO: 446           moltype = AA   length = 6
FEATURE                  Location/Qualifiers
REGION                   1..6
                         note = Synthetic
source                   1..6
                         mol_type = protein
                         organism = synthetic construct
SEQUENCE: 446
QNITSY                                                                    6

SEQ ID NO: 447           moltype =    length =
SEQUENCE: 447
000

SEQ ID NO: 448           moltype =    length =
SEQUENCE: 448
000

SEQ ID NO: 449           moltype = DNA   length = 30
FEATURE                  Location/Qualifiers
misc_feature             1..30
                         note = Synthetic
source                   1..30
                         mol_type = other DNA
                         organism = synthetic construct
SEQUENCE: 449
caacagagtt tcagtagtcc tccgatcacc                                         30

SEQ ID NO: 450           moltype = AA   length = 10
FEATURE                  Location/Qualifiers
REGION                   1..10
                         note = Synthetic
source                   1..10
                         mol_type = protein
                         organism = synthetic construct
SEQUENCE: 450
QQSFSSPPIT                                                               10

SEQ ID NO: 451           moltype = DNA   length = 348
FEATURE                  Location/Qualifiers
misc_feature             1..348
                         note = Synthetic
source                   1..348
                         mol_type = other DNA
                         organism = synthetic construct
SEQUENCE: 451
caggtgcagc tgcaggagtc gggcccagga ctggtgaagc cttcggagac cctgtccctc        60
acctgcactg tctctggtgg ctccatcagt agttactact ggagctggat ccggcagccc       120
ccagggaagg gactggaatg gattgggtac atctattaca gtgggagcgc caactacaac       180
ccctccctca agagtcgagt caccatatca gtagacacgt ccaagaacca gttctccctg       240
aagctaagct ctgtgaccgc tgcggacacg gccgtgtatt actgtgtgag agaccgggac       300
ctactccttg accactgggg ccagggaacc ctggtcaccg tctcctca                    348

SEQ ID NO: 452           moltype = AA   length = 116
FEATURE                  Location/Qualifiers
REGION                   1..116
                         note = Synthetic
source                   1..116
                         mol_type = protein
                         organism = synthetic construct
SEQUENCE: 452
QVQLQESGPG LVKPSETLSL TCTVSGGSIS SYYWSWIRQP PGKGLEWIGY IYYSGSANYN        60
PSLKSRVTIS VDTSKNQFSL KLSSVTAADT AVYYCVRDRD LLLDHWGQGT LVTVSS           116

SEQ ID NO: 453           moltype = DNA   length = 24
FEATURE                  Location/Qualifiers
misc_feature             1..24
                         note = Synthetic
source                   1..24
                         mol_type = other DNA
                         organism = synthetic construct
SEQUENCE: 453
ggtggctcca tcagtagtta ctac                                               24

SEQ ID NO: 454           moltype = AA   length = 8
FEATURE                  Location/Qualifiers
REGION                   1..8
                         note = Synthetic
```

```
source                    1..8
                          mol_type = protein
                          organism = synthetic construct
SEQUENCE: 454
GGSISSYY                                                               8

SEQ ID NO: 455            moltype = DNA  length = 21
FEATURE                   Location/Qualifiers
misc_feature              1..21
                          note = Synthetic
source                    1..21
                          mol_type = other DNA
                          organism = synthetic construct
SEQUENCE: 455
atctattaca gtgggagcgc c                                               21

SEQ ID NO: 456            moltype = AA  length = 7
FEATURE                   Location/Qualifiers
REGION                    1..7
                          note = Synthetic
source                    1..7
                          mol_type = protein
                          organism = synthetic construct
SEQUENCE: 456
IYYSGSA                                                                7

SEQ ID NO: 457            moltype = DNA  length = 30
FEATURE                   Location/Qualifiers
misc_feature              1..30
                          note = Synthetic
source                    1..30
                          mol_type = other DNA
                          organism = synthetic construct
SEQUENCE: 457
gtgagagacc gggacctact ccttgaccac                                      30

SEQ ID NO: 458            moltype = AA  length = 10
FEATURE                   Location/Qualifiers
REGION                    1..10
                          note = Synthetic
source                    1..10
                          mol_type = protein
                          organism = synthetic construct
SEQUENCE: 458
VRDRDLLLDH                                                            10

SEQ ID NO: 459            moltype = DNA  length = 324
FEATURE                   Location/Qualifiers
misc_feature              1..324
                          note = Synthetic
source                    1..324
                          mol_type = other DNA
                          organism = synthetic construct
SEQUENCE: 459
gacatccaga tgacccagtc tccatcctcc ctgtctgcat ctgtaggaga cagagtcacc     60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta cccctccgat caccttcggc    300
caagggacac gactggagat taaa                                           324

SEQ ID NO: 460            moltype = AA  length = 108
FEATURE                   Location/Qualifiers
REGION                    1..108
                          note = Synthetic
source                    1..108
                          mol_type = protein
                          organism = synthetic construct
SEQUENCE: 460
DIQMTQSPSS LSASVGDRVT ITCRASQSIS SYLNWYQQKP GKAPKLLIYA ASSLQSGVPS     60
RFSGSGSGTD FTLTISSLQP EDFATYYCQQ SYSTPPITFG QGTRLEIK                 108

SEQ ID NO: 461            moltype = DNA  length = 18
FEATURE                   Location/Qualifiers
misc_feature              1..18
                          note = Synthetic
source                    1..18
                          mol_type = other DNA
                          organism = synthetic construct
```

```
SEQUENCE: 461
cagagcatta gcagctat                                                    18

SEQ ID NO: 462         moltype = AA    length = 6
FEATURE                Location/Qualifiers
REGION                 1..6
                       note = Synthetic
source                 1..6
                       mol_type = protein
                       organism = synthetic construct
SEQUENCE: 462
QSISSY                                                                  6

SEQ ID NO: 463         moltype =       length =
SEQUENCE: 463
000

SEQ ID NO: 464         moltype =       length =
SEQUENCE: 464
000

SEQ ID NO: 465         moltype = DNA   length = 30
FEATURE                Location/Qualifiers
misc_feature           1..30
                       note = Synthetic
source                 1..30
                       mol_type = other DNA
                       organism = synthetic construct
SEQUENCE: 465
caacagagtt acagtacccc tccgatcacc                                       30

SEQ ID NO: 466         moltype = AA    length = 10
FEATURE                Location/Qualifiers
REGION                 1..10
                       note = Synthetic
source                 1..10
                       mol_type = protein
                       organism = synthetic construct
SEQUENCE: 466
QQSYSTPPIT                                                             10
```

DIELS-ALDER CONJUGATION METHODS

CROSS-REFERENCE TO RELATED APPLICATIONS

This application claims the benefit under 35 U.S.C. § 119(e) of U.S. Provisional Application No. 63/010,903, filed on Apr. 16, 2020, which is incorporated herein by reference in its entirety for all purposes.

FIELD OF DISCLOSURE

The present disclosure relates to protein-payload conjugates (e.g., antibody-drug conjugates), pharmaceutical compositions, and methods of treating disease therewith. Also provided are specific and efficient methods for producing protein-payload constructs utilizing a combination of transglutaminase and Diels-Alder techniques. In certain embodiments, methods are provided for specific and efficient reaction of a glutaminyl-modified antibody and reactive payload.

SEQUENCE LISTING

The instant application contains a Sequence Listing which has been submitted electronically in XML format and is hereby incorporated by reference in its entirety. Said XML copy, created on Jul. 5, 2023, is named 250298_000489_SL.xml and is 558,894 bytes in size.

BACKGROUND OF THE DISCLOSURE

Protein conjugates such as, antibody conjugates, utilize the selective binding of a binding agent to deliver a payload to targets within tissues of subjects. The payload can be a therapeutic moiety that is capable of taking action at the target, or an imaging agent moiety, e.g. capable of increasing the contrast of structures or fluids within the body for either diagnostic or therapeutic purposes.

Several techniques for conjugating linkers and payloads to antibodies are available. Many conjugates are prepared by non-selective covalent linkage to cysteine or lysine residues in the antibody. This non-selective technique can result in a heterogeneous mixture of products with conjugations at different sites and with different numbers of conjugations per antibody. Thus, there is a need in the art for methods and techniques that provide site-selective antibody conjugation.

There is a need in the art for additional safe and effective targeting agents that can bind to various antigens to provide enhanced the treatment of diseases such as cancer, infectious disease, inflammatory disease, and immune system disorders for use in monotherapy and combination therapies. In certain embodiments, the present disclosure meets the needs and provides other advantages.

The foregoing discussion is presented solely to provide a better understanding of the nature of the problems confronting the art and should not be construed in any way as an admission as to prior art nor should the citation of any reference herein be construed as an admission that such reference constitutes "prior art" to the instant application.

SUMMARY OF THE DISCLOSURE

Various non-limiting aspects and embodiments are described below.

In one aspect, the present disclosure provides a compound having a structure according to Formula (I):

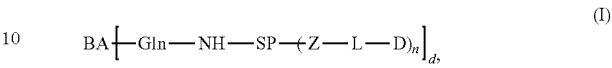

(I)

wherein: BA is a binding agent; Gln is a glutamine residue; SP is absent or a spacer; Z is a Diels-Alder adduct; L is a linker; D is a therapeutic and/or imaging agent moiety; n is an integer from 1 to 3; wherein when n is 2 or 3, Z, L and D may be the same or different; and d is an integer from 1 to 6.

In one embodiment, D is a therapeutic moiety, wherein the therapeutic moiety is a maytansinoid, a tubulysin, an auristatin, a dolastatin, a camptothesin, a pyrrolobenzodiazepine, an antibiotic, an antiviral agent, an anti-inflammatory agent, an immunomodulator, an antifungal agent, a steroid, or an analogue or derivative thereof, or D is an imaging agent moiety.

In one embodiment, D is a therapeutic moiety, wherein the therapeutic moiety is a maytansinoid, a tubulysin, an auristatin, a dolastatin, a camptothesin, a pyrrolobenzodiazepine, an antibiotic, an antiviral agent, an anti-inflammatory agent, an immunomodulator, an antifungal agent, or an analogue or derivative thereof.

In one aspect, the present disclosure provides a compound having a structure according to Formula (I):

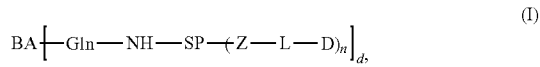

(I)

wherein: BA is a binding agent; Gln is a glutamine residue; SP is absent or a spacer; Z is a Diels-Alder adduct; L is a linker; D is a therapeutic moiety, wherein the therapeutic moiety is a maytansinoid, a tubulysin, an auristatin, a dolastatin, a camptothesin, a pyrrolobenzodiazepine, an antibiotic, an antiviral agent, an anti-inflammatory agent, an immunomodulator, an antifungal agent, a steroid, or an analogue or derivative thereof, or D is an imaging agent moiety; n is an integer from 1 to 3; wherein when n is 2 or 3, Z, L and D may be the same or different; and d is an integer from 1 to 6.

In one embodiment, the compound is according to Formula (1A):

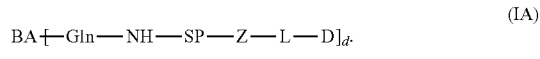

(IA)

In one embodiment, the compound is according to Formula (1B):

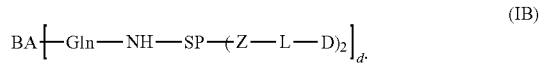

(IB)

In one embodiment, n is 1 or 2. In one embodiment, where n is 2, the two moieties D are the same. In one embodiment, where n is 2, the two moieties D are different. In one embodiment, where n is 2, the two Diels-Alder adducts Z are the same. In one embodiment, where n is 2, the two Diels-Alder adducts Z are different.

In one aspect, the present disclosure provides a compound having a structure according to Formula (II):

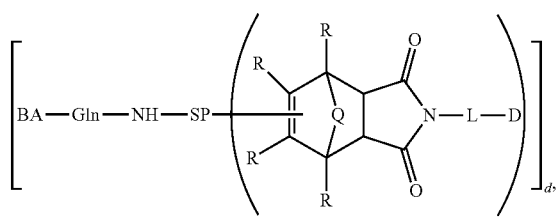

(II)

wherein: BA is a binding agent; Gln is a glutamine residue; SP is absent or a spacer; Q a CHR, (CHR)$_2$, or O bridge; R is independently at each occurrence H or an electron donating group (e.g., C$_{1-3}$ alkyl, —OC$_{1-3}$ alkyl, or —NHC$_{1-3}$ alkyl); L is a linker; D is a therapeutic moiety, wherein the therapeutic moiety is a maytansinoid, a tubulysin, an auristatin, a dolastatin, a camptothesin, a pyrrolobenzodiazepine, an antibiotic, an antiviral agent, an anti-inflammatory agent, an immunomodulator, an antifungal agent, a steroid, or an analogue or derivative thereof, or D is an imaging agent moiety; n is an integer from 1 to 3; and d is an integer from 1 to 6.

In one embodiment, the compound is according to Formula (IIA):

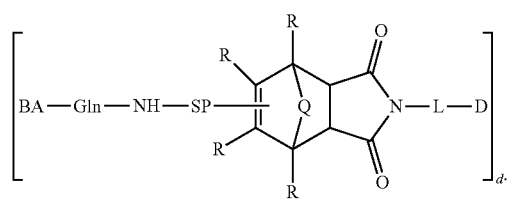

(IIA)

In one embodiment, the compound is according to Formula (IIB):

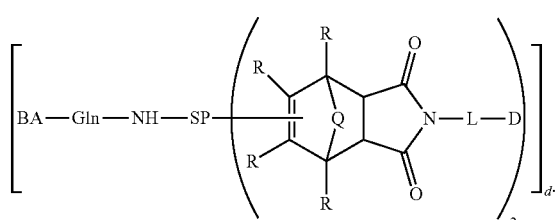

(IIB)

In one embodiment, the two moieties D are the same. In one embodiment, the two moieties D are different.

In one embodiment, the compound is according to Formula (IIIA):

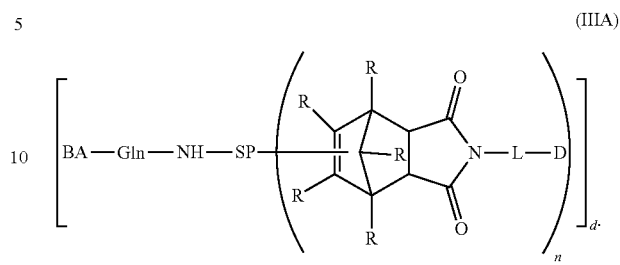

(IIIA)

In one embodiment, the compound is according to Formula (IIIB):

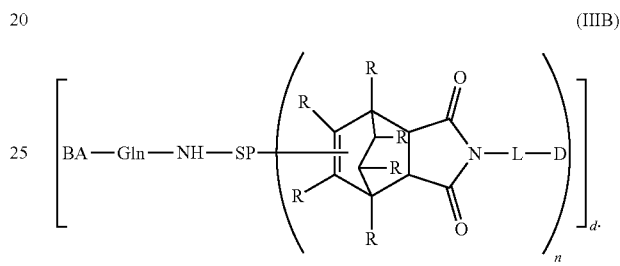

(IIIB)

In one embodiment, the compound is according to Formula (IIIC):

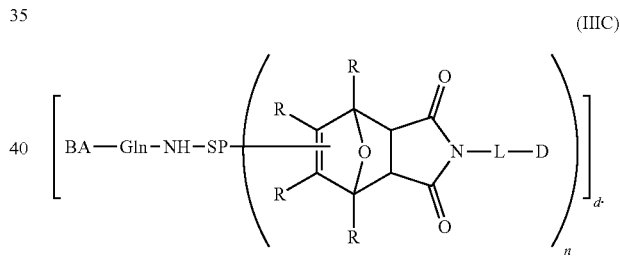

(IIIC)

In one embodiment of any of the above, R is H at each occurrence.

In another embodiment, at least one R is not H. In one embodiment, at least one R is C$_{1-3}$ alkyl. In one embodiment, at least one R is OC$_{1-3}$ alkyl. In one embodiment, at least one R is —NH—C$_{1-3}$ alkyl. In one embodiment, at least one R is methyl. In one embodiment, at least one R is OCH$_3$.

In one aspect, the present disclosure provides a compound having a structure according to Formula (IV):

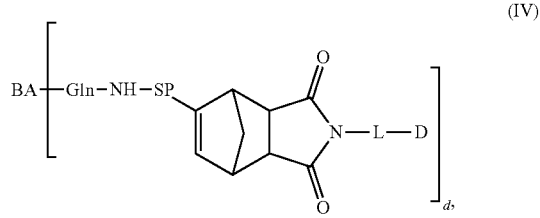

(IV)

wherein: BA is a binding agent; Gln is a glutamine residue; SP is absent or a spacer; L is a linker; D is a therapeutic moiety, wherein the therapeutic moiety is a maytansinoid, a tubulysin, an auristatin, a dolastatin, a camptothesin, a pyrrolobenzodiazepine, an antibiotic, an antiviral agent, an anti-inflammatory agent, an immunomodulator, an antifungal agent, a steroid, or an analogue or derivative thereof, or D is an imaging agent moiety; and d is an integer from 1 to 6.

In an embodiment of a compound of any of the above formulas, BA is an antibody, or an antigen-binding fragment thereof. In a further embodiment, BA is a monoclonal humanized antibody. In a further embodiment, BA is a HER-2 antibody, an antigen-binding fragment thereof, a MSR1 antibody, or an antigen-binding fragment thereof.

In an embodiment of a compound of any of the above formulas, Gln is independently at each occurrence Q295 or N297Q.

In an embodiment of any one of the preceding compounds, d is 2, 4, or 6. In a certain embodiment, d is 2. In a certain embodiment, d is 4.

In an embodiment of any one of the preceding compounds, D is a therapeutic moiety, wherein the therapeutic moiety is an auristatin, a pyrrolobenzodiazepine (PBD), a maytansinoid, an ansamycin antibiotic, or an analogue or derivative thereof.

In an embodiment of any one of the preceding compounds, D is a therapeutic moiety, wherein the therapeutic moiety is monomethyl auristatin E (MMAE), PBD-1, rifamycin, or an analogue or derivative thereof.

The compound according to any one of the preceding compounds, D is an imaging agent moiety, wherein the imaging agent comprises a dye (e.g., a fluorescent dye), a chelator, a radionuclide, or an oligonucleotide. In one embodiment, D comprises a fluorescent dye.

In one embodiment, D is an Alexa Fluor fluorescent dye selected from the group consisting of Alexa Fluor 647, Alexa Fluor 488, Alexa Fluor 594, Alexa Fluor 555, and Alexa Fluor 568. In one particular embodiment, D is Alexa Fluor 647.

In an embodiment of any one of the preceding compounds, SP comprises one or more of: —(CH$_2$)$_u$—, C(O)—, —NH—, —(CH$_2$)$_u$—NH—C(O)—, —(CH$_2$)$_u$—C(O)—NH—, —(CH$_2$)$_u$—C(O)—NH—(CH$_2$)$_v$—, —(CH$_2$—CH$_2$—O)$_v$—, —(CH$_2$)$_u$—(O—CH$_2$—CH$_2$)$_v$—C(O)—NH—, —(CH$_2$—CH$_2$—O)$_v$—(CH$_2$)$_u$—C(O)—NH—(CH$_2$)$_u$—, —NH—(CH$_2$)$_u$—, —NH—(CH$_2$)$_u$—C(O)—, —NH—(CH$_2$)$_u$—C(O)—NH—(CH$_2$)$_v$—, —NH—(CH$_2$—CH$_2$—O)$_v$—, —NH—(CH$_2$—CH$_2$—O)$_v$—C(O)—, —NH—(CH$_2$—CH$_2$—O)$_v$—(CH$_2$)$_u$—, —NH—(CH$_2$—CH$_2$—O)$_v$—(CH$_2$)$_u$—C(O)—, —NH—(CH$_2$—CH$_2$—O)$_v$—(CH$_2$)$_u$—C(O)—NH—(CH$_2$)$_u$—, —(CH$_2$)$_u$—NH—C(O)—, —(CH$_2$)$_u$—C(O)—NH—(CH$_2$—CH$_2$—O)$_v$—C(O)—NH—, —NH—(CH$_2$)$_u$—C(O)—NH—,

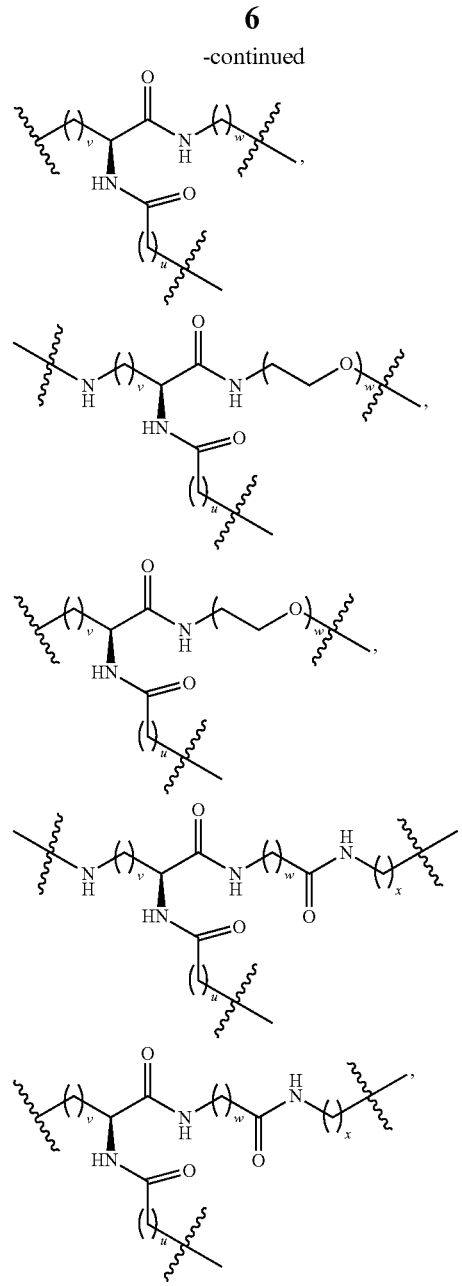

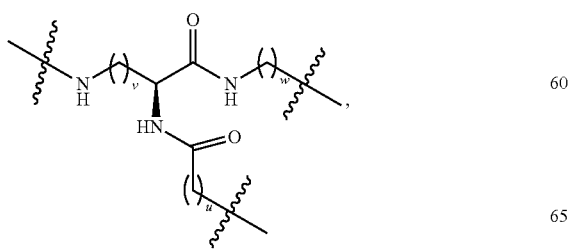

or combinations thereof; and wherein subscripts u, v, w, and x are independently an integer from 1 to 20. In one embodiment, subscripts u, v, w, and x are independently an integer from 1 to 12. In a further embodiment, SP is —(CH$_2$)$_u$—; wherein the subscript u is an integer from 1 to 5.

In one embodiment, SP is

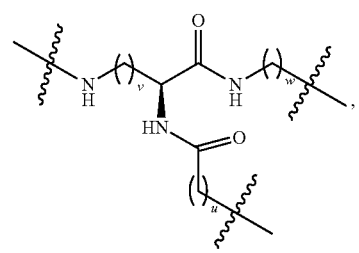

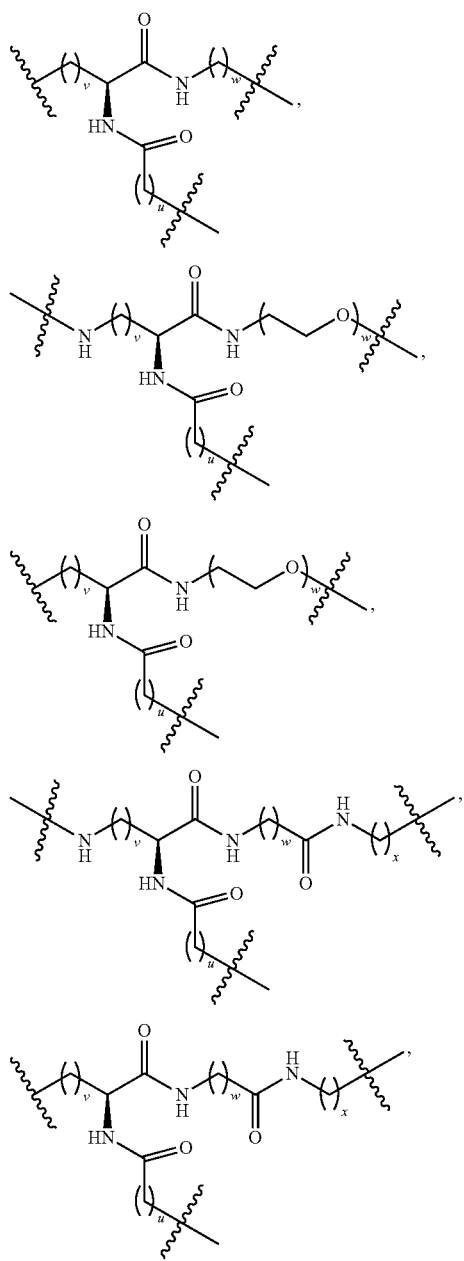

wherein subscripts u, v, w, and x are independently an integer from 1 to 12. In one embodiment, SP is

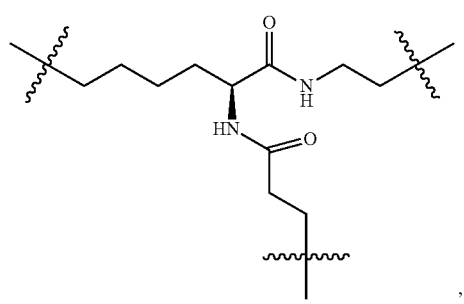

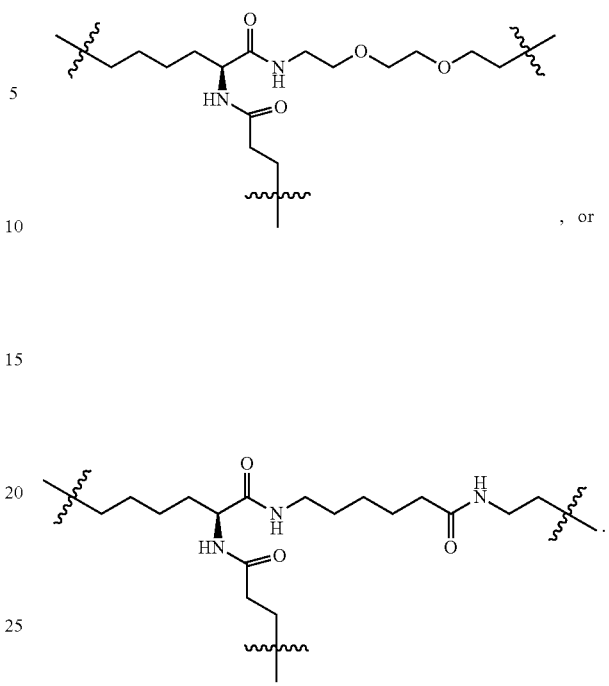

In one embodiment of any of the above, the two moieties D are the same. In one embodiment of any of the above, the two moieties D are different.

The compound according to any one of the preceding formulas, wherein Z is a moiety according to Formula 2a:

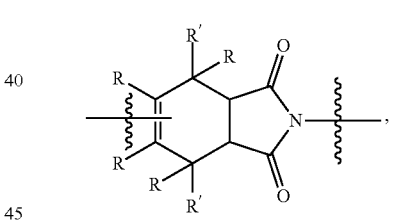

wherein R' is independently H, $C_{1-3}$ alkyl, or two R' together constitute a CHR, $(CHR)_2$, or O bridge, and wherein R is independently at each occurrence H, $C_{1-3}$ alkyl, or —$OC_{1-3}$ alkyl, or —NH—$C_{1-3}$ alkyl.

In an embodiment of any one of the preceding compounds, Z is a moiety according to formula 2a:

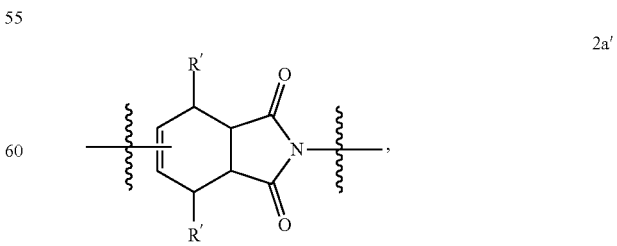

wherein R' are independently H, $C_{1-3}$ alkyl, or two R' together constitute a $CH_2$, $CH_2CH_2$, or O bridge.

In a further embodiment, Z is a moiety according to any one of formulas 2a-1-2a-3:
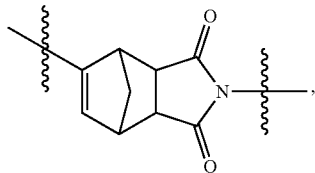
2a-1
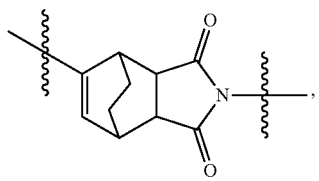
2a-2
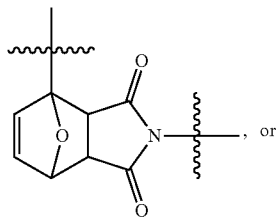
2a-3, or
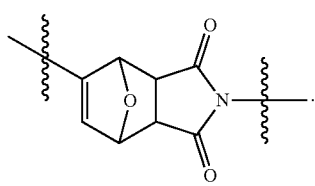
2a-3'
In a further embodiment, Z is a moiety according to formula 2a-1:
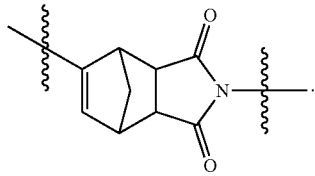
2a-1
In one embodiment, at least one R is not H. In one embodiment, Z is a moiety according to any one of formulas 2a-4-2a-6:
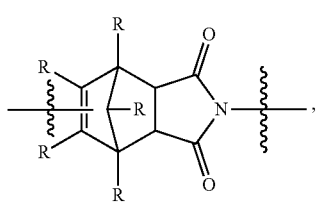
2a-4
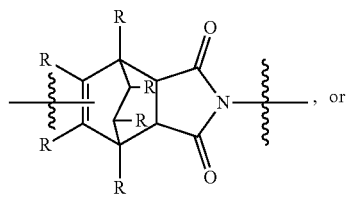
2a-5
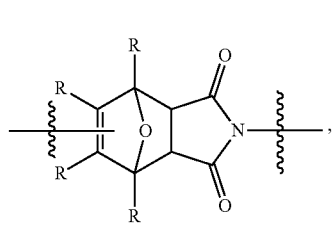
2a-6
wherein at least one R is not H. In one embodiment, Z is a moiety according to any one of formulas 2a-7-2a-12:
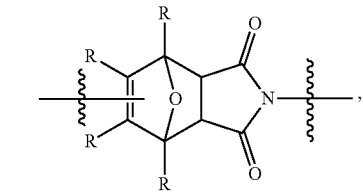
2a-7
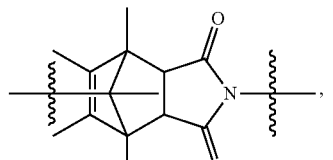
2a-8
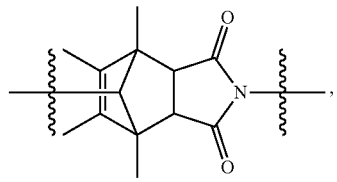
2a-9
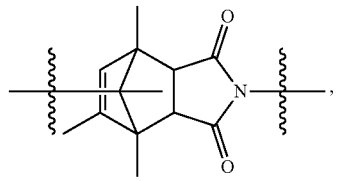
2a-10
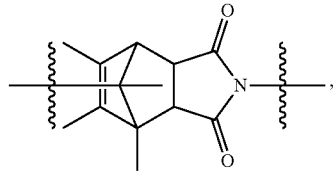
2a-11
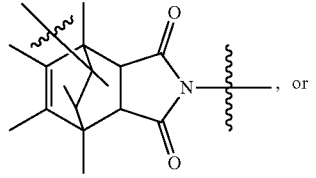

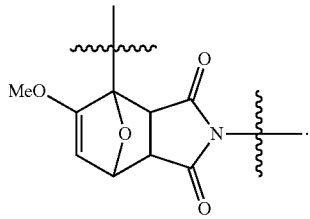

In one embodiment, the moiety Z is independently at each occurrence selected from 2a-1-2a-12.

In one embodiment wherein a compound comprises two moieties Z, one moiety Z is 2a-7 and the other moiety Z is 2a-11. In one embodiment wherein a compound comprises two moieties Z, one moiety Z is 2a-7 and the other moiety Z is 2a-12.

In one embodiment, the fragment —SP—Z— is selected from,

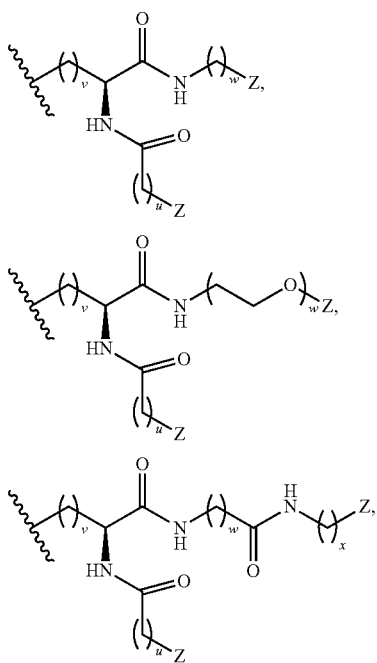

wherein the two moieties Z are the same.

In one embodiment, the fragment —SP—Z— is selected from,

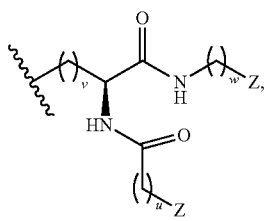

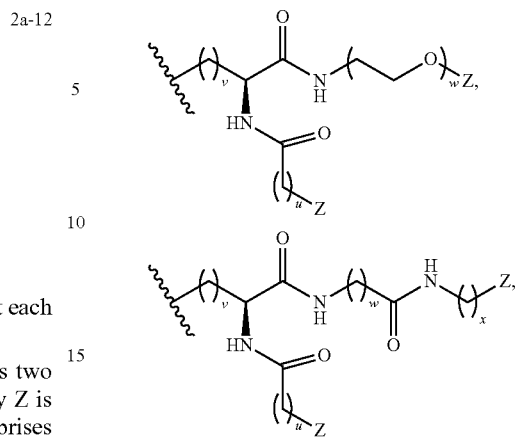

wherein the two moieties Z are different.

In an embodiment of any one of the preceding compounds, L comprises one or more amino acid. In an additional embodiment, L further comprises one or more: —NH—, —S—, —O—, —(CH$_2$)$_n$—, —(CH$_2$—CH$_2$—O—)$_m$—, —C(O)—, —NH—CH$_2$O—CH$_2$—C(=O)—NH—,

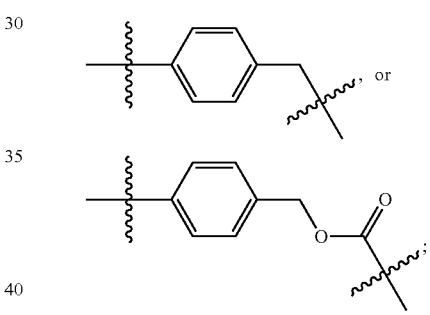

wherein subscripts m and n are independently at each occurrence an integer from 0 to 20. In one embodiment, the one or more amino acid is glycine, serine, alanine, valine, phenylalanine, proline, or citrulline. In a further embodiment, one or more amino acid is valine-citrulline (-VC-), or valine-alanine (-VA-).

In an embodiment of any one of the preceding compounds, L is:

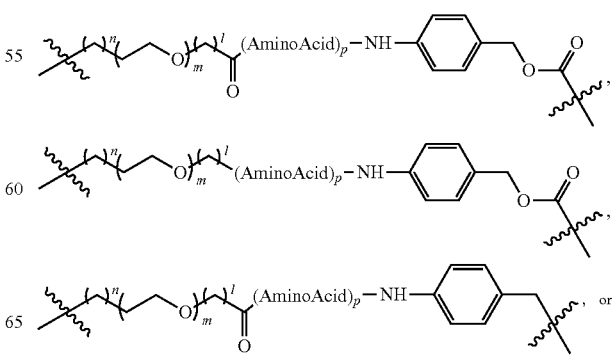

13

-continued

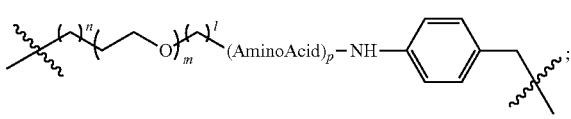

wherein l, m and n are independently at each occurrence an integer from 0 to 20; and p is an integer from 0 to 4.

In an embodiment of any one of the preceding compounds, L is:

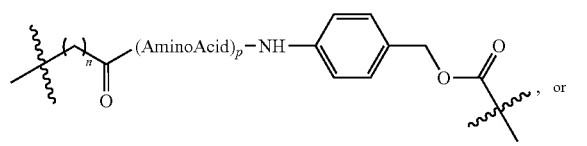, or

14

-continued

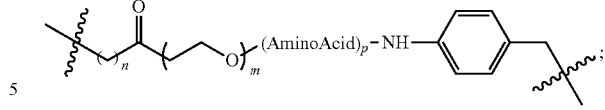

wherein n is an integer from 1 to 6; m is an integer from 2 to 10; p is an integer from 1 to 3, and the amino acid is independently at each occurrence valine, citrulline or alanine.

In an embodiment of any one of the preceding compounds, the therapeutic and/or imaging agent moiety D is attached to linker L via a tertiary amino group.

In an embodiment of a compound of formula I, the fragment

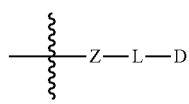

is according to Formula (I-DA):

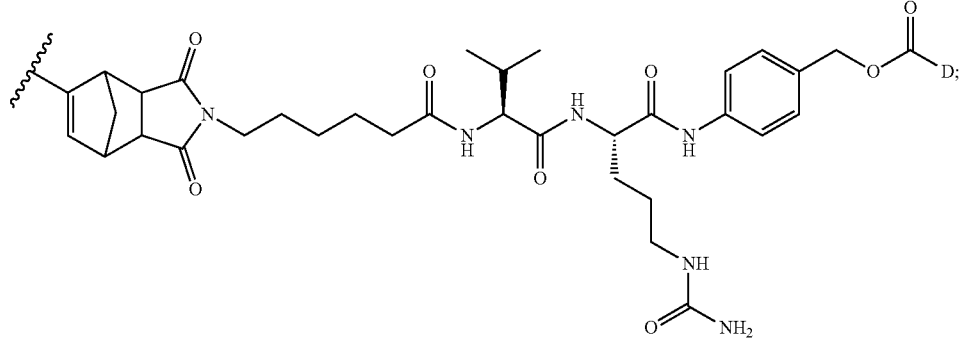

Formula (I-DA)

wherein the

is the bond to the spacer or binding agent, and wherein the therapeutic and/or imaging moiety D is attached via an amino group. In a further embodiment, D is a maytansinoid or a maytansinoid analogue as described herein.

In an embodiment of a compound of formula I, the fragment

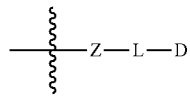

is according to Formula (I-A1):

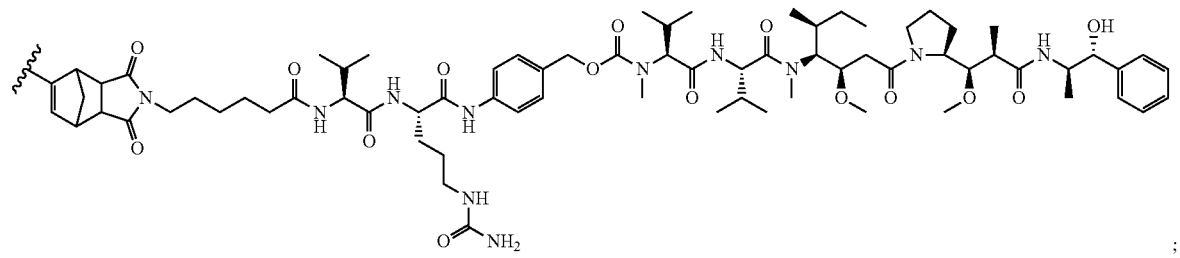

Formula (I-A1)

wherein the

is the bond to the spacer or binding agent.

In an embodiment of a compound of formula I, the fragment

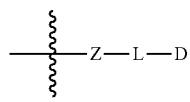

is according to Formula (I-A11):

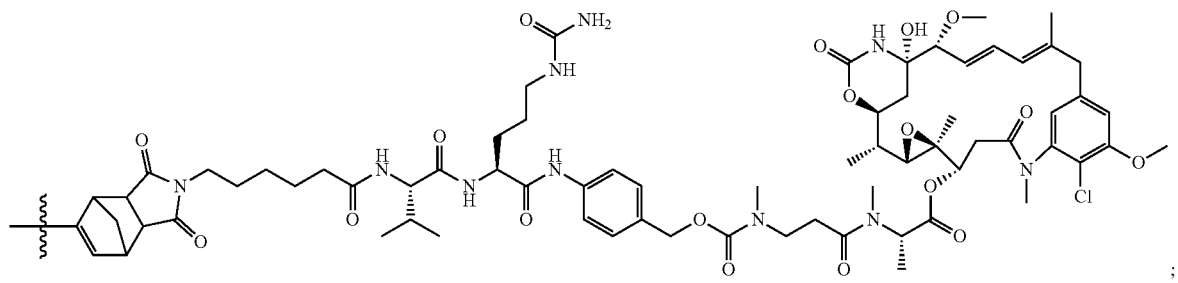

Formula (I-A11)

wherein the

is the bond to the spacer or binding agent.

In an embodiment of a compound of formula I, the fragment

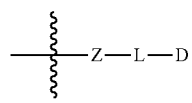

is according to Formula (I-DB):

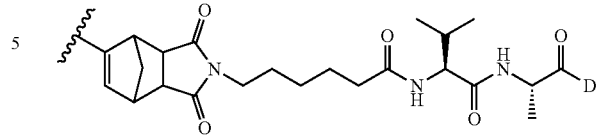

Formula (I-DB); wherein the

is the bond to the spacer or binding agent, and wherein the moiety D is attached via an amino group. In an embodiment of a compound of formula I-B, D is a pyrrolobenzodiazepine (PBD) or analogue or derivative thereof as described herein. In an embodiment of a compound of formula I-B, D is PBD-1 or analogue or derivative thereof as described herein:

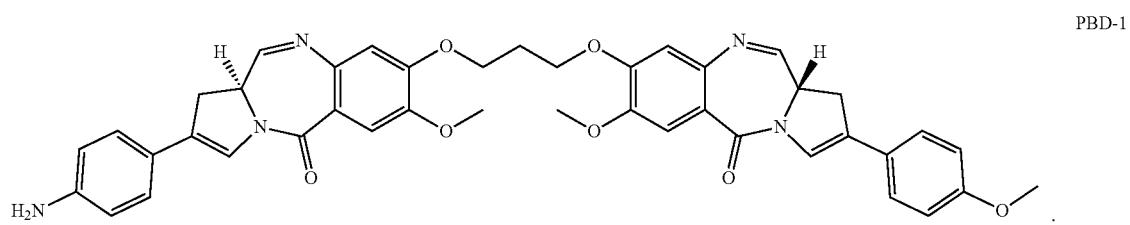

PBD-1

In an embodiment of a compound of formula I, the fragment

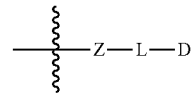

is according to Formula (I-B1):

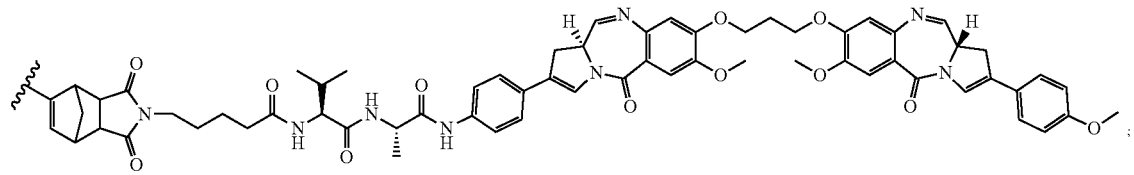

Formula (I-B1)

wherein the

is the bond to the spacer or binding agent.

In an embodiment of a compound of formula I, the fragment

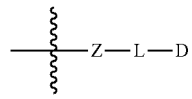

is according to Formula (I-DC):

Formula (I-DC)

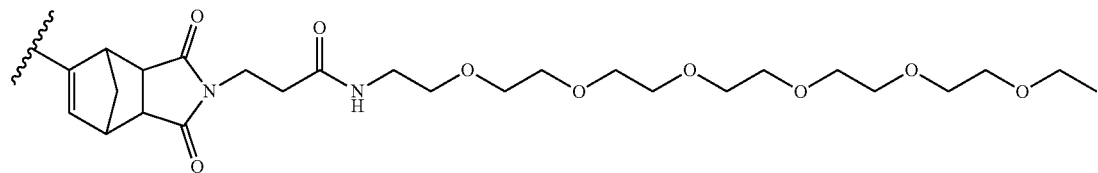

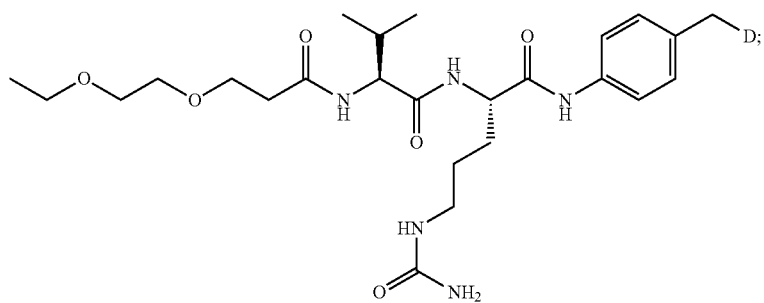

wherein the

is the bond to the spacer or binding agent, and wherein the moiety D is attached via an amino group. In a further embodiment, D is a rifamycin or an analogue or derivative thereof.

In an embodiment of a compound of formula I, the fragment

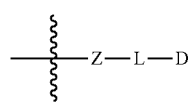

is according to Formula (I-C1):
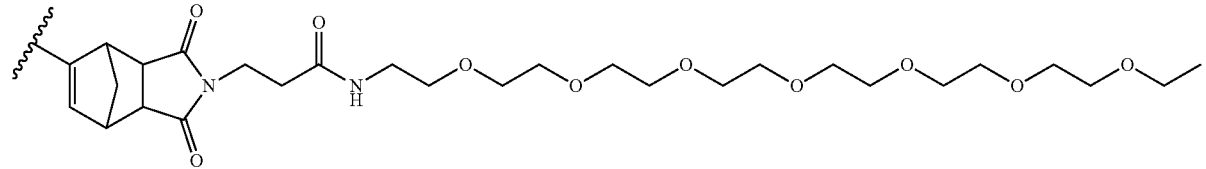
Formula (I-C1)
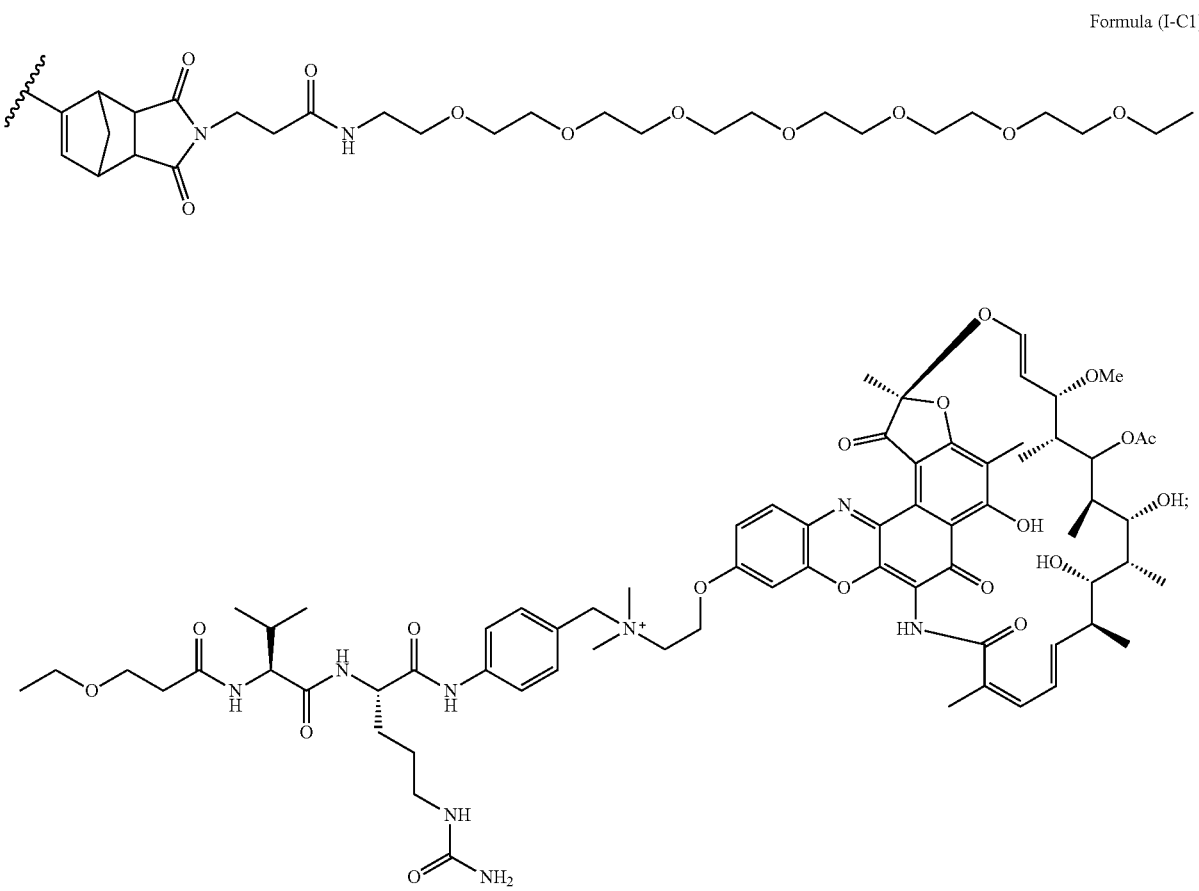
wherein the
is the bond to the spacer or binding agent.
In an embodiment of a compound of formula I, the fragment
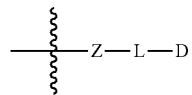
is according to Formula (I-C2):
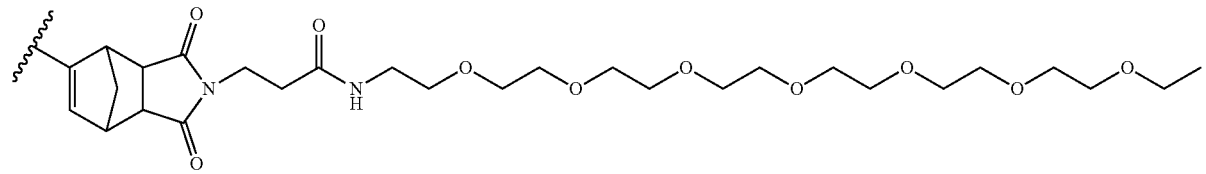
Formula (I-C2)

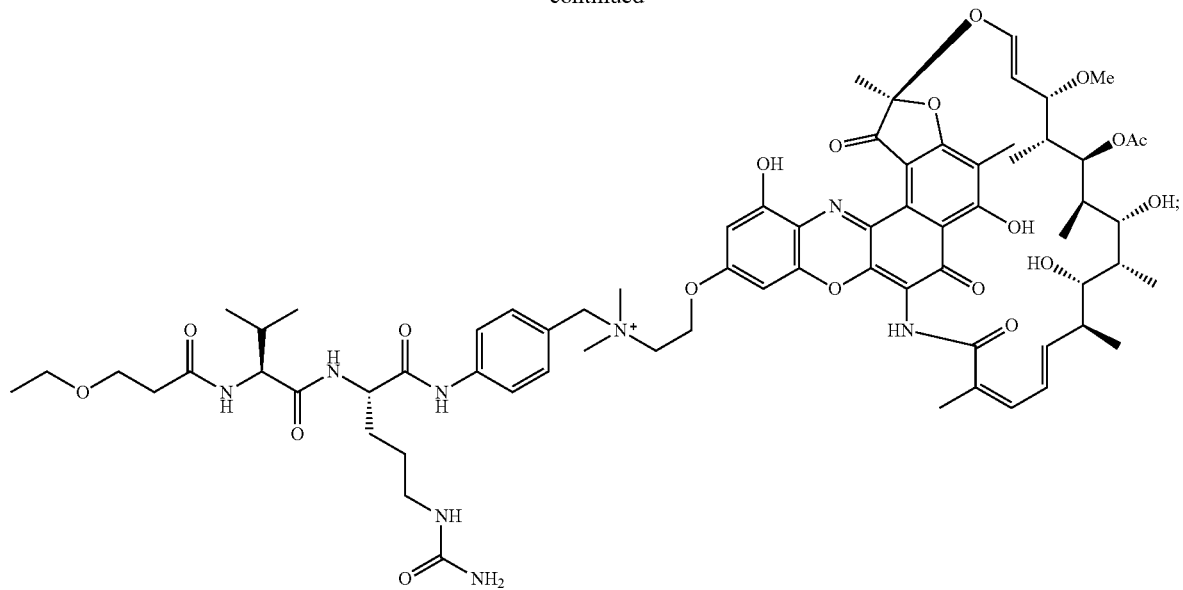

wherein the

is the bond to the spacer or binding agent.

In an embodiment of any of the preceeding compounds according to Formula (II), BA is a HER-2 antibody, an antigen-binding fragment thereof, a MSR1 antibody, or an antigen-binding fragment thereof; and D is a therapeutic moiety, wherein the therapeutic moiety is monomethyl auristatin E (MMAE), PBD-1, rifamycin, or an analogue or derivative thereof, or D is an imaging agent moiety Alexa Fluor 647.

In an embodiment of any of the preceeding compounds, the compound has a structure according to any one of Formulas (I-A1')-(I-A10'):

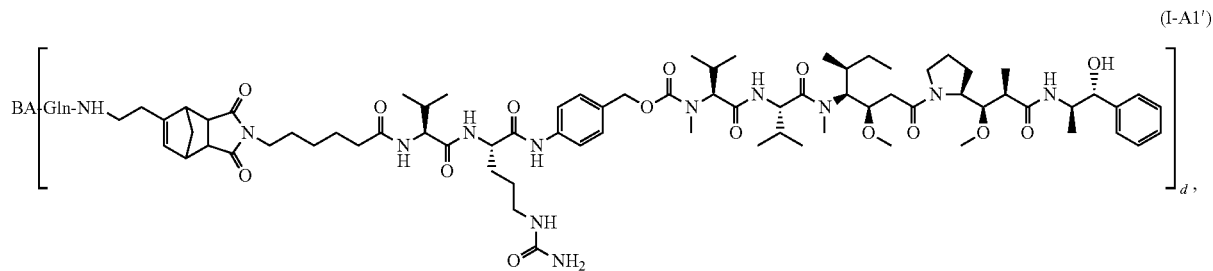

(I-A1')

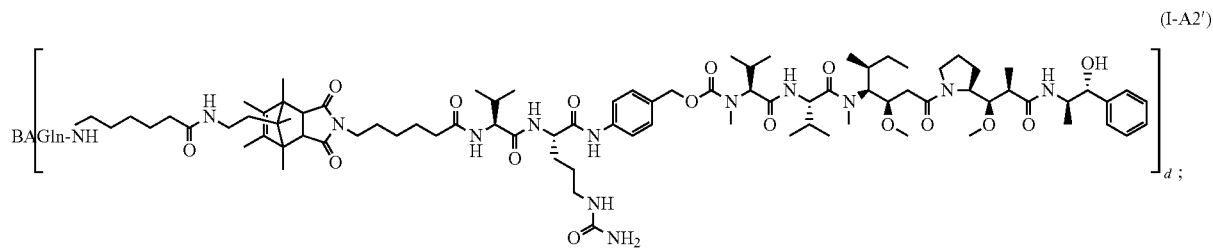

(I-A2')

-continued
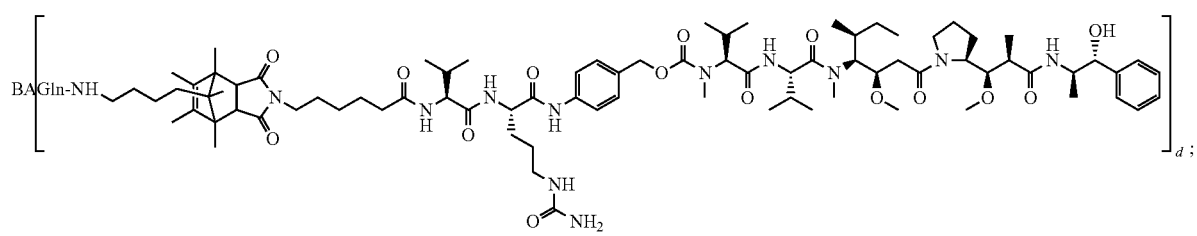
(I-A3′)
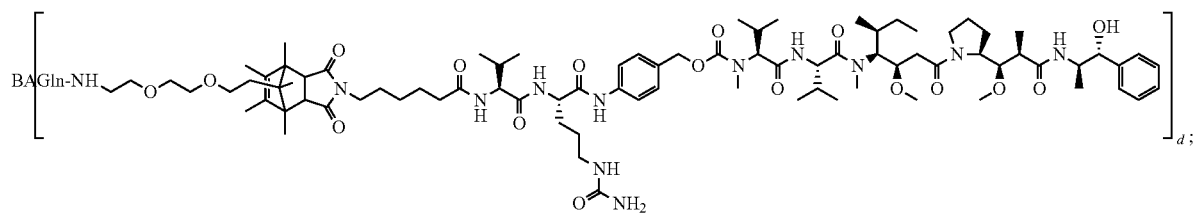
(I-A4′)
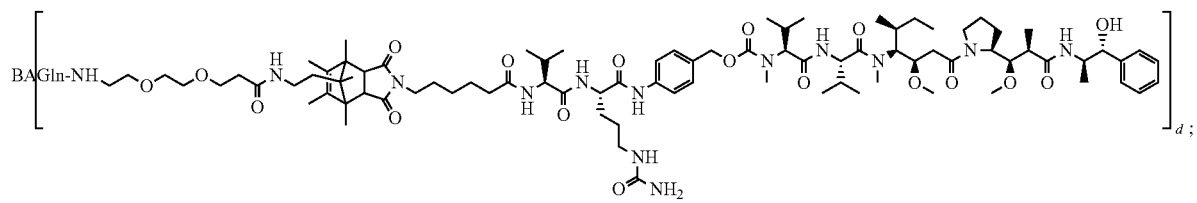
(I-A5′)
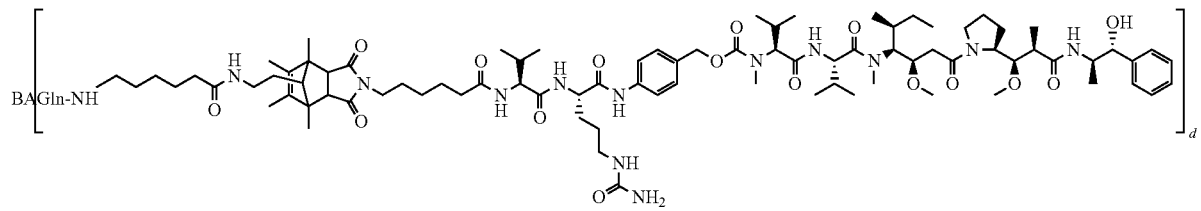
(I-A6′)
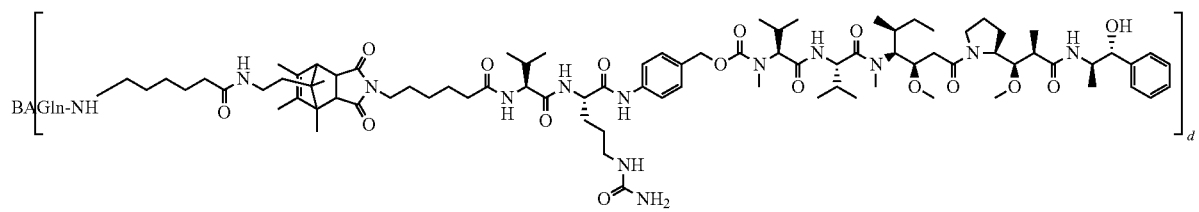
(I-A6″)
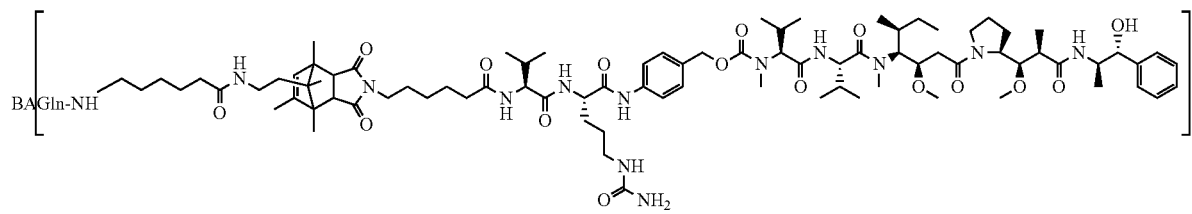
(I-A6‴)

-continued
(I-A6′, I-A6″, and I-A6‴);
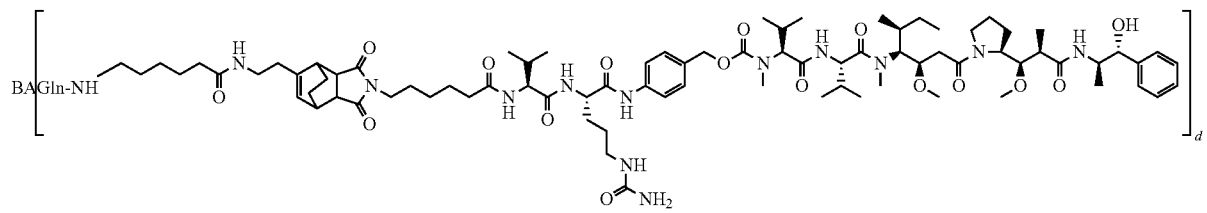
I-A7′
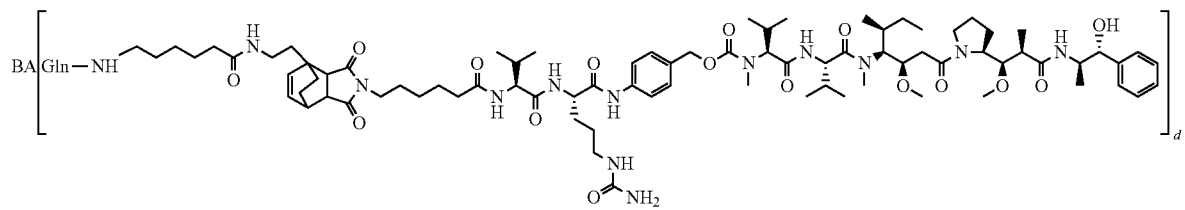
I-A7″
(I-A7′ and I-A7″);
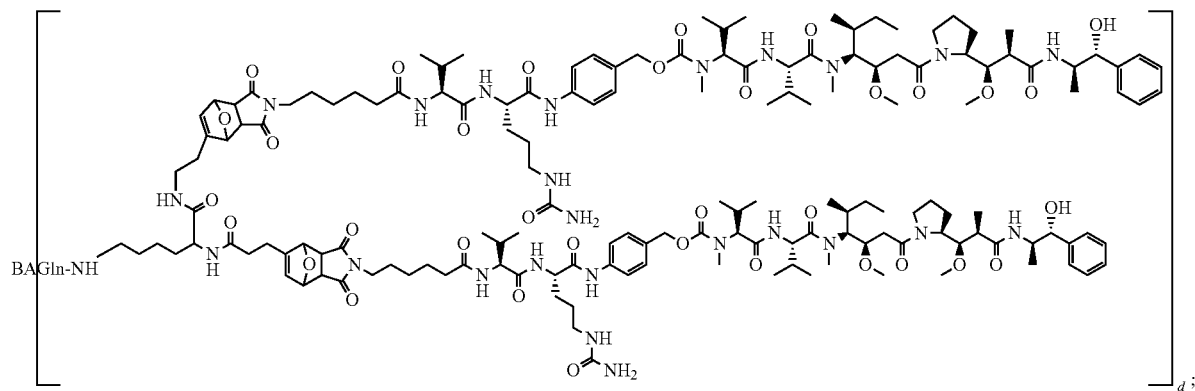
(I-A8′)
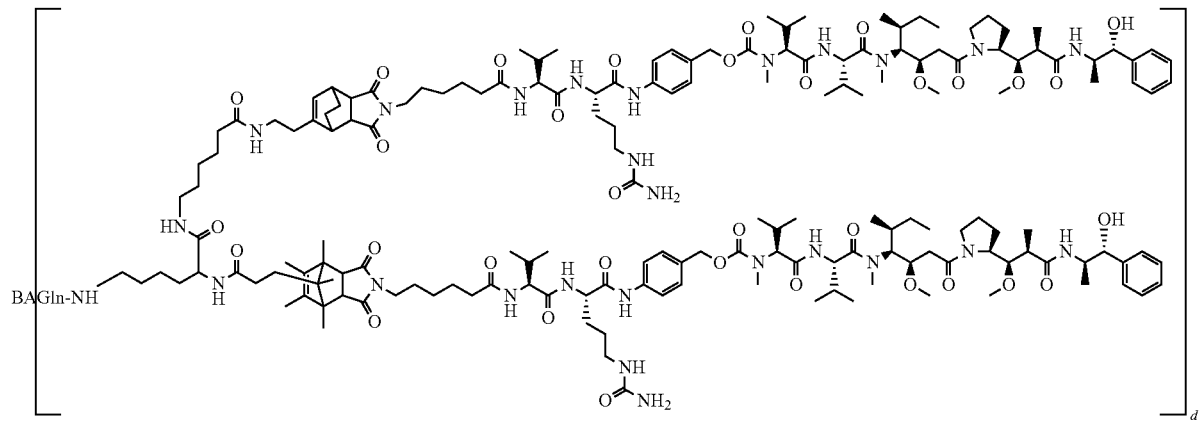
I-A9′

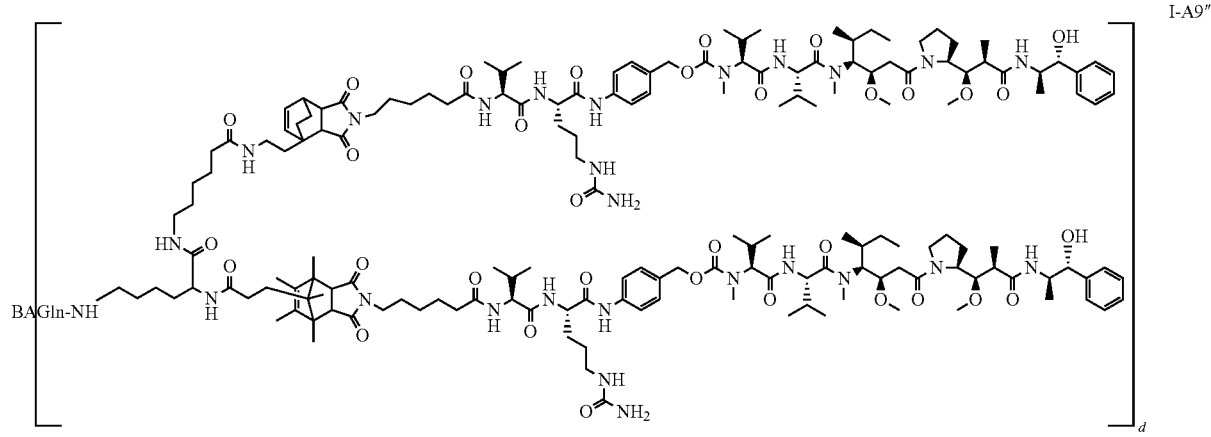
(I-A9′ and I-A9″); or
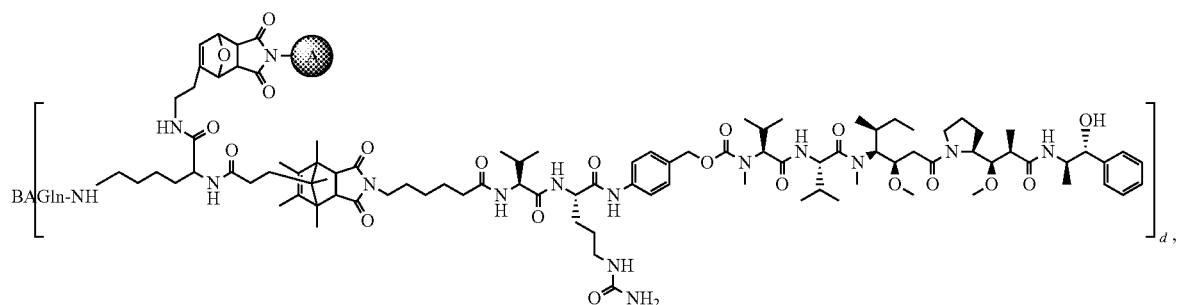
(I-A10′),
wherein d is an integer from 1 to 6.
In an embodiment of any of the preceeding compounds, the compound has a structure according to Formula (I-A11′):
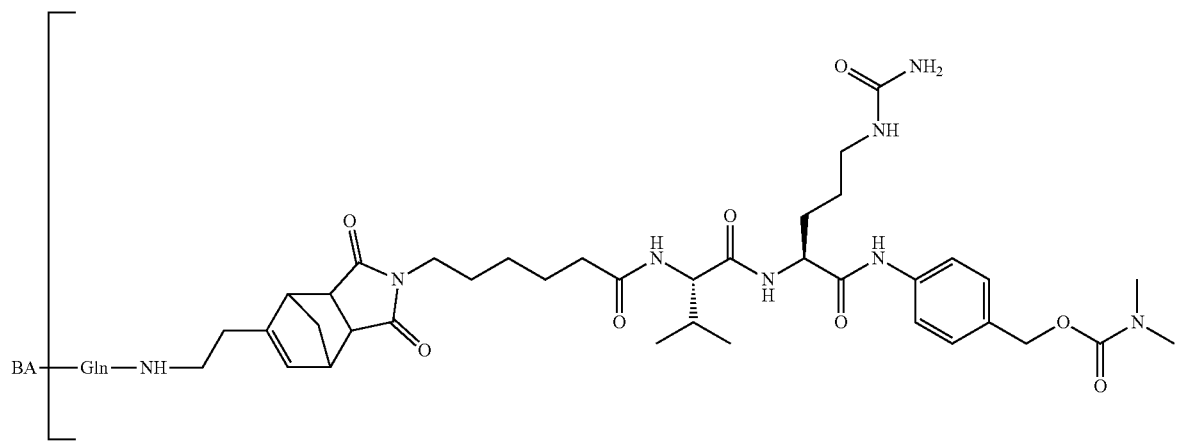

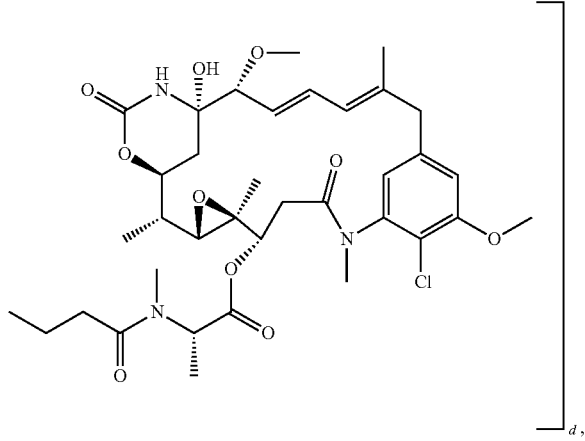
wherein d is an integer from 1 to 6.
In an embodiment of any of the preceeding compounds, the compound has a structure according to Formula (I-B):
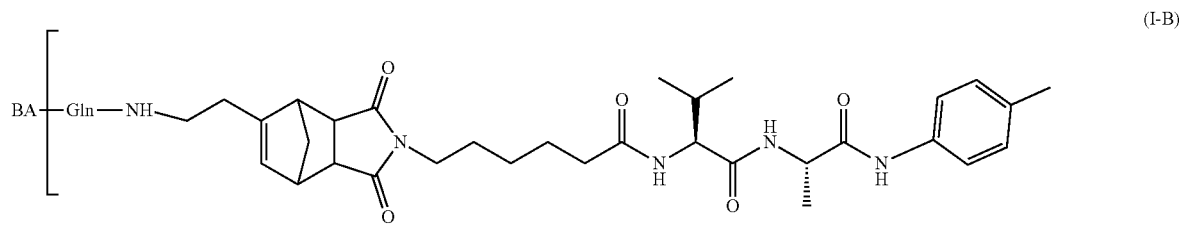
(I-B)
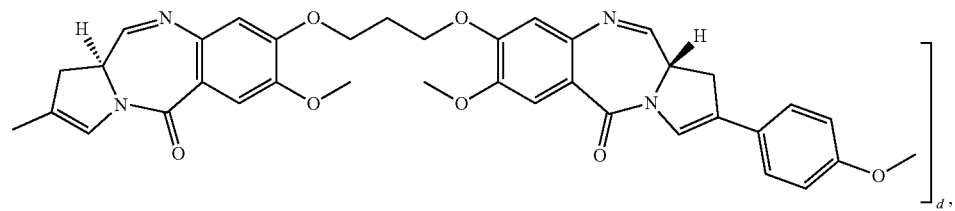
wherein d is an integer from 1 to 6.
In an embodiment of any of the preceeding compounds, the compound has a structure according to Formula (I-C)
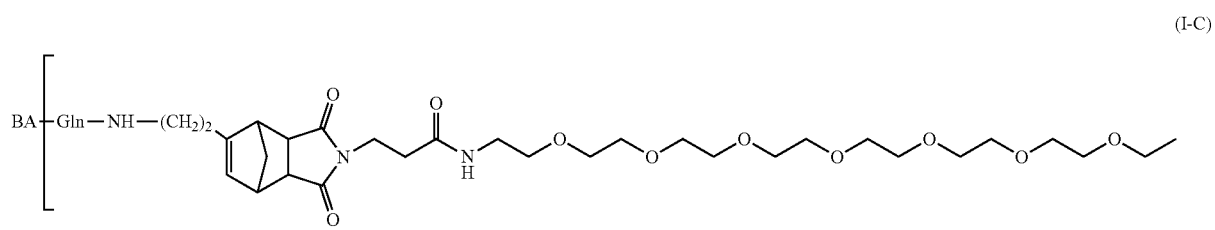
(I-C)

-continued

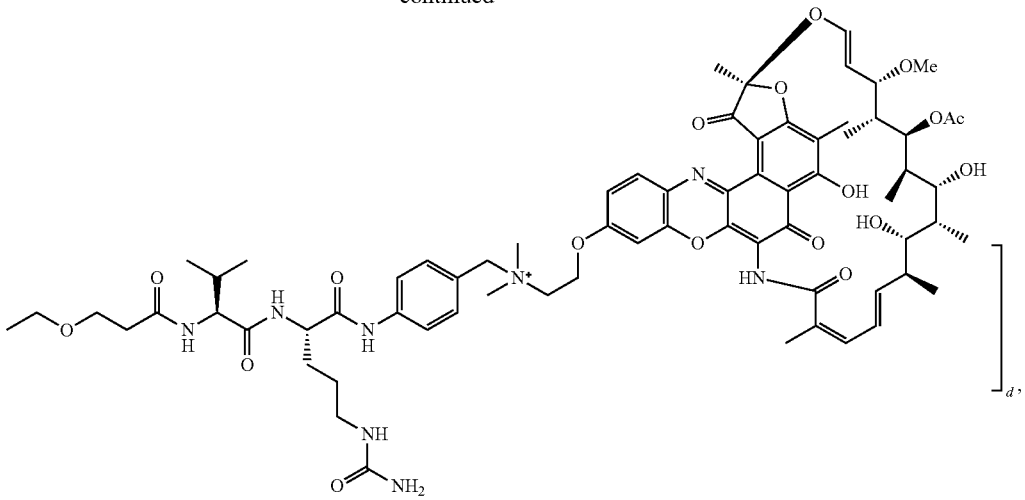

wherein d is an integer from 1 to 6.

In one aspect, the present disclosure provides a composition comprising a population of compounds according to any one the preceding compounds, having a drug-antibody ratio (DAR) of about 0.5 to about 8.0. In a further embodiment, the composition comprises a population of compounds having a DAR of about 1.0 to about 2.5. In a further embodiment, the composition comprises a population of compounds having a DAR of about 2. In a further embodiment, the composition comprises a population of compounds having a DAR of about 3.0 to about 4.5. In a further embodiment, the composition comprises a population of compounds having a DAR of about 4.

In one aspect of the present disclosure is provided a method of producing the compound according to any one of the preceding embodiments, the method comprising the steps of:
a.) contacting: i) a compound having a structure according to Formula (V-x):

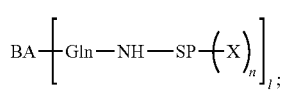 (V-x)

wherein:
BA is a binding agent;
SP is absent or a spacer;
X is a moiety that comprises a diene;
I is an integer from 1 to 6; and
n is an integer from 1 to 3; wherein when n is 2 or 3, Z, L and D may be the same or different;
with ii) a compound according to Formula (VI-y):

Y-L-D    (VI-y);

wherein:
Y is a moiety that comprises a dienophile;
L is a linker; and
D is a therapeutic moiety, wherein the therapeutic moiety is a maytansinoid, a tubulysin, an auristatin, a dolastatin, a camptothesin, a pyrrolobenzodiazepine, an antibiotic, an antiviral agent, an anti-inflammatory agent, an immunomodulator, an antifungal agent, a steroid, or an analogue or derivative thereof, or D is an imaging agent moiety; and b.) isolating the produced compound.

In one embodiment, n is 1 or 2. In one embodiment, n is 1, i.e. the compound has a structure

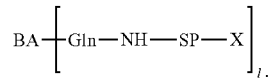

In one embodiment, n is 2, i.e., the compound has a structure

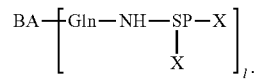

In one embodiment, the above method comprises preparing a compound having a structure the according to Formula (V-x) comprising steps of:

1.) contacting i) a binding agent having at least one acceptor glutamine residue and ii) a compound according to formula V-x2:

 (V-x2)

in the presence of transglutaminase (TG), wherein:
SP is absent or a spacer; and
X is a moiety that comprises a diene, wherein the two X moieties are the same; and 2.) isolating the produced compound.

In one embodiment, the above method comprises preparing a compound having a structure according to Formula (V-x) comprising the steps of:

1.) contacting i) a binding agent having at least one acceptor glutamine residue and ii) a compound according to formula V-x2:

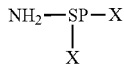
(V-x2)

in the presence of transglutaminase (TG), wherein:
SP is absent or a spacer; and
X is a moiety that comprises a diene, wherein the two X moieties are different; and 2.) isolating the produced compound.

In one embodiment, X is independently at each occurrence selected from

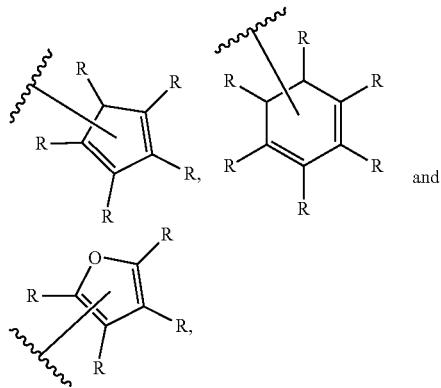

wherein R is independently at each occurrence H or an electron donating group (e.g., $C_{1-3}$ alkyl, —$OC_{1-3}$ alkyl, or —$NHC_{1-3}$ alkyl).

In one embodiment of the above method, R is H at each occurrence.

In one embodiment of the above method, at least one R is not H. In one embodiment of the above method, at least one R is $C_{1-3}$ alkyl. In one embodiment of the above method, at least one R is $OC_{1-3}$ alkyl. In one embodiment of the above method, at least one R is —$NHC_{1-3}$ alkyl. In one embodiment of the above method, at least one R is methyl. In one embodiment of the above method, at least one R is $OCH_3$.

In one embodiment, X is

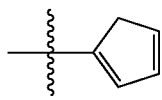

and Y is

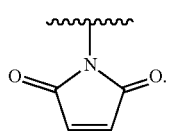 [SMILES: *N1C(=O)C=CC1=O]

In another aspect, the present disclosure provides a method comprising the steps of:
a.) contacting: i) a compound having a structure according to Formula (V-x):

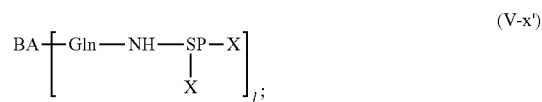
(V-x')

wherein:
BA is a binding agent;
SP is absent or a spacer;
X is a moiety that comprises a diene;
I is an integer from 1 to 6;
with ii) a compound according to Formula (VI-y):

Y-L-D      (VI-y);

wherein:
Y is a moiety that comprises a dienophile;
L is a linker; and
D is a therapeutic moiety, wherein the therapeutic moiety is a maytansinoid, a tubulysin, an auristatin, a dolastatin, a camptothesin, a pyrrolobenzodiazepine, an antibiotic, an antiviral agent, an anti-inflammatory agent, an immunomodulator, an antifungal agent, a steroid, or D is an imaging agent moiety, or an analogue or derivative thereof;
to produce a compound having a structure according to Formula (V-x'z):

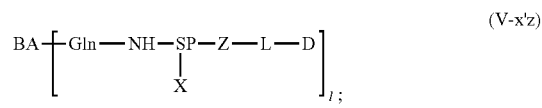
(V-x'z)

b.) contacting the compound according to Formula (V-x'z) with a compound according to Formula (VI-y): Y-L-D (VI-y); and
c.) isolating the produced compound of Formula (1B).

In one embodiment, the two X moieties are the same. In another embodiment, the two X moieties are different.

In one embodiment, the D moiety of step a.) is different from the D moiety of step b.). In one embodiment, the D moiety of step a.) is the same as the D moiety of step b.).

In one embodiment, step a.) is performed at a pH of about 7.0 to about 7.6. In one embodiment, step a.) is performed at a pH of about 7.2 to about 7.4. In one embodiment, step a.) is performed at a pH of about 7.2.

In one embodiment, step b.) is performed at a pH of about 5.0 to about 6.0. In one embodiment, step b.) is performed at a pH of about 5.3 to about 5.7. In one embodiment, step b.) is performed at a pH of about 5.5.

In one embodiment, the method further comprises a buffer exchange step after step a.) and before step b.).

In one embodiment, X is independently at each occurrence selected from

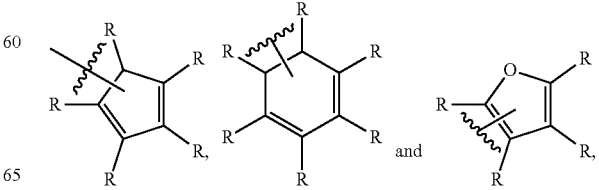

wherein R is independently at each occurrence H or an electron donating group (e.g., $C_{1-3}$ alkyl, —$OC_{1-3}$ alkyl, or —$NHC_{1-3}$ alkyl).

In one embodiment of the above method, R is H at each occurrence.

In one embodiment of the above method, at least one R is not H. In one embodiment of the above method, at least one R is $C_{1-3}$ alkyl. In one embodiment of the above method, at least one R is $OC_{1-3}$ alkyl. In one embodiment of the above method, at least one R is —$NHC_{1-3}$ alkyl. In one embodiment of the above method, at least one R is methyl. In one embodiment of the above method, at least one R is $OCH_3$.

In one embodiment, the preceeding method comprises preparing a compound having a structure according to Formula (IV-x) comprising the steps of:

1.) contacting i) a binding agent having at least one acceptor glutamine residue and ii) a compound according to formula IV-x1:

$NH_2$—SP—X    (IV-x1) in the presence of transglutaminase (TG), wherein:

SP is absent or a spacer; and
X is a moiety that comprises a diene; and

2.) isolating the produced compound.

In a further embodiment of the preceding method, X is

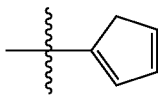 [SMILES: *C1=CC=CC1]

and Y is

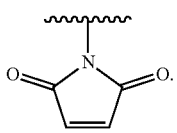 [SMILES: *N1C(=O)C=CC1=O]

In one aspect of the present disclosure is provided a method of producing the compound according to any one of the preceding embodiments, the method comprising the steps of:

a.) contacting: i) a compound having a structure according to Formula (IV-y):

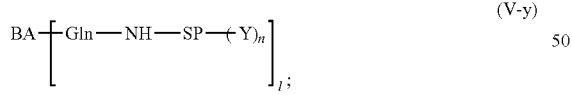

wherein:
BA is a binding agent;
SP is absent or a spacer;
Y is a moiety that comprises a dienophile;
I is an integer from 1 to 6; and
n is an integer from 1 to 3;
with ii) a compound according to Formula (VI-x):

X-L-D    (V-x), wherein:

X is a moiety that comprises a diene;
L is a linker; and
D is a therapeutic moiety, wherein the therapeutic moiety is a maytansinoid, a tubulysin, an auristatin, a dolastatin, a camptothesin, a pyrrolobenzo-diazepine, an antibiotic, an antiviral agent, an anti-inflammatory agent, an immunomodulator, an antifungal agent, a steroid, or D is an imaging agent moiety, or an analogue or derivative thereof; and b.) isolating the produced compound.

In one embodiment, the preceeding method comprises preparing a compound having a structure according to Formula (V-y) comprising the steps of:

1.) contacting i) the binding agent having at least one acceptor glutamine residue and ii) a compound according to formula V-y1:

$NH_2$—SP—Y    (V-y1) in the presence of transglutaminase (TGase), wherein:

SP is absent or a spacer;
Y is a moiety that comprises a dienophile; and

2.) isolating the produced compound.

In one embodiment, the preceding method comprises preparing a compound having a structure according to Formula (V-y) comprising the steps of:

1.) contacting i) the binding agent having at least one acceptor glutamine residue and ii) a compound according to formula V-y2:

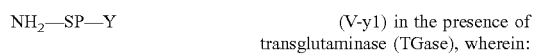

in the presence of transglutaminase (TGase), wherein:
SP is absent or a spacer;
Y is a moiety that comprises a dienophile, wherein the two Y moieties are the same; and 2.) isolating the produced compound.

In one embodiment, the preceding method comprises preparing a compound having a structure according to Formula (V-y) comprising the steps of:

1.) contacting i) the binding agent having at least one acceptor glutamine residue and ii) a compound according to formula V-y2:

in the presence of transglutaminase (TGase), wherein:
SP is absent or a spacer;
Y is a moiety that comprises a dienophile, wherein the two Y moieties are different; and 2.) isolating the produced compound.

In a further embodiment of the preceeding method, X is

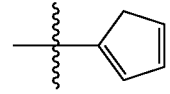 [SMILES: *C1=CC=CC1]

and Y is

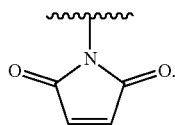 [SMILES: *N1C(=O)C=CC1=O]

In an embodiment of any one of the preceding methods, the binding agent is aglycosylated.

In an embodiment of any one of the preceding methods, the binding agent is deglycosylated prior to step 1.

In an embodiment of the preceding methods, BA is a HER-2 antibody, an antigen-binding fragment thereof, a MSR1 antibody or an antigen-binding fragment thereof.

In an embodiment of the preceding methods, Gln is independently at each occurrence Q295 or N297Q.

In an embodiment of the preceding methods, d is 2 or 4. In a further embodiment, d is 2. In another embodiment, d is 4.

In an embodiment of the preceding methods, SP is one or more of —(CH$_2$)$_u$—, —((CH$_2$)$_u$—O—)$_v$—, —NH—, —C(O)—, or combinations thereof, wherein subscripts u and v are independently at each occurrence an integer from 1 to 20. In a further embodiment SP is one or more of —(CH$_2$)$_u$—, C(O)—, —NH—, —(CH$_2$)$_u$—NH—C(O)—, —(CH$_2$)$_u$—C(O)—NH—, —(CH$_2$)$_u$—C(O)—NH—(CH$_2$)$_v$—, —(CH$_2$—CH$_2$—O)$_v$—, —(CH$_2$)$_u$—(O—CH$_2$—CH$_2$)$_v$—C(O)—NH—, —(CH$_2$—CH$_2$—O)$_v$—(CH$_2$)$_u$—C(O)—NH—(CH$_2$)$_u$—, —NH—(CH$_2$)$_u$—, —NH—(CH$_2$)$_u$—C(O)—, —NH—(CH$_2$)$_u$—C(O)—NH—(CH$_2$)—, —NH—(CH$_2$—CH$_2$—O)—, —NH—(CH$_2$—CH$_2$—O)$_v$—C(O)—, —NH—(CH$_2$—CH$_2$—O)$_v$—(CH$_2$)$_u$—, —NH—(CH$_2$—CH$_2$—O)$_v$—(CH$_2$)$_u$—C(O)—, —NH—(CH$_2$—CH$_2$—O)$_v$—(CH$_2$)$_u$—C(O)—NH—(CH$_2$)$_u$—, —(CH$_2$)$_u$—NH—C(O)—, —(CH$_2$)$_u$—C(O)—NH—(CH$_2$—CH$_2$—O)$_v$—C(O)—NH—, —NH—(CH$_2$)$_u$—C(O)—NH—, or combinations thereof; wherein subscripts u and v are independently an integer from 1 to 20. In a further embodiment, SP is —(CH$_2$)$_u$—; wherein the subscript u is an integer from 1 to 5.

In one embodiment, SP is

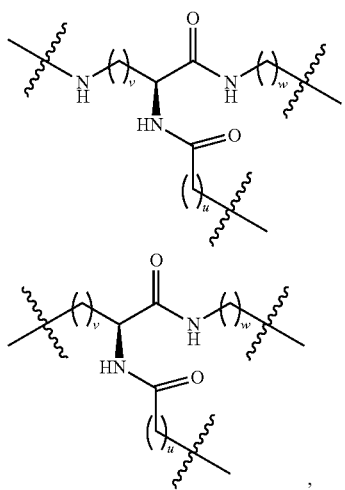

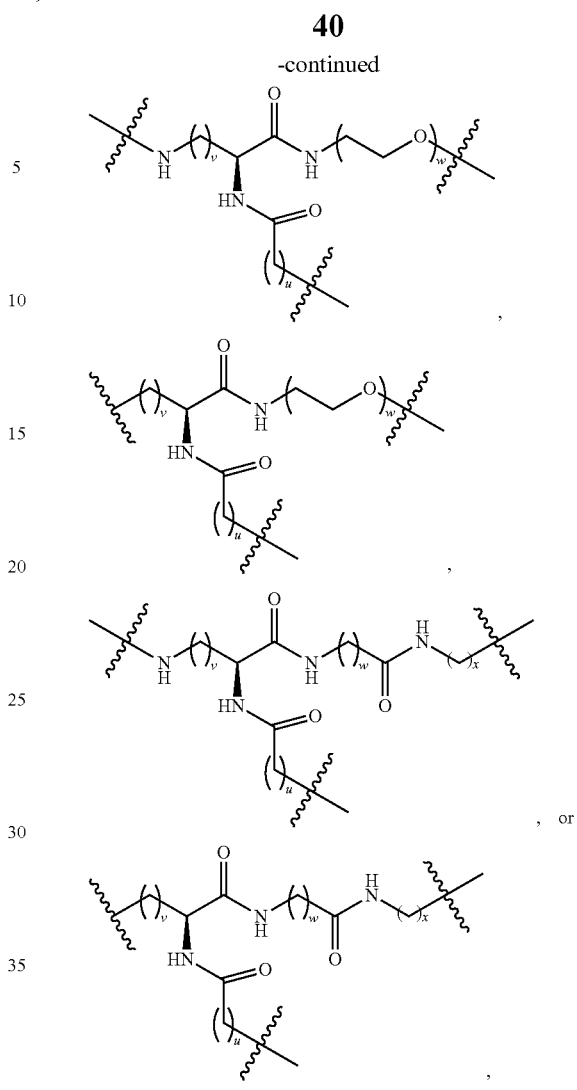

wherein subscripts u, v, w, and x are independently an integer from 1 to 12.

In one embodiment, SP is

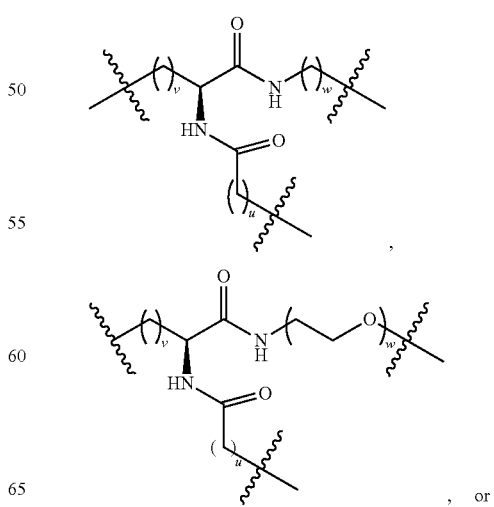

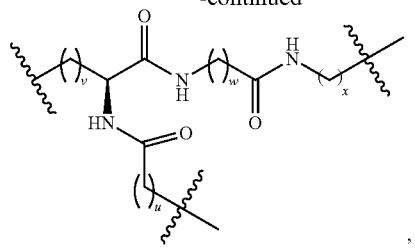
wherein subscripts u, v, w, and x are independently an integer from 1 to 12.
In one embodiment, SP is
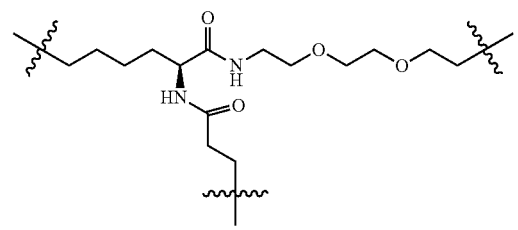
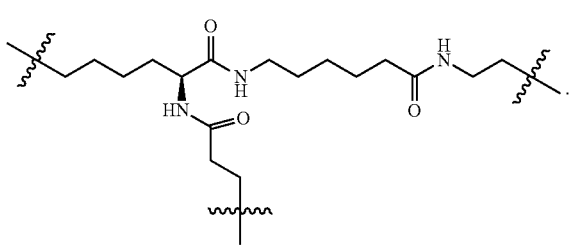
, or
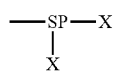
In one embodiment,
$$-SP-X \atop X$$
is
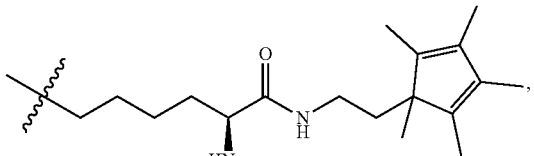
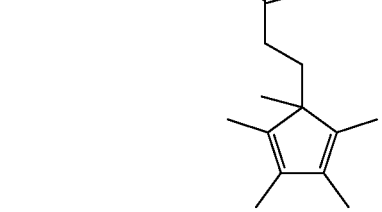
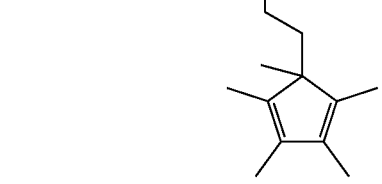
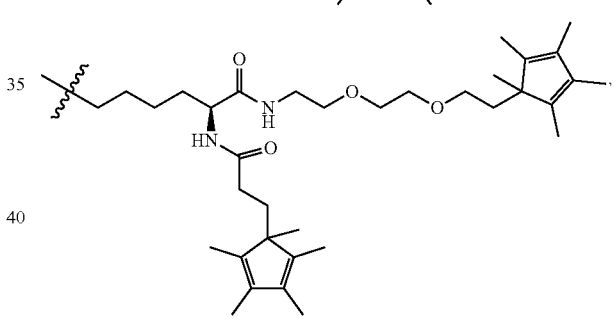
, or
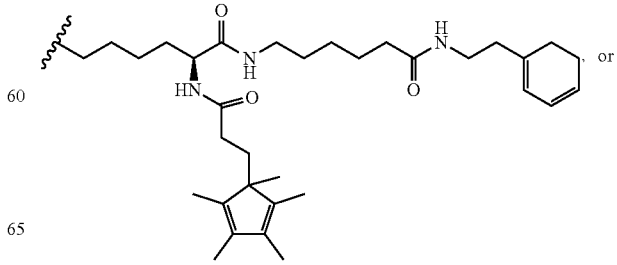

-continued

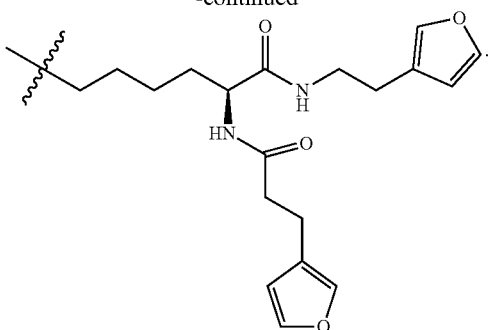

In an embodiment of the preceding methods, X is a diene moiety according to formula 3 or 4 below:

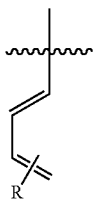

3

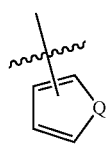

4 wherein R is H or $C_{1-3}$ alkyl; and Q is $CH_2$, $CH_2CH_2$, or O. In a further embodiment, X is a diene moiety according to formula 4a below:

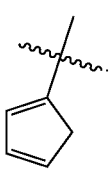

4a

In an embodiment of the preceding methods, Y is a dienophile moiety according to formula 5 or 6:

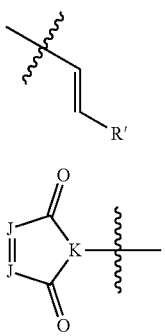

5

6 wherein: R' is H or $C_{1-3}$ alkyl; J is independently at each occurrence CH or N; and K is CH, N,

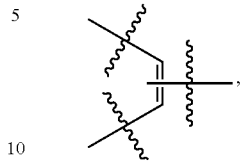

or NH—N. In a further embodiment, Y is a dienophile moiety according to formula 6a:

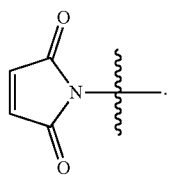

6a

In an embodiment of the preceding methods, L comprises one or more amino acids. In an additional embodiment, L further comprises one or more of —NH—, —S—, —O—, —(CH$_2$)$_n$—, —(CH$_2$—O—)$_m$—, —C(O)—,

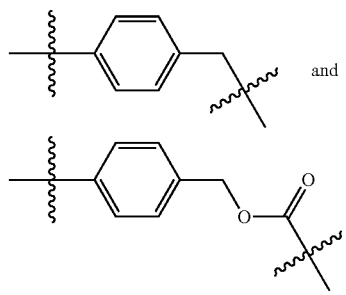

and

In a particular embodiment, the amino acid is glycine, serine, alanine, valine, phenylalanine, proline or citrulline.

In an embodiment of the preceding methods, L comprises

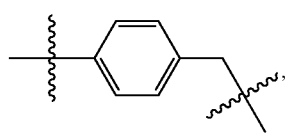

and D comprises a tertiary amine that is linked covalently to the methylene moiety of L, forming a quaternary ammonium moiety.

In an embodiment of the preceding methods, D is a therapeutic moiety, wherein the therapeutic moiety is an auristatin, a pyrrolobenzodiazepine (PBD), an ansamycin antibiotic, or an analogue or derivative thereof.

In an embodiment of the preceding methods, D is a therapeutic moiety, wherein the therapeutic moiety is monomethyl auristatin E (MMAE), PBD-1, rifamycin, or an analogue or derivative thereof.

In an embodiment of the preceding methods, BA is a HER-2 antibody, an antigen-binding fragment thereof, a MSR1 antibody, or an antigen-binding fragment thereof; X is a diene moiety according to formula 4a below:

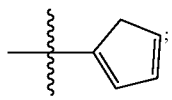

Y is a dienophile moiety according to formula 6a:

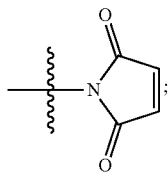

and D is a therapeutic moiety, wherein the therapeutic moiety is monomethyl auristatin E (MMAE), PBD-1, rifamycin; and an analogue or derivative thereof, or D is an imaging agent moiety Alexa Fluor 647.

In an embodiment of the preceding methods, comprising the steps of:
a.) producing a compound by:
  1.) contacting i) the binding agent having at least one acceptor glutamine residue and ii) a compound according to formula V-x1a:

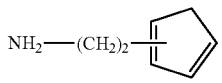

in the presence of transglutaminase (TGase), wherein the binding agent is a deglycosylated HER-2 antibody, an antigen-binding fragment thereof, a MSR1 antibody, or an antigen-binding fragment thereof;
  2.) isolating the produced compound; and
b.) contacting the compound of step a.) with a compound according to Formula (VI-A), (VI-B) or (VI-C) below:

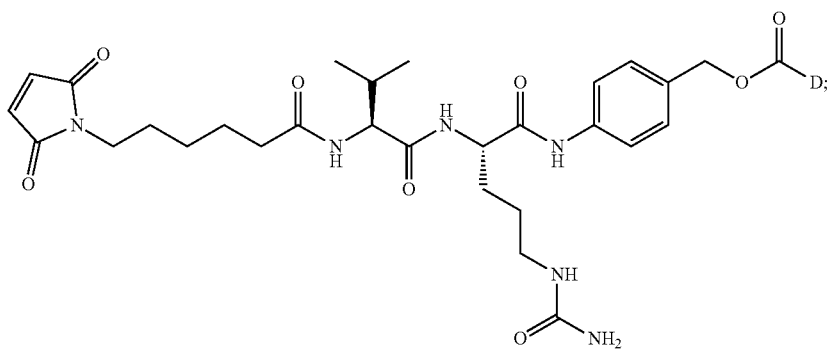

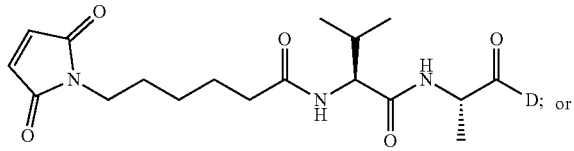

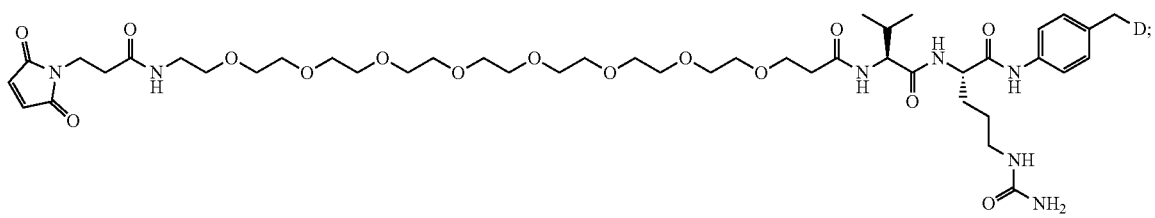

wherein D is a therapeutic moiety, wherein the therapeutic moiety is monomethyl auristatin E (MMAE), PBD-1, rifamycin, or an analogue or derivative thereof attached via an amino group of the therapeutic moiety; and c.) isolating the produced compound.

In one aspect, the present disclosure provides a compound produced by any one of the preceding methods.

In one aspect, the present disclosure provides a pharmaceutical composition comprising the compound according to any one of the provided embodiments, or the composition according to any one of the provided embodiments, and a diluent, a carrier, and/or an excipient. In one embodiment, the composition is a parenteral formulation.

In one aspect, the present disclosure provides a method of treating a condition in a subject in need thereof comprising administering to the subject a therapeutically effective amount of a composition comprising a compound according to any one of the provided embodiments, the composition according to any one of the provided embodiments, or a pharmaceutical composition according to any one of the provided embodiments. In one embodiment of the preceding method, the condition is cancer. In a further embodiment of the preceding method, the condition is HER2+ breast cancer. In one embodiment of the preceding method, BA is a HER2 antibody, or an antigen-binding fragment thereof. In one embodiment of the preceding method, D is a cytotoxic agent.

In one embodiment of the preceding method of treating a condition in a subject, the cancer is characterized by primary and/or metastatic tumors arising in one or more of: the prostate, bladder, cervix, lung, colon, kidney, breast, pancreas, stomach, uterus, and ovary. In one embodiment of the preceding method, the cancer is prostate cancer, bladder cancer, cervical cancer, lung cancer, colon cancer, kidney cancer, breast cancer, pancreatic cancer, stomach cancer, uterine cancer, or ovarian cancer.

In one embodiment of the preceding method of treating a condition in a subject, D is selected from: dolastatins, auristatins, maytansinoids, pyrrolobenzodiazepines and tubulin-interacting agents. In a further embodiment, D is MMAE or PDB.

In one embodiment of the preceding method of treating a condition in a subject, the condition is an infection. In a further embodiment, BA is a MSR1 antibody, or an antigen-binding fragment thereof. In a further embodiment, D is rifamycin or an analogue or derivative thereof. In a further embodiment, the condition is a bacterial infection. In a further embodiment, the condition is a viral infection.

In one embodiment of the preceding method of treating a condition in a subject, the condition is an inflammatory condition. In a further embodiment, BA is a MSR1 antibody, or an antigen-binding fragment thereof. In a further embodiment, the condition is an immune system disorder. In a further embodiment, the inflammatory condition is: hypercalcemia due to cancer, Meniere's disease, a migraine headache, a cluster headache, a severe aphthous ulcer, laryngitis, severe tuberculosis, a Herxheimer reaction to syphilis, a decompensated heart failure, allergic rhinitis or nasal polyps.

These and other aspects of the present disclosure will become apparent to those skilled in the art after a reading of the following detailed description, including the appended claims.

DETAILED DESCRIPTION

Detailed embodiments of the present disclosure are disclosed herein; however, it is to be understood that the disclosed embodiments are merely illustrative of the disclosure that can be embodied in various forms. In addition, each of the examples given in connection with the various embodiments of the disclosure is intended to be illustrative, and not restrictive. Therefore, specific structural and functional details disclosed herein are not to be interpreted as limiting, but merely as a representative basis for teaching one skilled in the art to variously employ the present disclosure. It is to be understood that this disclosure is not limited to particular methods and experimental conditions described, as such methods and conditions can vary. It is also to be understood that the terminology used herein is for the purpose of describing particular embodiments only, and is not intended to be limiting, since the scope of the present disclosure will be limited only by the appended claims.

Definitions

Unless defined otherwise, all technical and scientific terms used herein have the same meaning as commonly understood by one of ordinary skill in the art to which this disclosure belongs. As used herein, the term "about," when used in reference to a particular recited numerical value, means that the value can vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present disclosure, particular methods and materials are now described. All patents, applications and non-patent publications mentioned in this specification are incorporated herein by reference in their entireties.

Ranges can be expressed herein as from "about" or "approximately" one particular value and/or to "about" or "approximately" another particular value. When such a range is expressed, another embodiment includes from the one particular value and/or to the other particular value.

By "comprising" or "containing" or "including" is meant that at least the named compound, element, particle, or method step is present in the composition or article or method, but does not exclude the presence of other compounds, materials, particles, or method steps, even if the other such compounds, material, particles, or method steps have the same function as what is named.

The terms "treat" or "treatment" of a state, disorder or condition include: (1) preventing, delaying, or reducing the incidence and/or likelihood of the appearance of at least one clinical or sub-clinical symptom of the state, disorder or condition developing in a subject that can be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

A "subject" or "patient" or "individual" or "animal", as used herein, refers to humans, veterinary animals (e.g., cats, dogs, cows, horses, sheep, pigs, etc.) and experimental animal models of diseases (e.g., mice, rats). In one embodiment, the subject is a human.

As used herein the term "effective" applied to dose or amount refers to that quantity of a compound or pharmaceutical composition that is sufficient to result in a desired activity upon administration to a subject in need thereof. Note that when a combination of active ingredients is administered, the effective amount of the combination may or may not include amounts of each ingredient that would have been effective if administered individually. The exact amount required will vary from subject to subject, depending on the species, age, and general condition of the subject, the severity of the condition being treated, the particular drug or drugs employed, the mode of administration, and the like.

The phrase "pharmaceutically acceptable", as used in connection with compositions of the disclosure, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

The phrase "pharmaceutically acceptable salt", as used in connection with compositions of the disclosure, refers to any salt suitable for administration to a patient. Suitable salts include, but are not limited to, those disclosed in. Berge et al., "Pharmaceutical Salts", *J. Pharm. Sci.*, 1977, 66:1, incorporated herein by reference. Examples of salts include, but are not limited to, acid derived, base derived, organic, inorganic, amine, and alkali or alkaline earth metal salts, including but not limited to calcium salts, magnesium salts, potassium salts, sodium salts, salts of hydrochloric acid, hydrobromic acid, sulfuric acid, nitric acid, phosphoric acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methane sulfonic acid, ethane sulfonic acid, p toluene sulfonic acid, salicylic acid, and the like. In some examples, a payload described herein (e.g., a rifamycin analog described herein) comprises a tertiary amine, where the nitrogen atom in the tertiary amine is the atom through which the payload is bonded to a linker or a linker-spacer. In such instances, bonding to the tertiary amine of the payload yields a quaternary amine in the linker-payload molecule. The positive charge on the quaternary amine can be balanced by a counter ion (e.g., chloro, bromo, iodo, or any other suitably charged moiety such as those described herein).

The phrase "therapeutically effective amount," as used herein, refers to an amount that produces the desired effect for which it is administered. The exact amount will depend on the purpose of the treatment, and will be ascertainable by one skilled in the art using known techniques (see, for example, Lloyd (1999) *The Art, Science and Technology of Pharmaceutical Compounding*).

The term "minimum inhibitory concentration" ("MIC") refers to the lowest concentration of an antimicrobial that will inhibit the visible growth of a microorganism after overnight incubation. Assay for determining MIC are known. One method is as described in the Examples below.

Certain groups, moieties, substituents, and atoms are depicted with a wavy line. The wavy line can intersect or cap a bond or bonds. The wavy line indicates the atom through which the groups, moieties, substituents, or atoms are bonded. For example, a phenyl group that is substituted with a propyl group depicted as:

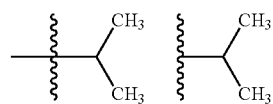

has the following structure:

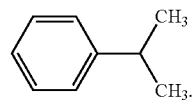

Certain groups, moieties, substituents, and atoms are depicted with a floating bond connection to another group or moiety, e.g., a ring moiety. The floating bond which intersects another bond indicates that the group, moiety, substituent or atom may be attached to any unspecified atom of the other group or moiety, e.g., the ring moiety, where it is chemically possible. For example, in the following structure:

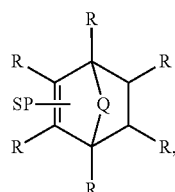

the substituent SP may be attached to the ring at any position on the ring where it is chemically possible.

The term "electron donating group", as used herein, is given its ordinary meaning in the art, i.e. an atom or a functional group that donates some of its electron density into a conjugated π system via resonance (mesomerism) or inductive effects (or induction) thus making the π system more nucleophilic. As a result of these electronic effects, an aromatic ring to which such a group is attached is more likely to participate in electrophilic substitution reaction. Non-limiting examples of electron donating groups include substituted and unsubstituted amines, hydroxy-, alkoxy, alkyl, vinyl, aryl, acylamino, acyloxy, alkylthio, alkylphosphino, and fluoro groups.

As used herein, the term "alkyl" is given its ordinary meaning in the art and may include saturated aliphatic groups, including straight-chain alkyl groups, branched-chain alkyl groups, cycloalkyl groups, alkyl substituted cycloalkyl groups, and cycloalkyl substituted alkyl groups. In certain embodiments, a straight chain or branched chain alkyl has about 1-20 carbon atoms in its backbone (e.g., C1-C20 for straight chain, C2-C20 for branched chain), and alternatively, about 1-10 carbon atoms, or about 1 to 6 carbon atoms. In some embodiments, a cycloalkyl ring has from about 3-10 carbon atoms in their ring structure wherein such rings are monocyclic or bicyclic, and alternatively about 5, 6 or 7 carbons in the ring structure. In some embodiments, an alkyl group may be a lower alkyl group, wherein a lower alkyl group comprises 1-4 carbon atoms (e.g., C1-C4 for straight chain lower alkyls).

As used herein, the term "alkenyl" refers to an alkyl group, as defined herein, having one or more double bonds.

As used herein, the term "alkynyl" refers to an alkyl group, as defined herein, having one or more triple bonds.

The term "heteroalkyl" is given its ordinary meaning in the art and refers to alkyl groups as described herein in which one or more carbon atoms is replaced with a heteroatom (e.g., halogen, oxygen, nitrogen, sulfur, and the like). Examples of heteroalkyl groups include, but are not limited to, alkoxy, poly(ethylene glycol)-, alkyl-substituted amino, tetrahydrofuranyl, piperidinyl, morpholinyl, etc.

As used herein, "aromatic" refers to a monocyclic or polycyclic, aromatic or heteroaromatic ring which may have from 5 to 20 ring atoms, and optionally may have from 1 to 20 heteroatom substituents. In some embodiments, the aromatic groups may optionally have from 1 to 10 heteroatom substituents. In some embodiments, the aromatic groups may optionally have from 1 to 5 heteroatom substituents. In some embodiments, the aromatic groups are monocyclic or polycyclic aromatic rings, such as cyclopentadienyl, phenyl, naphthyl or anthracenyl. In some embodiments, aromatic groups are monocyclic or polycyclic aromatic rings having from 5 to 10 ring atoms. In some embodiments, aromatic groups are monocyclic aromatic rings containing from 5 to 6 carbon atoms, such as phenyl and cyclopentadienyl. In one particular embodiment, an aromatic group is a phenyl group.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present disclosure, "aryl" refers to an aromatic ring system which includes, but not limited to, phenyl, biphenyl, naphthyl, binaphthyl, anthracyi and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The expressions "MSR1," "hMSR1" and the like, as used herein, refer to the human single-pass, trimeric type II transmembrane glycoprotein pattern recognition receptor comprising (i) the amino acid sequence as set forth in NCBI accession No. NP_002436.1, (ii) the amino acid sequence as set forth in NCBI accession No. NP_619729.1, and/or (iii) the amino acid sequence as set forth in NCBI accession No. NP_619730.1, which represent the various types and isoforms of class A macrophage scavenger receptors. The expression "MSR1" includes both monomeric and multimeric MSR1 molecules. As used herein, the expression "monomeric human MSR1" means a MSR1 protein or portion thereof that does not contain or possess any multimerizing domains and that exists under normal conditions as a single MSR1 molecule without a direct physical connection to another MSR1 molecule.

The expression"HER2" or "human epidermal growth factor receptor 2" refers to a member of the human epidermal growth factor receptor family. Amplification or overexpression of this oncogene has been shown to play an important role in the development and progression of certain aggressive types of breast cancer. In recent years the protein has become an important biomarker and target of therapy for approximately 30% of breast cancer patient. The amino acid sequence of HER2 is set forth as SEQ ID NO: 49. All references to proteins, polypeptides and protein fragments herein are intended to refer to the human version of the respective protein, polypeptide or protein fragment unless explicitly specified as being from a non-human species. Thus, the expression "HER2" means human HER2 unless specified as being from a non-human species, e.g., "mouse HER2," "monkey HER2," etc.

The phrase "an antibody that binds HER2" or an "anti-HER2 antibody" includes antibodies and antigen-binding fragments thereof that specifically recognize HER2.

All amino acid abbreviations used in this disclosure are those accepted by the United States Patent and Trademark Office as set forth in 37 C.F.R. § 1.822 (B)(J).

The term "protein" means any amino acid polymer having more than about 20 amino acids covalently linked via amide bonds. As used herein, "protein" includes biotherapeutic proteins, recombinant proteins used in research or therapy, trap proteins and other Fc-fusion proteins, chimeric proteins, antibodies, monoclonal antibodies, human antibodies, bispecific antibodies, antibody fragments, nanobodies, recombinant antibody chimeras, scFv fusion proteins, cytokines, chemokines, peptide hormones, and the like. Proteins can be produced using recombinant cell-based production systems, such as the insect bacculovirus system, yeast systems (e.g, Pichia sp.), mammalian systems (e.g., CHO cells and CHO derivatives like CHO-K1 cells).

All references to proteins, polypeptides and protein fragments herein are intended to refer to the human version of the respective protein, polypeptide or protein fragment unless explicitly specified as being from a non-human species. Thus, the expression "MSR1" means human MSR1 unless specified as being from a non-human species, e.g., "mouse MSR1," "monkey MSR1," etc.

The amino acid sequence of an antibody can be numbered using any known numbering schemes, including those described by Kabat et al., ("Kabat" numbering scheme); Al-Lazikani et al., 1997, *J. Mol. Biol.*, 273:927-948 ("Chothia" numbering scheme); MacCallum et al., 1996, *J. Mol. Biol.* 262:732-745 ("Contact" numbering scheme); Lefranc et al., Dev. Comp. *Immunol.*, 2003, 27:55-77 ("IMGT" numbering scheme); and Honegge and Pluckthun, *J. Mol. Biol.*, 2001, 309:657-70 ("AHo" numbering scheme). Unless otherwise specified, the numbering scheme used herein is the Kabat numbering scheme. However, selection of a numbering scheme is not intended to imply differences in sequences where they do not exist, and one of skill in the art can readily confirm a sequence position by examining the amino acid sequence of one or more antibodies. Unless stated otherwise, the "EU numbering scheme" is generally used when referring to a residue in an antibody heavy chain constant region (e.g., as reported in Kabat et al., supra).

The term "glutaminyl-modified antibody" refers to an antibody with at least one covalent linkage from a glutamine side chain to a primary amine compound of the present disclosure. In particular embodiments, the primary amine compound is linked through an amide linkage on the glutamine side chain. In certain embodiments, the glutamine is an endogenous glutamine. In other embodiments, the glutamine is an endogenous glutamine made reactive by polypeptide engineering (e.g., via amino acid deletion, insertion, substitution, or mutation on the polypeptide). In additional embodiments, the glutamine is polypeptide engineered with an acyl donor glutamine-containing tag (e.g., glutamine-containing peptide tags, Q-tags or TGase recognition tag).

The term "TGase recognition tag" refers to a sequence of amino acids comprising an acceptor glutamine residue and that when incorporated into (e.g. appended to) a polypeptide sequence, under suitable conditions, is recognized by a TGase and leads to cross-linking by the TGase through a reaction between an amino acid side chain within the sequence of amino acids and a reaction partner. The recognition tag may be a peptide sequence that is not naturally present in the polypeptide comprising the TGase recognition tag. In some embodiments, the TGase recognition tag comprises at least one Gln. In some embodiments, the TGase recognition tag comprises an amino acid sequence XXQX (SEQ ID NO: 467), wherein X is any amino acid (e.g., conventional amino acid Leu, Ala, Gly, Ser, Val, Phe, Tyr, His, Arg, Asn, Glu, Asp, Cys, Gin, Ile, Met, Pro, Thr, Lys, or Trp or nonconventional amino acid). In some embodiments, the acyl donor glutamine-containing tag comprises an amino acid sequence selected from the group consisting of LLQGG (SEQ ID NO:468), LLQG (SEQ ID NO:469), LSLSQG (SEQ ID NO:470), GGGLLQGG (SEQ ID NO:471), GLLQG (SEQ ID NO:472), LLQ, GSPLAQSHGG (SEQ ID NO:473), GLLQGGG (SEQ ID NO:474), GLLQGG (SEQ ID NO:475), GLLQ (SEQ ID NO:476), LLQLLQGA (SEQ ID NO:477), LLQGA (SEQ ID NO:478), LLQYQGA (SEQ ID NO:479), LLQGSG (SEQ ID NO:480), LLQYQG (SEQ ID NO:481), LLQLLQG (SEQ ID NO:482), SLLQG (SEQ ID NO:483), LLQLQ (SEQ ID NO:484), LLQLLQ (SEQ ID NO:485), and LLQGR (SEQ ID NO:486). See for example, WO2012059882, the entire contents of which are incorporated herein.

In some embodiments, a TGase recognition tag is derived from a myc peptide that can be introduced to a variety of polypeptides, including but not limited to antibodies. See, e.g., U.S. Ser. No. 10/036,010 the entire contents of which are incorporated herein. In some embodiments, the Myc-Tag sequence is: EQKLISEEDL (N-Glu-Gln-Lys-Leu-Ile-Ser-Glu-Glu-Asp-Leu-C, SEQ ID NO:487).

The term "antibody," as used herein, means any antigen-binding molecule or molecular complex comprising at least one complementarity determining region (CDR) that specifically binds to or interacts with a particular antigen. The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or VH) and a heavy chain constant region. The heavy chain constant region comprises three domains, CH1, CH2, and CH3. Each light chain comprises a light chain variable region (abbreviated herein as LCVR or VL) and a light chain constant region. The light chain constant region comprises one domain (CL1). The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. In different embodiments, the FRs of the antibody (or antigen-binding portion thereof) can be identical to the human germline sequences, or can be naturally or artificially modified. An amino acid consensus sequence can be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody can be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA can be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g., monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain can be of any size or amino acid composition and will generally comprise at least one CDR which is adjacent to or in frame with one or more framework sequences. In antigen-binding fragments having a VH domain associated with a VL domain, the VH and VL domains can be situated relative to one another in any suitable arrangement. For example, the variable region can be dimeric and contain VH—VH, VH-VL or VL-VL dimers.

Alternatively, the antigen-binding fragment of an antibody can contain a monomeric VH or VL domain.

In certain embodiments, an antigen-binding fragment of an antibody can contain at least one variable domain covalently linked to at least one constant domain. Non-limiting, exemplary configurations of variable and constant domains that can be found within an antigen-binding fragment of an antibody of the present description include: (i) VH-CH1; (ii) VH-CH2; (iii) VH-CH3; (iv) VH-CH1-CH2; (V) VH-CH1-CH2-CH3; (vi) VH-CH2-CH3; (vii) VH-CL; (viii) VL-CH1; (ix) VL-CH2; (x) VL-CH3; (xi) VL-CH1-CH2; (xii) VL-CH1-CH2-CH3; (xiii) VL-CH2-CH$_3$; and (xiv) VL-CL. In any configuration of variable and constant domains, including any of the exemplary configurations listed herein, the variable and constant domains can be either directly linked to one another or can be linked by a full or partial hinge or linker region. A hinge region can consist of at least 2 (e.g., 5, 10, 15, 20, 40, 60, or more) amino acids which result in a flexible or semi-flexible linkage between adjacent variable and/or constant domains in a single polypeptide molecule.

Moreover, an antigen-binding fragment of an antibody of the present description can comprise a homo-dimer or hetero-dimer (or other multimer) of any of the variable and constant domain configurations listed herein in non-covalent association with one another and/or with one or more monomeric VH or VL domain (e.g., by disulfide bond(s)).

As with full antibody molecules, antigen-binding fragments can be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, can be adapted for use in the context of an antigen-binding fragment of an antibody of the present description using routine techniques available in the art.

The antibodies of the present description can function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the description in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al. (1998) *Proc. Natl. Acad. Sci.* (USA) 95:652-656). The constant region of an antibody is important in the ability of an antibody to fix complement and mediate cell-dependent cytotoxicity. Thus, the isotype of an antibody can be selected on the basis of whether it is desirable for the antibody to mediate cytotoxicity.

In certain embodiments, the antibodies of the description, e.g., anti-HER2 antibodies or anti-MSR1 antibodies, are human antibodies. The term "human antibody," as used herein, is intended to include antibodies having variable and constant regions derived from human germline immunoglobulin sequences. The human antibodies of the description can include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

The antibodies can, in some embodiments, be recombinant human antibodies. The term "recombinant human antibody," as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (See, e.g., Taylor et al. (1992) *Nucl. Acids Res.* 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification. The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) *Molecular Immunology* 30: 105) to levels typically observed using a human IgG1 hinge. The instant description encompasses antibodies having one or more mutations in the hinge, CH2 or CH3 region which can be desirable, for example, in production, to improve the yield of the desired antibody form.

The antibodies of the description can be isolated or purified antibodies. An "isolated antibody" or "purified antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present description. For example, an antibody that has been purified from at least one component of a reaction or reaction sequence, is a "purified antibody" or results from purifying the antibody. An isolated antibody also includes an antibody in situ within a recombinant cell. Isolated antibodies are antibodies that have been subjected to at least one purification or isolation step. According to certain embodiments, an isolated antibody or purified antibody can be substantially free of other cellular material and/or chemicals.

The antibodies disclosed herein can comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present description includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the VH and/or VL domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived).

Furthermore, the antibodies of the present description can contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, improved drug-to-antibody ratio (DAR) for antibody-drug conjugates, etc. Antibodies and antigen-binding fragments obtained in this general manner are encompassed within the present description.

The amino acid sequence of an antibody can be numbered using any known numbering schemes, including those described by Kabat et al., ("Kabat" numbering scheme); Al-Lazikani et al., 1997, *J. Mol. Biol.*, 273:927-948 ("Chothia" numbering scheme); MacCallum et al., 1996, *J. Mol. Biol.* 262:732-745 ("Contact" numbering scheme); Lefranc et al., Dev. Comp. *Immunol.*, 2003, 27:55-77 ("IMGT" numbering scheme); and Honegge and Plückthun, *J. Mol. Biol.*, 2001, 309:657-70 ("AHo" numbering scheme). Unless otherwise specified, the numbering scheme used herein is the Kabat numbering scheme. However, selection of a numbering scheme is not intended to imply differences in sequences where they do not exist, and one of skill in the art can readily confirm a sequence position by examining the amino acid sequence of one or more antibodies. Unless stated otherwise, the "EU numbering scheme" is generally used when referring to a residue in an antibody heavy chain constant region (e.g., as reported in Kabat et al., supra).

The term "aglycosylated antibody" refers to an antibody that does not comprise a glycosylation sequence that might interfere with a transglutamination reaction, for instance an antibody that does not have saccharide group at N297 on one or more heavy chains. In particular embodiments, an antibody heavy chain has an N297 mutation. In other words, the antibody is mutated to no longer have an asparagine residue at position 297 according to the EU numbering system as disclosed by Kabat et al. In particular embodiments, an antibody heavy chain has an N297Q or an N297D mutation. Such an antibody can be prepared by site-directed mutagenesis to remove or disable a glycosylation sequence or by site-directed mutagenesis to insert a glutamine residue at site apart from any interfering glycosylation site or any other interfering structure. Such an antibody also can be isolated from natural or artificial sources.

The term "deglycosylated antibody" refers to an antibody in which a saccharide group at N297 was removed, thereby facilitating Q295 transglutamination. In particular embodiments, provided herein are processes that encompass an additional step of deglycosylating an antibody, for instance an N297 antibody.

The term "epitope" refers to an antigenic determinant that interacts with a specific antigen binding site in the variable region of an antibody molecule known as a paratope. A single antigen can have more than one epitope. Thus, different antibodies can bind to different areas on an antigen and can have different biological effects. Epitopes can be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope can include moieties of saccharides, phosphoryl groups, or sulfonyl groups on the antigen.

The terms "conjugated protein" or "conjugated antibody" as used herein refers to a protein or an antibody covalently linked to one or more chemical moieties. The chemical moiety can include an amine compound of the present disclosure. Linkers (L) and payloads (D) suitable for use with the present disclosure are described in detail herein. In particular embodiments, a conjugated antibody comprising a therapeutic moiety is an antibody-drug conjugate (ADC), also referred to as an antibody-payload conjugate, or an antibody-linker-payload conjugate.

The term "Drug-to-Antibody Ratio" or (DAR) is the average number of therapeutic moieties, e.g., drugs, conjugated to a binding agent of the present disclosure.

The term "Linker Antibody Ratio" or (LAR), also denoted as the lower case l in some embodiments, is the average number of reactive primary amine compounds conjugated to a binding agent of the present disclosure. Such binding agents, e.g., antibodies, can be conjugated with primary amine compounds comprising a suitable diene or dienophile. The resulting binding agent, which is functionalized with a diene or dienophile can subsequently react with a therapeutic comprising the corresponding diene or dienophile via the Diels-Alder reaction.

The term "glutaminyl-modified antibody" refers to an antibody with at least one covalent linkage from a glutamine side chain to a chemical moiety. The chemical moiety can be any moiety deemed suitable by the practitioner of skill, e.g., the amine compounds of the present disclosure. In particular embodiments, the chemical moiety is linked through an amide linkage on the glutamine side chain.

The phrase "pharmaceutically acceptable amount" refers to an amount effective or sufficient in treating, reducing, alleviating, or modulating the effects or symptoms of at least one health problem in a subject in need thereof. For example, a pharmaceutically acceptable amount of an antibody or antibody-drug conjugate is an amount effective for modulating a biological target using the antibody or antibody-drug-conjugates provided herein. Suitable pharmaceutically acceptable amounts include, but are not limited to, from about 0.001% up to about 10%, and any amount in between, such as about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, or about 10% of an antibody or antibody-drug-conjugate provided herein.

The phrase "initial pH" refers to the pH of a component or reactant for a reaction before the component or reactant is added to the reaction mixture. For example, the initial pH of a buffer solution is 7.74 before the buffer solution is added to a reaction mixture.

The phrase "reaction pH" refers to the pH of a reaction after all reaction components or reactants have been added.

The term "pharmaceutically acceptable" means approved by a regulatory agency of the United States Federal or State government or listed in the U.S. Pharmacopeia or other generally recognized pharmacopeia for use in animals, and more particularly in humans.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule can, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity can be adjusted upwards to correct for the conservative nature of the substitution. Means for making this adjustment are well-known to those of skill in the art. See, e.g., Pearson (1994) Methods Mol. Biol. 24: 307-331. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. In some embodiments, conservative amino acids substitution groups are: valine-leucine-isoleucine, phenylalanine-tyrosine, lysine-arginine, alanine-valine, glutamate-aspartate, and asparagine-glutamine.

Alternatively, a conservative replacement is any change having a positive value in the PAM250 log-likelihood matrix disclosed in Gonnet et al. (1992) Science 256: 1443-1445. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another particular algorithm when comparing a sequence of the description to a database containing a large number of sequences from different organisms is the computer program BLAST, especially BLASTP or TBLASTN, using default parameters. See, e.g., Altschul et al. (1990) *J. Mol. Biol.* 215:403-410 and Altschul et al. (1997) *Nucleic Acids Res.* 25:3389-402.

As used herein, "therapeutically effective amount" refers to an amount (of a compound) that is sufficient to provide a therapeutic benefit to a patient in the treatment or management of a disease or disorder, or to delay or minimize one or more symptoms associated with the disease or disorder.

Compounds of the Disclosure

Protein-Payload Conjugate Compounds

According to the foregoing objective and others, the present disclosure provides protein-payload conjugate compounds, e.g., protein-drug conjugate compounds, precursors and intermediates thereof, pharmaceutical compositions, and methods for treating certain diseases in a subject in need of such treatment. According to the disclosure, the protein-payload conjugate compounds provided herein comprise a glutaminyl-modified binding agent conjugated with a primary amine compound linked to a therapeutic or an imaging agent moiety wherein the linker comprises a Diels-Alder adduct, which is a substituted cyclohexene derivative as described herein.

The term "protein-payload conjugate" as used herein refers to a compound comprising a binding agent according to the present disclosure, (e.g., an antibody or a fragment thereof), having one or more glutamine residues conjugated to one or more compounds of the present disclosure comprising i) a Diels-Alder adduct and ii) a therapeutic or an imaging agent moiety. Illustrative non-limiting examples include Formula (IA), (IB) and (IC) described herein.

The term "protein-drug conjugate" as used herein refers to a compound comprising a binding agent according to the present disclosure, (e.g., an antibody or a fragment thereof), having one or more glutamine residues conjugated to one or more compounds of the present disclosure comprising i) a Diels-Alder adduct and ii) a therapeutic moiety. Illustrative non-limiting examples include Formula (IA), (IB) and (IC) described herein. In specific embodiments of a protein-drug conjugate, wherein the binding agent is an antibody, (e.g., a monoclonal antibody), the term "antibody drug conjugate" or ADC is optionally used.

According to the present disclosure, a protein-payload conjugate compound is provided comprising the components as illustrated in the structure according to Formula (A):

(A)

wherein: BA is a binding agent as described herein; Gln is a glutamine residue; Z comprises a Diels-Alder adduct as described herein; D is a therapeutic moiety or an imaging agent moiety as described herein, n is an integer from 1 to 4, and d is an integer from 1 to 10. In certain embodiments, the protein-drug conjugate compound of Formula A can also include additional linkers and spacers known to practitioners in the art.

Generally, the Diels-Alder reaction is a chemical reaction between a conjugated diene and an alkene or alkyne, commonly termed a dienophile (also spelled dienophile), to form a cyclohexene derivative, also referred to herein as a "Diels-Alder adduct".

While not being bound by theory, the Diels-Alder reaction is considered a [4+2]-cycloaddition of a conjugated diene and a dienophile (an alkene or alkyne), an electrocyclic reaction that involves the 4 π-electrons of the diene and 2 π-electrons of the dienophile. The driving force of the reaction is thought to be the formation of new σ-bonds, which are energetically more stable than the π-bonds. A non-limiting example of the Diels-Alder reaction and the resulting adduct is illustrated in Scheme I, below.

Scheme I

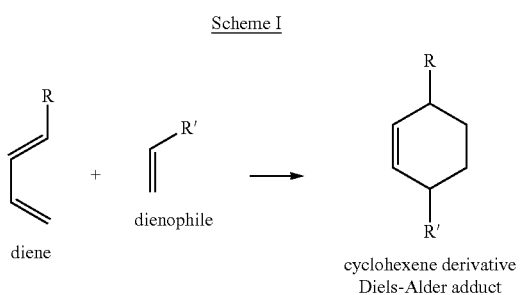

diene  dienophile  cyclohexene derivative Diels-Alder adduct

The term "Diels-Alder adduct," Z, of the present disclosure encompasses any divalent cyclohexene derivative, independent of the synthetic steps taken to produce the substituted cyclohexene derivative. That is to say, the Diels-Alder adduct term as used herein is not limited to the literal product of the Diels-Alder reaction, but includes structures that could be produced (or would be expected to be produced) by the Diels-Alder reaction.

In certain embodiments, Diels-Alder Adduct Z comprises a moiety according to formula 1 or 2:

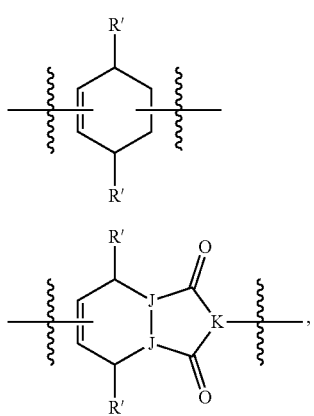

wherein R' are independently at each occurrence H, $C_{1-3}$ alkyl, or two R' together constitute a CHR, $(CHR)_2$, or O bridge; J is independently at each occurrence CH or N; and K is N,

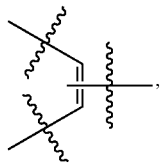

or NH—N; and R is independently at each occurrence H or an electron donating group.

In certain embodiments, the present disclosure provides a protein-drug conjugate compound having the structure according to Formula (I):

$$BA\!-\!\![Gln\!-\!NH\!-\!SP\!-\!(Z\!-\!L\!-\!D)_n]_d, \quad (I)$$

wherein: BA is a binding agent as described herein; Gln is a glutamine residue; SP is an optional spacer as described herein; Z comprises a Diels-Alder adduct as described herein; L is a linker according to the present disclosure; D is a therapeutic and/or imaging agent moiety as described herein, n is an integer from 1 to 4, and d is an integer from 1 to 10.

In certain embodiments, the present disclosure provides a protein-drug conjugate compound having the structure according to Formula (IA):

$$BA\!-\!\![Gln\!-\!NH\!-\!SP\!-\!Z\!-\!L\!-\!D]_d, \quad (IA)$$

wherein: BA is a binding agent as described herein; Gln is a glutamine residue; SP is an optional spacer as described herein; Z comprises a Diels-Alder adduct as described herein; L is a linker according to the present disclosure; D is a therapeutic and/or imaging agent moiety as described herein, and d is an integer from 1 to 10.

In certain embodiments, the present disclosure provides a protein-drug conjugate compound having the structure according to Formula (II):

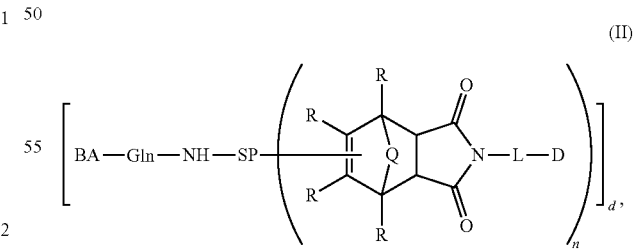

wherein: BA is a binding agent as described herein; Gln is a glutamine residue; SP is absent or a spacer as described herein; Q a CHR, $(CHR)_2$, or O bridge; R is independently at each occurrence H or an electron donating group; L is a linker according to the present disclosure; D is a therapeutic and/or imaging agent moiety as described herein, n is an integer from 1 to 4, and d is an integer from 1 to 10.

In certain embodiments, the present disclosure provides a protein-drug conjugate compound having the structure according to Formula (II):

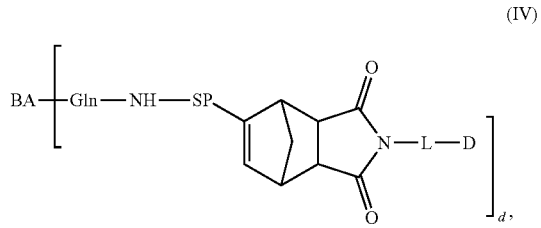

(IV)

wherein: BA is a binding agent as described herein; Gln is a glutamine residue; SP is absent or a spacer as described herein; L is a linker according to the present disclosure; D is a therapeutic and/or imaging agent moiety as described herein, and d is an integer from 1 to 10.

Binding Agents

In one embodiment, the effectiveness of the protein-drug conjugate embodiments described herein depend on the selectivity of the binding agent to bind its binding partner. In one embodiment of the present disclosure, the binding agent is any molecule capable of binding with some specificity to a given binding partner. In one embodiment, the binding agent is within a mammal where the interaction can result in a therapeutic use. In an alternative embodiment, the binding agent is in vitro where the interaction can result in a diagnostic use. In some aspects, the binding agent is capable of binding to a cell or cell population.

Suitable binding agents of the present disclosure include proteins that bind to a binding partner, wherein the binding agent comprises one or more glutamine residues. Suitable binding agents include, but are not limited to, antibodies, lymphokines, hormones, growth factors, viral receptors, interleukins, or any other cell binding or peptide binding molecules or substances.

In one embodiment the binding agent is an antibody. In certain embodiments, the antibody is selected from monoclonal antibodies, polyclonal antibodies, antibody fragments (Fab, Fab', and F(ab)2, minibodies, diabodies, tribodies, and the like). Antibodies herein can be humanized using methods described in U.S. Pat. No. 6,596,541 and US Publication No. 2012/0096572, each incorporated by reference in their entirety. In certain embodiments of the protein-drug conjugate compounds of the present disclosure, BA is a humanized monoclonal antibody. For example, BA can be a monoclonal antibody that binds HER2 or MSR1.

In the present disclosure, the antibody can be any antibody deemed suitable to the practitioner of skill. In some embodiments, the antibody comprises at least one glutamine residue in at least one polypeptide chain sequence. In certain embodiments, the antibody comprises one or more Gln295 residues. In certain embodiments, the antibody comprises two heavy chain polypeptides, each with one Gln295 residue. In further embodiments, the antibody comprises one or more glutamine residues at a site other than a heavy chain 295. Such antibodies can be isolated from natural sources or engineered to comprise one or more glutamine residues. Techniques for engineering glutamine residues into an antibody polypeptide chain are within the skill of the practitioners in the art. In certain embodiments, the antibody is aglycosylated.

The antibody can be in any form known to those of skill in the art. In certain embodiments, the antibody comprises a light chain. In certain embodiments, the light chain is a kappa light chain. In certain embodiments, the light chain is a lambda light chain.

In certain embodiments, the antibody comprises a heavy chain. In some aspects, the heavy chain is an IgA. In some aspects, the heavy chain is an IgD. In some aspects, the heavy chain is an IgE. In some aspects, the heavy chain is an IgG. In some aspects, the heavy chain is an IgM. In some aspects, the heavy chain is an IgG1. In some aspects, the heavy chain is an IgG2. In some aspects, the heavy chain is an IgG3. In some aspects, the heavy chain is an IgG4. In some aspects, the heavy chain is an IgA1. In some aspects, the heavy chain is an IgA2.

In some embodiments, the antibody is an antibody fragment. In some aspects, the antibody fragment is an Fv fragment. In some aspects, the antibody fragment is a Fab fragment. In some aspects, the antibody fragment is a F(ab')2 fragment. In some aspects, the antibody fragment is a Fab' fragment. In some aspects, the antibody fragment is an scFv (sFv) fragment. In some aspects, the antibody fragment is an scFv-Fc fragment.

In some embodiments, the antibody is a monoclonal antibody. In some embodiments, the antibody is a polyclonal antibody.

In some embodiments, the antibody is a chimeric antibody. In some embodiments, the antibody is a humanized antibody. In some embodiments, the antibody is a human antibody.

The antibody can have binding specificity for any antigen deemed suitable to those of skill in the art. In certain embodiments, the antigen is a transmembrane molecule (e.g., receptor) or a growth factor. Exemplary antigens include, but are not limited to, molecules such as renin; a growth hormone, including human growth hormone and bovine growth hormone; growth hormone releasing factor; parathyroid hormone; thyroid stimulating hormone; lipoproteins; alpha1-antitrypsin; insulin A-chain; insulin B-chain; proinsulin; follicle stimulating hormone; calcitonin; luteinizing hormone; glucagon; clotting factors such as factor vmc, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-I-alpha); a serum albumin, such as human serum albumin; Muellerian-inhibiting substance; relaxin A-chain; relaxin B-chain; prorelaxin; mouse gonadotropin-associated peptide; a microbial protein, such as beta-lactamase; DNase; 19E; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-β; platelet-derived growth factor (PDGF); fibroblast growth factor such as aFGF and bFGF; fibroblast growth factor receptor 2 (FGFR2), epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -2 (IGF-I and IGF-2); des(I-3)-IGF-I (brain IGF-I), insulin-like growth factor binding proteins, EpCAM, GD3, FLT3, PSMA, PSCA, MUCI, MUCI6, STEAP, CEA, TENB2, EphA receptors, EphB receptors, folate receptor, FOLRI, mesothelin, cripto, alphavbeta6, integrins, VEGF, VEGFR, EGFR, transferrin receptor, IRTAI, IRTA2, IRTA3, IRTA4, IRTA5; CD proteins such as CD2, CD3, CD4, CD5, CD6, CD8, CDII, CDI4, CDI9, CD20, CD21, CD22, CD25, CD26, CD28, CD30, CD33, CD36, CD37, CD38, CD40, CD44, CD52, CD55, CD56, CD59, CD70, CD79, CD80, CD81, CD103, CD105, CD134, CD137, CD138, CDI52, or an antibody which binds to one or more tumor-associated antigens or cell-surface receptors disclosed in US Publication No. 2008/0171040 or US Publication No. 2008/0305044 and incorporated in their entirety by reference; erythropoietin; osteoinductive factors; immunotoxins; a bone morphogenetic protein (BMP); an interferon, such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the HIV envelope; transport proteins; homing receptors; addressins; regulatory proteins; integrins, such as CDIIa, CDIIb, CDIIc, CDI8, an ICAM, VLA-4 and VCAM; a tumor associated antigen such as AFP, ALK, B7H4, BAGE proteins, β-catenin, brc-abl, BRCA1, BORIS, CA9 (carbonic anhydrase IX), caspase-8, CD20, CD40, CD123, CDK4, CEA, CLEC12A, c-kit, cMET, CTLA4, cyclin-B1, CYP1B1, EGFR, EGFRvIII, endoglin, Epcam, EphA2, ErbB2/Her2, ErbB3/Her3, ErbB4/Her4, ETV6-AML, Fra-1, FOLR1, GAGE proteins (e.g., GAGE-1, -2), GD2, GD3, GloboH, glypican-3, GM3, gp100, Her2, HLA/B-raf, HLA/EBNA1, HLA/k-ras, HLA/MAGE-A3, hTERT, IGF1R, LGR5, LMP2, MAGE proteins (e.g., MAGE-1, -2, -3, -4, -6, and -12), MART-1, mesothelin, ML-IAP, Muc1, Muc16 (CA-125), MUM1, NA17, NGEP, NY-BR1, NY-BR62, NY-BR85, NY-ESO1, OX40, p15, p53, PAP, PAX3, PAX5, PCTA-1, PDGFR-α, PDGFR-β, PDGF-A, PDGF-B, PDGF-C, PDGF-D, PLAC1, PRLR, PRAME, PSCA, PSGR, PSMA (FOLH1), RAGE proteins, Ras, RGS5, Rho, SART-1, SART-3, STEAP1, STEAP2, STn, survivin, TAG-72, TGF-β, TMPRSS2, Tn, TNFRSF17, TRP-1, TRP-2, tyrosinase, and uroplakin-3, and fragments of any of the herein-listed polypeptides.

Exemplary antigens also include, but are not limited to, BCMA, SLAMF7, B7H4, GPNMB, UPK3A, and LGR5. Exemplary antigens also include, but are not limited to, MUC16, PSMA, STEAP2, and HER2.

In some embodiments, the antigens include prolactin receptor (PRLR) or prostate-specific membrane antigen (PSMA). In some embodiments, the antigens include MUC16. In some embodiments, the antigens include STEAP2. In some embodiments, the antigens include PSMA. In some embodiments, the antigens include HER2. In some embodiments, the antigen is prolactin receptor (PRLR) or prostate-specific membrane antigen (PSMA). In some embodiments, the antigen is MUC16. In some embodiments, the antigens include PSMA. In some embodiments, the antigen is HER2. In some embodiments, the antigen is STEAP2.

Binding agents also include ankyrin repeat proteins, interferons, lymphokines such as IL-2 or IL-3, hormones like insulin and glucocorticoids, growth factors such as EGF, transferrin, fibronectin type III, etc.

Some embodiments herein are target specific for therapeutic or diagnostic use. In one embodiment, binding agents are prepared to interact with and bind to antigens defined as tumor antigens, which include antigens specific for a type of tumor or antigens that are shared, overexpressed or modified on a particular type of tumor. Examples include: alpha-actinin-4 with lung cancer, ARTC1 with melanoma, BCR-ABL fusion protein with chronic myeloid leukemia, B-RAF, CLPP or Cdc27 with melanoma, CASP-8 with squamous cell carcinoma, and hsp70-2 with renal cell carcinoma as well as the following shared tumor-specific antigens, for example: BAGE-1, GAGE, GnTV, KK-LC-1, MAGE-A2, NA88-A, TRP2-INT2. In some embodiments, the antigen is PRLR or HER2. In some embodiments, the antibody binds STEAP2, MUC16, EGFR, EGFRVIII, FGR2, or PRLR.

Anti-HER2 Antibodies Suitable for Protein-Drug Conjugates

In some embodiments, the antibody is an anti HER2 antibody. In some embodiments, the antibody is trastuzumab, pertuzumab (2C4) or margetuximab (MGAH22). In some embodiment, the antibody is trastuzumab. According to certain embodiments, protein-drug conjugates, e.g., ADCs, according to the disclosure comprise anti-HER2 antibody. In some embodiment, the antibody binds HER2, including those described in WO 2019/212965 A1.

Anti-MSR1 Antibodies Suitable for Protein-Drug Conjugates

A protein-drug conjugate according to the present disclosure optionally comprises an anti-MSR1 antibody, e.g., full-length (for example, an IgG1 or IgG4 antibody), or an antigen-binding portion (for example, a Fab, F(ab')2 or scFv fragment), and is optionally modified to affect functionality, e.g., to eliminate residual effector functions (Reddy et al., 2000, *J. Immunol.* 164:1925-1933).

Embodiments of antibody-drug conjugates described herein can comprise anti-MSR1 antibodies listed in Tables 1 and 2. Table 1 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the exemplary anti-MSR1 antibodies. Table 2 sets forth the nucleic acid sequence identifiers of the HCVRs, LCVRs, HCDR1, HCDR2 HCDR3, LCDR1, LCDR2 and LCDR3 of the exemplary anti-MSR1 antibodies.

Further suitable antibodies or antigen-binding fragments thereof that specifically bind MSR1 comprise an HCVR and an LCVR amino acid sequence pair (HCVR/LCVR) comprising any of the HCVR amino acid sequences listed in Table 1 paired with any of the LCVR amino acid sequences listed in Table 1. Certain embodiments relate to antibody-drug conjugates comprising antibodies, or antigen-binding fragments thereof, comprising an HCVR/LCVR amino acid sequence pair contained within any of the exemplary anti-MSR1 antibodies listed in Table 1. In some embodiments, the HCVR/LCVR amino acid sequence pair is selected from the group consisting of: 2/10, 23/42, 50/58; 90/98, and 282/290.

Suitable antibodies or antigen-binding fragments thereof for the antibody-drug conjugates described herein include those that specifically bind MSR1 and comprise a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

Further suitable antibodies or antigen-binding fragments thereof that specifically bind MSR1 comprise a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

Further suitable antibodies or antigen-binding fragments thereof that specifically bind MSR1 comprise a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

Suitable antibodies or antigen-binding fragments thereof for the antibody-drug conjugates described herein include those that specifically bind MSR1 and comprise a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

Further suitable antibodies or antigen-binding fragments thereof that specifically bind MSR1 comprise a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

Further suitable antibodies or antigen-binding fragments thereof that specifically bind MSR1 comprise a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

Further suitable antibodies or antigen-binding fragments thereof that specifically bind MSR1 comprise an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. Certain embodiments relate to antibodies, or antigen-binding fragments thereof, comprising an HCDR3/LCDR3 amino acid sequence pair contained within any of the exemplary anti-MSR1 antibodies listed in Table 1. In some embodiments, the HCDR3/LCDR3 amino acid sequence pair is selected from the group consisting of: 8/16, 40/48, 56/64; 96/104, and 288/296.

Suitable antibodies or antigen-binding fragments thereof for the antibody-drug conjugates described herein include those that specifically bind MSR1 and comprise a set of six CDRs (i.e., HCDR1-HCDR2-HCDR3-LCDR1-LCDR2-LCDR3) contained within any of the exemplary anti-MSR1 antibodies listed in Table 1. In certain embodiments, the HCDR1-HCDR2-HCDR3-LCDR1-LCDR2-LCDR3 amino acid sequences set is selected from the group consisting of: 4-6-8-12-14-16; 36-38-40-44-46-48; 52-54-56-60-62-64; 92-94-96-100-102-104, and 284-286-288-292-294-296.

In a related embodiment, suitable antibodies, or antigen-binding fragments thereof that specifically bind MSR1 comprise a set of six CDRs (i.e., HCDR1-HCDR2-HCDR3-LCDR1-LCDR2-LCDR3) contained within an HCVR/LCVR amino acid sequence pair as defined by any of the exemplary anti-MSR1 antibodies listed in Table 1. For example, the present disclosure includes suitable antibodies or antigen-binding fragments thereof that specifically bind MSR1 and comprise the HCDR1-HCDR2-HCDR3-LCDR1-LCDR2-LCDR3 amino acid sequences set contained within an HCVR/LCVR amino acid sequence pair selected from the group consisting of: 2/10, 23/42, 50/58, 90/98, and 282/290. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

Also provided herein are nucleic acid molecules encoding anti-MSR1 antibodies or portions thereof for the preparation of antibody-drug conjugates described herein. For example, provided herein are nucleic acid molecules encoding any of the HCVR amino acid sequences listed in Table 1; in certain embodiments the nucleic acid molecule can comprise a polynucleotide sequence selected from any of the HCVR nucleic acid sequences listed in Table 2, or a substantially similar sequence thereof having at least 90%, at least 95%, at least 98% or at least 99% sequence identity thereto.

Also provided herein are nucleic acid molecules encoding any of the LCVR amino acid sequences listed in Table 1; in certain embodiments the nucleic acid molecule can comprise a polynucleotide sequence selected from any of the LCVR nucleic acid sequences listed in Table 2, or a substantially similar sequence thereof having at least 90%, at least 95%, at least 98% or at least 99% sequence identity thereto.

Also provided herein are nucleic acid molecules encoding any of the HCDR1 amino acid sequences listed in Table 1; in certain embodiments the nucleic acid molecule can comprise a polynucleotide sequence selected from any of the HCDR1 nucleic acid sequences listed in Table 2, or a substantially similar sequence thereof having at least 90%, at least 95%, at least 98% or at least 99% sequence identity thereto.

Also provided herein are nucleic acid molecules encoding any of the HCDR2 amino acid sequences listed in Table 1; in certain embodiments the nucleic acid molecule can comprise a polynucleotide sequence selected from any of the HCDR2 nucleic acid sequences listed in Table 2, or a substantially similar sequence thereof having at least 90%, at least 95%, at least 98% or at least 99% sequence identity thereto.

Also provided herein are nucleic acid molecules encoding any of the HCDR3 amino acid sequences listed in Table 1; in certain embodiments the nucleic acid molecule can comprise a polynucleotide sequence selected from any of the HCDR3 nucleic acid sequences listed in Table 2, or a substantially similar sequence thereof having at least 90%, at least 95%, at least 98% or at least 99% sequence identity thereto.

Also provided herein are nucleic acid molecules encoding any of the LCDR1 amino acid sequences listed in Table 1; in certain embodiments the nucleic acid molecule can comprise a polynucleotide sequence selected from any of the LCDR1 nucleic acid sequences listed in Table 2, or a substantially similar sequence thereof having at least 90%, at least 95%, at least 98% or at least 99% sequence identity thereto.

Also provided herein are nucleic acid molecules encoding any of the LCDR2 amino acid sequences listed in Table 1; in certain embodiments the nucleic acid molecule can comprise a polynucleotide sequence selected from any of the LCDR2 nucleic acid sequences listed in Table 2, or a substantially similar sequence thereof having at least 90%, at least 95%, at least 98% or at least 99% sequence identity thereto.

Also provided herein are nucleic acid molecules encoding any of the LCDR3 amino acid sequences listed in Table 1; in certain embodiments the nucleic acid molecule can comprise a polynucleotide sequence selected from any of the LCDR3 nucleic acid sequences listed in Table 2, or a substantially similar sequence thereof having at least 90%, at least 95%, at least 98% or at least 99% sequence identity thereto.

Also provided herein are nucleic acid molecules encoding an HCVR, wherein the HCVR can comprise a set of three CDRs (i.e., HCDR1-HCDR2-HCDR3), wherein the HCDR1-HCDR2-HCDR3 amino acid sequence set is as defined by any of the exemplary anti-MSR1 antibodies listed in Table 1.

Also provided herein are nucleic acid molecules encoding an LCVR, wherein the LCVR can comprise a set of three CDRs (i.e., LCDR1-LCDR2-LCDR3), wherein the LCDR1-LCDR2-LCDR3 amino acid sequence set is as defined by any of the exemplary anti-MSR1 antibodies listed in Table 1.

Also provided herein are nucleic acid molecules encoding both an HCVR and an LCVR, wherein the HCVR can comprise an amino acid sequence of any of the HCVR amino acid sequences listed in Table 1, and wherein the LCVR can comprise an amino acid sequence of any of the LCVR amino acid sequences listed in Table 1. In certain embodiments, the nucleic acid molecule can comprise a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 2, or a substantially similar sequence thereof having at least 90%, at least 95%, at least 98% or at least 99% sequence identity thereto. In certain embodiments according to this aspect of the disclosure, the nucleic acid molecule encodes an HCVR and LCVR, wherein the HCVR and LCVR are both derived from the same anti-MSR1 antibody listed in Table 1, such as H1H21234N.

Also provided herein are recombinant expression vectors capable of expressing a polypeptide comprising a heavy or light chain variable region of a HER2 or an anti-MSR1 antibody for the preparation of antibody-drug conjugates described herein. For example, embodiments include recombinant expression vectors comprising any of the nucleic acid molecules mentioned herein, i.e., nucleic acid molecules encoding any of the HCVR, LCVR, and/or CDR sequences as set forth in Table 1. Also included within the scope of the present disclosure are host cells into which such vectors have been introduced, as well as methods of producing the antibodies or portions thereof for the preparation of antibody-drug conjugates described herein by culturing the host cells under conditions permitting production of the antibodies or antibody fragments, and recovering the antibodies and antibody fragments so produced.

Suitable anti-MSR1 antibodies for the antibody-drug conjugates described herein include those that have a modified glycosylation pattern. In some embodiments, an antibody is modified to remove undesirable glycosylation sites. In alternative embodiments, an antibody lacks a fucose moiety present on the oligosaccharide chain, for example, to increase antibody dependent cellular cytotoxicity (ADCC) function (see Shield et al. (2002) *JBC* 277:26733). In other embodiments, galactosylation is modified in order to modify complement dependent cytotoxicity (CDC).

According to certain embodiments, antibody-drug conjugates according to the disclosure comprise anti-MSR1 antibodies comprising an Fc domain comprising one or more mutations which enhance or diminish antibody binding to the FcRn receptor, e.g., at acidic pH as compared to neutral pH. For example, provided herein are antibody-drug conjugates comprising anti-MSR1 antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations can result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification can comprise a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, embodiments include antibody-drug conjugates comprising anti-MSR1 antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present disclosure.

Heavy and Light Chain Variable Region Amino Acid and Nucleic Acid Sequences

Table 1 sets forth the amino acid sequence identifiers of the heavy and light chain variable regions and CDRs of selected anti-MSR1 antibodies described herein. The corresponding nucleic acid sequence identifiers are set forth in Table 2.

TABLE 1

Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1H21227N | 2 | 4 | 6 | 8 | 10 | 12 | 14 | 16 |
| H1H21228N | 18 | 20 | 22 | 24 | 26 | 28 | 30 | 32 |
| H1H21231N | 34 | 36 | 38 | 40 | 42 | 44 | 46 | 48 |
| H1H21234N | 50 | 52 | 54 | 56 | 58 | 60 | 62 | 64 |
| H1H21235N | 66 | 68 | 70 | 72 | 74 | 76 | 78 | 80 |
| H1H25685N | 82 | 84 | 86 | 88 | 90 | 92 | 94 | 96 |
| H1H25690N | 98 | 100 | 102 | 104 | 106 | 108 | 110 | 112 |
| H1H25695N | 114 | 116 | 118 | 120 | 122 | 124 | 126 | 128 |
| H1H25700N | 130 | 132 | 134 | 136 | 138 | 140 | 142 | 144 |
| H1H27729P | 146 | 148 | 150 | 152 | 154 | 156 | 158 | 160 |
| H1H27731P | 162 | 164 | 166 | 168 | 170 | 172 | 174 | 176 |
| H1H27732P | 178 | 180 | 182 | 184 | 186 | 188 | 190 | 192 |
| H1H27734P | 194 | 196 | 198 | 200 | 202 | 204 | 206 | 208 |
| H1H27736P | 210 | 212 | 214 | 216 | 218 | 220 | 222 | 224 |
| H1H27739P | 226 | 228 | 230 | 232 | 234 | 236 | 238 | 240 |
| H1H27747P | 242 | 244 | 246 | 248 | 250 | 252 | 254 | 256 |
| H1H27749P | 258 | 260 | 262 | 264 | 266 | 268 | 270 | 272 |
| H1H27751P | 274 | 276 | 278 | 280 | 282 | 284 | 286 | 288 |
| H1H27754P | 290 | 292 | 294 | 296 | 298 | 300 | 302 | 304 |
| H1H27756P | 306 | 308 | 310 | 312 | 314 | 316 | 318 | 320 |
| H1H27760P2 | 322 | 324 | 326 | 328 | 90 | 92 | 94 | 96 |
| H1H27761P2 | 330 | 332 | 334 | 336 | 90 | 92 | 94 | 96 |
| H1H27762P2 | 338 | 340 | 342 | 344 | 90 | 92 | 94 | 96 |
| H1H27766P2 | 346 | 348 | 350 | 352 | 90 | 92 | 94 | 96 |
| H1H27771P2 | 354 | 356 | 358 | 360 | 362 | 364 | 366 | 368 |
| H1xH27759P2 | 370 | 372 | 374 | 376 | 90 | 92 | 94 | 96 |
| H1xH27773P2 | 378 | 380 | 382 | 384 | 362 | 364 | 366 | 368 |
| H1xH27778P2 | 386 | 388 | 390 | 392 | 362 | 364 | 366 | 368 |
| H1xH29273P2 | 394 | 396 | 397 | 400 | 90 | 92 | 94 | 96 |
| H1xH29282P2 | 402 | 404 | 406 | 408 | 90 | 92 | 94 | 96 |
| H1xH29283P2 | 410 | 412 | 414 | 416 | 90 | 92 | 94 | 96 |
| H2M21229N | 420 | 422 | 424 | 426 | 428 | 430 | 432 | 434 |
| H2M21230N | 436 | 438 | 440 | 442 | 444 | 446 | 448 | 450 |
| H2M21232N | 452 | 454 | 456 | 458 | 460 | 462 | 464 | 466 |

TABLE 2

Nucleic Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1H21227N | 1 | 3 | 5 | 7 | 9 | 11 | 13 | 15 |
| H1H21228N | 17 | 19 | 21 | 23 | 25 | 27 | 29 | 31 |
| H1H21231N | 33 | 35 | 37 | 39 | 41 | 43 | 45 | 47 |
| H1H21234N | 49 | 51 | 53 | 55 | 57 | 59 | 61 | 63 |
| H1H21235N | 65 | 67 | 69 | 71 | 73 | 75 | 77 | 79 |
| H1H25685N | 81 | 83 | 85 | 87 | 89 | 91 | 93 | 95 |
| H1H25690N | 97 | 99 | 101 | 103 | 105 | 107 | 109 | 111 |
| H1H25695N | 113 | 115 | 117 | 119 | 121 | 123 | 125 | 127 |
| H1H25700N | 129 | 131 | 133 | 135 | 137 | 139 | 141 | 143 |
| H1H27729P | 145 | 147 | 149 | 151 | 153 | 155 | 157 | 159 |
| H1H27731P | 161 | 163 | 165 | 167 | 169 | 171 | 173 | 175 |
| H1H27732P | 177 | 179 | 181 | 183 | 185 | 187 | 189 | 191 |
| H1H27734P | 193 | 195 | 197 | 199 | 201 | 203 | 205 | 207 |
| H1H27736P | 209 | 211 | 213 | 215 | 217 | 219 | 221 | 223 |
| H1H27739P | 225 | 227 | 229 | 231 | 233 | 235 | 237 | 239 |
| H1H27747P | 241 | 243 | 245 | 247 | 249 | 251 | 253 | 255 |
| H1H27749P | 257 | 259 | 261 | 263 | 265 | 267 | 269 | 271 |
| H1H27751P | 273 | 275 | 277 | 279 | 281 | 283 | 285 | 287 |
| H1H27754P | 289 | 291 | 293 | 295 | 297 | 299 | 301 | 303 |
| H1H27756P | 305 | 307 | 309 | 311 | 313 | 315 | 317 | 319 |
| H1H27760P2 | 321 | 323 | 325 | 327 | 89 | 91 | 93 | 95 |
| H1H27761P2 | 329 | 331 | 333 | 335 | 89 | 91 | 93 | 95 |
| H1H27762P2 | 337 | 339 | 341 | 343 | 89 | 91 | 93 | 95 |
| H1H27766P2 | 345 | 347 | 349 | 351 | 89 | 91 | 93 | 95 |
| H1H27771P2 | 353 | 355 | 357 | 359 | 361 | 363 | 365 | 367 |
| H1xH27759P2 | 369 | 371 | 373 | 375 | 89 | 91 | 93 | 95 |
| H1xH27773P2 | 377 | 379 | 381 | 383 | 361 | 363 | 365 | 367 |

TABLE 2-continued

Nucleic Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1xH27778P2 | 385 | 387 | 389 | 391 | 361 | 363 | 365 | 367 |
| H1xH29273P2 | 393 | 395 | 397 | 399 | 89 | 91 | 93 | 95 |
| H1xH29282P2 | 401 | 403 | 405 | 407 | 89 | 91 | 93 | 95 |
| H1xH29283P2 | 409 | 411 | 413 | 415 | 89 | 91 | 93 | 95 |
| H2M21229N | 419 | 421 | 423 | 425 | 427 | 429 | 431 | 433 |
| H2M21230N | 435 | 437 | 439 | 441 | 443 | 445 | 447 | 449 |
| H2M21232N | 451 | 453 | 455 | 457 | 459 | 461 | 463 | 465 |

Antibodies are typically referred to herein according to the following nomenclature: Fc prefix (e.g. "H1H," "H2aM," etc.), followed by a numerical identifier (e.g. "21227," "21228," "21231," etc.), followed by a "P," "N," or "P2" suffix, as shown in Tables 1 and 2. Thus, according to this nomenclature, an antibody can be referred to herein as, e.g., "H1H21227N," "H2aM21228N," "H1H27729P," "H1H27760P2," etc. The prefix on the antibody designations used herein indicate the particular Fc region isotype of the antibody. In particular, an "H1H" antibody has a human IgG1 Fc (all variable regions are fully human as denoted by the first 'H' in the antibody designation), while an "H2aM" antibody has a mouse IgG2a Fc. As will be appreciated by a person of ordinary skill in the art, an antibody having a particular Fc isotype can be converted to an antibody with a different Fc isotype (e.g., an antibody with a mouse IgG4 Fc can be converted to an antibody with a human IgG1, etc.), but in any event, the variable domains (including the CDRs)—which are indicated by the numerical identifiers shown in Tables 1 and 2—will remain the same, and the binding properties are expected to be identical or substantially similar regardless of the nature of the Fc domain.

Antibody Modifications. The anti-MSR1 antibodies described in herein (e.g., H1H21234N) were produced with the original human Fcγ portion, as well as a version with an N297Q single point mutation for all three anti-MSR1 antibodies. All other antibodies described herein were made with an N297Q single point mutation in human Fcγ portion.

In some embodiments, the protein drug conjugates are produced in accordance with known methods to yield conjugates, comprising the components as illustrated in the structure according to Formula (B):

BA―[Z―D]$_d$, (B)

wherein: BA is a binding agent as described herein; Z comprises a Diels-Alder adduct as described herein; D is a therapeutic and/or imaging agent moiety as described herein, and d is an integer from 1 to 10. In certain embodiments, the protein-drug conjugate compound of Formula B can also include additional linkers and spacers known to practitioners in the art.

In certain embodiments, the present disclosure provides a protein-drug conjugate compound having the structure according to Formula (BI):

BA―[SP―Z―L―D]$_d$, (BI)

wherein: BA is a binding agent as described herein; SP is an optional spacer as described herein; Z comprises a Diels-Alder adduct as described herein; L is a linker according to the present disclosure; D is a therapeutic and/or imaging agent moiety as described herein, and d is an integer from 1 to 10.

In certain embodiments, the present disclosure provides a protein-drug conjugate compound having the structure according to Formula (BII):

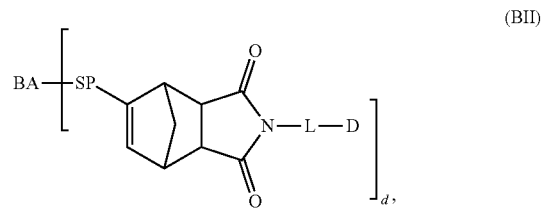

(BII)

wherein: BA is a binding agent as described herein; SP is absent or a spacer as described herein; L is a linker according to the present disclosure; D is a therapeutic and/or imaging agent moiety as described herein, and d is an integer from 1 to 10.

Techniques and linkers for conjugating to residues of an antibody or antigen binding fragment are known in the art. Exemplary amino acid attachments that can be used in the context of this aspect, e.g., lysine (see, e.g., U.S. Pat. No. 5,208,020; US 2010/0129314; Hollander et al., *Bioconjugate Chem.*, 2008, 19:358-361; WO 2005/089808; U.S. Pat. No. 5,714,586; US 2013/0101546; and US 2012/0585592), cysteine (see, e.g., US 2007/0258987; WO 2013/055993; WO 2013/055990; WO 2013/053873; WO 2013/053872; WO 2011/130598; US 2013/0101546; and U.S. Pat. No. 7,750,116), selenocysteine (see, e.g., WO 2008/122039; and Hofer et al., *Proc. Natl. Acad. Sci., USA*, 2008, 105:12451-12456), formyl glycine (see, e.g., Carrico et al., *Nat. Chem. Biol.*, 2007, 3:321-322; Agarwal et al., *Proc. Natl. Acad. Sci., USA*, 2013, 110:46-51, and Rabuka et al., *Nat. Protocols*, 2012, 10:1052-1067), non-natural amino acids (see, e.g., WO 2013/068874, and WO 2012/166559), and acidic amino acids (see, e.g., WO 2012/05982). Lysine conjugation can also proceed through NHS (N-hydroxy succinimide). Linkers can also be conjugated to cysteine residues, including cysteine residues of a cleaved interchain disulfide bond, by forming a carbon bridge between thiols (see, e.g., U.S. Pat. Nos. 9,951,141, and 9,950,076). Linkers can also be conjugated to an antigen-binding protein via attachment to carbohydrates (see, e.g., US 2008/0305497, WO 2014/065661, and Ryan et al., *Food & Agriculture Immunol.*, 2001, 13:127-130) and disulfide linkers (see, e.g., WO 2013/085925, WO 2010/010324, WO 2011/018611, and Shaunak et al., *Nat. Chem. Biol.*, 2006, 2:312-313). Site specific conjugation techniques can also be employed to direct conjugation to particular residues of the antibody or antigen binding protein (see, e.g., Schumacher et al. *J Clin Immunol* (2016) 36 (Suppl 1): 100). In specific embodiments discussed in more detail below, Site specific conjugation techniques, include glutamine conjugation via transglutaminase (see e.g., Schibli, Angew Chemie Inter Ed. 2010, 49, 9995).

Transglutaminase Mediated Site Specific Conjugation

In some embodiments, the protein drug conjugates are produced in accordance with known methods to provide glutaminyl modified proteins. Techniques for conjugating the primary amine compounds are known in the art. Site specific conjugation techniques are employed herein to direct conjugation to glutamine using glutamine conjugation via transglutaminase (see e.g., Schibli, *Angew Chemie* Inter Ed. 2010, 49, 9995).

Primary amine-comprising compounds of the present disclosure can be conjugated to one or more glutamine residues via transglutaminase-based chemo-enzymatic conjugation (see, e.g., Dennler et al., *Protein Conjugate Chem.* 2014, 25, 569-578, and WO 2017/147542). For example, in the presence of transglutaminase, one or more glutamine residues of an antibody can be coupled to a primary amine linker compound. Briefly, in some embodiments, a binding agent having a glutamine residue (e.g., a Gln295, i.e. Q295 residue) is treated with a primary amine compound, described in more detail below, in the presence of the enzyme transglutaminase. In certain embodiments, the binding agent is aglycosylated. In certain embodiments, the binding agent is deglycosylated.

In certain embodiments, the binding agent comprises at least one glutamine residue in at least one polypeptide chain sequence. In certain embodiments, the binding agent comprises two heavy chain polypeptides, each with one Gln295 residue. In further embodiments, the binding agent comprises one or more glutamine residues at a site other than a heavy chain 295. In some embodiments, a binding agent, such as an antibody, can be prepared by site-directed mutagenesis to insert a glutamine residue at a site without resulting in disabled antibody function or binding. For example, included herein are antibodies bearing Asn297Gln (N297Q) mutation(s) as described herein. In some embodiments, an antibody having a Gln295 residue and/or an N297Q mutation contains one or more additional naturally occurring glutamine residues in their variable regions, which can be accessible to transglutaminase and therefore capable of conjugation to a linker or a linker-payload. An exemplary naturally occurring glutamine residue can be found, e.g., at Q55 of the light chain. In such instances, the binding agent, e.g., antibody, conjugated via transglutaminase can have a higher than expected DAR value (e.g., a DAR higher than 4). Any such antibodies can be isolated from natural or artificial sources.

In certain embodiments of the disclosure, the DAR is from 1, 2, 3, 4, 5, 6, 7, or 8 drug molecules per antibody. In some embodiments, the DAR is from 1 to 8. In some embodiments, the DAR is from 1 to 6. In certain embodiments, the DAR is from 2 to 4. In some cases, the DAR is from 2 to 3. In certain cases, the DAR is from 0.5 to 3.5. In some embodiments, the DAR is about 1, or about 1.5, or about 2, or about 2.5, or about 3, or about 3.5.

Primary Amine Compounds

The primary amine compound useful for the transglutaminase mediated coupling of a binding agent (e.g., an antibody or antigen binding compound) comprising a glutamine residue can be any primary amine deemed useful by the practitioner of ordinary skill.

Reactive Primary Amine Compounds

In certain embodiments, the primary amine compound comprises a reactive group capable of further reaction after transglutamination. In these embodiments, the glutaminyl-modified protein (e.g., antibody) is capable of further reaction with a reactive payload compound or a reactive linker-payload compound, as disclosed herein, to form a protein-payload conjugate. More specifically, the reactive payload compound or the reactive linker-payload compound comprise a reactive group that is capable of reacting with the reactive group of the primary amine compound. In certain embodiments, a reactive group according to the present disclosure comprises a moiety that is capable of undergoing a Diels-Alder cycloaddition. In certain embodiments, the reactive group is a diene. In certain embodiments, the reactive group is a dienophile. In certain embodiments of the present disclosure a reactive group is compatible with the binding agent and transglutamination reaction conditions.

In certain embodiments according to the present disclosure, a reactive primary amine compound, $NH_2$—SP—W, is provided, wherein SP is optional and comprises a spacer; and W comprises a diene or a dienophile. In certain embodiments, W comprises a diene (X) or a dienophile (Y) as defined herein.

Diene, X

Certain embodiments of the present disclosure comprise a diene moiety X according to formula 3 or 4 below:

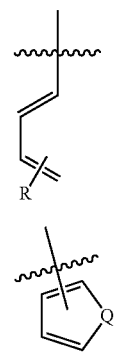

wherein R is H or $C_{1-3}$ alkyl; and Q is $CH_2$, $CH_2CH_2$, or O.

Certain embodiments of the present disclosure comprise a diene moiety X according to a structure selected from:

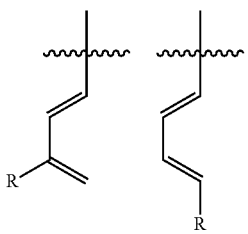

wherein R is H or an electron donating group.

Certain non-limiting embodiments of the present disclosure comprise a diene moiety X according to a structure selected from:

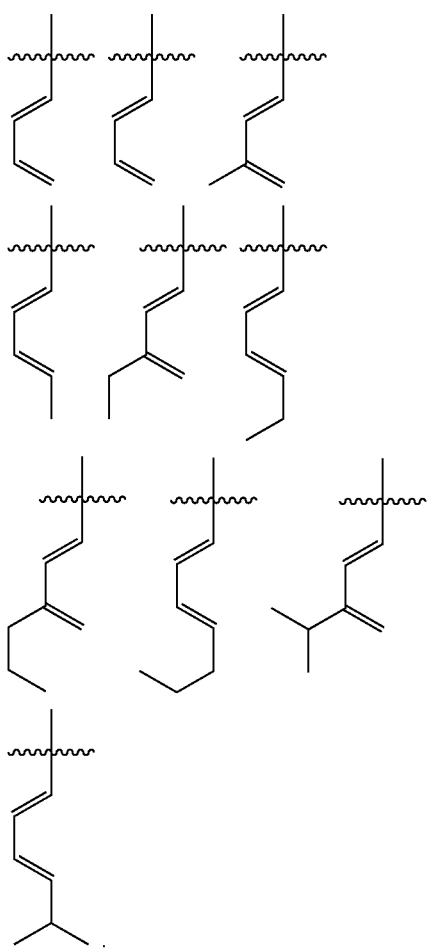

Certain embodiments of the present disclosure comprise a diene moiety X according to a structure selected from:

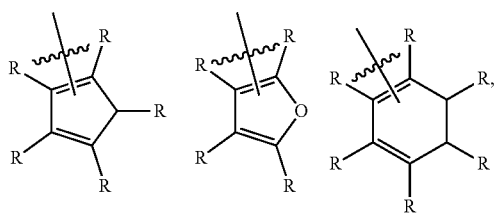

wherein R is independently at each occurrence H or an electron donating group.

Certain embodiments of the present disclosure comprise a diene moiety X according to a structure selected from:

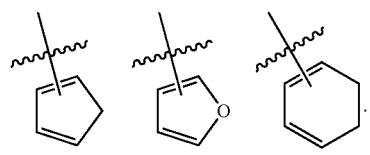

Certain embodiments of the present disclosure comprise a diene moiety X according to a structure selected from:

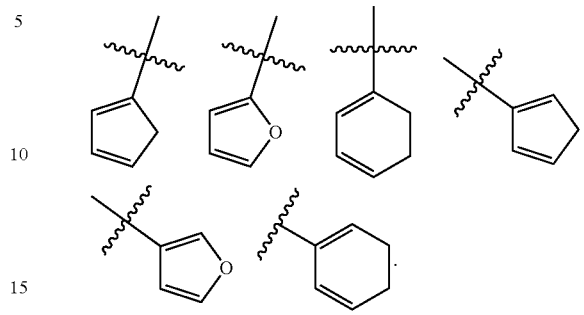

Certain embodiments of the present disclosure comprise cyclopentadiene or methyl-substituted cyclopentadiene, according to one of the structures below:

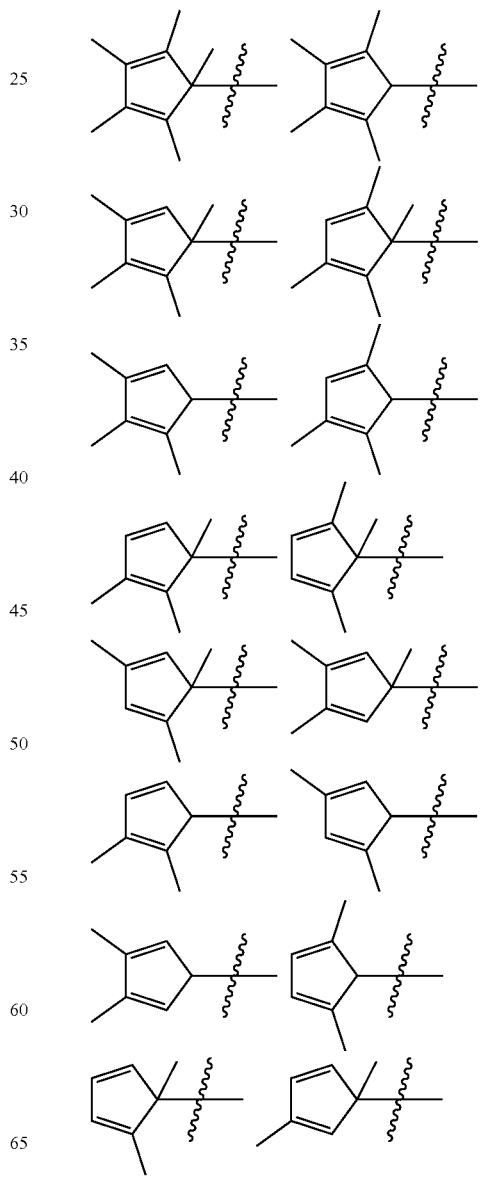

-continued

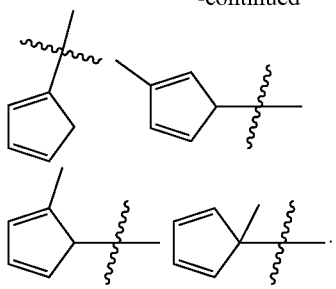

In embodiments according to the present disclosure, a reactive primary amine compound NH$_2$—SP—X is provided, wherein SP is optional and comprises a spacer; and X is a moiety that comprises a diene.

In certain embodiments according to the present disclosure, a reactive primary amine compound according to the following structures is provided:

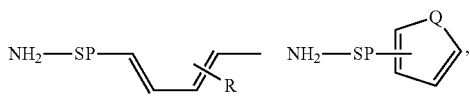

wherein R is H or C$_{1-3}$ alkyl; and Q is CH$_2$, CH$_2$CH$_2$, or O.

In certain embodiments according to the present disclosure, a reactive primary amine compound according to the following structures is provided:

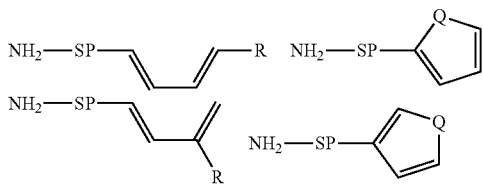

wherein R is H or C$_{1-3}$ alkyl, and Q is CH$_2$, CH$_2$CH$_2$, or O.

In certain embodiments according to the present disclosure, a reactive primary amine compound according to the following structures is provided:

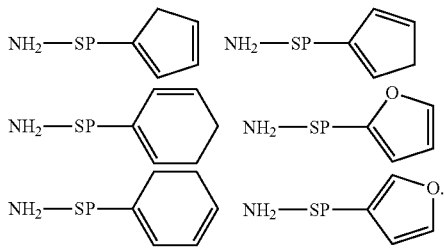

In certain embodiments, the reactive primary amine compound is according to one of the following structures, or is a mixture thereof:

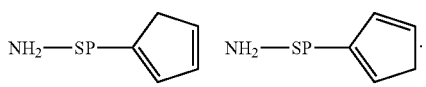

Dienophile, Y

Certain embodiments of the present disclosure comprise a dienophile moiety Y according to formula 5 or 6 below:

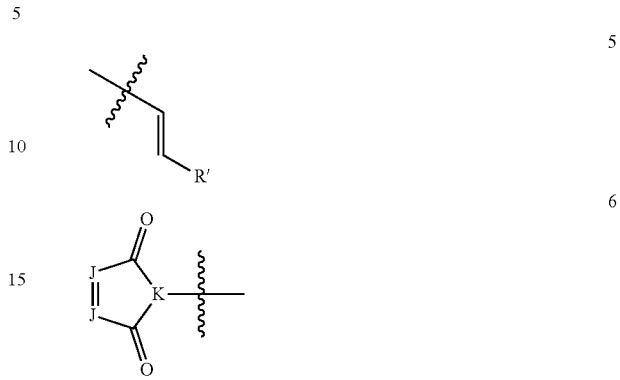

wherein: R' is H or C$_{1-3}$ alkyl; J is independently at each occurrence CH or N; and K is CH, N,

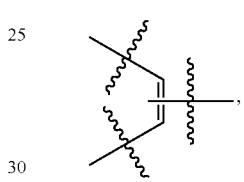

or NH—N.

Certain non-limiting embodiments of the present disclosure comprise a dienophile moiety Y according to one of the following structures:

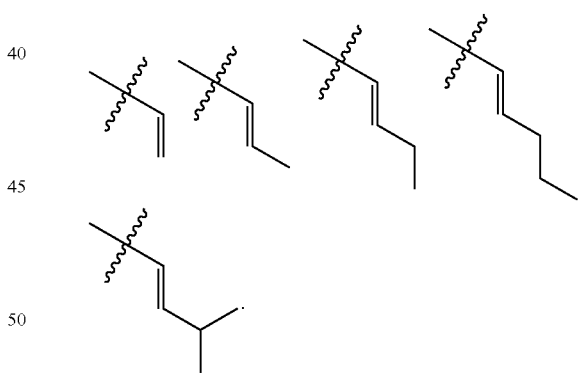

Certain embodiments of the present disclosure comprise a dienophile moiety Y according to one of the following structures:

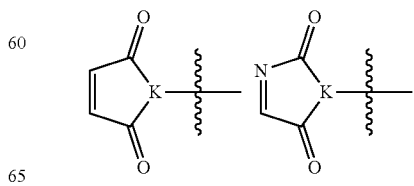

wherein K is CH, N,

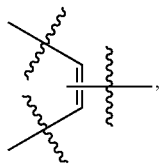

or NH—N.

Certain embodiments of the present disclosure comprise a dienophile moiety Y according to one of the following structures:

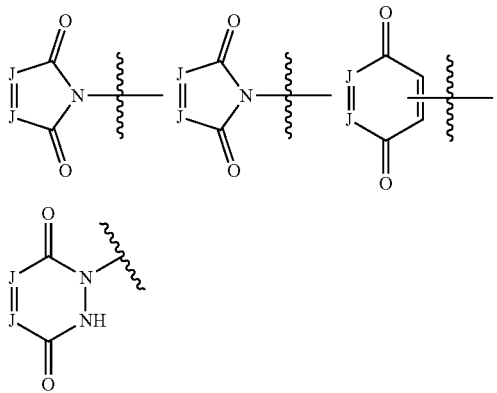

wherein: J is independently at each occurrence CH or N.

Certain non-limiting embodiments of the present disclosure comprise a dienophile moiety Y according to one of the following structures:

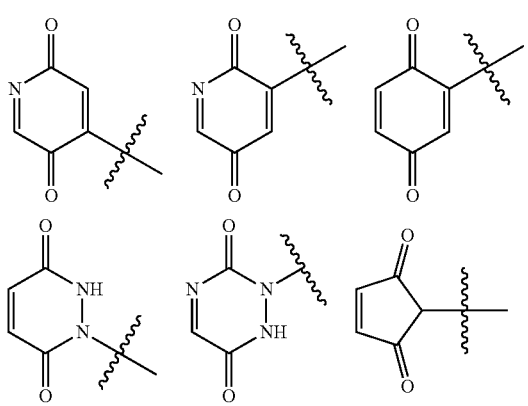

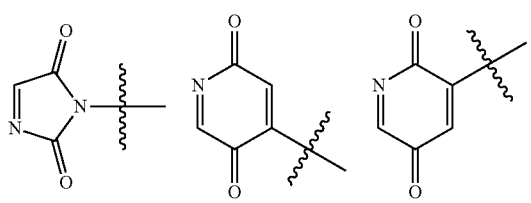

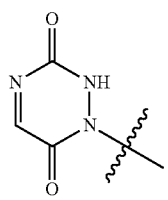

In certain embodiments, a dienophile moiety comprises a maleimide according to formula 6a:

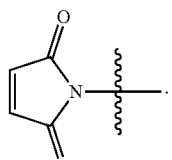

In further embodiments, a reactive primary amine compound NH$_2$—SP—Y is provided, wherein SP is optional and comprises spacer; and Y is a moiety that comprises a dienophile.

In certain embodiments, the reactive primary amine compound comprises a dienophile according to one of the structures: following

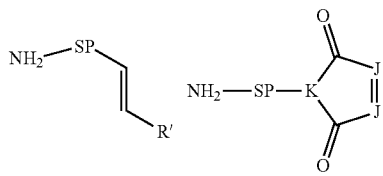

wherein: R' is H or C$_{1-3}$ alkyl; J is independently at each occurrence CH or N; and K is CH, N,

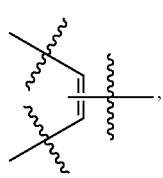

or NH—N.

In certain embodiments, the reactive primary amine compound comprises a dienophile according to one of the following structures:

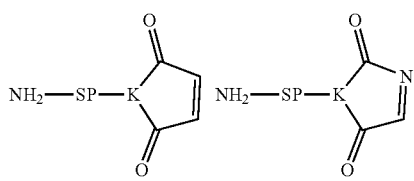

wherein K is CH, N,

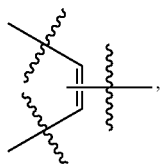

or NH—N.

In certain embodiments, the reactive primary amine compound comprises a dienophile according to one of the following structures:

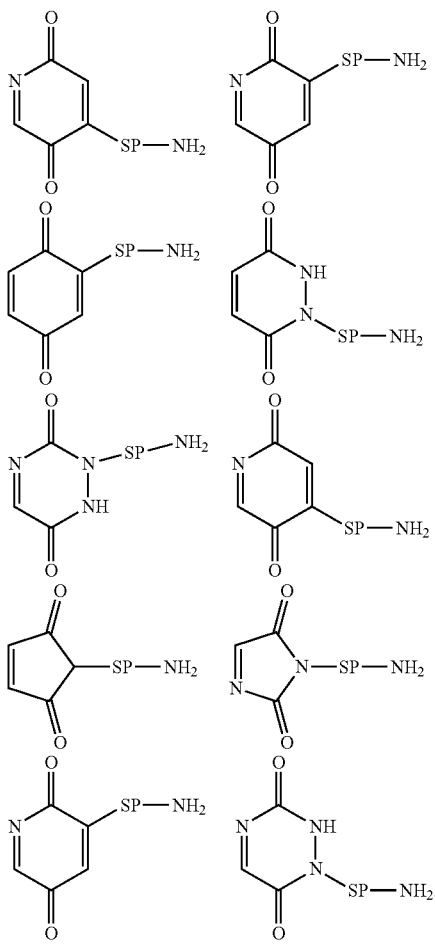

In certain embodiments, the reactive primary amine compound comprises a maleimide according to the following structure:

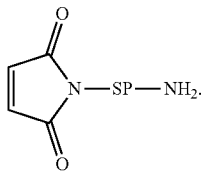

Spacers SP

In certain embodiments described herein SP is optionally present and comprises a spacer selected from the group consisting of —$(CH_2)_u$—, —$((CH_2)_u$—O—$)_v$—, —NH—, —C(O)—, and combinations thereof, wherein subscripts u and v are independently at each occurrence an integer from 1 to 20 and wherein the spacer connectivity can be configured in a forward direction, e.g., $H_2N$—$((CH_2)_u$—O—$)_v$—W, or in a reverse direction, e.g., $H_2N$—(—O—$(CH_2)_u)_v$—W.

In certain embodiments, SP comprises one connecting group which covalently binds to a diene or a dienophile, or a Diels-Alder adduct. Such SP is known as "linear".

In other embodiments, SP comprises two connecting groups which covalently bind to two dienes or dienophiles, or two Diels-Alder adducts. In other embodiments, SP comprises three connecting groups which covalently bind to three dienes or dienophiles, or three Diels-Alder adducts. Such SP is known as "branched".

In one embodiment, SP is covalently bound to one diene. In one embodiment, SP is covalently bound to one Diels-Alder adduct.

In one embodiment, SP is covalently bound to two dienes. In one embodiment, SP is covalently bound to two Diels-Alder adducts. In this scenario, the SP may be bound to two dienes or Diels-Alder adducts that are the same or different from each other. In one embodiment, the SP is bound to two different dienes. In another embodiment, the SP is bound to two different Diels-Alder adducts.

Examples of branched SP include but are not limited to

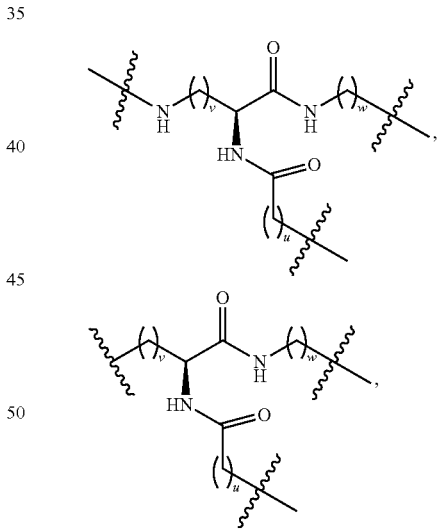

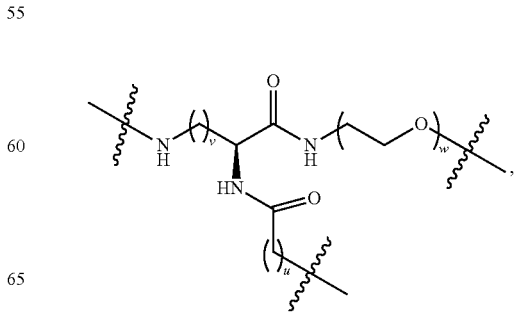

-continued

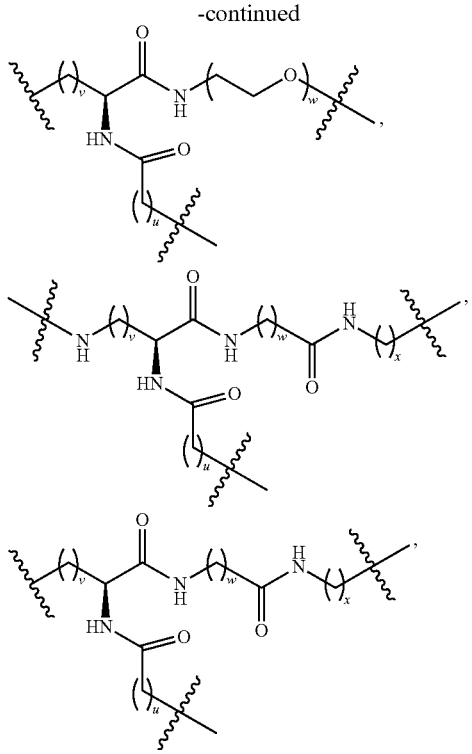

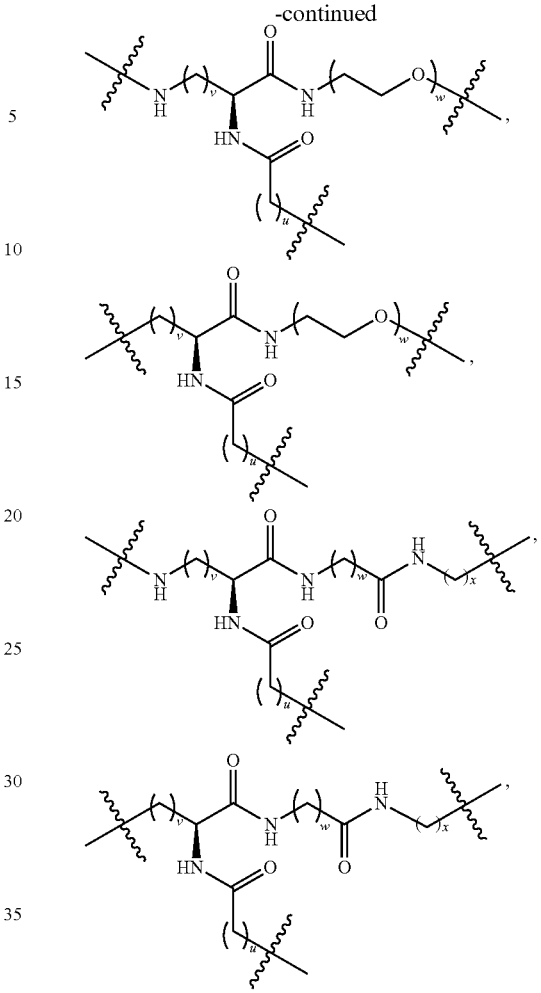

wherein subscripts u, v, w, and x are independently an integer from 1 to 20.

In certain embodiments of the present disclosure, SP comprises a spacer selected from —(CH$_2$)$_u$—, C(O)—, —NH—, —(CH$_2$)$_u$—NH—C(O)—, —(CH$_2$)$_u$—C(O)—NH—, —(CH$_2$)$_u$—C(O)—NH—(CH$_2$)$_v$—, —(CH$_2$—CH$_2$—O)$_v$—, —(CH$_2$)$_u$—(O—CH$_2$—CH$_2$)$_v$—C(O)—NH—, —(CH$_2$—CH$_2$—O)$_v$—(CH$_2$)$_u$—C(O)—NH—(CH$_2$)$_u$—, —NH—(CH$_2$)$_u$—, —NH—(CH$_2$)$_u$—C(O)—, —NH—(CH$_2$)$_u$—C(O)—NH—(CH$_2$)$_v$—, —NH—(CH$_2$—CH$_2$—O)$_v$—, —NH—(CH$_2$—CH$_2$—O)$_v$—C(O)—, —NH—(CH$_2$—CH$_2$—O)$_v$—(CH$_2$)$_u$—, —NH—(CH$_2$—CH$_2$—O)$_v$—(CH$_2$)$_u$—C(O)—, —NH—(CH$_2$—CH$_2$—O)$_v$—(CH$_2$)$_u$—C(O)—NH—(CH$_2$)$_u$—, —(CH$_2$)$_u$—NH—C(O)—, —(CH$_2$)$_u$—C(O)—NH—(CH$_2$—CH$_2$—O)$_v$—C(O)—NH—, —NH—(CH$_2$)$_u$—C(O)—NH—,

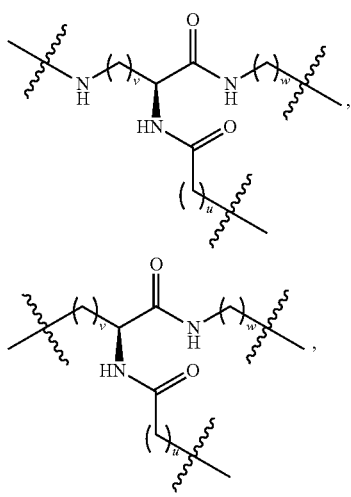

and combinations thereof; wherein subscripts u, v, w and x are independently an integer from 1 to 20.

In certain embodiments of the present disclosure, SP is —(CH$_2$)$_2$—.

In particular embodiments, SP is a divalent polyethylene glycol (PEG) group having from 1 to 20 PEG monomers. As used herein, "PEG #" refers to a divalent ethylene glycol moiety attached via a terminal oxygen atom and a terminal carbon atom, where # is from 1 to 100. For example, when # is 1, then PEG 1 is —OCH$_2$CH$_2$— or —CH$_2$CH$_2$O—; when # is two, then PEG 2 is —OCH$_2$CH$_2$—OCH$_2$CH$_2$— or —CH$_2$CH$_2$O—CH$_2$CH$_2$O—; and when # is three, then PEG 3 is —OCH$_2$CH$_2$OCH$_2$CH$_2$—OCH$_2$CH$_2$— or —CH$_2$CH$_2$O—CH$_2$CH$_2$O—CH$_2$CH$_2$O—. In certain embodiments SP is PEG 8, comprising 8 PEG monomers.

In certain embodiments, the primary amine-spacer compound is according to one of the following formulas:

H$_2$N—(CH$_2$)$_u$—W;

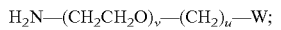

H$_2$N—(CH$_2$CH$_2$O)$_v$—(CH$_2$)$_u$—W;

H$_2$N—(CH$_2$)$_u$—N(H)C(O)—(CH$_2$)$_u'$—W;

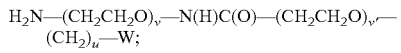

H$_2$N—(CH$_2$CH$_2$O)$_v$—N(H)C(O)—(CH$_2$CH$_2$O)$_v'$—(CH$_2$)$_u$—W;

H$_2$N—(CH$_2$)$_u$—C(O)N(H)—(CH$_2$)$_u'$—W;

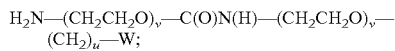

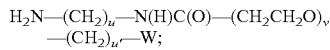

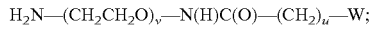

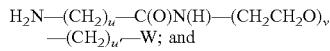

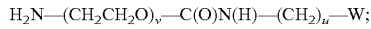

where each subscripts of u, u', v and v' is independently an integer selected from 1 to 12, and W comprises a diene (X) or a dienophile (Y) as defined above.

In certain embodiments, the primary amine-spacer compound is selected from the following:

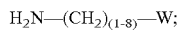

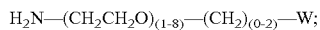

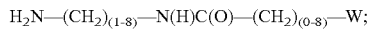

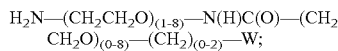

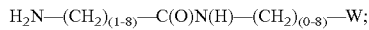

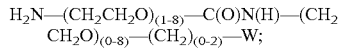

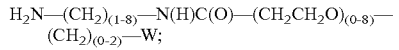

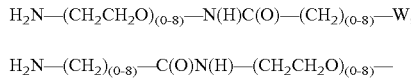

H$_2$N—(CH$_2$)$_{(0-8)}$—C(O)N(H)—(CH$_2$CH$_2$O)$_{(0-8)}$—(CH$_2$)$_{(0-2)}$—W; and

H$_2$N—(CH$_2$CH$_2$O)$_{(0-8)}$—C(O)N(H)—(CH$_2$)$_{(0-8)}$—W;

where W comprises a diene (X) or a dienophile (Y) as defined above.

In certain embodiments, any of the alkyl or alkylene (i.e., —CH$_2$—) groups can optionally be substituted, for example with C$_{1-8}$ alkyl, methylformyl, or —SO$_3$H. In certain embodiments, the alkyl groups are unsubstituted.

Glutaminyl-Modified Protein

Provided herein are glutaminyl-modified proteins, e.g., antibodies, comprising a binding agent conjugated with one or more reactive primary amine compounds as defined herein.

In certain embodiments, an aglycosylated antibody is contacted with a reactive primary amine compound according to the present disclosure, to produce a glutaminyl-modified antibody, as discussed in more detail herein. In certain embodiments, a deglycosylated antibody is reacted with a reactive primary amine compound to produce a glutaminyl-modified antibody. For the purposes of this description, the deglycosylated antibody can be obtained or produced from any source or by any technique deemed suitable by those of skill in the art. In certain embodiments, the antibody is deglycosylated according to step (1), below. In further embodiments, it is sufficient that the deglycosylated or aglycosylated antibody comprise at least one glutamine residue that is sufficiently free of interfering glycosylation, or other structures, to be available for reaction with transglutaminase, as described below.

The reactive primary amine compound can be any primary amine that is capable of forming a covalent bond with a glutamine residue in the presence of transglutaminase and comprising the reactive group W (including X and Z), as described herein. Useful primary amines are described in a section herein.

In certain embodiments, a glutaminyl-modified protein (e.g., antibody) according to the present disclosure has a structure according to Formula (V-W):

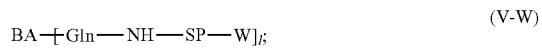  (V-W)

wherein: BA is a binding agent; SP is absent or a spacer; W comprises a diene or dienophile moiety, and I is an integer from 1 to 10.

In certain embodiments, a reactive glutaminyl-modified protein (e.g., antibody) according to the present disclosure has a structure according to Formula (V-X):

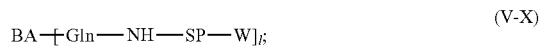  (V-X)

wherein: BA is a binding agent; SP is absent or a spacer; X is a moiety that comprises a diene, and I is an integer from 1 to 10.

In certain embodiments, a reactive glutaminyl-modified protein (e.g., antibody) according to the present disclosure has a structure according to Formula (V-Y):

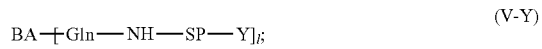  (V-Y)

wherein: BA is a binding agent; SP is absent or a spacer; Y is a moiety that comprises a dienophile, and I is an integer from 1 to 10.

In certain embodiments, a reactive glutaminyl-modified protein (e.g., antibody) according to the present disclosure has a structure according to Formula (V-X1):

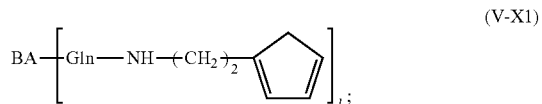  (V-X1)

wherein: BA is a binding agent; and I is an integer from 1 to 10. In certain embodiments, BA is trastuzumab. In certain embodiments, BA is anti-MSR1 antibody, such as H1H21234N.

In certain embodiments, a reactive glutaminyl-modified protein (e.g., antibody) according to the present disclosure has a structure according to Formula (V-X2):

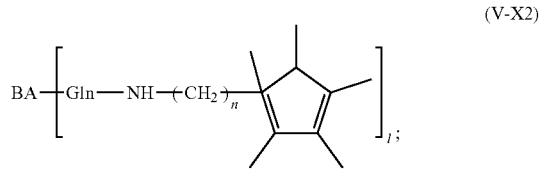  (V-X2)

wherein: BA is a binding agent, and l and n are independently an integer from 1 to 10. In certain embodiments, BA is trastuzumab. In certain embodiments, BA is anti-MSR1 antibody, such as H1H21234N.

In certain embodiments, a reactive glutaminyl-modified protein (e.g., antibody) according to the present disclosure has a structure according to Formula (V-X3):

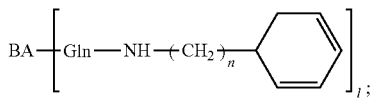
(V-X3)

wherein: BA is a binding agent, and l and n are independently an integer from 1 to 10. In certain embodiments, BA is trastuzumab. In certain embodiments, BA is anti-MSR1 antibody, such as H1H21234N.

In certain embodiments, a reactive glutaminyl-modified protein (e.g., antibody) according to the present disclosure has a structure according to Formula (V-X4):

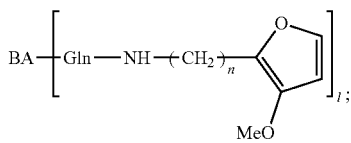
(V-X4)

wherein: BA is a binding agent, and l and n are independently an integer from 1 to 10. In certain embodiments, BA is trastuzumab. In certain embodiments, BA is anti-MSR1 antibody, such as H1H21234N.

In certain embodiments of the disclosure, the linker-antibody ratio or LAR (e.g., abbreviated as the lower case letter "l", e.g., in Formulas V-W, V-X and V-Y, above) is from 1, 2, 3, 4, 5, 6, 7, or 8 drug molecules per antibody. In some embodiments, the LAR is from 1 to 8. In some embodiments, the LAR is from 1 to 6. In certain embodiments, the LAR is from 2 to 4. In some cases, the LAR is from 2 to 3. In certain cases, the LAR is from 0.5 to 3.5. In some embodiments, the LAR is about 1, or about 1.5, or about 2, or about 2.5, or about 3, or about 3.5.

In certain embodiments according to the present disclosure, l is an integer from 1 to 10, 1 to 9, 1 to 8, 1 to 7, 1 to 6, 1 to 5, 1 to 4, 1 to 3, 1 to 2, 2 to 10, 2 to 9, 2 to 8, 2 to 7, 2 to 6, 2 to 5, 2 to 4, 2 to 3, 3 to 10, 3 to 9, 3 to 8, 3 to 7, 3 to 6, 3 to 5, 3 to 4, 4 to 10, 4 to 9, 4 to 8, 4 to 7, 4 to 6, or 4 to 5. In certain embodiments, l is an integer from 1 to 4, 1 to 3, 1 to 2, 2 to 4, 2 to 3, or 3 to 4. In certain embodiments, l is 2. In certain embodiments, d is 3. In certain embodiments, l is 4. In some embodiments, l is 4.

In certain embodiments, BA can comprise two or four glutamine residues. In certain embodiments, BA can comprise a Q295 residue. In certain embodiments, BA can comprise an N297Q mutation. In certain embodiments, BA can comprise Q295 and N297Q. In such embodiments, because BA can be dimeric, BA has four glutamine residues for transglutaminase with reactive primary amine compounds. In such embodiments, l is 1 to 4. In certain embodiments, l is 2. In certain embodiments, l is 3. In certain embodiments, l is 4.

A reactive glutaminyl-modified protein (e.g., antibody) of Formula (IV-X) is useful, for example, for undergoing a Diels-Alder cycloaddition reaction with a reactive linker-payload molecule, e.g., Y-L-D, to form a protein-drug conjugate.

A reactive glutaminyl-modified protein (e.g., antibody) of Formula (IV-Y) is useful, for example, for undergoing a Diels-Alder cycloaddition reaction with a reactive linker-payload molecule, e.g., X-L-D, to form a protein-drug conjugate.

Reactive Linker-Payload Compounds

In some embodiments, the reactive linker-payload compound is a compound according to the formula W-L-D, wherein the reactive linker-payload compound comprises a divalent linker L, a reactive group W, and a payload D, wherein W is capable of reacting with the reactive group of a glutaminyl-modified protein (e.g., antibody) as described herein. As discussed in the present disclosure are methods comprising the step of contacting a reactive glutaminyl-modified protein (e.g., BA-[Gln-NH—SP—W]$_l$) with a reactive linker-payload compound (e.g., W-L-D) to from a protein-drug conjugate as described herein, (e.g., BA-[Gln-NH—SP—Z-L-D]$_d$).

In certain embodiments, a reactive linker-payload compound of the present disclosure comprises a diene (X) as defined in the section herein. In certain embodiments, the reactive linker-payload compound comprises a dienophile (Y) as defined in the section herein.

In certain embodiments according to the present disclosure the reactive linker-payload is according to of the following structures:

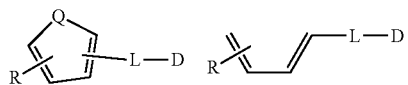

wherein R is H or electron donating group; and Q is CH$_2$, CH$_2$CH$_2$, or O; wherein L is a linker as defined herein and D is a therapeutic and/or imaging agent moiety as defined herein.

In certain embodiments according to the present disclosure the reactive linker-payload is according to of the following structures:

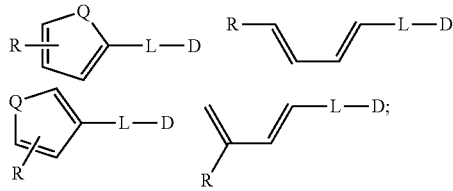

wherein R is H or C$_{1-3}$ alkyl, and Q is CH$_2$, CH$_2$CH$_2$, or O; wherein L is a linker as defined herein and D is a therapeutic and/or imaging agent moiety as defined herein.

In certain embodiments, the reactive linker-payload compound is according to one of the following structures:

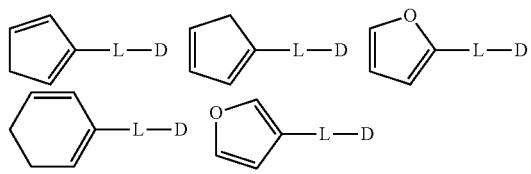

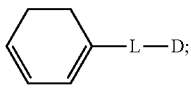

wherein L is a linker as defined herein and D is a therapeutic and/or imaging agent moiety as defined herein.

In certain embodiments, the reactive linker-payload compound is according to one of the following structures, or a mixture thereof:

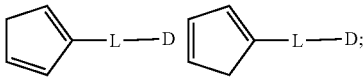

wherein L is a linker as defined herein and D is a therapeutic and/or imaging agent moiety as defined herein.

In certain embodiments, reactive linker-payload compound is according to one of the following structures:

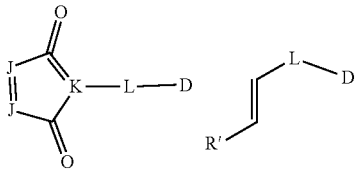

wherein: R' is H or $C_{1-3}$ alkyl; J is independently at each occurrence CH or N; and K is CH, N,

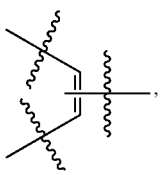

or NH—N; wherein L is a linker as defined herein and D is a therapeutic and/or imaging agent moiety as defined herein.

In certain embodiments, the reactive linker-payload compound is according to one of the following structures:

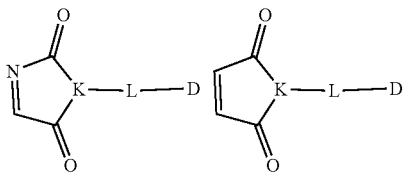

wherein K is CH, N,

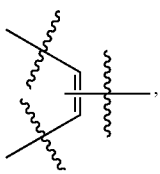

or NH—N; wherein L is a linker as defined herein and D is a therapeutic and/or imaging agent moiety as defined herein.

In certain embodiments, the reactive linker-payload compound is according to one of the following structures:

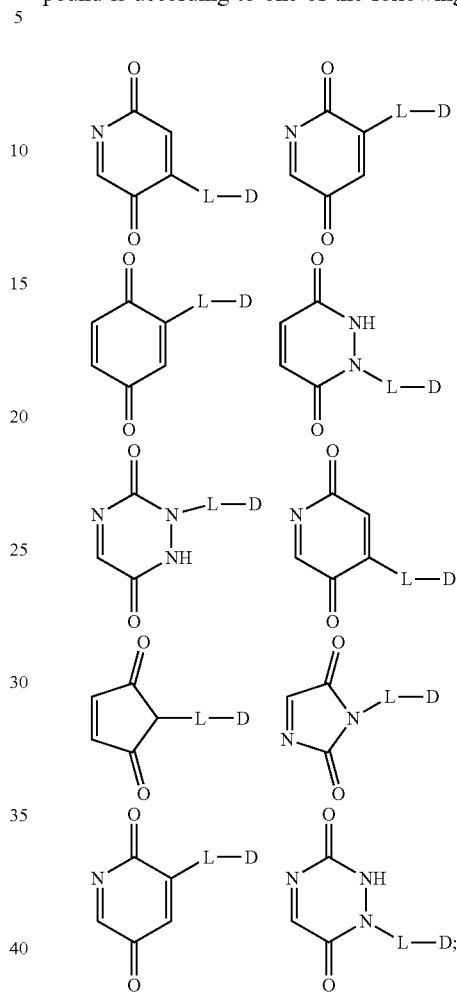

wherein L is a linker as defined herein and D is a moiety as defined herein.

In certain embodiments, the reactive linker-payload compound comprises a maleimide moiety. In certain embodiments, the reactive linker-payload compound is according to the following structure:

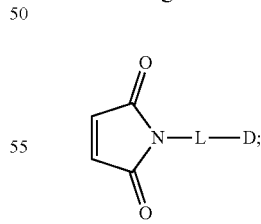

wherein L is a linker as defined herein and D is a moiety as defined herein.

Linker

As used herein, "linker" or "linker unit" refers to any divalent moiety -L- that covalently links a reactive group, e.g., W, X, or Y, or Diels-Alder adduct Z, to one or more therapeutic moieties D, as described herein. Generally, suitable linkers for the antibody conjugates and therapeutic moieties described herein are those that are sufficiently stable to exploit the circulating half-life of the antibody and, at the same time, capable of releasing its payload after antigen-mediated internalization of the conjugate. Generally, linkers can also include any spacer described herein.

Linkers can be cleavable or non-cleavable. Cleavable linkers include linkers that are cleaved by intracellular metabolism following internalization, e.g., cleavage via hydrolysis, reduction, or enzymatic reaction. Non-cleavable linkers include linkers that release an attached payload via lysosomal degradation of the antibody following internalization.

In some embodiments, suitable linkers include, but are not limited to, acid-labile linkers, hydrolysis-labile linkers, enzymatically cleavable linkers, reduction labile linkers, self-immolative linkers, and non-cleavable linkers. In certain embodiments, the linker is a cleavable linker. According to other embodiments, the linker is a non-cleavable linker.

Suitable linkers also include, but are not limited to, those that are or comprise one or more amino acids, glucuronides, succinimide-thioethers, polyethylene glycol (PEG) units, hydrazones, mal-caproyl units, dipeptide units, valine-citrulline units, valine-alanine units and para-aminobenzyl units. Any linker molecule or linker technology known in the art can be used to create or construct an ADC of the present disclosure. Exemplary linkers that can be used in the context of the present disclosure include, linkers that comprise or consist of e.g., MC (6-maleimidocaproyl), MP (maleimidepropionyl), val-cit (valine-citrulline), val-ala (valine-alanine), val-gly (valine-glycine), dipeptide site in protease-cleavable linker, ala-phe (alanine-phenylalanine), dipeptide site in protease-cleavable linker, p-aminobenzyl, p-aminobenzyloxycarbonyl, SPP (N-Succinimidyl 4-(2-pyridylthio) pentanoate), SMCC (N-Succinimidyl 4-(N-maleimidomethyl)cyclohexane-1 carboxylate), SIAB (N-Succinimidyl (4-iodo-acetyl)aminobenzoate), and variants and combinations thereof. Additional examples of linkers that can be used in the context of the present disclosure are provided, e.g., in U.S. Pat. No. 7,754,681 and in Ducry, Bioconjugate Chem., 2010, 21:5-13, and the references cited therein, the contents of which are incorporated by reference herein in their entireties.

In some embodiments, the linker comprises one or more amino acids. Suitable amino acids include natural, non-natural, standard, non-standard, proteinogenic, non-proteinogenic, and L- or D-alpha-amino acids. In some embodiments, the linker comprises alanine, valine, glycine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, or a combination thereof.

In some embodiments, the linker comprises two or more amino acids, also referred to as a peptide. In certain embodiments, the linker comprises two amino acids, also referred to as a dipeptide, selected from the group consisting of valine-citrulline, citrulline-valine, lysine-phenylalanine, phenylalanine-lysine, valine-asparagine, asparagine-valine, threonine-asparagine, serine-asparagine, asparagine-serine, phenylalanine-asparagine, asparagine-phenylalanine, leucine-asparagine, asparagine-leucine, isoleucine-asparagine, asparagine-isoleucine, glycine-asparagine, asparagine-glycine, glutamic acid-asparagine, asparagine-glutamic acid, citrulline-asparagine, asparagine-citrulline, alanine-asparagine, and asparagine-alanine. In certain embodiments, the peptide is valine-citrulline; citrulline-valine; valine-alanine; alanine-valine; valine-glycine, or glycine-valine. In some embodiments, the linker comprises valine and citrulline. In some embodiments, the linker comprises valine and alanine.

In certain embodiments, the linker comprises an amino acid or peptide and one or more selected from: —NH—, —S—, —O—, —(CH$_2$)$_n$—, —(CH$_2$—CH$_2$—O—)$_m$—, —C(O)—, —NH—CH$_2$—O—CH$_2$—C(=O)—NH—,

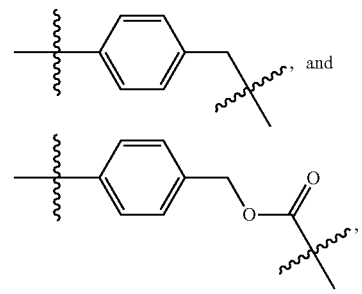

wherein subscripts n and m are independently an integer from 1 to 20.

In further embodiments, the linker comprises an amino acid or peptide and one or more selected from —(CH$_2$)$_n$—NH—C(O)—, —(CH$_2$)$_n$—C(O)—NH—, —(CH$_2$—CH$_2$—O)$_m$—, —(CH$_2$)$_n$—(O—CH$_2$—CH$_2$)$_m$—C(O)—NH—, —NH—(CH$_2$)$_n$—, —NH—(CH$_2$)$_n$—C(O)—, —NH—(CH$_2$—CH$_2$—O)$_m$—, —NH—(CH$_2$—CH$_2$—O)$_m$—C(O)—, —NH—(CH$_2$—CH$_2$—O)$_m$—(CH$_2$)$_n$—, —NH—(CH$_2$—CH$_2$—O)$_m$—(CH$_2$)$_n$—C(O)—, —(CH$_2$)$_n$—NH—C(O)—, —NH—(CH$_2$)$_n$—C(O)—NH—, —NH—CH$_2$—O—CH$_2$—C(=O)—NH—and combinations thereof; wherein subscripts n and m are independently an integer from 1 to 20. In certain embodiments subscripts n and m are independently an integer from 1 to 10. In certain embodiments subscripts n and m are independently an integer from 1 to 5.

In some embodiments, the linker comprises a self-immolative group. The self-immolative group can be any such group known to those of skill. In particular embodiments, the self-immolative group is

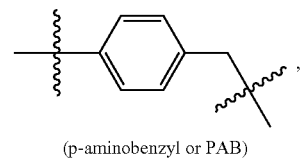 [SMILES: *Cc1ccc(*)cc1]

(p-aminobenzyl or PAB)

or a derivative thereof. Useful derivatives include

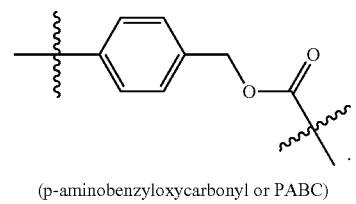 [SMILES: *C(=O)OCc1ccc(*)cc1]

(p-aminobenzyloxycarbonyl or PABC)

Those of skill will recognize that a self-immolative group is capable of carrying out a chemical reaction which releases the remaining atoms of a linker from a payload (i.e., a therapeutic moiety or an imaging agent moiety). As used herein, the term "self-immolative linker" refers to a chemical moiety that is capable of covalently linking together two chemical moieties. In some embodiments, the linker will separate from the therapeutic moiety or an imaging agent moiety if its bond to the first moiety is cleaved. In certain embodiments, the self-immolating moiety connects the therapeutic moiety, (e.g., drug) and a dipeptide unit of a linker. Upon cleavage of the peptide sequence by an intracellular enzyme, the self-immolating moiety cleaves itself from the drug moiety such that the drug moiety is in an underivatized and active form.

The PAB and PABC linker units are also referred to as an electronic cascade spacer. The amide bond linking the carboxy terminus of a peptide unit and the para-aminobenzyl of PAB can be a substrate and cleavable by certain proteases. The aromatic amine becomes electron-donating and initiates an electronic cascade that leads to the expulsion of the leaving group, which releases the free drug after elimination of carbon dioxide (de Groot, et al (2001) *Journal of Organic Chemistry* 66(26): 8815-8830). Upon cleavage of a peptide bond adjacent to the PAB/PABC, i.e. by an intracellular enzyme, the drug is released from the ligand whereby no remaining portion of the linker is bound (de Groot, et al (2002) *Molecular Cancer Therapeutics* 1(11):901-911; de Groot, et al (1999) *J. Med. Chem.* 42(25):5277-5283).

In some embodiments, the linker comprising an amino acid or peptide can be enzymatically cleaved by one or more enzymes, including a cancer or tumor-associated protease, to liberate the moiety (-D), which in one embodiment is protonated in vivo upon release to provide a therapeutic moiety. In certain embodiments, the one or more amino acids or peptide comprise natural amino acids. In other embodiments, the amino acid or peptide comprises non-natural amino acids.

In certain embodiments, the linker comprises a structure selected from:

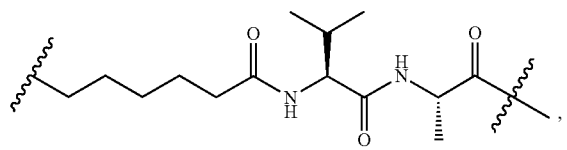

,

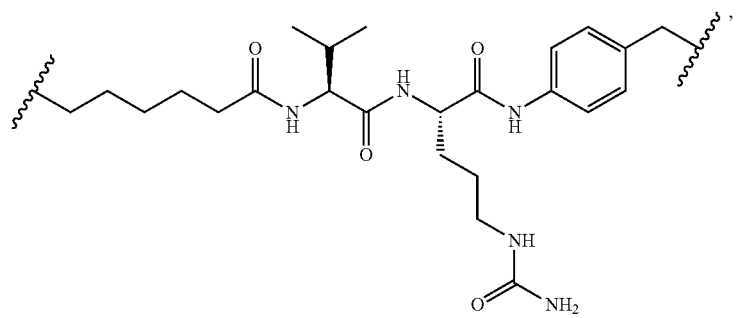

,

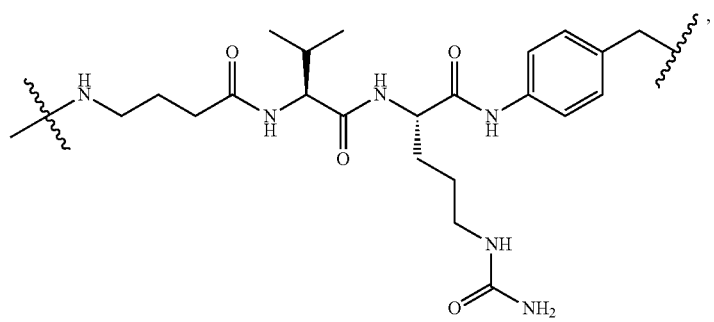

,

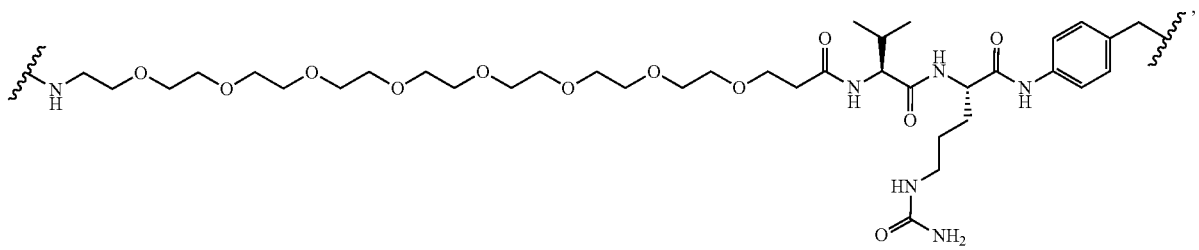

,

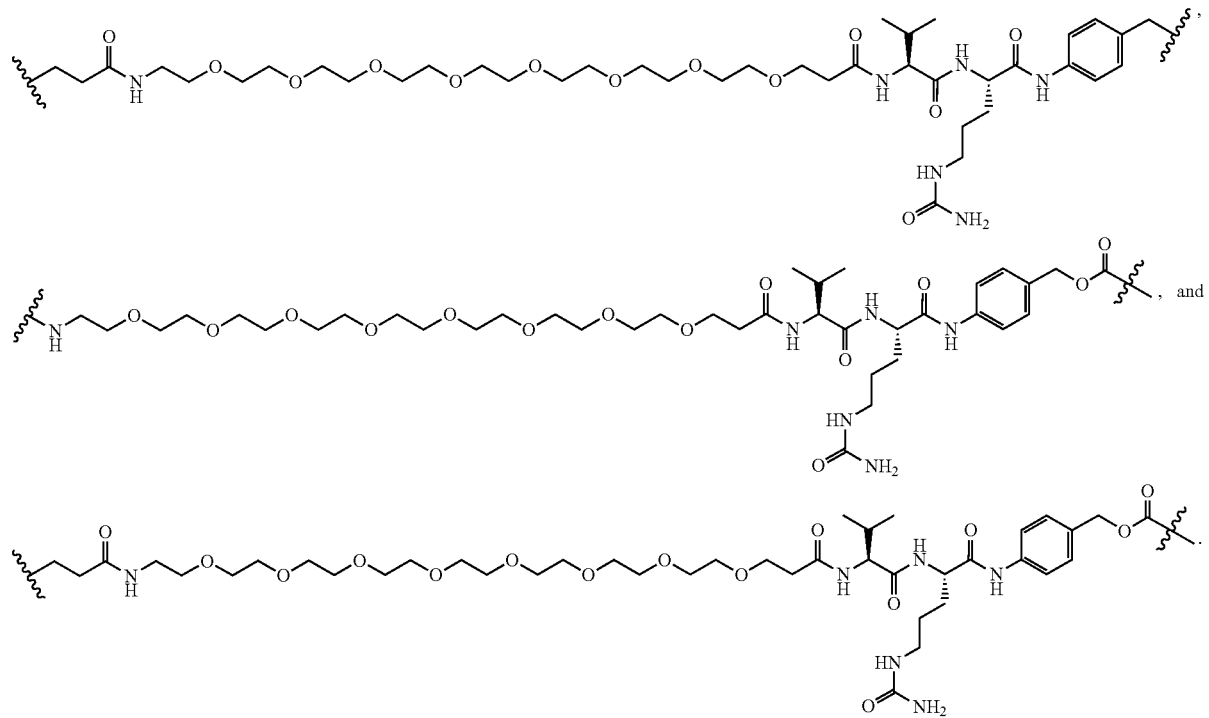
In certain embodiments, the linker comprises a structure selected from:
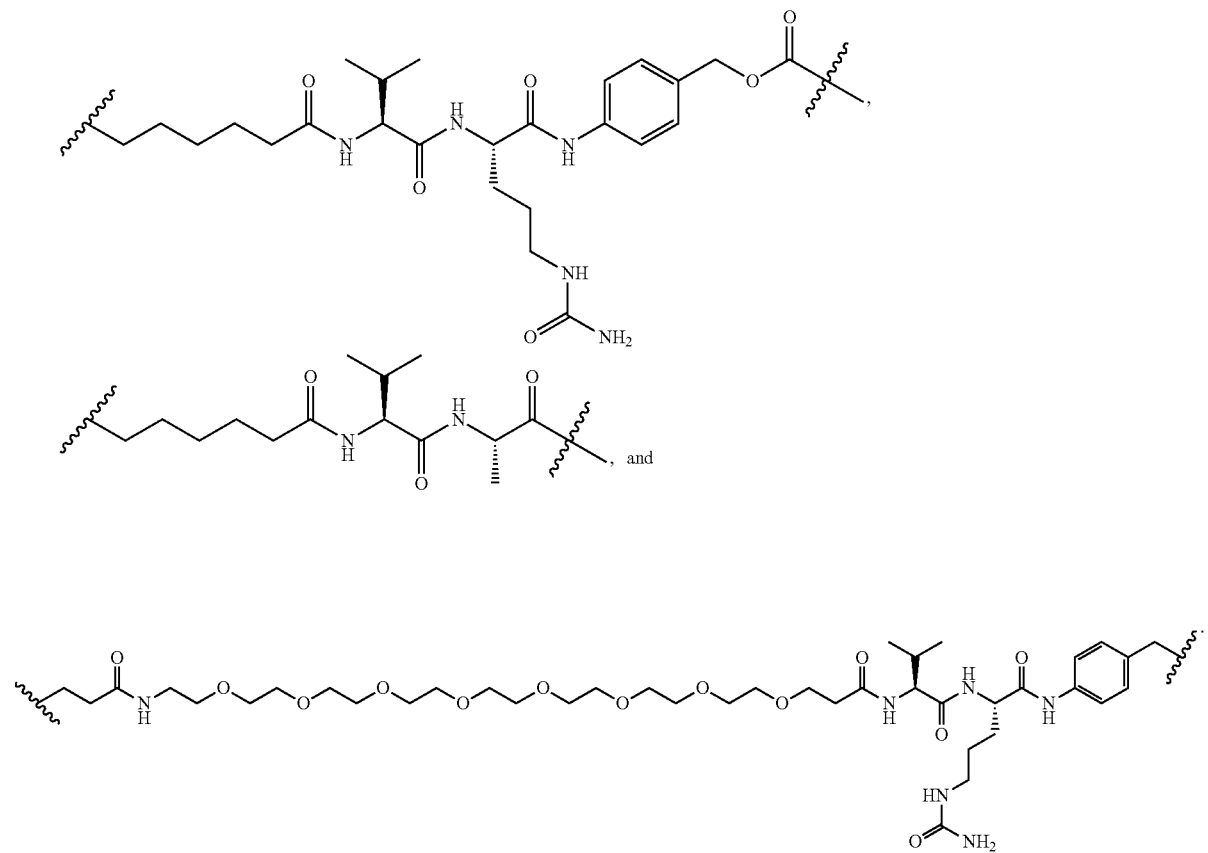

In certain embodiments, the moiety D comprises an amino group that is the point of attachment to linker L. Such a moiety can be denoted as $D_N$. In certain embodiments of the present disclosure comprising $D_N$, the amino group is linked to a self-immolative moiety in the linker.

In certain embodiments according to the present disclosure, the reactive linker-payload compound is according to the following structure, wherein the moiety denoted as $D_N$ comprises an amino group that is the point of attachment to the linker:

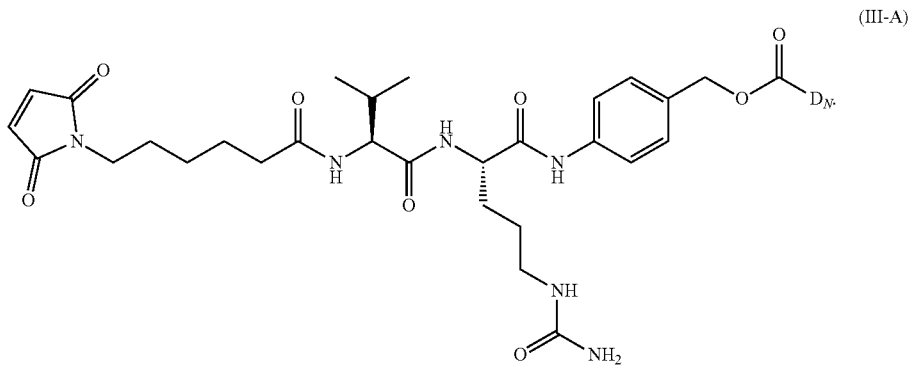

(III-A)

In further embodiments of the reactive linker-payload compounds of Formula (III-A), $D_N$ is a maytansinoid or a maytansinoid analog.

In certain embodiments according to the present disclosure, the reactive linker-payload compound is according to the following structure wherein the moiety denoted as $D_N$ comprises an amino group that is the point of attachment to the linker:

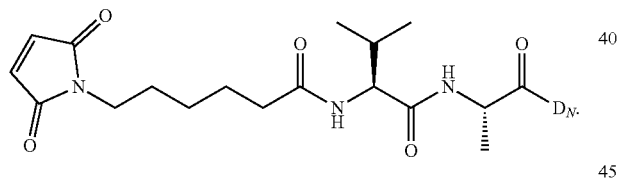

(III-B)

In further embodiments of the reactive linker-payload compounds of Formula (III-B), $D_N$ is a pyrrolobenzodiazepine (PBD) or analogue or derivative thereof. In one embodiment, $D_N$ is PBD-1.

In certain embodiments according to the present disclosure, the reactive linker-payload compound is according to the following structure wherein the moiety denoted as $D_N$ comprises an amino group that is the point of attachment to the linker:

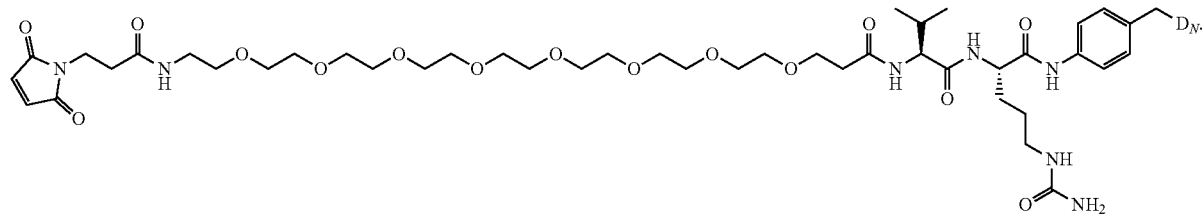

(III-C)

In further embodiments of the reactive linker-payload compounds of Formula (III-C), $D_N$ is a rifamycin or an analog or a derivative thereof.

In some embodiments, a payload $D_N$ described herein (e.g., a rifamycin analog) comprises a tertiary amine, where the nitrogen atom in the tertiary amine is the atom through which the payload is bonded to a linker. In such instances, bonding to the tertiary amine of the payload yields a quaternary amine in the linker-payload molecule. The positive charge on the quaternary amine can be balanced by a counter ion (e.g., chloro, bromo, iodo, or any other suitably charged moiety such as those described herein).

Such an example includes the embodiment wherein the reactive linker-payload molecule comprises a rifamycin analog and is according to Formula (III-C1) below:

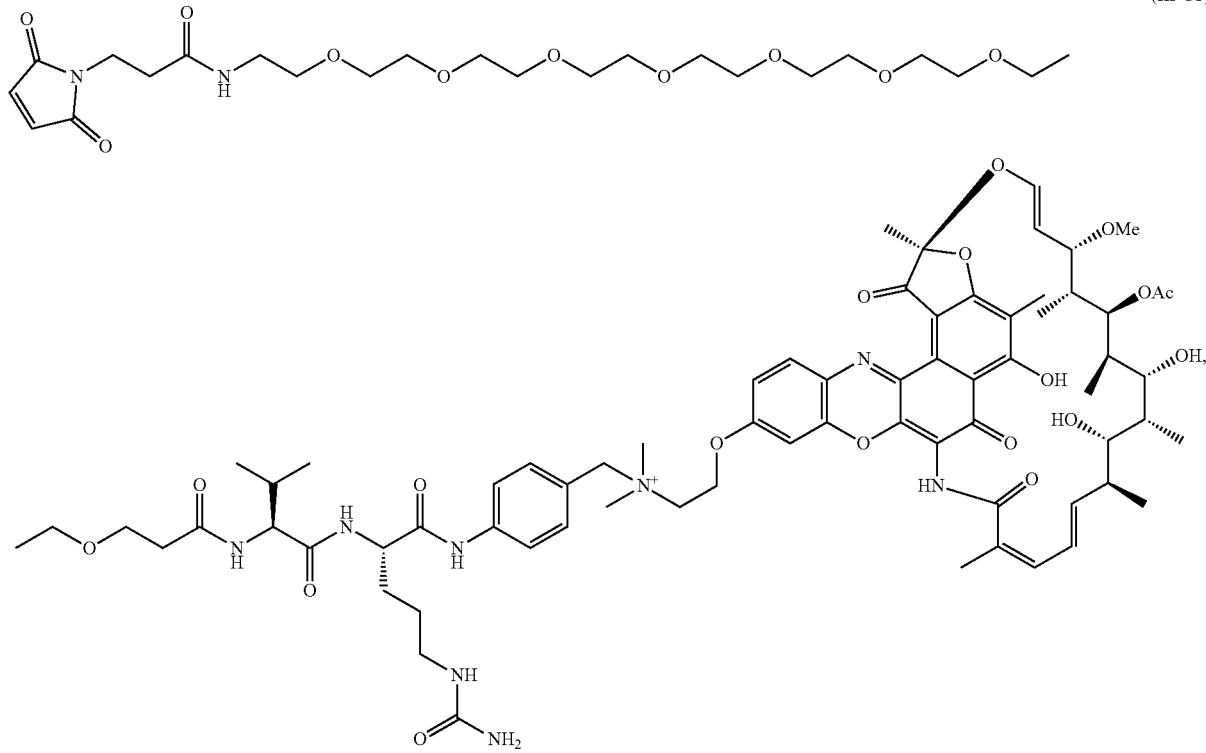

(III-C1)

also referred to herein as mal-PEG8-VC-PABQ-Rifanalog.

In certain embodiments, when a PAB moiety links to a secondary amine nitrogen which is endogenous to a therapeutic and/or imaging agent moiety to form a quaternary amine, as illustrated in Formula (III-C1), the linker is referred to as a PABQ linker.

In some embodiments having a payload $D_N$ described herein (e.g., MMAE), the reactive linker-payload molecule is according to Formula (III-A1) below.

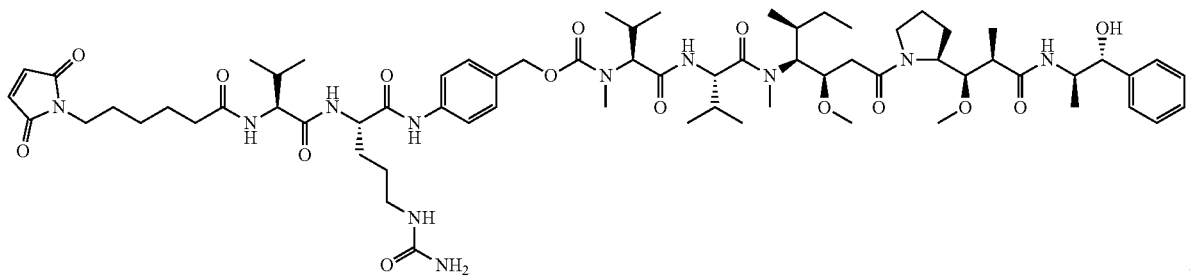 [SMILES: CC[C@H](C)[C@@H]([C@@H](CC(=O)N1CCC[C@H]1[C@H](OC)[C@@H](C)C(=O)N[C@H](C)[C@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCCCCN2C(=O)C=CC2=O)C(C)C)cc1)C(C)C]

In some embodiments having a payload $D_N$ described herein (e.g., PBD-1), the reactive linker-payload molecule is according to Formula (III-B1) below:

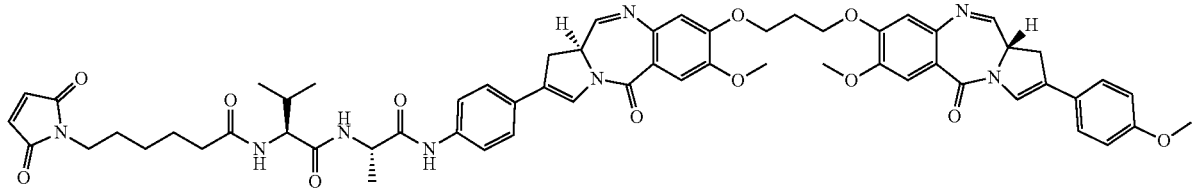 [SMILES: COc1ccc(C2=CN3C(=O)c4cc(OC)c(OCCCOc5cc6c(cc5OC)C(=O)N5C=C(c7ccc(NC(=O)[C@H](C)NC(=O)[C@@H](NC(=O)CCCCCN8C(=O)C=CC8=O)C(C)C)cc7)C[C@H]5C=N6)cc4N=C[C@@H]3C2)cc1]

In certain embodiments, the present disclosure provides a protein-drug conjugate compound having the structure according to Formula (I-N):

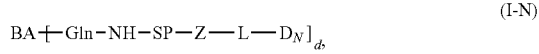

(I-N)

wherein: BA is a binding agent as described herein; Gln is a glutamine residue; SP is an optional spacer as described herein; Z comprises a Diels-Alder adduct as described herein; L is a linker according to the present disclosure; $D_N$ is a therapeutic and/or imaging agent moiety comprising an amino group that is point of attachment to the linker L, and d is an integer from 1 to 10.

In certain embodiments, the present disclosure provides a protein-drug conjugate compound having the structure according to Formula (IV-N):

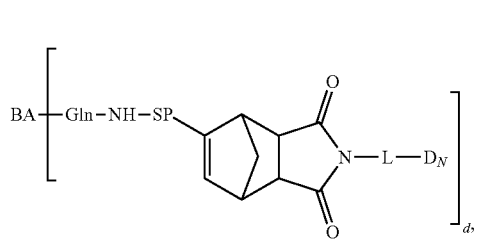

(IV-N)

In some embodiments, the fragment

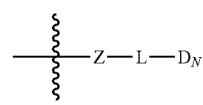

is according to Formula (IV-NA):

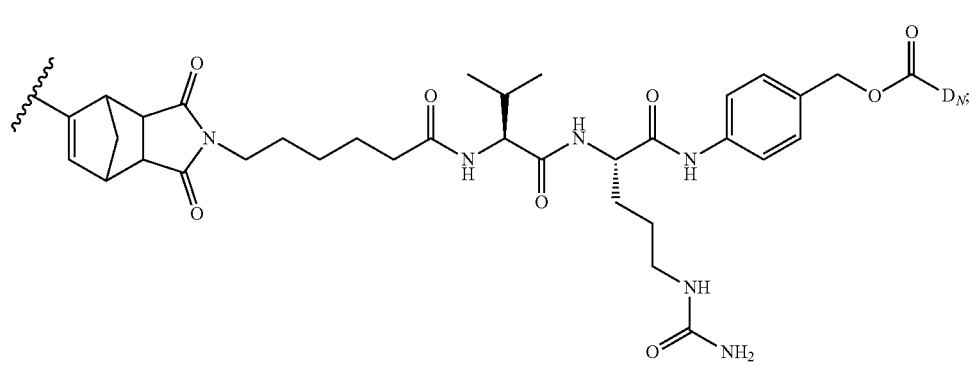

Formula (IV-NA)

wherein the

is the bond to the optional spacer or binding agent fragment.

In further embodiments of the reactive linker-payload compounds of Formula (IV-NA), DN is a maytansinoid or a maytansinoid analogue as described herein.

In some embodiments, the fragment

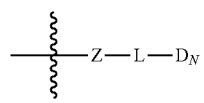

is according to Formula (IV-NA1):

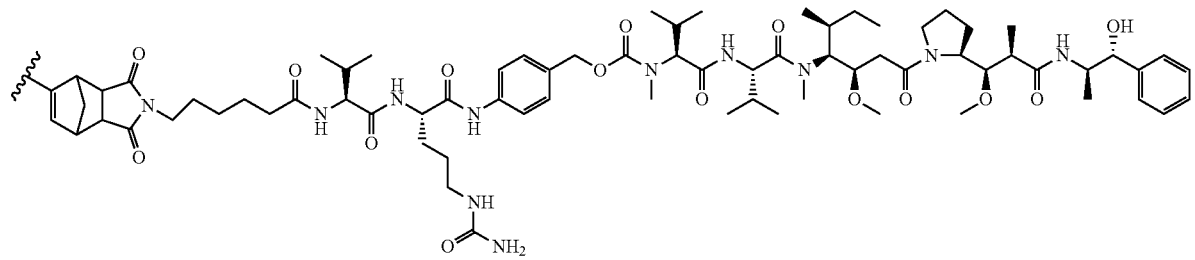 [SMILES: *C1=CC2CC1C1C(=O)N(CCCCCC(=O)N[C@H](C(=O)N[C@@H](CCCNC(N)=O)C(=O)Nc3ccc(COC(=O)N(C)[C@H](C(=O)N[C@H](C(=O)N(C)[C@@H]([C@@H](C)CC)[C@@H](CC(=O)N4CCC[C@H]4[C@H](OC)[C@@H](C)C(=O)N[C@H](C)[C@H](O)c4ccccc4)OC)C(C)C)C(C)C)cc3)C(C)C)C(=O)C21]

In some embodiments, the fragment

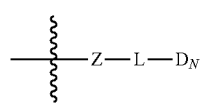

is according to Formula (IV-NB):

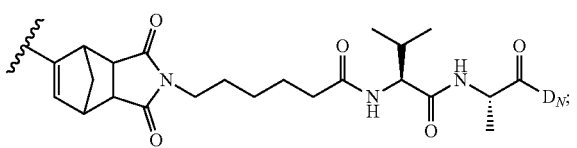

Formula (IV-NB)

wherein the

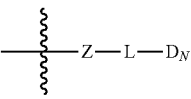

is the bond to the optional spacer or binding agent fragment.

In further embodiments of the reactive linker-payload compounds of Formula (IV-NB), $D_N$ is a pyrrolobenzodiazepine (PBD) or an analogue or derivative thereof as described herein. In one embodiment, $D_N$ is PBD-1.

In some embodiments, the fragment $$\text{---}\overset{\xi}{\underset{\xi}{\xi}}\text{---}Z\text{---}L\text{---}D_N$$

is according to Formula (IV-NB1):

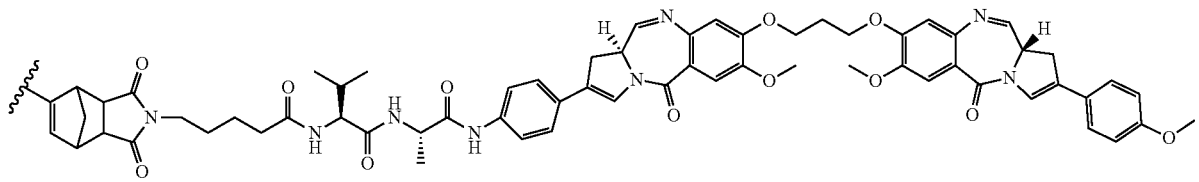 [SMILES: *C1=CC2CC1C1C(=O)N(CCCCC(=O)N[C@H](C(=O)N[C@@H](C)C(=O)Nc3ccc(C4=CN5C(=O)c6cc(OC)c(OCCCOc7cc8c(cc7OC)C(=O)N7C=C(c9ccc(OC)cc9)C[C@H]7C=N8)cc6N=C[C@@H]5C4)cc3)C(C)C)C(=O)C21]

Formula (IV-NB1); wherein the

is the bond to the optional spacer or binding agent fragment.

In some embodiments, the fragment

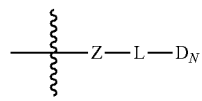

is according to Formula (IV-NC):

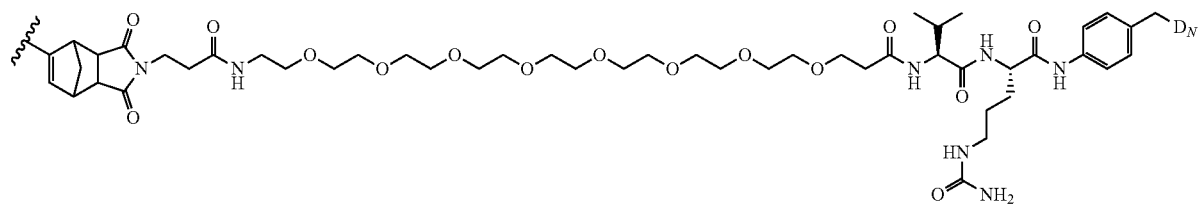

Formula (IV-NC); wherein the

is the bond to the optional spacer or binding agent fragment.

In further embodiments of the reactive linker-payload compounds of Formula (IV-NC), $D_N$ is a rifamycin or an analogue or derivative thereof as described herein.

In some embodiments, the fragment

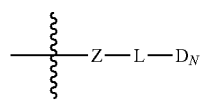

is according to Formula (IV-NC1):

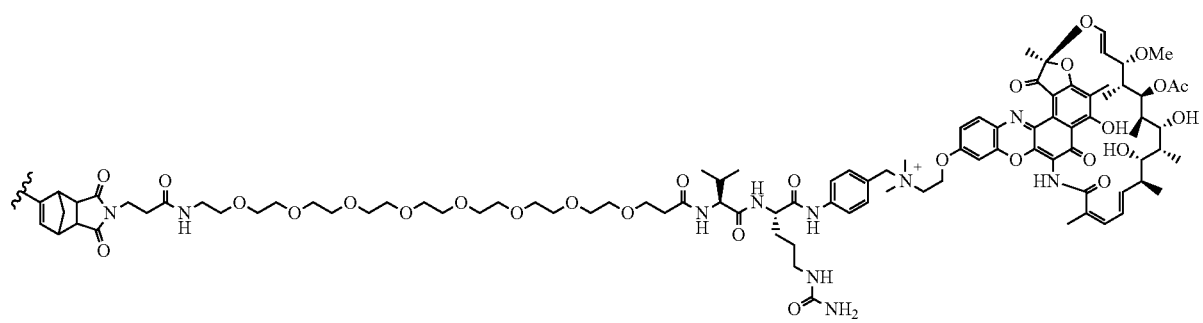

wherein the

is the bond to the spacer or binding agent.

In some embodiments, the fragment

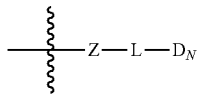

is according to Formula (IV-NC2):

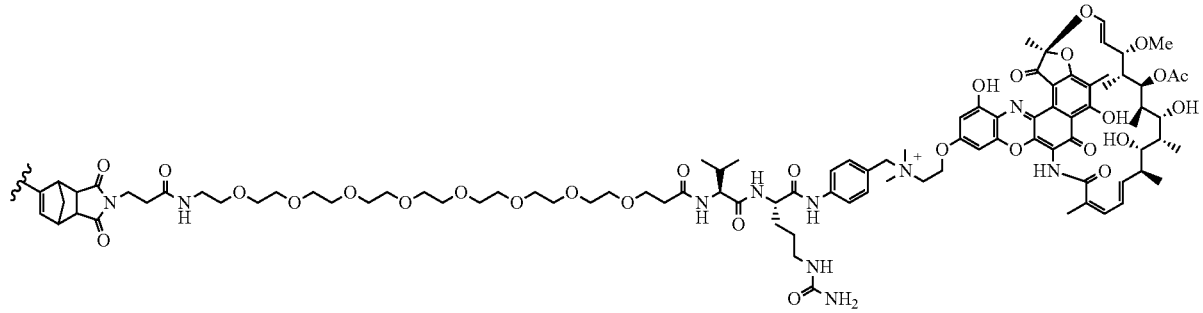

wherein the

is the bond to the spacer or binding agent.

Therapeutic Moieties—D

In embodiments of the present disclosure, D can be any therapeutic and/or imaging agent moiety deemed useful. In one aspect, therapeutic moieties are compounds that result in the inhibition, retardation, reduction, and/or prevention of cell growth. Therapeutic moieties can also result in cell death via necrosis or apoptosis.

Illustrative therapeutic moieties for use in conjugate compounds described herein include: dolastatins and their peptidic analogs and derivatives, auristatins, which are highly potent antimitotic agents that have been shown to have anticancer and antifungal activity. See, e.g., U.S. Pat. No. 5,663,149 and Pettit et al., *Antimicrob. Agents Chemother.* 42:2961-2965 (1998). Exemplary dolastatins and auristatins include, but are not limited to, auristatin E, auristatin EB (AEB), auristatin EFP (AEFP), monomethyl auristatin F (MMAF), monomethyllauristatin-D (MMAD), monomethyl auristatin E (MMAE), and 5-benzoylvaleric acid-AE ester (AEVB). In certain embodiments, the dolastatin derivative or analog is MMAF.

Illustrative therapeutic moieties for use in conjugate compounds described herein include: maytansinoids (e.g., DM1, DM4, etc.), auristatins (e.g., MMAE, MMAD, MMAF, etc.), duocarmycin (e.g., MGBA), dolastatin, toxoids, and other chemotherapeutically effective drugs.

In one embodiment the therapeutic moiety is a maytansinoid or a maytansinoid analog. Exemplary maytansinoids for use herein are described in Widdison et al., *J. Med. Chem.*, 2006, 49, 4392-4408, incorporated by reference herein for all purposes.

In certain embodiments, the therapeutic moiety is DM1 (thiol-containing maytansinoid anti-microtubule agent).

Other specific examples of therapeutic moieties D, that can be used in the context of the provided protein-drug conjugates include, e.g., 1-dehydrotestosterone, 2-pyrrolino-doxorubicin, 5-fluorouracil, 6-mercaptopurine, 6-thioguanine, actinomycin D, anthracycline, anthramycin (AMC), bleomycin, busulfan, calicheamicins, carmustine cisplatin, colchicin, cyanomorpholino-doxorubicin, cyclophosphamide, cytarabine, cytochalasin B, dactinomycin, daunorubicin, decarbazine, dibromomannitol, dihydroxy anthracin dione, doxorubicin, emetine, epirubicin, ethidium bromide, etoposide, gramicidin D, glucocorticoids, lidocaine, lomustine (CCNU), mechlorethamine, melphalan, methotrexate, mithramycin, mitomycin, mitoxantrone, morpholino-doxorubicin, procaine, propranolol, puromycin, pyrrolobenzodiazepines, sibiromycin, streptozotocin, taxol, tenoposide, tetracaine, thioepa chlorambucil, trichothecenes, tubulysin, vincristine, and stereoisomers, isosteres, analogs or derivatives of any of the foregoing.

In certain embodiments of the present disclosure, therapeutic moiety D comprises a cytotoxic agent. Cytotoxic agents include any agent that is detrimental to the growth, viability or propagation of cells, including, but not limited to, tubulin-interacting agents and DNA-damaging agents. Examples of suitable cytotoxic agents and chemotherapeutic agents that can be conjugated to anti-HER2 antibodies or anti-MSR1 antibodies in accordance with this aspect of the disclosure include, e.g., 1-(2chloroethyl)-1,2-dimethanesulfonyl hydrazide, 1,8-dihydroxy-bicyclo[7.3.1]trideca-4, 9-diene-2,6-diyne-13-one, 1-dehydrotestosterone, 5-fluorouracil, 6-mercaptopurine, 6-thioguanine, 9-amino camptothecin, actinomycin D, amanitins, aminopterin, anguidine, anthracycline, anthramycin (AMC), auristatins, bleomycin, busulfan, butyric acid, calicheamicins (e.g., calicheamicin g1), camptothecin, carminomycins, carmustine, cemadotins, cisplatin, colchicin, combretastatins, cyclophosphamide, cytarabine, cytochalasin B, dactinomycin, decarbazine, diacetoxypentyldoxorubicin, dibromomannitol, dihydroxy anthracin dione, disorazoles, dolastatin (e.g., dolastatin 10), doxorubicin, duocarmycin, echinomycins, eleutherobins, emetine, epothilones, esperamicin, estramustines, ethidium bromide, etoposide, fluorouracils, geldanamycins, gramicidin D, glucocorticoids, irinotecans, kinesin spindle protein (KSP) inhibitors, leptomycins, leurosines, lidocaine, lomustine (CCNU), maytansinoids, mechlorethamine, melphalan, mercatopurines, methopterins, methotrexate, mithramycin, mitomycin, mitoxantrone, N8-acetyl spermidine, podophyllotoxins, procaine, propranolol, pteridines, puromycin, pyrrolobenzodiazepines (PBDs), rhizoxins, streptozotocin, tallysomycins, taxol, tenoposide, tetracaine, thioepa chlorambucil, tomaymycins, topotecans, tubulysin, vinblastine, vincristine, vindesine, vinorelbines, and derivatives of any of the foregoing.

In certain embodiments, D is a therapeutic moiety selected from a maytansinoid, a tubulysin, an auristatin, a dolastatin, a camptothesin, a pyrrolobenzodiazepine, an antibiotic, an antiviral agent, an anti-inflammatory agent, an immunomodulator, an antifungal agent, a steroid, or an analogue or derivative thereof. In certain embodiments, D is an imaging agent moiety. In some embodiments, the imaging agent moiety comprises a dye, a chelator, a radionuclide, or an oligonucleotide.

In some embodiments the dye is a fluorescent dye. In some embodiments, D may be an Alexa Fluor fluorescent dye selected from the group consisting of Alexa Fluor 647, Alexa Fluor 488, Alexa Fluor 594, Alexa Fluor 555, and Alexa Fluor 568. In one embodiment, D is Alexa Fluor 647.

In some embodiments, D comprises a radionuclide. In one embodiment, D comprises one or more of $^{89}$Zr, $^{64}$Cu, $^{86}$Y, $^{11}$C, $^{18}$F, $^{68}$Ga, $^{52}$Mn, $^{55}$Co, $^{152}$Tb, $^{90}$Nb, $^{68}$Ga, $^{72}$As, or $^{69}$Ge.

In certain embodiments, the present disclosure provides antibody-drug conjugates (ADC) comprising an anti-HER2 antibody or antigen-binding fragments thereof and a therapeutic and/or imaging agent moiety D (i.e., "payload") (e.g., a cytotoxic agent), such as but not limited to DM1. In some embodiments, the an anti-HER2 antibody or antigen-binding fragment and the cytotoxic agent (such as, but not limited to DM1) are covalently attached via a linker ("L"). In certain embodiments, the ADC comprises an anti-HER2 antibody that is trastuzumab. In various embodiments, the ADC comprises an anti-HER2 antibody or antigen-binding fragment thereof that comprises the CDRs of a HCVR and a LCVR having the amino acid sequences set forth in WO 2019/212965 A1, and a maytansinoid, optionally DM1, optionally wherein the anti-HER2 antibody or antigen-binding fragment thereof and the maytansinoid are covalently attached via a linker, e.g., SMCC.

In various embodiments, the ADC comprises an anti-HER2 antibody or antigen-binding fragment thereof that comprises the CDRs of a HCVR and a LCVR having the amino acid sequences set forth in WO 2019/212965 A1.

According to another aspect, the present disclosure provides antibody-drug conjugates comprising an anti-HER2 antibody or antigen-binding fragment thereof, such as trastuzumab, and a therapeutic and/or imaging agent moiety (e.g., a cytotoxic agent). In some embodiments, the antibody or antigen-binding fragment and the cytotoxic agent are covalently attached via a linker, as discussed herein. In various embodiments, the anti-HER2 antibody or antigen-binding fragment can be any of the anti-HER2 antibodies or fragments described herein. In particular embodiments, the anti-HER2 antibody comprises trastuzumab.

According to certain embodiments, the cytotoxic agent that is conjugated to an anti-HER2 antibody, such as trastuzumab, is a maytansinoid such as DM1 or DM4, a tomaymycin derivative, or a dolastatin derivative. According to certain embodiments, the cytotoxic agent that is conjugated to an anti-HER2 antibody is an auristatin such as MMAE, MMAF, or derivatives thereof. Other cytotoxic agents known in the art are contemplated within the scope of the present disclosure, including, e.g., protein toxins such ricin, C. difficile toxin, pseudomonas exotoxin, ricin, diphtheria toxin, botulinum toxin, bryodin, saporin, pokeweed toxins (i.e., phytolaccatoxin and phytolaccagenin), and others such as those set forth in Sapra et al., Pharmacol. & Therapeutics, 2013, 138:452-469.

In certain embodiments, the cytotoxic agent is an auristatin. Suitable auristatins include MMAE, MMAF and derivatives thereof. In one embodiment, the auristatin is MMAE. In one embodiment, MMAE or derivative thereof has the following structure:

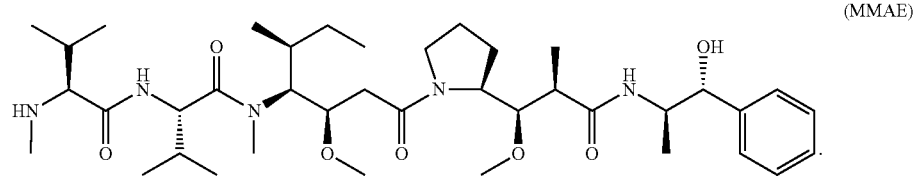 [SMILES: CC[C@H](C)[C@@H]([C@@H](CC(=O)N1CCC[C@H]1[C@H](OC)[C@@H](C)C(=O)N[C@H](C)[C@H](O)c1ccccc1)OC)N(C)C(=O)[C@@H](NC(=O)[C@@H](NC)C(C)C)C(C)C]

(MMAE)

In certain embodiments, the cytotoxic agent is a maytansinoid, e.g., derivative of maytansine. Suitable maytansinoids include DM1, DM4, or derivatives, stereoisomers, or isotopologues thereof. Suitable maytansinoids also include, but are not limited to, those disclosed in WO 2014/145090A1, WO 2015/031396A1, US 2016/0375147A1, and US 2017/0209591A1, incorporated herein by reference in their entireties.

In some embodiments, the maytansinoid has the following structure:

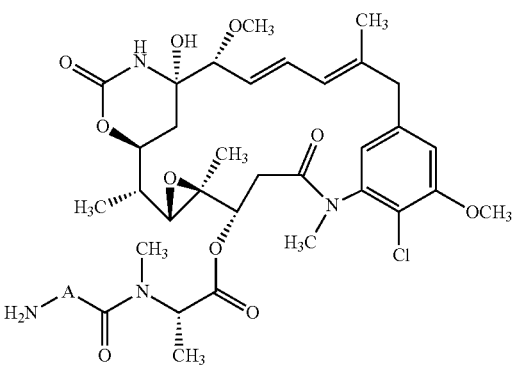

wherein A is an optionally substituted arylene or heteroarylene.

In some embodiments, the maytansinoid has the following structure:

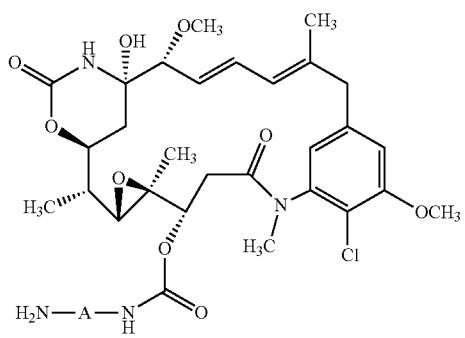

wherein A is an optionally substituted arylene or heteroarylene.

In some embodiments, the maytansinoid has the following structure:

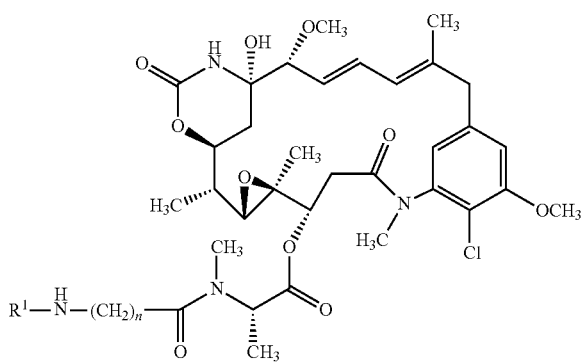

wherein n is an integer from 1-12 and $R^1$ is alkyl.

In some embodiments, the maytansinoid has the following structure:

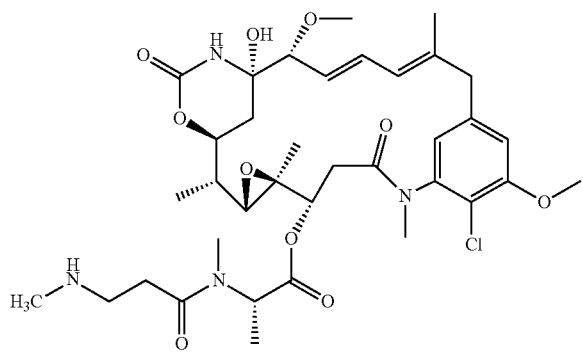

In certain embodiments, therapeutic moieties include small molecules that provide a therapeutic benefit through their delivery via MSR1 or HER2. In certain embodiments, D is the residue of a molecule selected from the group consisting of a steroid, an LXR modulator, or a rifamycin analog. In some cases, D is a steroid. In some cases, D is an LXR modulator. In some cases, D is an LXR agonist. In some embodiments, D is an LXR antagonist. Exemplary LXR modulator payloads are described, e.g., in U.S. Application No. 62/508,327, filed May 18, 2017 Bis-Octahydrophenanthrene Carboxamides And Protein Conjugates published as US 2018/0334426, which is incorporated herein by reference in its entirety.

In some embodiments, the therapeutic moiety D is a rifamycin analog, including any rifamycin analog described in U.S. Application Nos. 62/783,506, filed Dec. 21, 2018, 62/844,860, filed May 8, 2019, and Ser. No. 16/722,958, filed Dec. 20, 2019, which are incorporated herein by reference in their entirety. In some embodiments, the therapeutic moiety D is a rifamycin analogue or derivative, having the following structure:

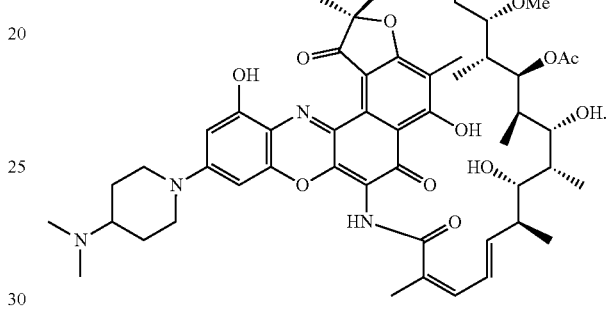

In one embodiment the therapeutic moiety is a tubulysin. The tubulysins, first isolated from mycobacterial culture broth, are a group of extremely potent tubulin polymerization inhibitors that rapidly disintegrate the cytoskeleton of dividing cells and induce apoptosis. Tubulysins are comprised of N-methyl-D-pipecolinic acid (Mep), L-isoleucine (Ile), and tubuvaline (Tuv), which contains an unusual N,O-acetal and a secondary alcohol or acetoxy group. Tubulysins A, B, C, G, and I contain the C-terminal tubutyrosine (Tut) alpha-amino acid, while D, E, F, and H instead have tubuphenylalanine (Tup) at this position (Steinmetz, H., et al. (2004), Isolation, Crystal and Solution Structure Determination, and Biosynthesis of Tubulysins—Powerful Inhibitors of Tubulin Polymerization from Myxobacteria. *Angewandte Chemie International Edition*, 43: 4888-4892).

In other embodiments, the therapeutic moiety is selected from pyrrolobenzodiazepines (PBDs). PBDs have the ability to recognize and bond to specific sequences of DNA; in certain embodiments the sequence is PuGPu. The first PBD antitumor antibiotic, anthramycin, was discovered in 1965 (Leimgruber, et al., J. Am. Chem. Soc, 87, 5793-5795 (1965); Leimgruber, et al., J. *Am. Chem. Soc.* 87, 5791-5793 (1965). Since then, a number of naturally occurring PBDs have been reported, and over 10 synthetic routes have been developed to a variety of analogues (Thurston, et al, Chem. Rev. 1994, 433-465 (1994); Antonow, D. and Thurston, D. E., *Chem. Rev.* 2011 11 1 (4), 2815-2864). Family members include abbeymycin (Hochlowski, et al., *J. Antibiotics,* 40, 145-148 (1987)), chicamycin (Konishi, et al., *J. Antibiotics,* 37, 200-206 (1984)), DC-81 (Japanese Patent 58-180 487; Thurston, et al., Chem. Brit, 26, 767-772 (1990); Bose, et al., *Tetrahedron,* 48, 751-758 (1992)), mazethramycin (Kuminoto, et al., *J. Antibiotics,* 33, 665-667 (1980)), neothramycins A and B (Takeuchi, et al., *J. Antibiotics,* 29, 93-96 (1976), porothramycin (Tsunakawa, et al., *J. Antibiotics,* 41, 1366-1373 (1988)), prothracarcin (Shimizu, et al, *J. Antibi-* otics, 29, 2492-2503 (1982); Langley and Thurston, *J. Org. Chem.*, 52, 91-97 (1987)), sibanomicin (DC-102)(Hara, et al., *J. Antibiotics*, 41, 702-704 (1988): Itoh, et al., *J. Antibiotics*, 41, 1281-1284 (1988)), sibiromycin (Leber, et al., *J. Am. Chem. Soc*, 110, 2992-2993 (1988)) and tomamycin (Arima, et al, *J. Antibiotics*, 25, 437-444 (1972).

In some embodiments, PBDs according to the present disclosure have the general structure:

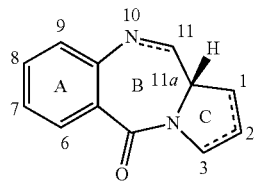

PBDs differ in the number, type and position of substituents, in both their aromatic A rings and pyrrolo C rings, and in the degree of saturation of the C ring. In the B-ring there is either an imine (N═C), a carbinolamine (NH—CH(OH), or a carbinolamine methyl ether (NH—CH(OMe)) at the N10-C1 1 position which is the electrophilic center responsible for alkylating DNA. All of the known natural products have an (S)-configuration at the chiral C1 1a position which provides them with a right-handed twist when viewed from the C ring towards the A ring. This gives them the appropriate three-dimensional shape for isohelicity with the minor groove of B-form DNA, leading to a snug fit at the binding site (Kohn, In *Antibiotics III*. Springer-Verlag, New York, pp. 3-11 (1975); Hurley and Needham-VanDevanter, *Acc. Chem. Res.*, 19, 230-237 (1986). Their ability to form an adduct in the minor groove, enables them to interfere with DNA processing, hence their use as antitumor agents.

In one particular embodiment, the therapeutic moiety D is the PBD compound of Formula PBD-1:

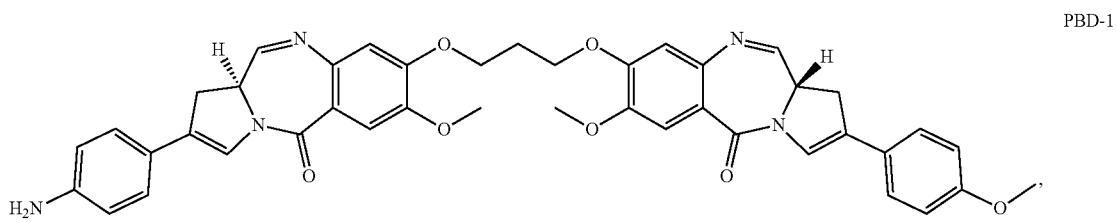 [SMILES: COc1ccc(C2=CN3C(=O)c4cc(OC)c(OCCCOc5cc6c(cc5OC)C(=O)N5C=C(c7ccc(N)cc7)C[C@H]5C=N6)cc4N=C[C@@H]3C2)cc1]

or an analog or derivative thereof.

In certain embodiments, the therapeutic moiety is an auristatin, a PBD or an ansamycin antibiotic such as rifamycin or an analogue or derivative thereof.

In certain embodiments, the therapeutic moiety is MMAE, PBD-1, or an antibiotic such as rifamycin or an analogue or derivative thereof.

In certain embodiments according to the present disclosure, the reactive linker-payload compound is according to the following structure, wherein the therapeutic moiety denoted as D is attached the linker via an amino group:

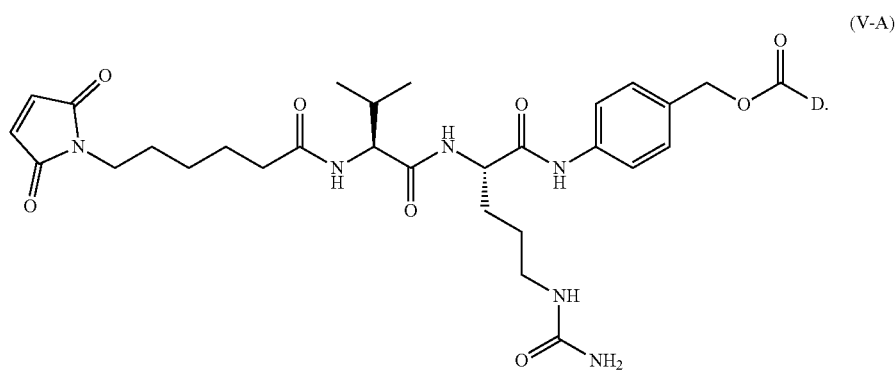

In further embodiments of the reactive linker-payload compounds of Formula (V-A), D is a maytansinoid or a maytansinoid analog.

In certain embodiments according to the present disclosure, the reactive linker-payload compound is according to the following structure wherein the therapeutic moiety denoted as D is attached the linker via an amino group:

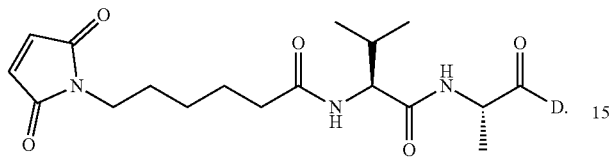

(V-B)

In further embodiments of the reactive linker-payload compounds of Formula (V-B), D is a pyrrolobenzodiazepine (PBD) or analogue or derivative thereof. In a particular embodiment, D is PBD-1.

In certain embodiments according to the present disclosure, the reactive linker-payload compound is according to the following structure wherein the therapeutic moiety denoted as D is attached the linker via an amino group:

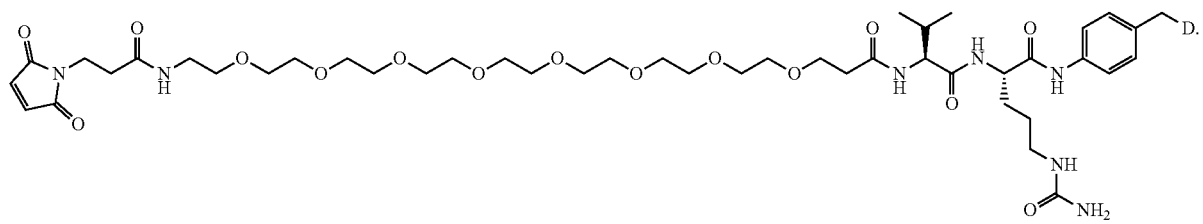

(V-C)

In further embodiments of the reactive linker-payload compounds of Formula (V-C), D is a rifamycin or an analogue or a derivative thereof.

In some embodiments, a payload D described herein (e.g., a rifamycin analog) comprises a tertiary amine, where the nitrogen atom in the tertiary amine is the atom through which the payload is bonded to a linker. In such instances, bonding to the tertiary amine of the payload yields a quaternary amine in the linker-payload molecule. The positive charge on the quaternary amine can be balanced by a counter ion (e.g., chloro, bromo, iodo, or any other suitably charged moiety such as those described herein). Such an example includes the embodiment wherein the reactive linker-payload molecule is according to Formula (V-C1) below:

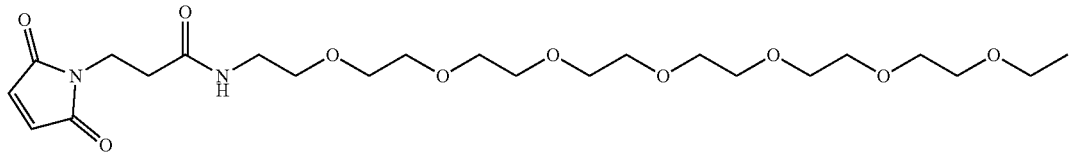

(V-C1)

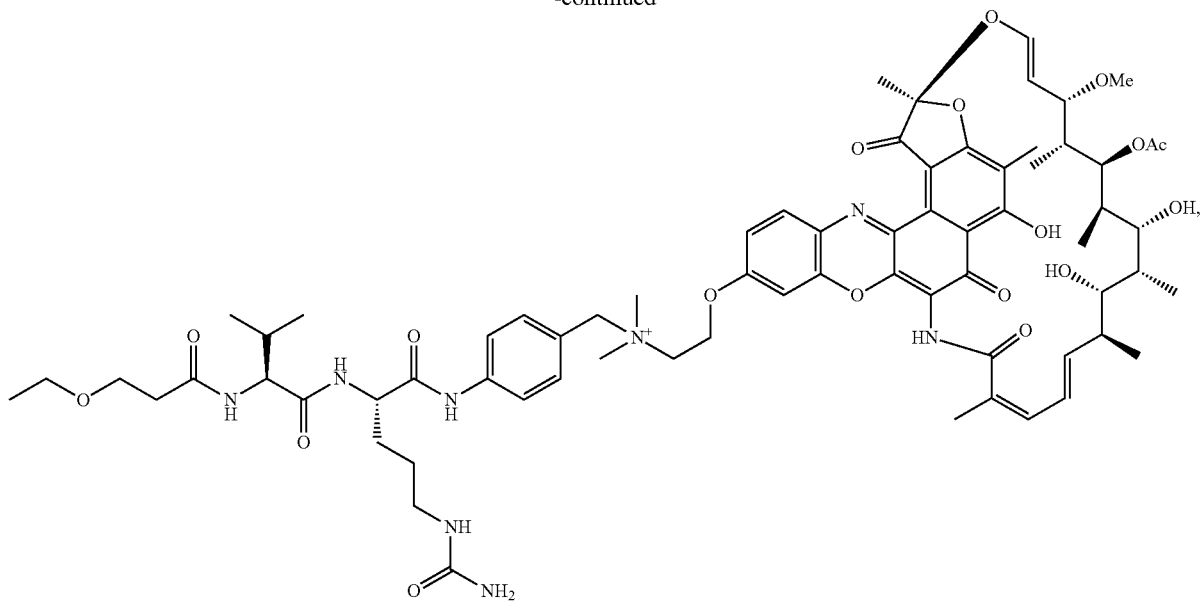
also referred to herein as mal-PEG8-VC-PABQ-Rifanalog.
In some embodiments having a payload D described herein (e.g., MMAE), the reactive linker-payload molecule is according to Formula (V-A1) below:
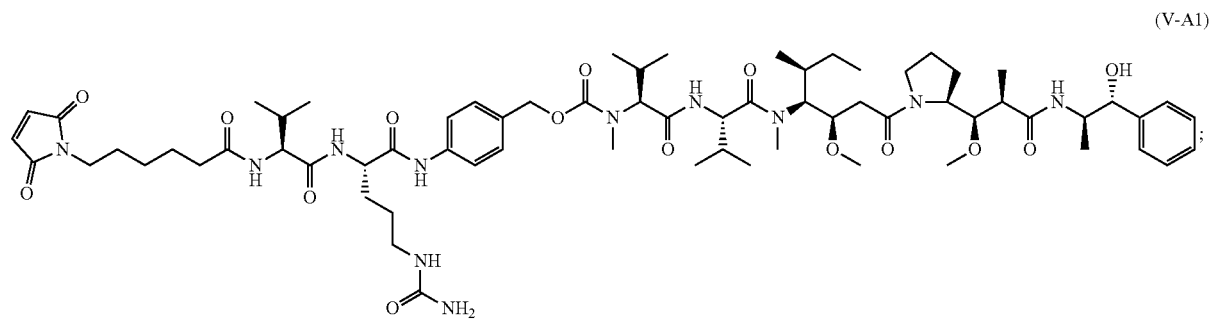 [SMILES: CC[C@H](C)[C@@H]([C@@H](CC(=O)N1CCC[C@H]1[C@H](OC)[C@@H](C)C(=O)N[C@H](C)[C@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCCCCN2C(=O)C=CC2=O)C(C)C)cc1)C(C)C]
(V-A1)
also referred to herein as mc-VC-PABC-MMAE.
In some embodiments having a payload D described herein, the reactive linker-payload molecule is according to Formula (V-A11) below:
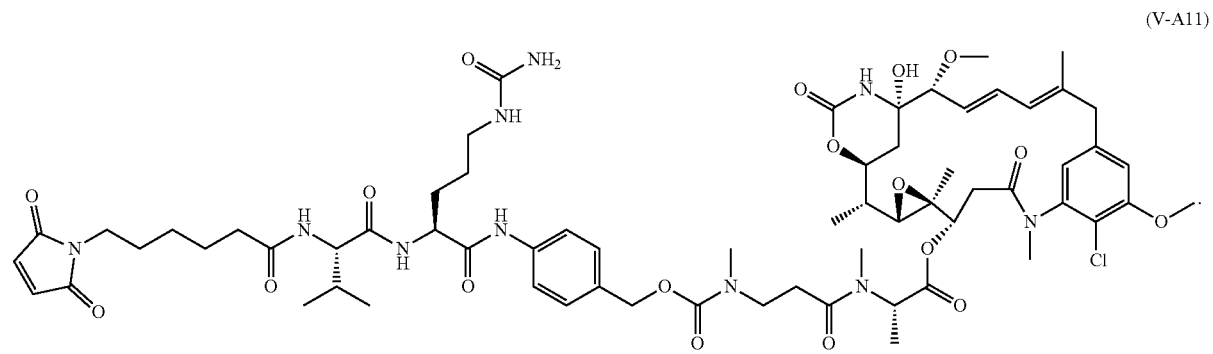 [SMILES: COc1cc2cc(c1Cl)N(C)C(=O)C[C@H](OC(=O)[C@H](C)N(C)C(=O)CCN(C)C(=O)OCc1ccc(NC(=O)[C@H](CCCNC(N)=O)NC(=O)[C@@H](NC(=O)CCCCCN3C(=O)C=CC3=O)C(C)C)cc1)[C@]1(C)O[C@H]1[C@H](C)[C@@H]1C[C@@](O)(NC(=O)O1)[C@H](OC)/C=C/C=C(\C)C2]
(V-A11)

In some embodiments having a payload D described herein (e.g., PBD, e.g., PBD-1), the reactive linker-payload molecule is according to Formula (V-B1) below:

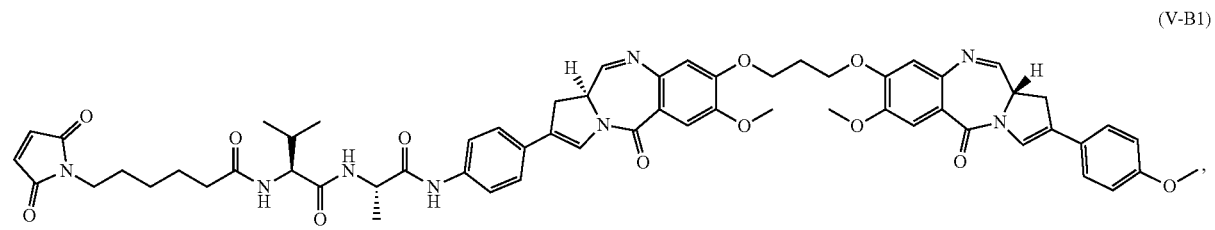 [SMILES: COc1ccc(C2=CN3C(=O)c4cc(OC)c(OCCCOc5cc6c(cc5OC)C(=O)N5C=C(c7ccc(NC(=O)[C@H](C)NC(=O)[C@@H](NC(=O)CCCCCN8C(=O)C=CC8=O)C(C)C)cc7)C[C@H]5C=N6)cc4N=C[C@@H]3C2)cc1]

(V-B1)

also referred to herein as mc-VA-PBD.

In some embodiments, the fragment

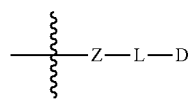

is according to Formula (I-DA):

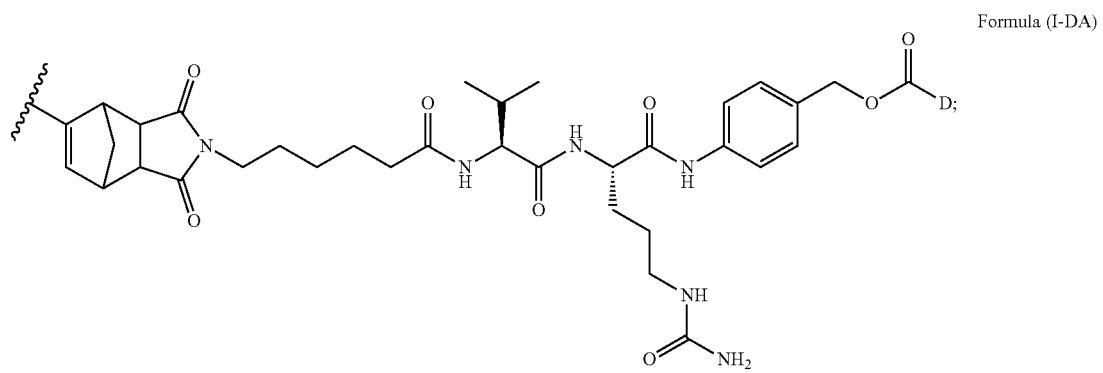

Formula (I-DA)

wherein the

is the bond to the spacer or binding agent.

In further embodiments of the reactive linker-payload compounds of Formula (I-DA), D is a maytansinoid or a maytansinoid analogue as described herein.

In some embodiments, the fragment

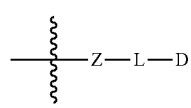

is according to Formula (I-A1):
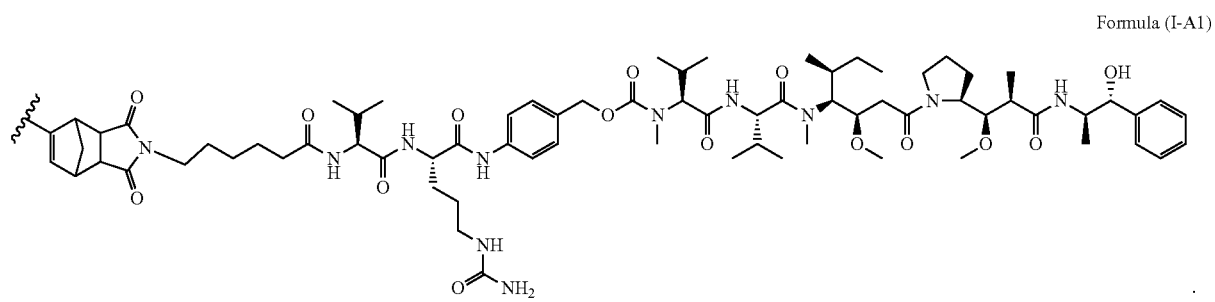 [SMILES: *C1=CC2CC1C1C(=O)N(CCCCCC(=O)N[C@H](C(=O)N[C@@H](CCCNC(N)=O)C(=O)Nc3ccc(COC(=O)N(C)[C@H](C(=O)N[C@H](C(=O)N(C)[C@@H]([C@@H](C)CC)[C@@H](CC(=O)N4CCC[C@H]4[C@H](OC)[C@@H](C)C(=O)N[C@H](C)[C@H](O)c4ccccc4)OC)C(C)C)C(C)C)cc3)C(C)C)C(=O)C21]
Formula (I-A1)
wherein the
is the bond to the spacer or binding agent.
In some embodiments, the fragment
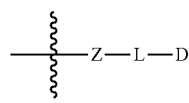
is according to Formula (I-A11):
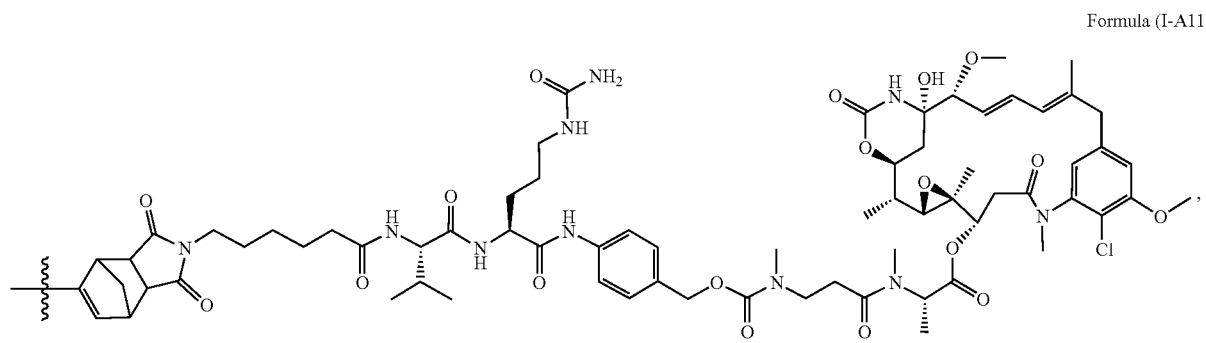 [SMILES: *C1=CC2CC1C1C(=O)N(CCCCCC(=O)N[C@H](C(=O)N[C@@H](CCCNC(N)=O)C(=O)Nc3ccc(COC(=O)N(C)CCC(=O)N(C)[C@@H](C)C(=O)O[C@H]4CC(=O)N(C)c5cc(cc(OC)c5Cl)C/C(C)=C/C=C/[C@@H](OC)[C@@]5(O)C[C@H](OC(=O)N5)[C@@H](C)[C@@H]5O[C@@]45C)cc3)C(C)C)C(=O)C21]
Formula (I-A11)
wherein the
is the bond to the spacer or binding agent.
In some embodiments, the fragment
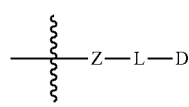

is according to Formula (I-DB):

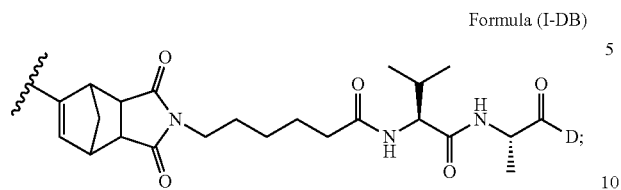

Formula (I-DB)

wherein the

is the bond to the spacer or binding agent.

In further embodiments of the reactive linker-payload compounds of Formula (I-DB), D is a pyrrolobenzodiazepine (PBD) or an analogue or derivative thereof as described herein. In one particular embodiment, D is PBD-1.

In some embodiments, the fragment

is according to Formula (I-B1):

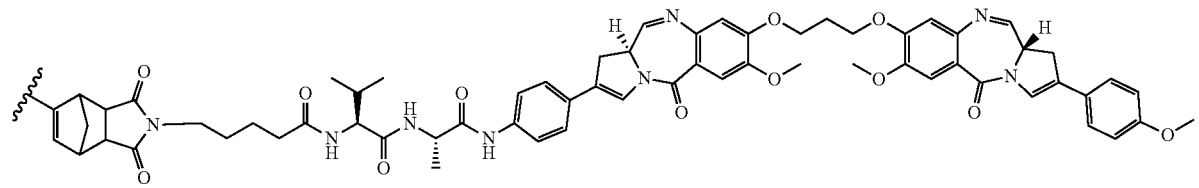

In some embodiments, the fragment

is according to Formula (I-DC):

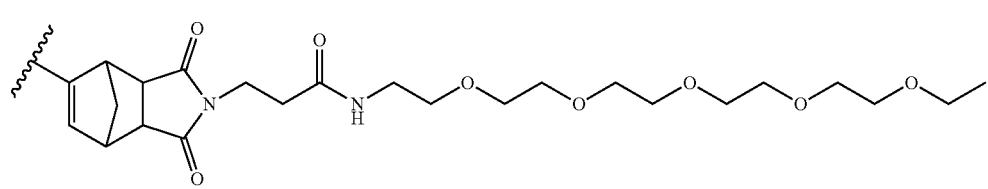

Formula (I-DC)

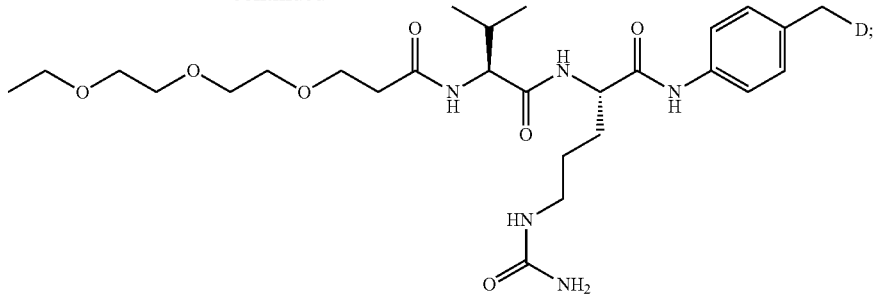
wherein the
is the bond to the spacer or binding agent.
In further embodiments of the reactive linker-payload compounds of Formula (I-DC), D is a rifamycin or an analogue or derivative thereof as described herein.
In some embodiments, the fragment
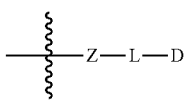
is according to Formula (I-C1):
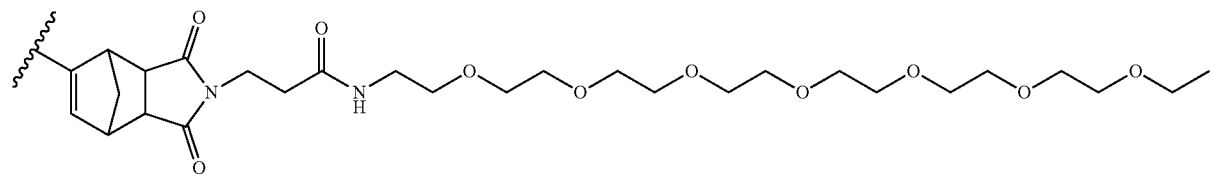
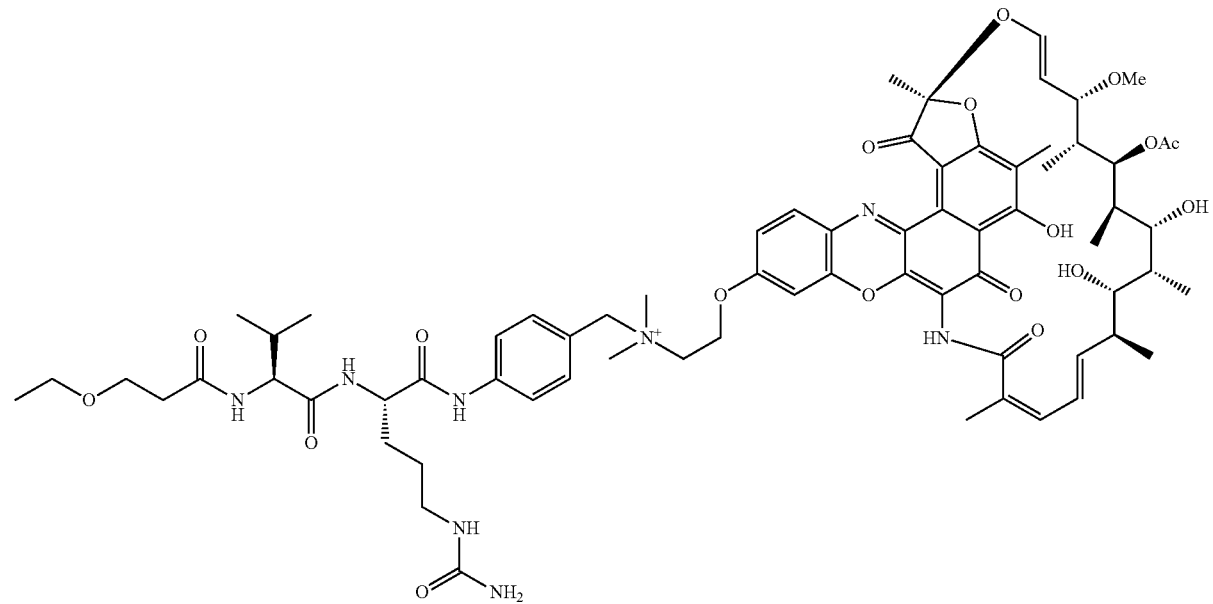

wherein the
is the bond to the spacer or binding agent.
In some embodiments, the fragment
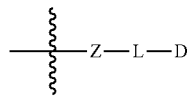
is according to Formula (I-C2):
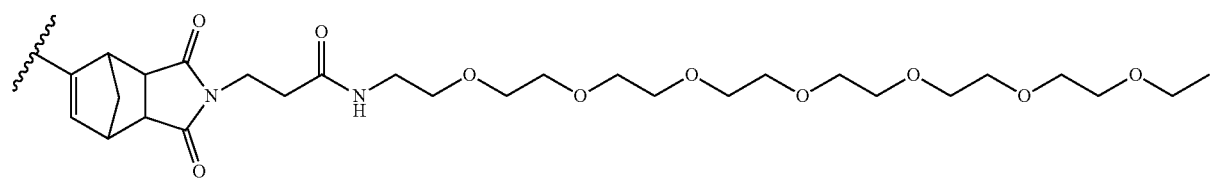
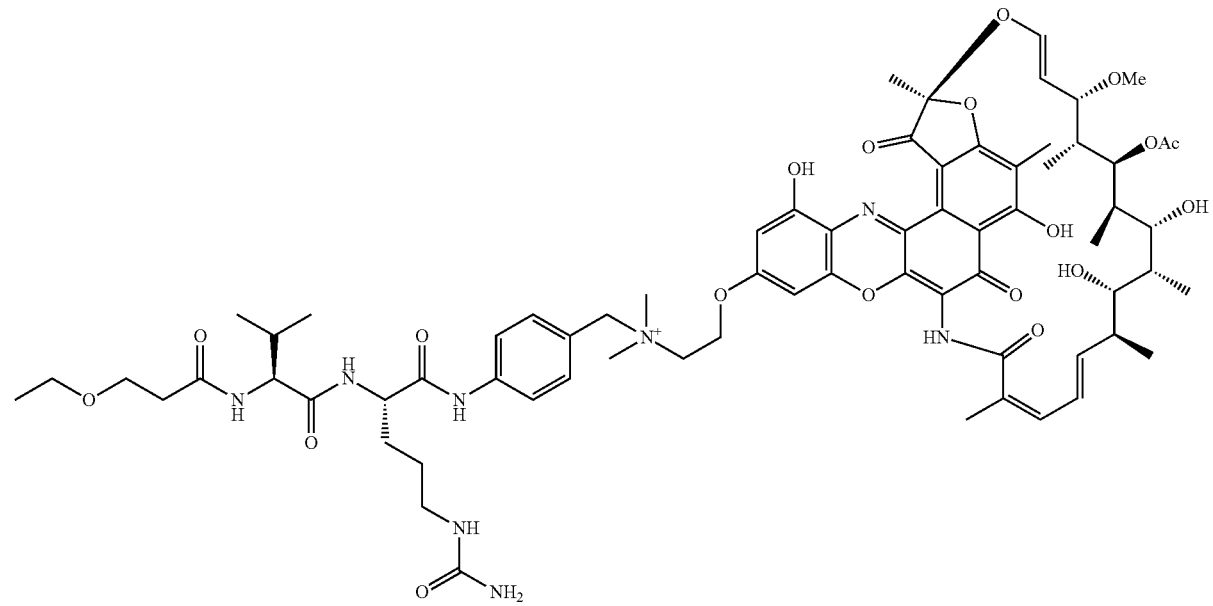
wherein the
is the bond to the spacer or binding agent.
In certain embodiments a protein-drug conjugate is provided having a structure according to Formulas (I-A1') through (I-A11'):

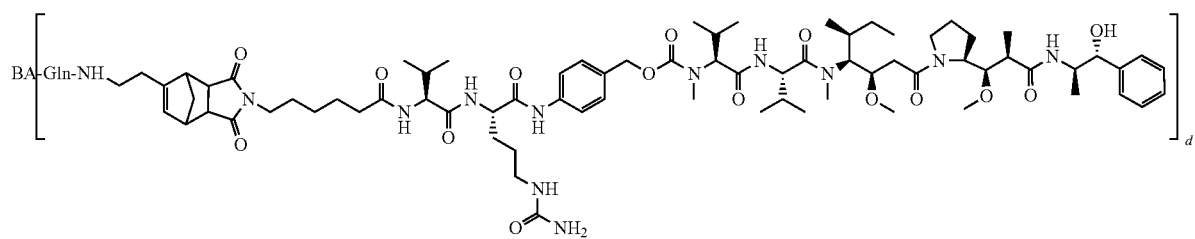
(I-A1', or BA-3-mc-VC-PABC-MMAE);
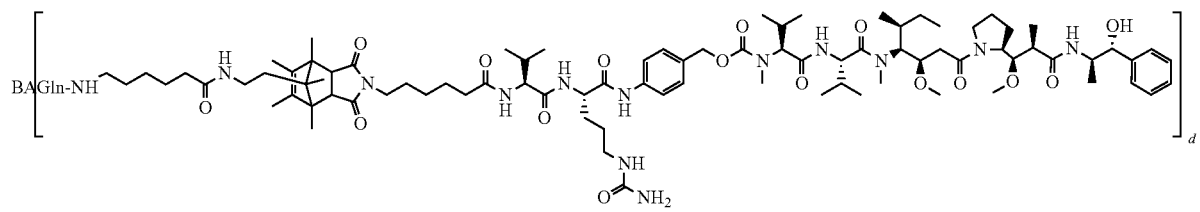
(I-A2', or BA-9-mc-VC-PABC-MMAE);
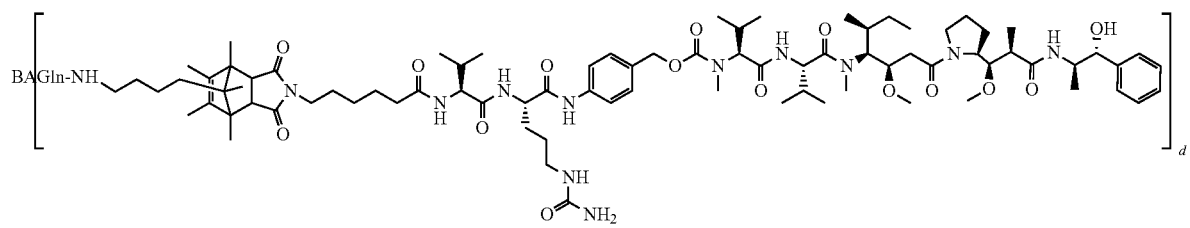
(I-A3', or BA-10-mc-VC-PABC-MMAE);
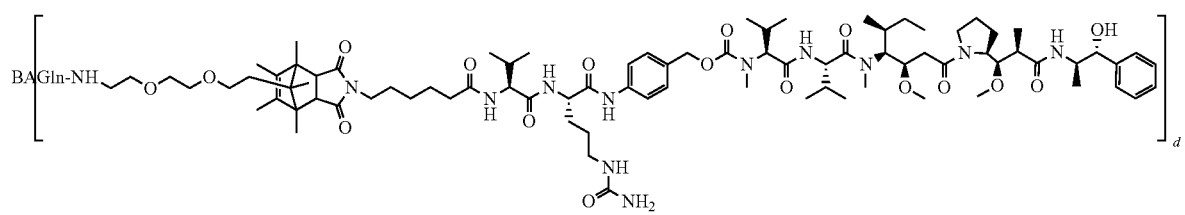
(I-A4', or BA-13-mc-VC-PABC-MMAE);
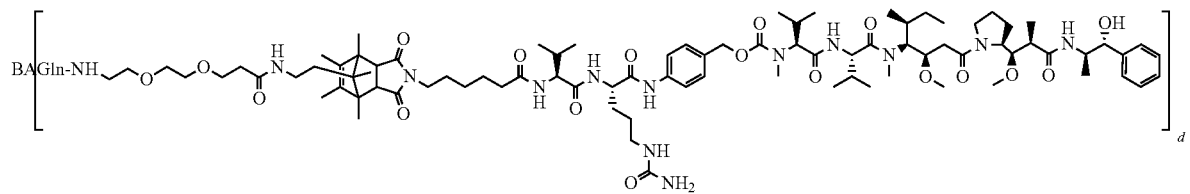
(I-A5', or BA-16-mc-VC-PABC-MMAE);

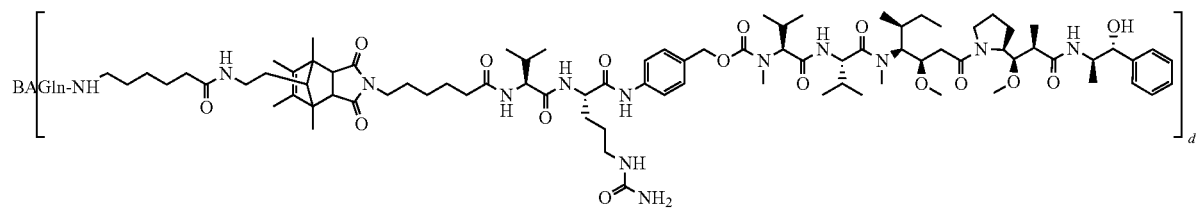
(I-A6′)
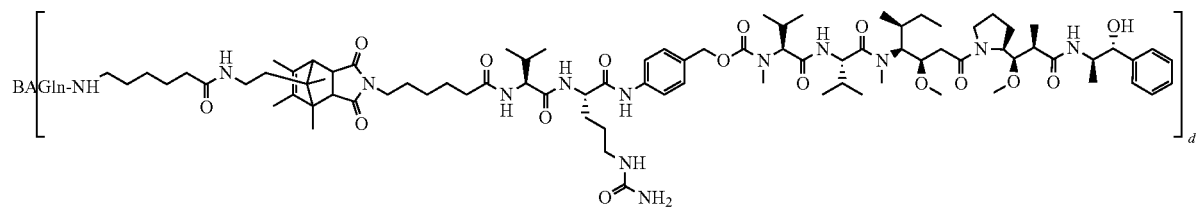
(I-A6″)
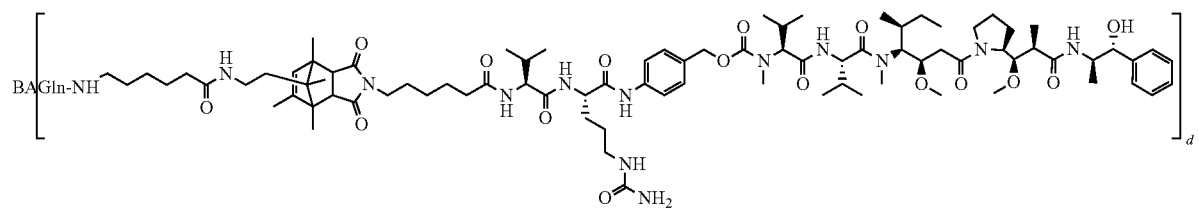
(I-A6‴)
(I-A6′, I-A6″, and I-A6‴, or BA-38-mc-VC-PABC-MMAE);
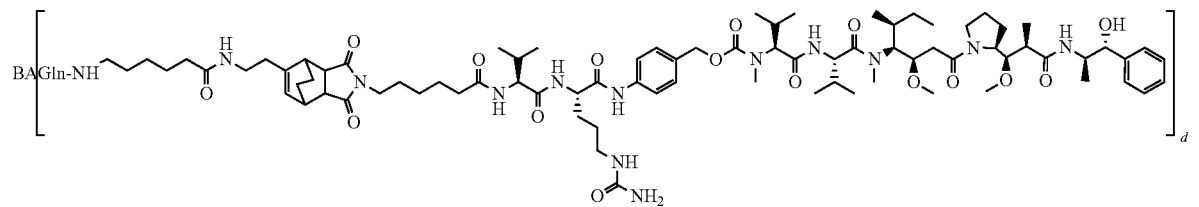
I-A7′
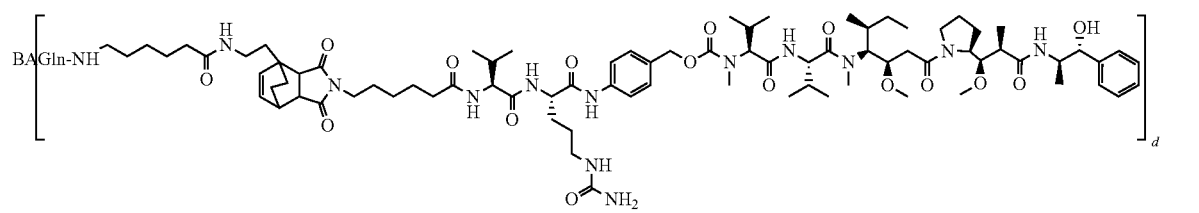
(I-A7″)
(I-A7′, I-A7″, or BA-44-mc-VC-PABC-MMAE);

-continued
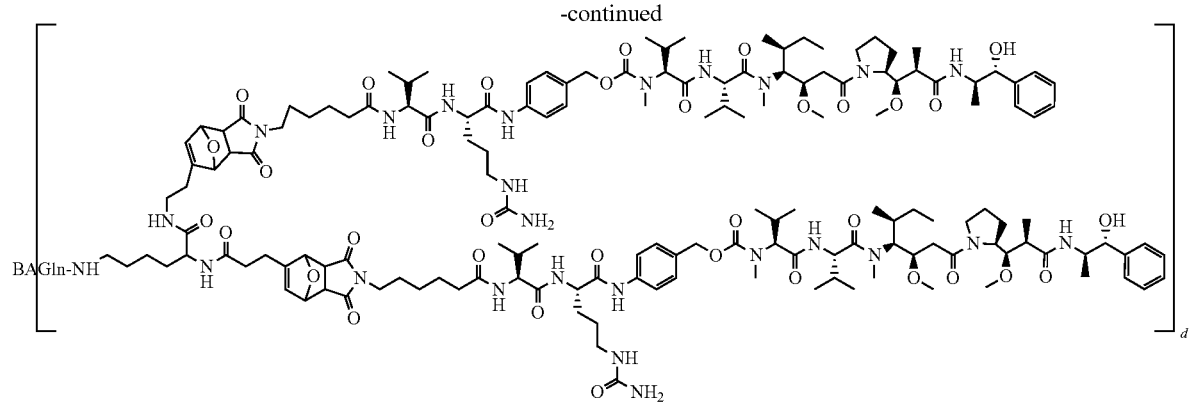
(I-A8′, or BA-48-mc-VC-PABC-MMAE);
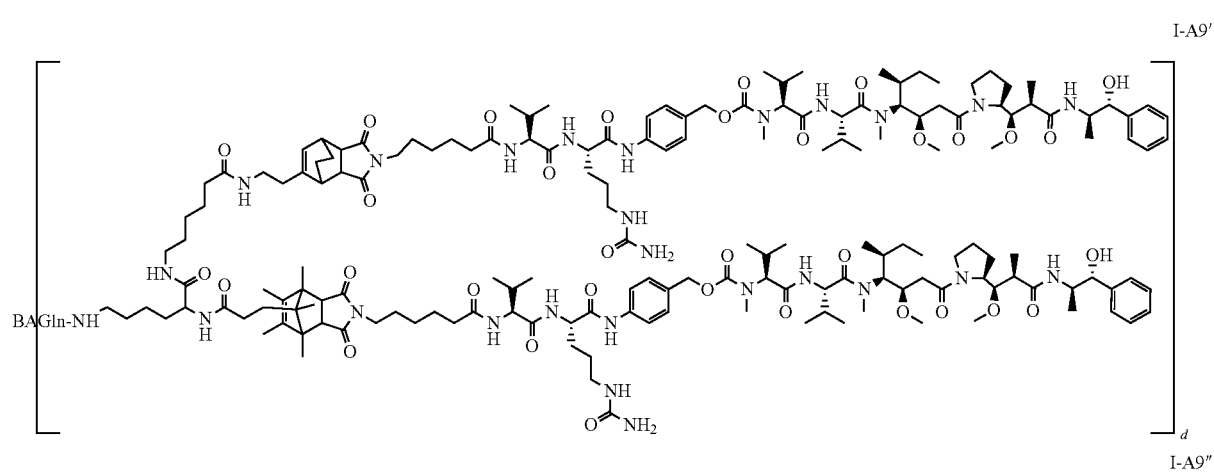
(I-A9′, I-A9″ or BA-46-mc-VC-PABC-MMAE);
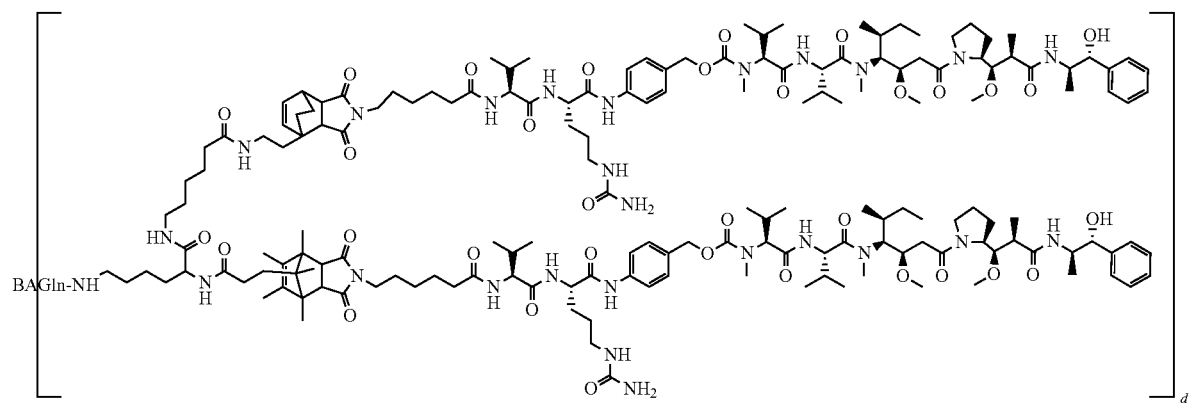
= Alexa Fluor 647
(I-A10′, or BA-27-mc-VC-PABC-MMAE-Alexa); and -continued

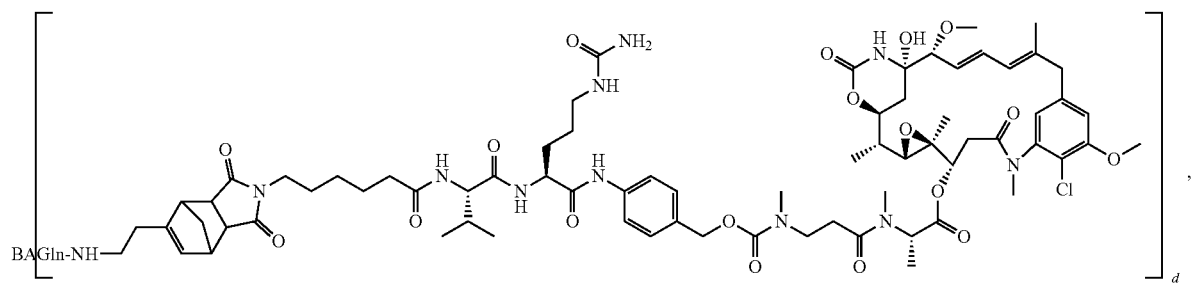
(I-A11')

wherein d is an integer from 1 to 6. In certain embodiments, BA is an antibody. In certain embodiments, BA is a monoclonal antibody. In certain embodiments, BA is a humanized monoclonal antibody. In certain embodiments, BA is an MSR1 antibody or an antigen-binding fragment thereof. In certain embodiments, BA is a HER2 antibody or an antigen-binding fragment thereof.

In certain embodiments a protein-drug conjugate is provided having a structure according to Formula (I-B1'):

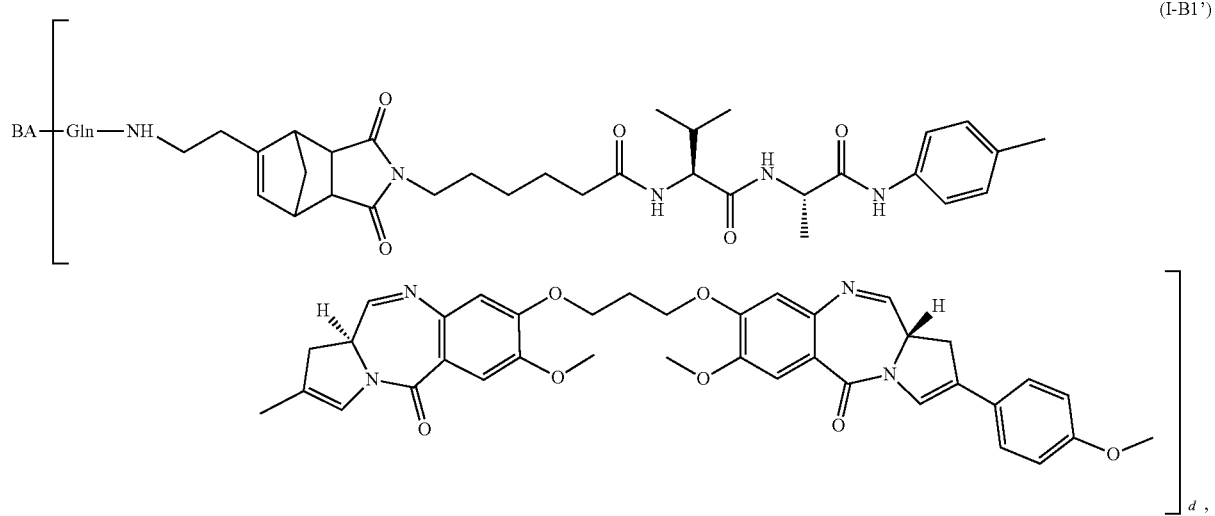
(I-B1')

wherein d is an integer from 1 to 4. wherein d is an integer from 1 to 6. In certain embodiments, BA is an antibody. In certain embodiments, BA is a monoclonal antibody. In certain embodiments, BA is a humanized monoclonal antibody. In certain embodiments, BA is an MSR1 antibody or an antigen-binding fragment thereof. In certain embodiments, BA is a HER2 antibody or an antigen-binding fragment thereof.

In certain embodiments a protein-drug conjugate is provided having a structure according to Formula (I-C1'):

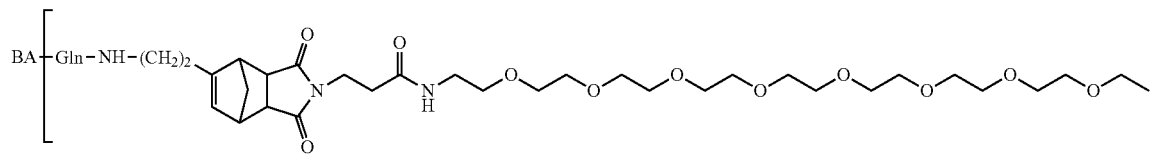
(I-C1')

-continued

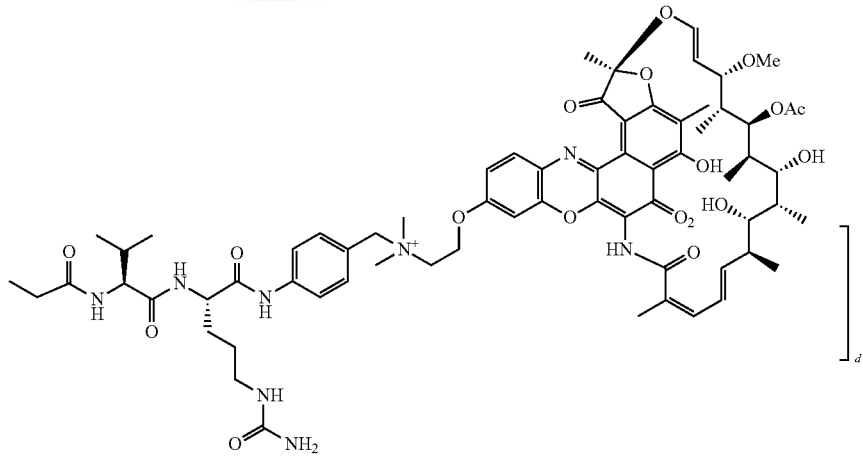

wherein d is an integer from 1 to 6. In certain embodiments, BA is an antibody. In certain embodiments, BA is a monoclonal antibody. In certain embodiments, BA is a humanized monoclonal antibody. In certain embodiments, BA is an MSR1 antibody or an antigen-binding fragment thereof. In certain embodiments, BA is a HER2 antibody or an antigen-binding fragment thereof. In certain embodiments, BA is trastuzumab.

Methods of Use

In another aspect, the protein-drug conjugates, e.g., ADCs, disclosed herein are useful, inter alia, for the treatment, prevention and/or amelioration of a disease, disorder or condition in need of such treatment.

In one embodiment, the protein-drug conjugates, e.g., ADCs, disclosed herein are useful for treating cancer. In another embodiment, the protein-drug conjugates, e.g., ADCs, disclosed herein are useful for treating an infection. In one embodiment, the protein-drug conjugates, e.g., ADCs, disclosed herein are useful for treating a bacterial infection. In another embodiment, the protein-drug conjugates, e.g., ADCs, disclosed herein are useful for treating a viral infection. In another embodiment, the protein-drug conjugates, e.g., ADCs, disclosed herein are useful for treating a fungal infection. In another embodiment, the protein-drug conjugates, e.g., ADCs, disclosed herein are useful for treating an inflammatory condition. In yet another embodiment, the protein-drug conjugates, e.g., ADCs, disclosed herein are useful for treating an immune system disorder.

In another aspect, the protein-payload conjugates disclosed herein are used, inter alia, for diagnostics and/or imaging. In one embodiment, the protein-payload conjugate according to the disclosure comprises an imaging agent moiety. Such an antibody may be used for, e.g., visualization of the distribution of the target protein within a sample, e.g., within a treated subject.

In some embodiments, the protein-drug conjugates according to the disclosure may comprise both a therapeutic moiety and an imaging agent moiety. In some embodiments, such conjugates may simultaneously be used to treat disease and to visualize the location of the protein's target in the body. In one non-limiting embodiment, such an antibody has the structure of Formula (I-A10'):

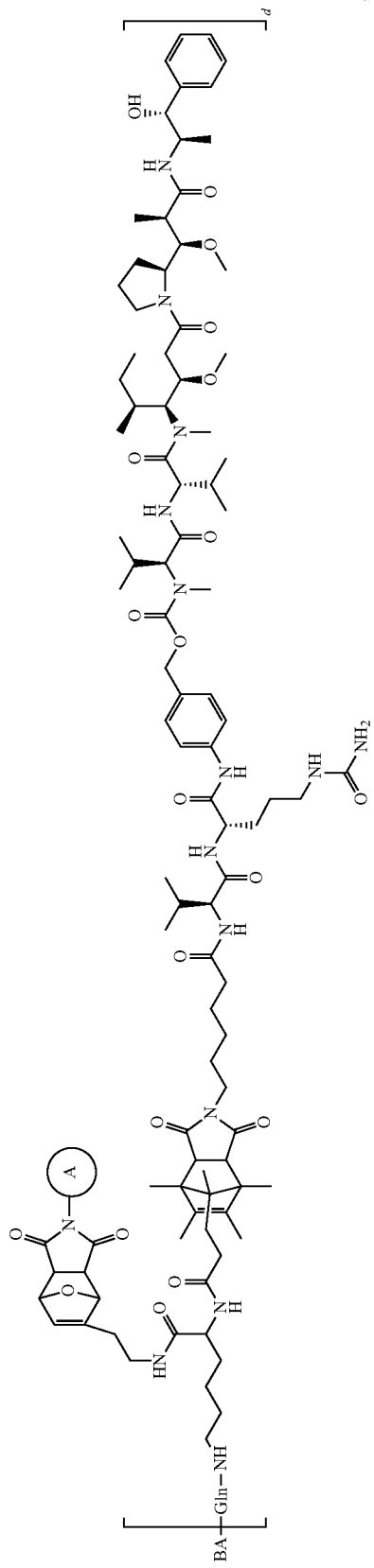

wherein d is an integer from 1 to 6.

Anti-HER2 Antibody-Drug Conjugates

In certain embodiments, the protein-drug conjugates, e.g., ADCs, disclosed herein are useful, inter alia, for the treatment, prevention and/or amelioration of any disease or disorder associated with or mediated by HER2 expression or activity, or treatable by binding HER2 without competing against modified LDL, or and/or promoting HER2 receptor internalization and/or decreasing cell surface receptor number.

The protein-drug conjugates of the present disclosure (and therapeutic compositions comprising the same) are useful, inter alia, for treating any disease or disorder in which stimulation, activation and/or targeting of an immune response would be beneficial. In particular, the anti-HER2 antibodies protein-drug conjugates of the present disclosure can be used for the treatment, prevention and/or amelioration of any disease or disorder associated with or mediated by HER2 expression or activity or the proliferation of HER2+ cells. The mechanism of action by which the therapeutic methods of the present disclosure are achieved include killing of the cells expressing HER2 in the presence of effector cells, for example, by CDC, apoptosis, ADCC, phagocytosis, or by a combination of two or more of these mechanisms. Cells expressing HER2 which can be inhibited or killed using the protein-drug conjugates of the present disclosure include, for example, breast tumor cells.

The protein-drug conjugates of the present disclosure can be used to treat, e.g., primary and/or metastatic tumors arising in the prostate, bladder, cervix, lung, colon, kidney, breast, pancreas, stomach, uterus, and/or ovary. In certain embodiments, the protein-drug conjugates of the present disclosure are used to treat one or more of the following cancers: prostate cancer, bladder cancer, cervical cancer, lung cancer, colon cancer, kidney cancer, breast cancer, pancreatic cancer, stomach cancer, uterine cancer, and ovarian cancer. According to certain embodiments of the present disclosure, the anti-HER2 antibodies or anti-HER2 are useful for treating a patient afflicted with a breast cancer cell that is IHC2+ or more. According to other related embodiments of the present disclosure, methods are provided comprising administering an anti-HER2 antibody as disclosed herein to a patient who is afflicted with a breast cancer cell that is IHC2+ or more. Analytic/diagnostic methods known in the art, such as tumor scanning, etc., can be used to ascertain whether a patient harbors a tumor that is castrate-resistant.

In certain embodiments, the present disclosure also includes methods for treating residual cancer in a subject. The term "residual cancer" means the existence or persistence of one or more cancerous cells in a subject following treatment with an anti-cancer therapy.

The protein-drug conjugates of the present disclosure (and therapeutic compositions comprising the same) are useful, inter alia, for treating any disease or disorder in which stimulation, activation and/or targeting of an immune response would be beneficial. In particular, protein-drug conjugates comprising the anti-HER2 antibodies of the present disclosure can be used for the treatment, prevention and/or amelioration of any disease or disorder associated with or mediated by HER2 expression or activity or the proliferation of HER2+ cells. The mechanism of action by which the therapeutic methods of the present disclosure are achieved include killing of the cells expressing HER2 in the presence of effector cells, for example, by CDC, apoptosis, ADCC, phagocytosis, or by a combination of two or more of these mechanisms. Cells expressing HER2 which can be inhibited or killed using the protein-drug conjugates of the present disclosure include, for example, breast tumor cells.

According to certain aspects, the present disclosure provides methods for treating a disease or disorder associated with HER2 expression (e.g., breast cancer) comprising administering one or more of the anti-HER2 protein-drug conjugates described elsewhere herein to a subject after the subject has been determined to have breast cancer (e.g., and IHC2+ breast cancer). For example, the present disclosure includes methods for treating breast cancer comprising administering protein-drug conjugate comprising an anti-HER2 antibody or antigen-binding molecule to a patient 1 day, 2 days, 3 days, 4 days, 5 days, 6 days, 1 week, 2 weeks, 3 weeks or 4 weeks, 2 months, 4 months, 6 months, 8 months, 1 year, or more after the subject has received hormone therapy (e.g., anti-androgen therapy).

In certain embodiments, the present disclosure also includes the use of an anti-HER2 antibody of the present disclosure in the manufacture of a medicament for the treatment of a disease or disorder (e.g., cancer) related to or caused by HER2-expressing cells. In one aspect, the present disclosure relates to a protein-drug conjugate comprising an anti-HER2 antibody or antigen-binding fragment, as disclosed herein, for use in medicine. In one aspect, the present disclosure relates to a compound comprising an antibody-drug conjugate (ADC) as disclosed herein, for use in medicine.

Anti-MSR1 Antibody-Drug Conjugates

In certain embodiments, the protein-drug conjugates, e.g., ADCs, disclosed herein are useful, inter alia, for the treatment, prevention and/or amelioration of any disease or disorder associated with or mediated by MSR1 expression or activity, or treatable by binding MSR1 without competing against modified LDL, or and/or promoting MSR1 receptor internalization and/or decreasing cell surface receptor number. For example, the antibodies and ADCs disclosed herein are useful for the treatment, attenuation, or amelioration of atherosclerosis, proliferative disorders, neurodegenerative disorders, and inflammation by targeting cells that express MSR1 and/or that respond to MSR1—mediated signaling, e.g., macrophages. In some embodiments, where the payload is a steroid, the disease, disorder, or condition is allergic state, including but not limited to asthma, atopic dermatitis, contact dermatitis, allergic dermatitis, drug hypersensitivity reactions, anaphylactic rhinitis, perennial or seasonal allergic rhinitis, and serum sickness; dermatologic diseases and conditions, including but not limited to skin itching, seborrheic dermatitis, neurodermatitis, eczema, bullous dermatitis herpetiformis, exfoliative erythroderma, mycosis fungoides, pemphigus, and severe erythema multiforme (Stevens-Johnson syndrome); endocrine disorders, including but not limited to primary or secondary adrenocortical insufficiency, congenital adrenal hyperplasia, hypercalcemia associated with cancer, and nonsuppurative thyroiditis; gastrointestinal diseases; hematologic disorders, including but not limited to acquired (autoimmune) hemolytic anemia, congenital (erythroid) hypoplastic anemia (Diamond-Blackfan anemia), idiopathic thrombocytopenia purpura in adults, pure red cell aplasia, and secondary thrombocytopenia; trichinosis; tuberculous meningitis with subarachnoid block or impending block; neoplastic diseases, including but not limited to leukemias and lymphomas; nervous system disorders, including but not limited to acute exacerbations of multiple sclerosis, cerebral edema associated with primary or metastatic brain tumor, craniotomy, or head injury; ophthalmic diseases, including but not limited to sympathetic ophthalmia, temporal arteritis, uveitis, xerophthalmia, and ocular inflammatory conditions unresponsive to topical corticosteroids; renal diseases, including but not limited to for inducing a diuresis or remission of proteinuria in idiopathic nephrotic syndrome or that due to lupus erythematosus; respiratory diseases, including but not limited to berylliosis, fulminating or disseminated pulmonary tuberculosis when used concurrently with appropriate antituberculous chemotherapy, idiopathic eosinophilic pneumonias, symptomatic sarcoidosis; and Rheumatic disorders, including but not limited to use as adjunctive therapy for short-term administration (to tide the patient over an acute episode or exacerbation) in acute gouty arthritis, acute rheumatic carditis, ankylosing spondylitis, psoriaticarthritis, rheumatoid arthritis, including juvenile rheumatoid arthritis, and for use in dermatomyositis, polymyositis, stomatitis, and systemic lupus erythematosus. In certain embodiments, provided herein are methods of treating or preventing arthritis.

In some embodiments, set forth herein is a method for treating a disease, disorder, or condition selected from an autoimmune disease, an allergy, arthritis, asthma, a breathing disorder, a blood disorder, a cancer, a collagen disease, a connective tissue disorders, a dermatological disease, an eye disease, an endocrine problem, an immunological disease, an inflammatory disease, an intestinal disorders, a gastrointestinal disease, a neurological disorder, an organ transplant condition, a rheumatoid disorder, a skin disorder, a swelling condition, a wound healing condition, and a combination thereof comprising administering a steroid payload or conjugate thereof described herein.

In some embodiments, the autoimmune disorder is selected from multiple sclerosis, autoimmune hepatitis, shingles, systemic lupus erythematosus (i.e., lupus), myasthenia gravis, Duchenne muscular dystrophy, and sarcoidosis. In some embodiments, the breathing disorder is selected from asthma, chronic respiratory disease, chronic obstructive pulmonary disease, bronchial inflammation, and acute bronchitis. In some embodiments, the cancer is selected from leukemia, lymphoblastic leukemia, acute lymphoblastic leukemia, chronic lymphoblastic some embodiments, the collagen disease is systemic lupus erythematosus. In some embodiments, the eye disease is keratitis. In some embodiments, the endocrine problem is selected from Addison's Disease, adrenal insufficiency, adrenal cortical dysfunction, adrenocortical, and congenital adrenal hyperplasia. In some embodiments, the inflammatory disease is selected from inflammation after cataract surgery, joint inflammation, immune inflammation, tendon inflammation, bursitis, epicondylitis, Crohn's disease, inflammatory bowels disease, lipid pneumonitis thyroiditis, urticaria (hives), pericarditis, nephrotic syndrome, and uveitis. In some embodiments, the intestinal disorder is selected from collagenous colitis, se. In some embodiments, the rheumatoid disorder is selected from rheumatoid arthritis, polymyalgia rheumatic, psoriatic arthritis, ankylosing spondylitis, and systemic lupus erythematosus. In some embodiments, the skin disorder is selected from psoriasis, eczema, and poison ivy. In some embodiments, the neurological disorder is chronic inflammatory demyelinating polyradiculoneuropathy.

In some embodiments, the compounds described herein are administered to a patient to treat an acute inflammatory event, including but not limited to shock, brain edema, and graft-vs-host disease. In some embodiments, the compounds described herein are administered to treat lymphocytic effects, including but not limited to those associated with hematological malignancies, e.g., leukemias, lymphomas, and myelomas.

In some embodiments, set forth herein is a method for reducing inflammation in a subject in need thereof, comprising administering to a subject in need thereof a therapeutically effective amount of a steroid or conjugate thereof described herein. In some embodiments, set forth herein is a method for modulating the immune system in a subject in need thereof, comprising administering to a subject in need thereof a therapeutically effective amount of a steroid or conjugate thereof described herein. In some embodiments, set forth herein is a method for modulating cortisol levels in a subject in need thereof, comprising administering to a subject in need thereof a therapeutically effective amount of a steroid or conjugate thereof described herein. In some embodiments, set forth herein is a method of reducing lymphocyte migration in a subject in need thereof, comprising administering to a subject in need thereof a therapeutically effective amount of a steroid or conjugate thereof described herein. In some embodiments, set forth herein is a method of treating hypercalcemia due to cancer, Meniere's disease, a migraine headache, a cluster headache, a severe aphthous ulcer, laryngitis, severe tuberculosis, a Herxheimer reaction to syphilis, a decompensated heart failure, allergic rhinitis or nasal polyps, comprising administering to a subject in need thereof a steroid payload or conjugate thereof described herein. In some embodiments, the compounds disclosed herein can be used for treating inflammatory bowel disease, Crohn's disease, or ulcerative colitis. In some embodiments, the disease, disorder, or condition is a chronic inflammatory condition, including but not limited to asthma, skin infections, and ocular infections. In some embodiments, compounds described herein are used for immunosuppression in patients undergoing organ transplantation.

In some embodiments, the steroid payloads and conjugates thereof described herein are administered to a patient to treat a nervous disorder associated with GR signaling, including but not limited to psychiatric disorders such as schizophrenia, drug addiction, post-traumatic stress disorder (PTSD), and mood disorders, substance abuse, stress, and anxiety.

In some embodiments, the steroid payloads and conjugates thereof described herein are administered to a patient to treat a visual system disorder, including but not limited to ocular inflammation (e.g., conjunctivitis, keratitis, uveitis), macular edema, and macular degeneration. In some embodiments, the steroid payloads and conjugates thereof described herein are administered to a patient to treat a cardiovascular disorder. In some embodiments, the steroid payloads and conjugates thereof described herein are administered to a patient to treat a glucose and/or liver metabolism disorder. In some embodiments, the steroid payloads and conjugates thereof described herein are administered to a patient to treat a musculoskeletal system disorder. In some embodiments, the steroid payloads and conjugates thereof described herein are administered to a patient to treat a cutaneous inflammatory condition, such as eczema and psoriasis.

The protein conjugates described herein provide a means for targeted delivery of its steroid payload to particular cells or organ systems, thereby reducing or preventing side effects that result from administration of the free unconjugated steroid payload. Examples of such potential side effects to be reduced or prevented include those listed in the approved drug label for Decadron® (dexamethasome), which is incorporated herein by reference in its entirety. In some embodiments, the side effect to be reduced or prevented is selected from elevation of blood pressure; sodium retention; water/fluid retention (edema, angioedema, pulmonary edema);

increased excretion of potassium; reversible hypothalamic-pituitary adrenal (HPA) axis suppression; potential corticosteroid insufficiency after withdrawal of treatment; susceptibility to infections; exacerbation of systemic fungal infections; worsening of severity of chickenpox in pediatric and adult patients; worsening of severity of measles in pediatric and adult patients; posterior subcapsular cataracts; glaucoma with possible damage to the optic nerves; enhancement of the establishment of secondary ocular infections due to bacteria, fungi, or -induced secondary adrenocortical insufficiency; increased risk of a perforation when active or latent peptic ulcers, diverticulitis, fresh intestinal anastomoses, and nonspecific ulcerative colitis, are present; peritoneal irritation following gastrointestinal perforation; decreased bone formation; increased bone resorption; inhibition of osteoblast function; inhibition of bone growth in pediatric patients; development of osteoporosis at any age; acute myopathy (possibly involving ocular and respiratory muscles, and potentially resulting in quadriparesis); elevation of creatinine kinase; psychic derangements, ranging from euphoria, insomnia, mood swings, personality changes, and severe depression, to frank psychotic manifestations; aggravation of existing emotional instability or psychotic tendencies; elevated intraocular pressure; bradycardia; cardiac arrest; cardiac arrhythmias; cardiac enlargement; circulatory collapse; congestive heart failure; fat embolism; hypertension; hypertrophic cardiomyopathy in premature infants; myocardial rupture following recent myocardial infarction; syncope; tachycardia; thromboembolism; thrombophlebitis; vasculitis; acne; allergic dermatitis; dry scaly skin; ecchymoses and petechiae; erythema; impaired wound healing; increased sweating; rash; striae; suppression of reactions to skin tests; thin fragile skin; thinning scalp hair; urticarial; decreased carbohydrate and glucose tolerance; development of cushingoid state; hyperglycemia; glycosuria; hirsutism; hypertrichosis; increased requirements for insulin or oral hypoglycemic agents in diabetes (insulin resistance); manifestations of latent diabetes mellitus; menstrual irregularities; secondary adrenocortical and pituitary unresponsiveness (particularly in times of stress; as in trauma; surgery; or illness); suppression of growth in pediatric patients; congestive heart failure in susceptible patients; fluid retention; hypokalemic alkalosis; potassium loss; sodium retention; abdominal distention; elevation in serum liver enzyme levels (usually reversible upon discontinuation); hepatomegaly; increased appetite; nausea; pancreatitis; peptic ulcer with possible perforation and hemorrhage; perforation of the small and large intestine (particularly in patients with inflammatory bowel disease); ulcerative esophagitis; negative nitrogen balance due to protein catabolismaseptic necrosis of femoral and humeral heads; loss of muscle mass; muscle weakness; osteoporosis; pathologic fracture of long bones; steroid myopathy; tendon rupture; vertebral compression fractures; convulsions; depression; emotional instability; euphoria; headache; increased intracranial pressure with papilledema (pseudotumor cerebri) usually following discontinuation of treatment; insomnia; mood swings; neuritis; neuropathy; paresthesia; personality changes; psychic disorders; vertigo; exophthalmos; glaucoma; increased intraocular pressure; posterior subcapsular cataracts; abnormal fat deposits; decreased resistance to infection; hiccups; increased or decreased motility and number of spermatozoa; malaise; moon face; and weight gain; and those side effects associated with drug-drug interactions. In some embodiments, the side effect to be reduced or prevented are those associated with drug-drug interactions. In some embodiments, the side effect to be reduced or prevented is associated with drug-drug interactions from the use of a corticosteroid with aminoglutethimide including diminishment of adrenal suppression by corticosteroids; amphotericin B injection and potassium-depleting agents, including development of hypokalemia, cardiac enlargement, and congestive heart failure; antibiotics including a significant decrease in corticosteroid clearance; anticholinesterases including producing severe weakness in patients with myasthenia gravis; oral anticoagulants including inhibition of response to warfarin; antidiabetics including increased blood glucose concentrations; antitubercular drugs including decreased serum concentrations of isoniazid; cholestyramine including increased clearance of corticosteroids; cyclosporine including increased activity of both cyclosporine and corticosteroids, and incidence of convulsions; dexamethasone suppression test (DST) interference including false-negative results in patients being treated with indomethacin; digitalis glycosides including increased risk of arrhythmias due to hypokalemia; ephedrine including enhancement of the metabolic clearance of corticosteroids, resulting in decreased blood levels and lessened physiologic activity; estrogens, including oral contraceptives, including decreased hepatic metabolism of certain corticosteroids and associated increase in their effect; hepatic enzyme inducers, inhibitors and substrates (drugs which induce cytochrome P450 3A4 (CYP 3A4) enzyme activity e.g., barbiturates, phenytoin, carbamazepine, rifampin), including enhancing of metabolism of corticosteroids; drugs which inhibit CYP 3A4 (e.g., ketoconazole, macrolide antibiotics such as erythromycin), including the potential for increased plasma concentrations of corticosteroids; drugs that are metabolized by CYP 3A4 (e.g., indinavir, erythromycin), including increase in their clearance, resulting in decreased plasma concentration; ketoconazole including decreased metabolism of certain corticosteroids by up to 60%, leading to increased risk of corticosteroid side effects, and inhibition of adrenal corticosteroid synthesis potentially causing adrenal insufficiency during corticosteroid withdrawal; nonsteroidal anti-inflammatory agents (NSAIDS), including increased risk of gastrointestinal side effects and increased clearance of salicylates; phenytoin, including increases or decreases in phenytoin level, altered seizure control; skin tests, including suppression of reactions to skin tests; thalidomide including toxic epidermal necrolysis; and vaccines including a diminished response to toxoids and live or inactivated vaccines due to inhibition of antibody response or potentiation of the replication of some organisms contained in live attenuated vaccines).

Thus, provided herein are methods for treating a disease, disorder, or condition associated with the glucocorticoid receptor comprising administering a conjugate of any of the Formulas as described above to a patient having said disease, disorder, or condition, wherein the side effects associated with administration of the free steroid payload of said conjugate is reduced. Furthermore, provided herein are methods of delivering a compound of any of the Formulas as described above to a cell comprising contacting said cell with a protein conjugate the compound of any of the Formulas as described above wherein the protein conjugate comprises an antibody or antigen binding fragment thereof that binds a surface antigen of said cell.

In some examples, where the payload is an LXR modulator, set forth herein is a method of treating a disease, disorder or condition comprising administering to a patient having said disorder a therapeutically effective amount of a compound and/or an ADC (e.g., ADCs of any of the Formulas as described above or a pharmaceutical composition thereof.

In some examples, set forth herein is a method of preventing a disease, disorder or condition comprising administering to a patient having said disorder a prophylactically effective amount of a compound and/or an ADC (e.g., ADCs of any of the Formulas as described above or a pharmaceutical composition thereof.

The proliferative disorder can be any proliferative disorder known to those of skill. In certain embodiments, proliferative disorders include, without limitation, oncology disorders, where the oncology disorder can be any cancer disorder known to those of skill. In certain embodiments, provided herein are methods of treating or preventing a melanoma. In certain embodiments, provided herein are methods of treating or preventing metastatic melanoma. In certain embodiments, provided herein are methods of treating or preventing lung cancer. In certain embodiments, provided herein are methods of treating or preventing EGFR-tyrosine kinase inhibitor resistant lung cancer. In certain embodiments, provided herein are methods of treating or preventing oral cancer. In certain embodiments, provided herein are methods of treating or preventing oral squamous cell carcinoma. In certain embodiments, provided herein are methods of treating or preventing prostate cancer. In certain embodiments, provided herein are methods of treating or preventing breast cancer.

The metabolic disease can be any metabolic disease known to those of skill. In certain embodiments, the metabolic disease is dyslipidemia. Dyslipidemia can be any dyslipidemia known to those of skill. In certain embodiments, dyslipidemia is selected from the group consisting of hyperlipidemia, hypercholesterolemia, hypertriglyceridemia, hyperlipoproteinemia, HDL deficiency, ApoA-I deficiency, and cardiovascular disease such as coronary artery disease (including, for example, treatment and prevention of angina, myocardial infarction, and sudden cardiac death); atherosclerosis (including, for example, treatment and prevention of atherosclerosis); and restenosis (including, for example, preventing or treating atherosclerotic plaques which develop as a consequence of medical procedures such as balloon angioplasty). In certain embodiments, provided herein are methods of treating or preventing diabetes.

The cardiovascular disease can be any cardiovascular disease known to those of skill. In certain embodiments, provided herein are methods of treating or preventing atherosclerosis. In certain embodiments, provided herein are methods of treating or preventing atherosclerosis derived from abnormal macrophage processing. In certain embodiments, provided herein are methods of treating or preventing atherosclerosis derived from the formation of oxidized low-density lipoproteins (oxLDLs), where marcrophages fail to process oxLDLs. In certain embodiments, provided herein are methods of treating or preventing ischemic heart disease. In certain embodiments, provided herein are methods of treating or preventing stroke. In certain embodiments, provided herein are methods of treating or preventing hypertensive heart disease. In certain embodiments, provided herein are methods of treating or preventing aortic aneurysm. In certain embodiments, provided herein are methods of treating or preventing endocarditis. In certain embodiments, provided herein are methods of treating or preventing peripheral artery disease. In certain embodiments, provided herein are methods of treating or preventing combinations of any of the diseases provided in this paragraph.

In some examples, set forth herein is a method for modulating the function of a nuclear receptor. By way of non-limiting example, the function can be selected from expression/secretion of inflammatory mediators (e.g. cytokines, chemokines), cholesterol regulation, cholesterol intake, cholesterol efflux, cholesterol oxidation, migration, chemotaxis, apoptosis and necrosis, an inflammatory activity, lipid regulation, apoptosis, migration, chemotaxis, gene transcription, and protein expression.

In some examples, set forth herein is a method of preventing a disease, disorder or condition comprising administering to a patient having said disorder a therapeutically effective amount of a compound and/or an ADC of any of the Formulas as described above, or a pharmaceutical composition thereof.

*S. aureus* is a facultative intracellular bacterium that can survive phagocytosis by macrophages and other cells types (Horn, J., et al., Inside job: *Staphylococcus aureus* host-pathogen interactions. *Int J Med Microbiol*, 2018. 308(6): p. 607-624; Jubrail, J., et al., Inability to sustain intraphagolysosomal killing of *Staphylococcus aureus* predisposes to bacterial persistence in macrophages. *Cell Microbiol*, 2016. 18(1): p. 80-96). Intravital imaging has demonstrated that macrophages can serve as a reservoir where *S. aureus* replicates and then seeds other organs during infection (Surewaard, B. G., et al., Identification and treatment of the *Staphylococcus aureus* reservoir in vivo. *J Exp Med*, 2016. 213(7): p. 1141-51). Most antibiotics do not penetrate cells, including macrophages, very well, indicating that the intracellular *S. aureus* reservoir can evade treatment with standard of care antibiotics (Lehar, S. M., et al., Novel antibody-antibiotic conjugate eliminates intracellular *S. aureus*. *Nature*, 2015. 527(7578): p. 323-8). However, liposomal formulation of vancomycin increased penetration of the antibiotic into macrophages and reduced *S. aureus* organ burden more effectively than standard of care vancomycin (Surewaard, B. G., et al., Identification and treatment of the *Staphylococcus aureus* reservoir in vivo. *J Exp Med*, 2016. 213(7): p. 1141-51). Together, these data indicate that delivering an antibiotic to macrophages can be an effective method to eliminate the intracellular *S. aureus* reservoir.

Antibiotic resistant *S. aureus* remains a public health problem and roughly 40% blood stream infections are caused by methicillin-resistant *S. aureus* (MRSA) in the USA. Few FDA approved treatment options exist for MRSA blood stream infections, with vancomycin remaining an antibiotic of choice. In spite of appropriate antibiotic treatment, mortality from *S. aureus* blood stream infections is ~18%, prompting investigation into combinations that can improve treatment.

The rifamycin class of antibiotics inhibit bacterial RNA polymerase (RNAP) and have potent activity against *S. aureus*. Monotherapy with this class of antibiotics, however, can lead to selection of a resistant population during treatment. Therefore, rifamycin antibiotics can be used in combination with first line antibiotics to improve outcomes, commonly in infections involving prostheses or foreign devices.

ADCs described herein comprising rifamycin analogs are useful for preventing or treating growth of a bacterium and/or bacterial infection in a subject. In some instances, the bacterium is a gram positive bacterium (a gram positive bacterium is the cause of the bacterial infection). In some instances, the bacterium is a penicillin-resistant bacterium (a penicillin-resistant bacterium is the cause of the bacterial infection). In some instances, the bacterium is a *Staphylococcus aureus*, methicillin resistant *Staphylococcus aureus*

(MRSA) bacterium (a MRSA bacterium is the cause of the bacterial infection). In some instances, the bacterium is a methicillin susceptible *Staphylococcus aureus* (MSSA) bacterium (a MSSA bacterium is the cause of the bacterial infection). In some instances, the bacterium is a vancomycin-resistant *Staphylococcus aureus* (VRSA) bacterium (a VRSA bacterium is the cause of the bacterial infection). In some instances, the bacterium is multi-drug resistant *M. tuberculosis* (a multi-drug resistant *M. tuberculosis* bacterium is the cause of the bacterial infection). In further instances, the bacterium is *Chlamydia trachomatis* resistant to, e.g., azithromycin (*Chlamydia trachomatis* resistant to, e.g., azithromycin is the cause of the bacterial infection). In more instances, the bacterium is *Clostridium difficile* resistant to, e.g., metronidazole, vancomycin, and/or fidaxomicin (*Clostridium difficile* resistant to, e.g., metronidazole, vancomycin, and/or fidaxomicin is the cause of the bacterial infection).

Provided herein is a method of preventing or treating cellulitis, bacteremia, dermonecrosis, eyelid infection, eye infection, neonatal conjunctivitis, osteomyelitis, impetigo, boils, scalded skin syndrome, food poisoning, pneumonia, surgical infection, urinary tract infection, burn infection, meningitis, endocarditis, septicemia, toxic shock syndrome, septic arthritis, mastitis, infection associated with a prosthetic joint, infection associated with a catheter, or infection associated with an implant, in a subject comprising administering to the subject an effective treatment amount of an antibody-drug conjugate comprising a rifamycin analog. Also provided herein is a method of preventing or treating an intracellular bacterial infection in a subject comprising administering to the subject an effective treatment amount of an antibody-drug conjugate of an antibody-drug conjugate comprising a rifamycin analog.

In some instances, provided herein are therapeutic methods comprising administration an anti-MSR1 antibody, an antigen-binding portion of an anti-MSR1 antibody, or an ADC comprising an anti-MSR1 antibody of MSR1 antigen-binding fragment thereof, to a subject in need thereof are useful for the treatment, and/or prevention of bacterial infection in a subject, and/or a disease or disorder or condition associated with Staphylococcal infection, for example, a *S. aureus* infection and/or for ameliorating at least one symptom associated with such disease, disorder or condition. Such disease, disorder or condition can be cellulitis, bacteremia, dermonecrosis, eyelid infection, eye infection, neonatal conjunctivitis, osteomyelitis, impetigo, boils, scalded skin syndrome, food poisoning, pneumonia, surgical infection, urinary tract infection, burn infection, meningitis, endocarditis, septicemia, toxic shock syndrome, or septic arthritis. In some instances, the subject has a prosthetic joint and the antibodies disclosed herein are used for treating and/or preventing *S. aureus* infection of the tissue surrounding the prosthetic joint. In some instances, the subject has a catheter and the antibodies disclosed herein are used for treating and/or preventing *S. aureus* infection of the catheter and/or the tissue surrounding the catheter. In some instances, the subject has a foreign body implanted, and the antibodies disclosed herein are used for treating and/or preventing *S. aureus* infection of the foreign body and/or the tissue surrounding the foreign body. In some instances, the subject has mastitis, and the antibodies disclosed herein are useful for treating mastitis.

In some instances, the rifamycin analogs and/or anti-MSR1 ADCs thereof are administered in combination with one or more additional antibiotics (e.g., antibiotics that can be used for MRSA infections) such as vancomycin, trimethoprim-sulfamethoxazole, tetracycline, doxycycline/minocycline, clindamycin, cephalosporins (e.g. cephalexin), nafcillin, fidaxomicin, linezolid, and the like, and/or any other suitable antibiotic(s). In some instances, the ADCs described herein comprising rifamycin analogs are administered in combination.

Also provided herein are methods of preventing or inhibiting growth of a bacterium comprising administration of an effective amount of an antibody-drug conjugate (ADC) comprising an anti-MSR1 antibody or MSR1 antigen-binding fragment thereof and a rifamycin analog.

Also provided herein are therapeutic methods comprising administration of an effective amount of an ADC comprising an anti-MSR1 antibody or MSR1 antigen-binding fragment thereof and a rifamycin analog, to a subject in need thereof. The therapeutic methods comprise administering a therapeutically effective amount of a pharmaceutical composition comprising an ADC comprising an anti-MSR1 antibody or MSR1 antigen-binding fragment thereof and a rifamycin analog to the subject. The disorder treated is any disease or condition which is improved, ameliorated, inhibited or prevented by targeting MSR1 and/or by the administration of an antibiotic agent. In some embodiments, the disease or condition is a proliferative disease, a metabolic disease, inflammation, a neurodegenerative disease, or disease, disorder, or condition associated with glucocorticoid receptor signaling. In some of such embodiments, the side effects associated with administration of the unconjugated rifamycin analog are reduced. Provided herein is the use of an anti-MSR1 antibody, an antigen-binding portion of an anti-MSR1 antibody, or an ADC comprising an anti-MSR1 antibody of MSR1 antigen-binding fragment thereof, described herein, such as H1H21234N, for the treatment of any disease disorder or condition described herein.

Also provided herein are therapeutic methods for treating, attenuating, or ameliorating a disease or disorder or condition associated with Staphylococcal infection, for example, a *S. aureus* infection and/or for ameliorating at least one symptom associated with such disease, disorder or condition, comprising administration of a rifamycin analog or an ADC comprising an anti-MSR1 antibody (such as H1H21234N) or MSR1 antigen-binding fragment thereof and a rifamycin analog, to a subject in need thereof. Such disease, disorder or condition can be cellulitis, bacteremia, dermonecrosis, eyelid infection, eye infection, neonatal conjunctivitis, osteomyelitis, impetigo, boils, scalded skin syndrome, food poisoning, pneumonia, surgical infection, urinary tract infection, burn infection, meningitis, endocarditis, septicemia, toxic shock syndrome, or septic arthritis. In some embodiments, the subject has a prosthetic joint and the rifamycin analogs or ADCs comprising an anti-MSR1 antibody or MSR1 antigen-binding fragment thereof and a rifamycin analog disclosed herein are used for treating and/or preventing *S. aureus* infection of the tissue surrounding the prosthetic joint. In some embodiments, the subject has a catheter and the rifamycin analogs or ADCs comprising an anti-MSR1 antibody or MSR1 antigen-binding fragment thereof and a rifamycin analog disclosed herein are used for treating and/or preventing *S. aureus* infection of the catheter and/or the tissue surrounding the catheter. In some embodiments, the subject has a foreign body implanted, and the rifamycin analogs or ADCs comprising an anti-MSR1 antibody or MSR1 antigen-binding fragment thereof and a rifamycin analog disclosed herein are used for treating and/or preventing *S. aureus* infection of the foreign body and/or the tissue surrounding the foreign body. In some embodiments, the subject has mastitis, and the antibodies disclosed herein are useful for treating mastitis. The therapeutic methods comprise administering a therapeutically effective amount of a pharmaceutical composition comprising a rifamycin analog or an ADC comprising an anti-MSR1 antibody or MSR1 antigen-binding fragment thereof and a rifamycin analog, to a subject in need thereof.

In another aspect, the present disclosure provides an antibody-drug conjugate comprising an antibody, or an antigen-binding fragment thereof, conjugated to the rifamycin analog compound of any of the embodiments of the disclosure via a linker or through a linker-spacer.

In one embodiment, the antibody, or the antigen-binding fragment thereof, binds macrophage scavenger receptor 1 (MSR1).

In one embodiment, the antibody, or the antigen-binding fragment thereof, can comprise:
 (i) a HCDR1 domain comprising an amino acid sequence selected from the group consisting of SEQ ID NOs: 4, 36, 52, 92, and 284;
 (ii) a HCDR2 domain comprising an amino acid sequence selected from the group consisting of SEQ ID NOs: 6, 38, 54, 94, and 286;
 (iii) a HCDR3 domain comprising an amino acid sequence selected from the group consisting of SEQ ID NOs: 8, 40, 56, 96, and 288;
 (iv) a LCDR1 domain comprising an amino acid sequence selected from the group consisting of SEQ ID NOs: 12, 44, 60, 100, and 292;
 (v) a LCDR2 domain comprising an amino acid sequence selected from the group consisting of SEQ ID NOs: 14, 46, 62, 102, and 294; and
 (vi) a LCDR3 domain comprising an amino acid sequence selected from the group consisting of SEQ ID NOs: 16, 48, 64, 104, and 296.

Pharmaceutical Compositions and Methods of Administration

Also provided are methods comprising administering to a subject in need thereof a therapeutic composition comprising a protein or antibody conjugate disclosed herein. The therapeutic composition can comprise any of conjugates described herein, and a pharmaceutically acceptable carrier or diluent.

The protein-drug conjugates of the description are useful, inter alia, for the treatment, prevention and/or amelioration of any disease or disorder associated with or mediated by their cognate antigen expression or activity, or treatable by blocking the interaction between their cognate antigen and receptor or ligand or otherwise inhibiting antigen activity and/or signaling, and/or promoting receptor internalization and/or decreasing cell surface receptor number. For example, protein-drug conjugates of the present description can be useful for the treatment of tumors that express their cognate antigens and/or that respond to antigen-mediated signaling. The antibodies and conjugates provided herein can also be used to treat primary and/or metastatic tumors arising in the brain and meninges, oropharynx, lung and bronchial tree, gastrointestinal tract, male and female reproductive tract, muscle, bone, skin and appendages, connective tissue, spleen, immune system, blood forming cells and bone marrow, liver and urinary tract, and special sensory organs such as the eye. In certain embodiments, the protein-drug conjugates of the description are used to treat one or more of the following cancers: renal cell carcinoma, pancreatic carcinoma, head and neck cancer, prostate cancer, malignant gliomas, osteosarcoma, colorectal cancer, gastric cancer (e.g., gastric cancer with MET amplification), malignant mesothelioma, multiple myeloma, ovarian cancer, small cell lung cancer, non-small cell lung cancer, synovial sarcoma, thyroid cancer, breast cancer, or melanoma.

In the context of the methods of treatment described herein, the protein-drug conjugates can be administered as a monotherapy (i.e., as the only therapeutic moiety) or in combination with one or more additional therapeutic moieties (examples of which are described elsewhere herein).

Provided herein are pharmaceutical (i.e., therapeutic) compositions comprising the protein-drug conjugates provided herein. The pharmaceutical compositions of the description are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™, Life Technologies, Carlsbad, Calif.), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) *J. Pharm. Sci. Technol.* 52:238-311.

The dose of protein-drug conjugate administered to a patient can vary depending upon the age and the size of the patient, target disease, conditions, route of administration, and the like. In certain embodiments, the dose is calculated according to body weight or body surface area. In an adult patient, it can be advantageous to intravenously administer the antibody of the present description normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering antibodies can be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical composition of the description, e.g., encapsulation in liposomes, microparticles, microcapsules, recombinant cells capable of expressing the mutant viruses, receptor mediated endocytosis (see, e.g., Wu et al., 1987, *J. Biol. Chem.* 262:4429-4432). Methods of introduction include, but are not limited to, intradermal, intramuscular, intraperitoneal, intravenous, subcutaneous, intranasal, epidural, and oral routes. The composition can be administered by any convenient route, for example by infusion or bolus injection, by absorption through epithelial or mucocutaneous linings (e.g., oral mucosa, rectal and intestinal mucosa, etc.) and can be administered together with other bio-logically active agents. Administration can be systemic or local.

A pharmaceutical composition of the present description can be delivered subcutaneously or intravenously with a standard needle and syringe. In addition, with respect to subcutaneous delivery, a pen delivery device readily has applications in delivering a pharmaceutical composition of the present description. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present description. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present description include, but are not limited to the SO-LOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.), and the HUMIRA™ Pen (Abbott Labs, Abbott Park, Ill.), to name only a few.

In certain situations, the pharmaceutical composition can be delivered in a controlled release system. In one embodiment, a pump can be used (see Langer, supra; Sefton, 1987, *CRC Crit. Ref. Biomed. Eng.* 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in *Medical Applications of Controlled Release*, supra, vol. 2, pp. 115-138). Other controlled release systems are discussed in the review by Langer, 1990, Science 249:1527-1533.

The injectable preparations can include dosage forms for intravenous, subcutaneous, intracutaneous and intramuscular injections, drip infusions, etc. These injectable preparations can be prepared by methods publicly known. For example, the injectable preparations can be prepared, e.g., by dissolving, suspending or emulsifying the antibody or its salt described herein in a sterile aqueous medium or an oily medium conventionally used for injections. As the aqueous medium for injections, there are, for example, physiological saline, an isotonic solution containing glucose and other auxiliary agents, etc., which can be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which can be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described herein are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, in certain embodiments the aforesaid antibody is contained in about 5 to about 100 mg and in about 10 to about 250 mg for the other dosage forms.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy.

Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo [4.3.0] nona-2,7, 9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-/V,/V-dimethylethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU1 1248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1 126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-1 1, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g. calicheamicin, calicheamicin gammal I, calicheamicin omegal I (Angew Chem. Intl. Ed. Engl. (1994) 33: 183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; antimetabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, OR); razoxane; rhizoxin; sizofiran; spirogermanium; tenuazonic acid; triaziquone; 2, 2', 2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-1 1; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifene citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idee), ofatumumab (ARZERRA®, GSK), pertuzumab (PERJETA™, OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Also included in the definition of "chemotherapeutic agent" are agents which modulate specific molecules or classes of molecule that are of particular importance in cancer pathology. Examples of specific molecules of interest are vEGF and EGFR (HER1, HER2, and/or HER3). An examples of a class of molecules of interest are the immune checkpoint modulators such as the anti PDL-1 or CTLA4 immune modulators. Examples of such suitable agents include antibodies, nucleic acids (e.g. ribozymes, siRNAs), and small molecules. In some embodiments the agents inhibit the expression and/or activity of the specific molecules. In some embodiments the agents activate the expression and/or activity of the specific molecules.

Humanized monoclonal antibodies with therapeutic potential as chemotherapeutic agents in combination with the conjugates of the disclosure include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

Pharmaceutical compositions according to the present disclosure, and for use according to the present disclosure, can comprise, in addition to the active ingredient, i.e. the protein-drug conjugate of the present disclosure, a pharmaceutically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration, which can be oral, or by injection, e.g. cutaneous, subcutaneous, or intravenous.

In another aspect, provided herein is a pharmaceutical composition comprising an antibody-drug conjugate comprising a recombinant human antibody or fragment thereof which specifically binds MSR1, further comprising a rifamycin analog, and a pharmaceutically acceptable carrier. In a related aspect, embodiments relate to a composition which is a combination of an antibody-drug conjugate comprising an anti-MSR1 antibody and further comprising a rifamycin analog, and a second therapeutic moiety. In one embodiment, the second therapeutic moiety is any agent that is advantageously combined with an antibody-drug conjugate comprising an anti-MSR1 antibody. In one embodiment, the second therapeutic moiety is an antibody-drug conjugate comprising an anti-MSR1 antibody conjugated to a second drug or a therapeutic moiety. Exemplary combination therapies, co-formulations, and ADCs involving the anti-MSR1 antibodies are disclosed elsewhere herein.

In certain embodiments, the present disclosure provides pharmaceutical compositions comprising the protein-drug conjugates of the present disclosure. The pharmaceutical compositions of the present disclosure are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, PA. These formulations include, for example, powders, pastes, ointments, jellies, waxes, oils, lipids, lipid (cationic or anionic) containing vesicles (such as LIPOFECTIN™, Life Technologies, Carlsbad, CA), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

In certain embodiments, the present disclosure includes methods comprising administering to a subject in need thereof a therapeutic composition comprising an anti-HER2 antibody or antigen-binding fragment thereof that specifically binds HER2. The therapeutic composition can comprise any of the antibodies or antigen-binding molecules as disclosed herein and a pharmaceutically acceptable carrier or diluent. The expression "a subject in need thereof" means a human or non-human animal that exhibits one or more symptoms or indicia of cancer (e.g., a subject expressing a tumor or suffering from any of the cancers mentioned herein below), or who otherwise would benefit from an inhibition or reduction in HER2 activity or a depletion of HER2+ cells (e.g., breast cancer cells).

In another aspect, the present disclosure provides a pharmaceutical composition comprising a recombinant human antibody or fragment thereof which specifically binds HER2 and a pharmaceutically acceptable carrier. In a related aspect, the present disclosure features a composition which is a combination of an anti-HER2 antibody and a second therapeutic moiety. In one embodiment, the second therapeutic moiety is any agent that is advantageously combined with an anti-HER2 antibody. Additional combination therapies and co-formulations involving the anti-HER2 antibodies of the present disclosure are disclosed elsewhere herein.

In another aspect, the present disclosure provides therapeutic methods for targeting/killing tumor cells expressing HER2 using an anti-HER2 antibody of the present disclosure, wherein the therapeutic methods comprise administering a therapeutically effective amount of a pharmaceutical composition comprising an anti-HER2 antibody of the present disclosure to a subject in need thereof. In some cases, the anti-HER2 antibodies (or antigen-binding fragments thereof) can be used for treating breast cancer, or can be modified to be more cytotoxic by methods, including but not limited to, modified Fc domains to increase ADCC (see e.g. Shield et al. (2002) JBC 277:26733), radioimmunotherapy, antibody-drug conjugates, or other methods for increasing the efficiency of tumor ablation.

Methods of Making the Compounds of the Disclosure

Techniques for conjugating primary amine compounds are known in the art. Site specific conjugation techniques are employed herein to direct conjugation to glutamine using glutamine conjugation via transglutaminase (see e.g., Schibli, *Angew Chemie* Inter Ed. 2010, 49, 9995). See also, WO 2017147542, the subject matter of which is expressly incorporated herein. Provided herein are methods of making glutaminyl-modified proteins and protein-drug conjugates (such as ADCs), as described herein and compositions useful in the provided methods, and compositions produced by the methods. Conjugated proteins are useful in assays, diagnostics, and therapies, including the treatment of cancer in subjects in need thereof.

In certain embodiments, the method comprises at least step (2) below wherein the reactive amine compound is a reactive linker-payload compound according to the present disclosure.

The methods comprise a transglutaminase reaction at a glutamine residue of an antibody. The antibody can be any antibody known to those of skill in the art. Useful antibodies are described in a section herein.

Those of skill will recognize that the antibody should comprise at least one glutamine residue. In certain embodiments, the antibody comprises a glutamine residue at one or more heavy chain positions numbered 295 in the EU numbering system. In the present disclosure, this position is referred to as glutamine 295, or as Gln295, or as Q295. Those of skill will recognize that this is a conserved glutamine residue in the wild type sequence of many antibodies. In other useful embodiments, the antibody can be engineered to comprise a glutamine residue. Techniques for modifying an antibody sequence to include a glutamine residue are within the skill of those in the art (See, e.g., Ausubel et al, *Current Protoc. Mol. Biol*).

In certain embodiments, the antibody comprises two glutamine residues, one in each heavy chain. In particular embodiments, the antibody comprises a Q295 residue in each heavy chain. In further embodiments, the antibody comprises one, two, three, four, five, six, seven, eight, or more glutamine residues. These glutamine residues can be in heavy chains, light chains, or in both heavy chains and light chains. These glutamine residues can be wild-type residues, or engineered residues. The antibodies can be prepared according to standard techniques.

Those of skill will recognize that antibodies are often glycosylated at residue N297, near residue Q295 in a heavy chain sequence. Glycosylation at residue N297 can interfere with a transglutaminase at residue Q295 (Dennler et al., supra), and affect drug-to-antibody ratios (DARs). Accordingly, in advantageous embodiments, the antibody is not glycosylated. In certain embodiments, the antibody is deglycosylated or aglycosylated.

In a deglycosylation step, the antibody can be deglycosylated by any technique apparent to those of skill in the art. In particular embodiments, a deglycosylated antibody is prepared by removing one or more oligosaccharides from the antibody. The deglycosylation can be carried out by any technique apparent to those of skill. In certain embodiments, the antibody is deglycosylated chemically. In certain embodiments, the antibody is deglycosylated enzymatically. In certain embodiments, the antibody can be deglycosylated by expression in a system that does not glycosylate polypeptides. Useful expression systems include, for example, prokaryotic expression systems.

In certain embodiments, provided herein are methods comprising the following step:

(1) deglycosylating the antibody.

The antibody can be deglycosylated by any technique deemed suitable by those of skill in the art. In certain embodiments, the antibody is contacted with a reagent capable of cleaving a bond between the antibody and an oligosaccharide. The reagent can be any reagent known to those of skill in the art. In particular embodiments, the reagent is an enzyme capable of cleaving a bond between an asparagine side chain and an N-linked oligosaccharide. In certain embodiments, the reagent is PNGase F, or peptide-N4-(N-acetyl-beta-glucosaminyl)asparagine amidase, or EC 3.5.1.52. Reagents such as PNGase F can be obtained from commercial sources. In certain embodiments, the reagent is Protein Deglycosylation Mix (New England Biolabs). The reagent is used in an amount suitable for the amount of glycosylated antibody and the reaction volume. In certain embodiments, about 0.4 units of reagent is used per about 1 µg of glycosylated antibody.

In certain embodiments, the deglycosylated antibody is isolated from the reaction mixture. The deglycosylated antibody can be isolated by any technique deemed suitable by those of skill. In particular embodiments, the deglycosylated antibody can be isolated by size exclusion chromatography, affinity chromatography, filtration, centrifugal ultrafiltration, or any other technique deemed suitable.

The antibody without interfering glycosylation is then reacted with a primary amine compound. In certain embodiments, an aglycosylated antibody is reacted with a primary amine compound to produce a glutaminyl-modified protein (e.g., antibody). In certain embodiments, a deglycosylated antibody is reacted with a primary amine compound to produce a glutaminyl-modified protein (e.g., antibody). For the purposes of this description, the deglycosylated antibody can be obtained or produced from any source or by any technique deemed suitable by those of skill in the art. In certain embodiments, the antibody is deglycosylated according to step (1), above. In further embodiments, it is sufficient that the deglycosylated or aglycosylated antibody comprise at least one glutamine residue that is sufficiently free of interfering glycosylation, or other structures, to be available for reaction with transglutaminase, as described below.

The primary amine can be any primary amine that is capable of forming a covalent bond with a glutamine residue in the presence of a transglutaminase. Useful primary amines are described in a section herein.

In another embodiment, provided are methods for producing a glutaminyl-modified antibody comprising the step:

(2) treating an antibody with a sufficient amount of a primary amine compound in the presence of transglutaminase at a reaction pH between about 7.0 and about 8.0 under conditions suitable for covalent coupling of the primary amine to a glutamine side chain in a polypeptide chain of the antibody. As discussed herein, the antibody can be deglycosylated, aglycosylated or otherwise free of interfering glycosylation.

In another embodiment, provided are methods for producing a glutaminyl-modified antibody comprising the steps of:

(i) adding the deglycosylated antibody or aglycosylated antibody to a solvent;

(ii) adding at least 5 molar equivalents of the primary amine compound;

(iii) adding the transglutaminase at a pH such that the reaction pH is between about 6.5 and about 8.5; and (iv) mixing the final reaction mixture.

In another embodiment, step (iv) comprises mixing the final reaction mixture for at least 4 hours. In certain embodiments, step (iv) comprises stirring the final reaction mixture. In other embodiments, step (iv) comprises shaking the reaction mixture.

The transglutaminase can be any transglutaminase deemed suitable by those of skill in the art. In certain embodiments, the transglutaminase is an enzyme that catalyzes the formation of an isopeptide bond between a free amino group on the primary amine compound and the acyl group on the side chain of a glutamine residue. Transglutaminase is also known as protein-glutamine-Y-glutamyltransferase. In particular embodiments, the transglutaminase is classified as EC 2.3.2.13. The transglutaminase can be from any source deemed suitable. In certain embodiments, the transglutaminase is a microbial transglutaminase. Useful transglutaminases have been isolated from *Streptomyces mobaraense, Streptomyces cinnamoneum, Streptomyces griseo-carneum, Streptomyces* and *lavendulae, Bacillus subtilis*. Non-microbial transglutaminases, including mammalian transglutaminases, can also be used. In certain embodiments, the transglutaminase can be produced by any technique or obtained from any source deemed suitable by the practitioner of skill. In particular embodiments, the transglutaminase is obtained from a commercial source.

In step (2), the reaction is typically carried out in a solvent. In certain embodiments, the solvent is selected from the group consisting of a water solution, such as a buffered solution or buffered water, saline water, buffered saline water, an organic solvent, water buffered with phosphate, HEPES, and MOPS. For example, in one embodiment, the solvent is BupH phosphate buffered saline.

In the reaction of step (2), the antibody can be at any concentration deemed suitable to the practitioner of skill. In certain embodiments, the antibody is present at a concentration from 0.1 to 5 mg/ml. In particular embodiments, the antibody is present at a concentration of about 0.1 mg/ml, about 0.2 mg/ml, about 0.3 mg/ml, about 0.4 mg/ml, about 0.5 mg/ml, about 0.6 mg/ml, about 0.7 mg/ml, about 0.8 mg/ml, about 0.9 mg/ml, about 1.0 mg/ml, about 1.1 mg/ml, about 1.2 mg/ml, about 1.3 mg/ml, about 1.4 mg/ml, about 1.5 mg/ml, about 1.6 mg/ml, about 1.7 mg/ml, about 1.8 mg/ml, about 1.9 mg/ml, about 2.0 mg/ml, about 2.5 mg/ml, about 3.0 mg/ml, about 3.5 mg/ml, about 4.0 mg/ml, about 4.5 mg/ml, or about 5.0 mg/ml.

The concentration of the primary amine compound can be any concentration deemed suitable by the practitioner of skill. In certain embodiments, the concentration of the primary amine compound determines the efficiency of the reaction (i.e., provides a useful DAR). The concentration of the primary amine compound can provide low amounts of high molecular weight side product and high DAR. In certain embodiments, the primary amine compound is at a concentration of at least about 34 molar equivalents, relative to the concentration of antibody. In certain embodiments, the primary amine compound is at a concentration of at least about 50 molar equivalents, relative to the concentration of antibody. In certain embodiments, the primary amine compound is at a concentration of at least about 75 molar equivalents, relative to the concentration of antibody. In certain embodiments, the primary amine compound is at a concentration of at least about 85 molar equivalents, relative to the concentration of antibody. In certain embodiments, the primary amine compound is at a concentration of at least about 100 molar equivalents, relative to the concentration of antibody. In certain embodiments, the primary amine compound is at a concentration of at least about 125 molar equivalents, relative to the concentration of antibody. In certain embodiments, the primary amine compound is at a concentration of at least about 150 molar equivalents, relative to the concentration of antibody. In certain embodiments, the primary amine compound is at a concentration of at least about 175 molar equivalents, relative to the concentration of antibody. In certain embodiments, the primary amine compound is at a concentration of at least about 200 molar equivalents, relative to the concentration of antibody. In certain embodiments, the primary amine compound is at a concentration of at least about 300 molar equivalents, relative to the concentration of antibody. In certain embodiments, the primary amine compound is at a concentration of at least about 400 molar equivalents, relative to the concentration of antibody. In certain embodiments, the primary amine compound is at a concentration of at least about 500 molar equivalents, relative to the concentration of antibody. In certain embodiments, the primary amine compound is at a concentration of at least about 600 molar equivalents, relative to the concentration of antibody. In certain embodiments, the primary amine compound is at a concentration of at least about 700 molar equivalents, relative to the concentration of antibody. In certain embodiments, the primary amine compound is at a concentration of at least about 800 molar equivalents, relative to the concentration of antibody. In certain embodiments, the primary amine compound is at a concentration of at least about 900 molar equivalents, relative to the concentration of antibody. In certain embodiments, the primary amine compound is at a concentration of at least about 1000 molar equivalents, relative to the concentration of antibody. Those of skill will recognize that the above ranges have an upper limit at the solubility of the primary amine compound. In certain embodiments, any of the above concentrations are less than about 500 molar equivalents or less than about 1000 molar equivalents.

The measure of U/mg deglycosylated antibody of transglutaminase can be any amount deemed suitable by the practitioner of skill. In certain embodiments, the transglutaminase is at about 0.5 to about 30 U/mg deglycosylated antibody. In certain embodiments, the transglutaminase is at about 0.5 to about 6 U/mg deglycosylated antibody. In certain embodiments, the transglutaminase is at about 1 to about 30 U/mg deglycosylated antibody. In certain embodiments, the transglutaminase is at least about 1.75 U/mg deglycosylated antibody. In certain embodiments, the transglutaminase is at about 2.2 U/mg deglycosylated antibody. In certain embodiments, the transglutaminase is at least about 2.5 U/mg deglycosylated antibody. In certain embodiments, the transglutaminase is at least about 3.5 U/mg deglycosylated antibody. In certain embodiments, the transglutaminase is at least about 5 U/mg deglycosylated antibody. In certain embodiments, the transglutaminase is at least about 10 U/mg deglycosylated antibody. In certain embodiments, the transglutaminase is at least about 25 U/mg deglycosylated antibody. In certain embodiments, the transglutaminase is at about 12 U/mg deglycosylated antibody for scale-up purposes.

The reaction of step (2) is carried out at any temperature deemed suitable by those of skill in the art. In particular embodiments, the reaction is conducted at any temperature from about 20° C. to about 40° C., from about 25° C. to about 40° C., or from about 25° C. to about 37° C. In particular embodiments, the reaction is at room temperature. In particular embodiments, the reaction is at about 25° C., about 30° C., about 35° C., or about 37° C.

The reaction of step (2) can be carried out in any volume deemed suitable by those of skill in the art and depends on the size of the reaction. In particular embodiments, the reaction volume is from about 10 µL to about 10 mL, from about 10 µL to about 5 mL, from about 10 µL to about 2.5 mL, from about 10 µL to about 1.0 mL, from about 10 µL to about 0.5 mL, from about 10 µL to about 250 µL, or from about 10 µL to about 100 µL.

The reaction of step (2) can proceed for any time deemed suitable for formation of the glutaminyl-modified antibody. In certain embodiments, the reaction proceeds for about 1 to about 48 hours. In particular embodiments, the reaction proceeds for about 1 hour, about 2 hours, about 3 hours, about 4 hours, about 5 hours, about 6 hours, about 6 hours, about 7 hours, about 8 hours, about 9 hours, about 10 hours, about 15 hours, about 20 hours, about 25 hours, about 30 hours, about 40 hours, or about 48 hours. In certain embodiments, the reaction proceeds for at least 4 hours, at least 18 hours, or at least 24 hours. Reaction progress can be monitored by standard techniques such as size-exclusion chromatography, mass spectrometry, MALDI, SDS-PAGE, Western blotting, and the like.

In certain embodiments, the glutaminyl-modified antibody is isolated or purified from the reaction mixture. The glutaminyl-modified antibody can be isolated or purified by any technique deemed suitable by those of skill. In particular embodiments, the glutaminyl-modified protein (e.g., antibody) can be isolated by chromatography, size-exclusion chromatography, affinity chromatography, or any other technique deemed suitable. For example, in one embodiment, the glutaminyl-modified antibody is purified by affinity chromatography. By way of further example, in one embodiment, the glutaminyl-modified antibody is purified by protein A chromatography. By way of further example, in one embodiment, the glutaminyl-modified antibody is purified by affinity chromatography and protein A chromatography.

In certain embodiments, the reaction of step (2) provides little or no high molecular weight side product. The high molecular weight side product would be a high molecular weight species comprising two or more heavy chain groups covalently bonded in a reaction that depends on the transglutaminase and/or the final reaction pH. In certain embodiments, the reaction of step (2) provides a composition comprising no detectable side product based on inspection of an SDS-PAGE gel, via visual inspection, staining, and/or other detection methods. In certain embodiments, the reaction of step (2) provides a composition comprising less than 10% side product relative to desired glutaminyl-modified antibody. In certain embodiments, the reaction of step (2) provides a composition comprising less than 5% side product relative to glutaminyl-modified antibody. In certain embodiments, the reaction of step (2) provides a composition comprising less than 4% side product relative to glutaminyl-modified antibody. In certain embodiments, the reaction of step (2) provides a composition comprising less than 3% side product relative to glutaminyl-modified antibody. In certain embodiments, the reaction of step (2) provides a composition comprising less than 2% side product relative to glutaminyl-modified antibody. In certain embodiments, the reaction of step (2) provides a composition comprising less than 1% side product relative to glutaminyl-modified antibody. In certain embodiments, the reaction of step (2) provides a composition comprising less than 1% cross-linked antibody relative to glutaminyl-modified antibody. Relative amounts can be calculated on a mass or molar basis.

In certain embodiments, the primary amine compound comprises a reactive group (referred to herein as a reactive amine linker, e.g., $H_2N$—SP—W) capable of further reaction after transglutamination. In these embodiments, the glutaminyl-modified antibody can be reacted with a reactive payload compound (e.g., W-D) or a reactive linker-payload compound (W-L-D) to form an antibody-payload conjugate. The reactive payload compound, the reactive linker compound, or the reactive linker-payload compound comprise a reactive group that is capable of reacting with the reactive group of the primary amine compound. In certain embodiments, the primary amine compound comprises a diene, and the reactive payload compound or the reactive linker-payload compound comprises a dienophile that react with the diene to form a Diels-Alder adduct. In certain embodiments, the primary amine compound comprises a dienophile that is capable of forming a Diels-Alder adduct with a diene, and the reactive payload compound or the reactive linker-payload compound comprises a diene.

Examples of useful reactive payload compounds and reactive linker-payload compounds are described in a section above.

Accordingly, provided herein are methods comprising the following step:
(3) reacting or treating the glutaminyl-modified antibody with a reactive linker-payload compound to form an antibody-payload conjugate.

The reaction can proceed under conditions deemed suitable by those of skill in the art. In certain embodiments, the glutaminyl-modified antibody is contacted or treated with the reactive linker-payload compound under conditions suitable for forming a bond between the glutaminyl-modified antibody and the linker-payload compound. In certain embodiments, the glutaminyl-modified antibody is contacted or treated with the reactive linker-payload compound under conditions suitable for forming a Diels-Alder adduct between the glutaminyl-modified antibody and the linker-payload compound. Suitable reaction conditions are well known to those in the art. Exemplary reactions are provided in the Examples below.

Additionally, provided herein are methods comprising the following step:
(3) reacting or treating the glutaminyl-modified antibody with a reactive payload compound to form an antibody-payload conjugate.

The reaction can proceed under conditions deemed suitable by those of skill in the art. In certain embodiments, the glutaminyl-modified antibody is contacted or treated with the reactive payload compound under conditions suitable for forming a bond between the glutaminyl-modified antibody and the payload. In certain embodiments, the glutaminyl-modified antibody is contacted or treated with the reactive payload compound under conditions suitable for forming a Diels-Alder adduct between the glutaminyl-modified antibody and the payload compound. Suitable reaction conditions are well known to those in the art. Exemplary reactions are provided in the Examples below.

In certain embodiments, provided herein are methods comprising the following steps:
(3a) reacting or treating the glutaminyl-modified antibody with a reactive linker compound to form an antibody-linker conjugate; and
(3b) reacting or treating the antibody-linker conjugate with a reactive payload compound to form an antibody-payload conjugate.

The reaction can proceed under conditions deemed suitable by those of skill in the art. In certain embodiments, the glutaminyl-modified antibody is contacted or treated with the reactive linker compound under conditions suitable for forming a bond between the glutaminyl-modified antibody and the linker. In certain embodiments, the antibody-linker conjugate is contacted or treated with the reactive payload compound under conditions suitable for forming a bond between the antibody-linker conjugate and the payload. In certain embodiments, the reactive linker compound comprises a first reactive group that reacts with the reactive group of the primary amine compounds described herein, and a second reactive group that is capable of reacting with a reactive payload compound or reactive linker-payload compound and is either (1) inert under the reaction conditions of step (3a) or (2) is protected with a protecting group to be inert under the reaction conditions of step (3a). Said protected second reactive group is deprotected and subjected to step (3b). Suitable reaction conditions and protecting group are well known to those in the art. Exemplary reactions are provided in the Examples below.

In certain embodiments, the antibody-drug conjugate isolated or purified from the reaction mixture. The antibody-drug conjugate can be isolated or purified by any technique deemed suitable by those of skill. In particular embodiments, the antibody-drug conjugate can be isolated by size exclusion chromatography, affinity chromatography, filtration, or any other technique deemed suitable.

In certain embodiments, the reaction of step (3), (3a), or (3b) provides little or no side product. The side product would be a high molecular weight species comprising two or more heavy chain polypeptides covalently bonded to each other in a reaction that depends on the transglutaminase and/or the final reaction pH. In certain embodiments, the reaction of step (3), (3a), or (3b) provides a composition comprising less than 10% side product relative to antibody-payload conjugate. In certain embodiments, the reaction of step (3), (3a), or (3b) provides a composition comprising less than 5% side product relative to antibody-payload conjugate. In certain embodiments, the reaction of step (3), (3a), or (3b) provides a composition comprising less than 4% side product relative to antibody-payload conjugate. In certain embodiments, the reaction of step (3), (3a), or (3b) provides a composition comprising less than 3% side product relative to antibody-payload conjugate. In certain embodiments, the reaction of step (3), (3a), or (3b) provides a composition comprising less than 2% side product relative to antibody-payload conjugate. In certain embodiments, the reaction of step (3), (3a), or (3b) provides a composition comprising less than 1% side product relative to antibody-payload conjugate. Relative amounts can be calculated on a mass or molar basis.

In some embodiments wherein the glutaminyl-modified antibody comprises two or more reactive units, e.g., when the SP is branched, step 3 may be repeated two or more times to functionalize the antibody with the same or different reactive payloads or linker-payloads.

In such embodiments, Step 3 may be performed two or more times at the same or different conditions, e.g., at the same or different pH.

In one non-limiting embodiment, wherein the SP is branched and comprises two dienes, Step 3 may be performed two times, where the first time the Step 3 is performed at a first pH, and the second time the Step 3 is performed at a second pH. In one embodiment, the first pH is about 6.7 to about 8.5, or about 7.0 to about 7.6, or about 7.2 to about 7.4, or about 7.2. In one embodiment, the second pH is about 4.5 to about 6.3, or about 5.0 to about 6.0, or about 5.5.

EXAMPLES

The following examples illustrate specific aspects of the instant description. The examples should not be construed as limiting, as the examples merely provide specific understanding and practice of the embodiments and their various aspects.

As used herein, the symbols and conventions used in the processes, and Examples, herein, are consistent with those used in the contemporary scientific literature, for example, the Journal of the American Chemical Society or the Journal of Biological Chemistry unless specified otherwise to the contrary. Specifically, but without limitation, the following abbreviations are used in the Examples and throughout the specification:

| Abbreviation | Term |
|---|---|
| ADC | Antibody-drug conjugate |
| Aglycosylated antibody | Antibody does not have any glycan |
| Da | Dalton |
| DAR | Drug to antibody ratio. |
| DCM | Dichloromethane |
| DIBAC | Dibenz[b,f]azocine, 11,12-didehydro-5,6-dihydro- or Dibenzocyclooctyne or Dibenz[b,f]azocine-5(6H)-butanoic acid, 11,12-didehydro |
| DIBAC-Suc | Dibenz[b,f]azocine-5(6H)-butanoic acid, 11,12-didehydro |
| DIBACT | 3H-Benzo[c]-1,2,3-triazolo[4,5-e][1]benzazocine, 8,9-dihydro- |
| DMSO | Dimethylsulfoxide |
| g | Gram |
| HATU | 2-(7-Aza-1H-benzotriazole-1-yl)-1,1,3,3-tetramethyluronium hexafluorophosphate |
| HC | Heavy chain of immunoglobulin |
| LC | Light chain of immunoglobulin |
| MC | Maleimidocaproyl |
| mg | Milligrams |
| min | Minutes |
| mL | Milliliters |
| mM | Millimolar |
| MMAE | Monomethyl auristatin E |
| MS | Mass spectrometry |
| MW | Molecular weight |
| nM | nanomolar |
| NMR | Nuclear magnetic resonance |

-continued

| Abbreviation | Term |
|---|---|
| PABC | Para-aminobezyloxy(carbonyl) |
| PAB | Para-aminobezyl |
| PBS | 10 mM sodium phosphate buffer and 150 mM sodium chloride |
| PEG | Polyethyleneglycol |
| ppm | Parts per million (chemical shift) |
| RP | Reversed phase |
| RT or rt | Room temperature |
| SDS-PAGE | Sodium dodecylsulfate polyacrylamide gel electrophoresis |
| TG | Transglutaminase |
| THF | Tetrahydrofuran |
| TOF | Time-of-flight |
| UPLC | Ultra-Performance Liquid Chromatography |
| VA | Valine-Aniline |
| VC | Valine-citrulline |
| μL | Microliters |
| μM | micromolar |

As used herein, the symbols and conventions used in these processes, schemes, and examples, regardless of whether a particular abbreviation is specifically defined, are consistent with those used in the contemporary scientific literature, for example, the Journal of the American Chemical Society or the Journal of Biological Chemistry.

General Methods

All the solvents used were purchased either from Sigma Aldrich or Fisher Scientific and were used without further purification. $^1$H-NMR spectra were recorded on a Varian Inova 300 MHz and 500 MHz NMR instruments. The chemical shifts (δ) are reported in ppm with respect to the NMR solvents used for analysis and are reported as s—singlet, d—doublet, t—triplet, q—quartet, dd—doublet of doublet, dt—doublet of triplet, dq—doublet of quartet, and m—multiplet. Coupling constants (J) are reported in hertz (Hz). Chromatographic purities were determined on an Agilent 1200 Series or 1100 Series LC/MS system with electrospray ionization source and triple-quad ion trap analyzer using a Merck Chromolith RP-18e analytical HPLC column (monolithic, 50×2 mm) and the following analytical HPLC method: injection volume 5 μL; flow rate 1 mL/min; 5→95% acetonitrile in water with 0.05% AcOH over 5 mins (Method A); or 0.1% TFA (Method B) over 5 mins; or: 1→30% acetonitrile in water with 0.1% TFA over 5 mins (Method C); Agilent diode array detector at wavelength=254, 220 or 195 nm; room temperature; or a Waters UPLC/MS-5SQD system using a Kinetex 1.7 □m C18 100 Å column (50×2.1 mm) and the following analytical UPLC method (Method D); injection volume 5 μL; flow rate 0.6 mL/min; 10→90% acetonitrile (containing 0.02% HCOOH) in water (containing 0.02% HCOOH) over 2.5 mins; full diode array detector; room temperature. Appropriate conjugates were analyzed using a Bruker ultraFleXtreme MALDI-TOF/TOF mass spectrometer. All starting materials and solvents were purchased commercially and used without purification, unless otherwise noted.

Example 1: Synthesis of 2-(cyclopenta-1,3-dien-1-yl)ethan-1-amine and 2-(cyclopenta-1,4-dien-1-yl)ethan-1-amine (3)

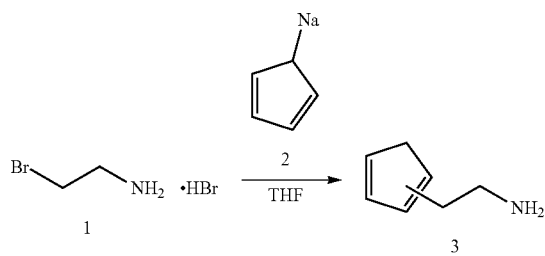

To a solution of 2-bromoethylamine hydrobromide (1) (1.01 g, 4.93 mmol), in THF (10 mL), under Ar, cooled at 0° C. for 5 min, was added sodium cyclopentadienylide (2) (5.0 ml of a 2.4 M solution in THF) dropwise over 5 min. The reaction mixture was allowed to stir while warming to 22° C. After 24 h, the reaction mixture was transferred to a separatory funnel and extracted with EtOAc (3×). The combined organics were washed with $H_2O$, then brine, dried over $Na_2SO_4$, filtered and concentrated. The resulting residue was purified by column chromatography (0→20% [1% $NH_4OH$ in MeOH] in DCM) to afford 311 mg of 3 (74% yield). LC/MS: retention time 0.214 min. (ESI) calculated for $C_7H_{12}N$: [M+H]$^+$ 110. found 110. $^1$H-NMR (500 MHZ; $CDCl_3$): δ 6.44-6.08 (m, 3H), 3.48 (s, 2H), 2.98 (t, J=1.5 Hz, 1H), 2.89 (dt, J=10.3, 6.8 Hz, 3H), 2.57-2.50 (m, 2H).

Example 2: Synthesis of 2-(pentamethylcyclopenta-1,3-dien-1-yl)ethan-1-amine (6) and 6-amino-N-(2-(1,2,3,4,5-pentamethylcyclopenta-2,4-dien-1-yl)ethyl)hexanamide oxalate (9)

Diels Alder linkers 6 and 9 were synthesized from Compound 1 as described below.

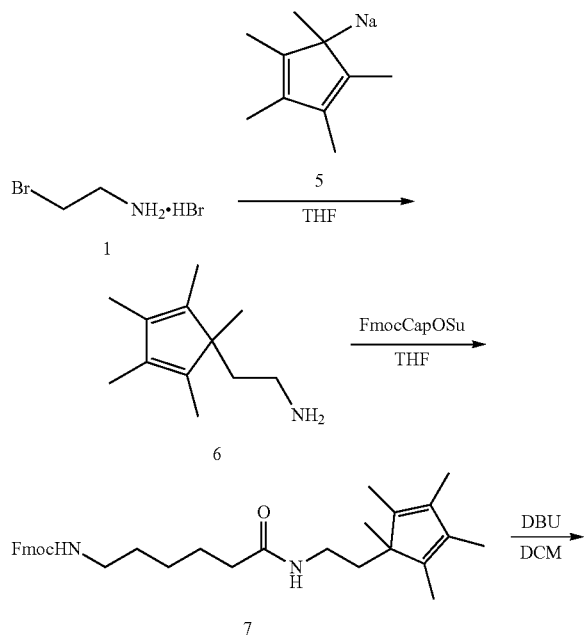

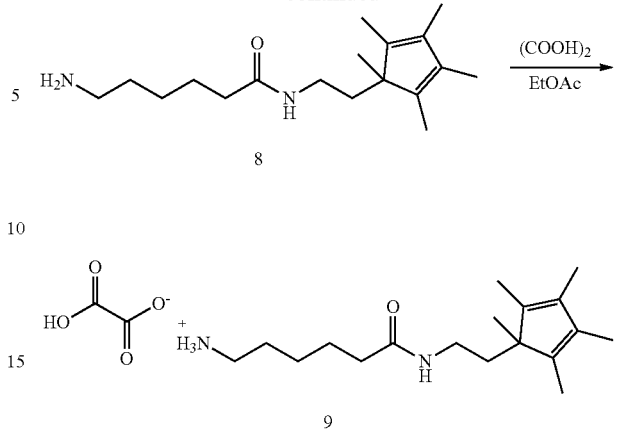

Step 1: To a solution of 2-bromoethylamine hydrobromide 1 (750 mg, 3.66 mmol), in anhydrous THF (10 mL), under Ar, cooled at 0° C. for 5 min, was added sodium 1,2,3,4,5-pentamethylcyclopentadienylide 5 (17.6 ml of a 0.5 M solution in THF) dropwise over 5 min. The reaction mixture was stirred while warming to 22° C. After 20 h, the reaction mixture was quenched with $H_2O$, transferred to a separatory funnel, and extracted with EtOAc (3×). The combined organics were washed with $H_2O$, then brine, dried over $MgSO_4$, filtered and concentrated. The resulting residue was purified by column chromatography (0→50% [0.1N $NH_3$ in MeOH] in DCM) to afford 615 mg of compound 6 (3.44 mmol, 94% yield) as a light tan semi-solid. LC/MS (Method B): retention time 1.94 min. (ESI) calculated for $C_{12}H_{22}N$: [M+H]$^+$ 180. found 180. $^1$H-NMR (500 MHz; $CDCl_3$): δ 2.05 (t, J=7.5 Hz, 2H), 1.75 (s, 6H), 1.70 (s, 6H), 1.60 (t, J=7.5 Hz, 2H), 1.23 (bs, 2H), 0.87 (s, 3H).

Step 2: To a solution of compound 6 (118 mg, 0.658 mmol), in THF (4.0 mL), under Ar, was added Fmoc-6-caproic acid NHS ester (326 mg, 0.724 mmol). After 1 h, the reaction was concentrated and purified by column chromatography (0→100% EtOAc in Hexanes) to afford 208 mg of compound 7 (0.404 mmol, 61% yield). LC/MS (Method A): retention time 4.38 min. (ESI) calculated for $C_{33}H_{43}N_2O_3$: [M+H]$^+$ 515. found 515.

Step 3: To a solution of compound 7 (208 mg, 0.404 mmol), in DCM (2.0 mL), under Ar, was added DBU (121 mL, 0.809 mmol). After 20 min, the reaction was concentrated and purified by column chromatography (0→100% [0.1M $NH_3$ in MeOH] in DCM) to afford 98.9 mg of compound 8 (0.339 mmol, 84% yield). LC/MS (Method B): retention time 1.02 min. (ESI) calculated for $C_{18}H_{33}N_2O$: [M+H]$^+$ 293. found 293.

Step 4: To a solution of compound 8 (98.9 mg, 0.339 mmol) in EtOAc (1 mL) was added saturated oxalic acid in EtOAc (~20 drops). Formed precipitate was filtered and washed with 5 mL EtOAc then dried under high vacuum to afford 70.8 mg of compound 9 (0.185 mmol, 47% yield) as a tan solid. LC/MS (Method B): retention time 0.21 min. (ESI) calculated for free base $C_{18}H_{33}N_2O$: [M+H]$^+$ 293. found 293. $^1$H-NMR (500 MHz; $CD_3OD$): δ 2.89 (t, J=7.6 Hz, 2H), 2.46-2.43 (m, 2H), 2.13 (t, J=7.4 Hz, 2H), 1.77 (s, 6H), 1.73 (s, 6H), 1.66-1.58 (m, 6H), 1.37 (quintet, J=7.7 Hz, 2H), 0.88 (s, 3H).

Example 3: Synthesis of 4-(1,2,3,4,5-pentamethyl-cyclopenta-2,4-dien-1-yl)butan-1-amine (10)

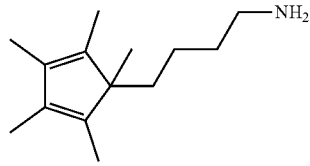
10

Compound 10 was synthesized using 4-bromobutylamine hydrobromide according to Step 1 in Example 2 to afford 157.0 mg of compound 10 (0.757 mmol, 58% yield) as a tan solid LC/MS (Method A): retention time 1.60 min. (ESI) calculated for $C_{14}H_{26}N$: $[M+H]^+$ 208. found 208. $^1$H-NMR (500 MHz; CDCl$_3$): δ 2.57 (t, J=7.0 Hz, 2H), 1.75 (s, 6H), 1.66 (s, 6H), 1.45 (bs, 2H), 1.37 (t, J=8.2 Hz, 2H), 1.29 (quintet, J=7.3 Hz, 2H), 0.85 (s, 3H), 0.62-0.55 (m, 2H).

Example 4: Synthesis of 2-(2-(2-(1,2,3,4,5-pentamethylcyclopenta-2,4-dien-1-yl)ethoxy)ethoxy)ethan-1-amine Acetate (13)

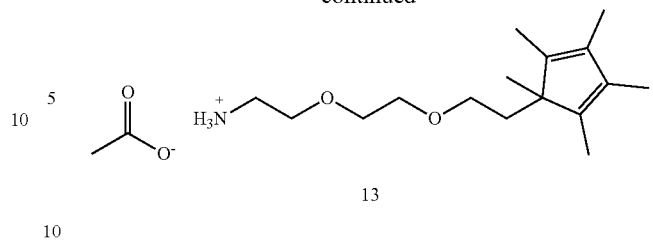
13

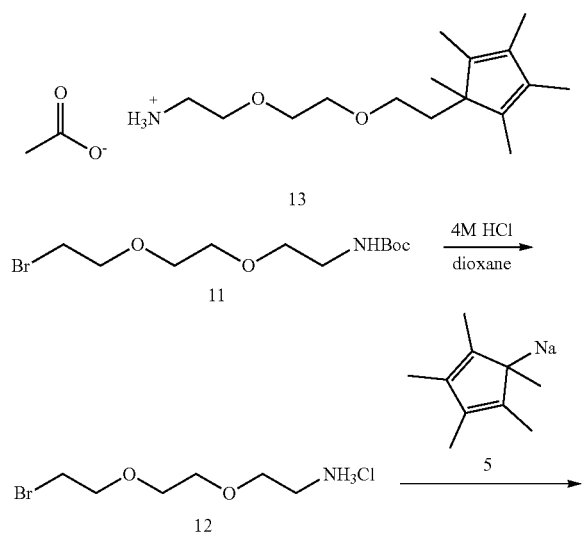

Step 1. Boc-amino-PEG$_2$-bromide 11 (32 mg, 0.103 mmol) was dissolved in 1,4-dioxane (1.0 mL), purged with Ar, then treated with 4 M HCl in 1,4-dioxane (0.26 mL, 1.029 mmol). After 1 d, the reaction was concentrated in vacuo, then dried on high vacuum for 3 h to afford crude compound 12 as a light-yellow oil.

Step 2. To a solution of crude 12 (0.103 mmol), in anhydrous THF (1.0 mL), under Ar, cooled at 0° C. for 5 min, was added sodium 1,2,3,4,5-pentamethylcyclopentadienylide 5 (0.6 ml, 0.309 mmol, 0.5 M solution in THF) dropwise over 5 min. The reaction mixture was stirred while warming to rt. After 20 h, the reaction mixture was quenched with H$_2$O, transferred to a separatory funnel, and extracted with EtOAc (3×). The combined organics were washed with H$_2$O, then brine, dried over MgSO$_4$, filtered and concentrated. The resulting residue was purified by column chromatography (0→50% [0.1N NH$_3$ in MeOH] in DCM), pure fractions were concentrated in vacuo. The free amine was then treated with 1 eq of AcOH, concentrated in vacuo and dried on high vacuum to afford 15 mg of compound 13 (0.0458 mmol, 45% yield) as a gold oil. LC/MS (Method A): retention time 1.90 min. (ESI) calculated for free base $C_{16}H_{30}NO_2$: $[M+H]^+$ 268.2. found 268.3. $^1$H NMR (500 MHz; CD$_3$OD) δ 3.51-3.72 (m, 6H) 3.42-3.47 (m, 2H) 3.06-3.15 (m, 2H) 2.75-2.81 (m, 2H) 1.74-1.81 (m, 9H) 1.63-1.74 (m, 7H) 0.85-0.91 (m, 3H).

Example 5: (2-(2-(3-oxo-3-((2-(1,2,3,4,5-pentamethylcyclopenta-2,4-dien-1-yl)ethyl)amino)propoxy)ethoxy)ethyl)-15-azaneyl Acetate (16)

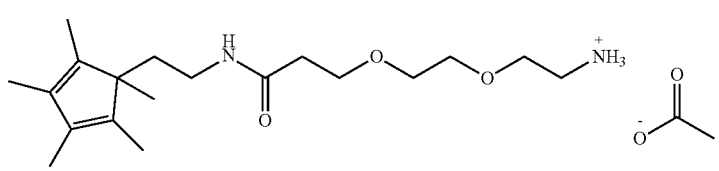
16

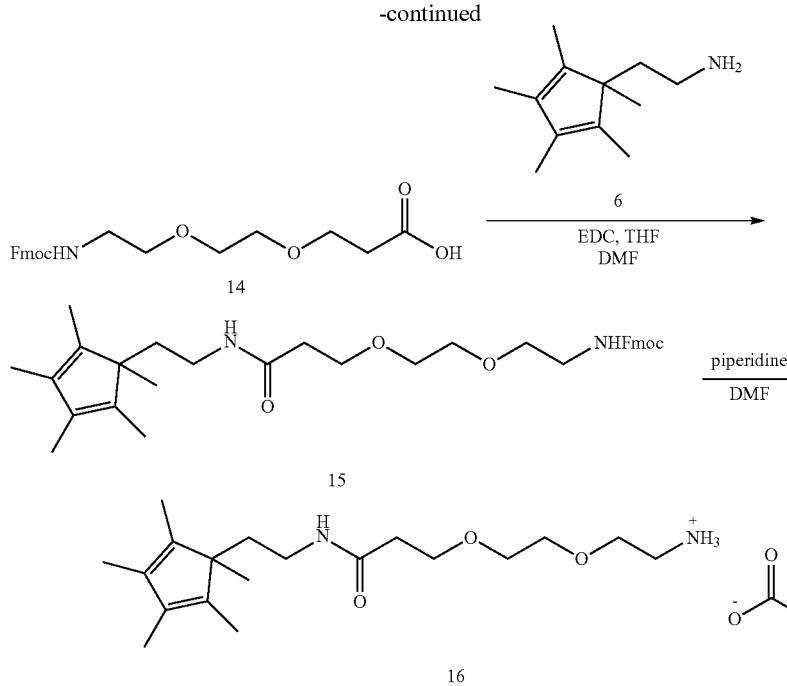

Step 1: To a solution of acid 14 (49 mg, 0.1228 mmol) in DMF (1.0 mL) were added a solution of amine 6 (20 mg, 0.1116 mmol) in THF (0.1 mL) and EDC (43 mg, 0.2232 mmol) at rt. After stirring for 18 h, the reaction was judged complete by LC/MS and purified directly by chromatography using $C_{18}Aq$ Isco column (30 g). Eluent: $CH_3CN$ in $H_2O$, each containing 0.05% of AcOH (0% to 100%). The fractions containing product were combined and lyophilized to afford 35 mg of compound 15 (0.0624 mmol, 56% yield) as a yellowish white solid. LC/MS (Method A): retention time 3.57 min. (ESI) calculated for $C_{34}H_{45}N_2O_5$: $[M+H]^+$ 561.3. found 561.3.

Step 2: Compound 15 (20.0 mg, 0.0357 mmol) was dissolved in DMF (0.7 mL) and then 5% piperidine in DMF (0.1 mL, 0.0525 mmol) was added. After 2 h, the reaction was judged complete by LC/MS and the mixture was purified directly by reverse phase on a $C_{18}Aq$ Isco column (30 g). Eluent: $CH_3CN$ in $H_2O$, each containing 0.05% of AcOH (0% to 100%). The fractions containing product were combined and lyophilized to afford 10.0 mg of compound 16 (0.0251 mmol, 70% yield) as a gold oil. LC/MS (Method A): retention time 1.69 min. (ESI) calculated for free base $C_{19}H_{35}N_2O_3$: $[M+H]^+$ 339.3. found 339.3. $^1H$ NMR (500 MHZ; $CD_3OD$) δ 3.69 (t, J=6.35 Hz, 2H) 3.59-3.63 (m, 5H) 3.55-3.58 (m, 2H) 2.88 (t, J=5.13 Hz, 2H) 2.41-2.49 (m, 2H) 2.36 (t, J=6.11 Hz, 2H) 1.89 (s, 1H) 1.77 (s, 6H) 1.68-1.75 (m, 7H) 1.58-1.68 (m, 2H) 0.88 (s, 3H).

Example 6: Synthesis of (S)-6-amino-N-(2-(1,2,3,4,5-pentamethylcyclopenta-2,4-dien-1-yl)ethyl)-2-(3-(1,2,3,4,5-pentamethylcyclopenta-2,4-dien-1-yl)propanamido)hexanamide Oxalate (23)

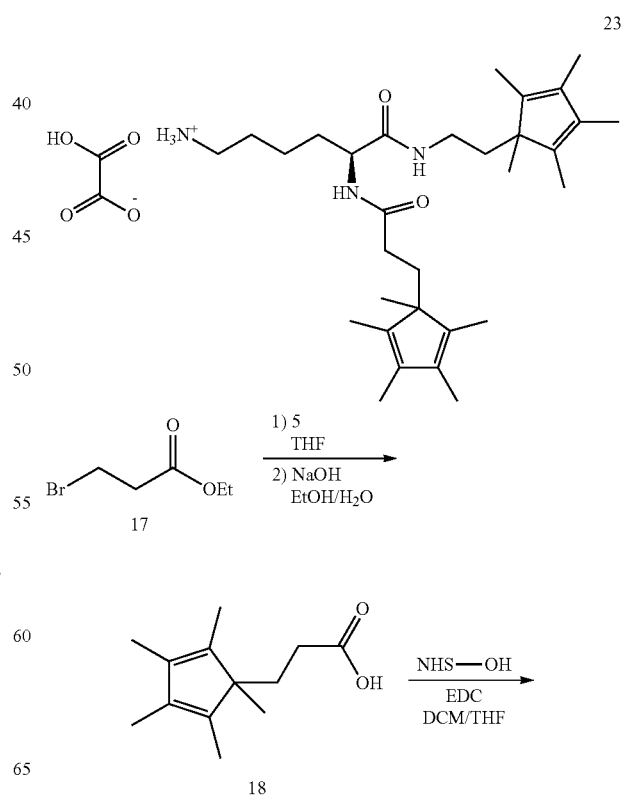

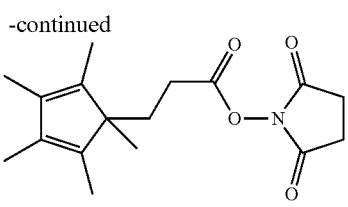

19

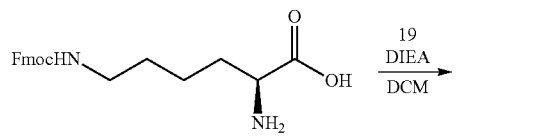

20

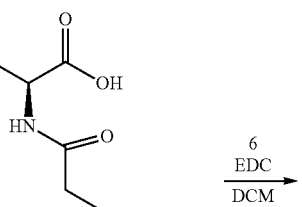

21

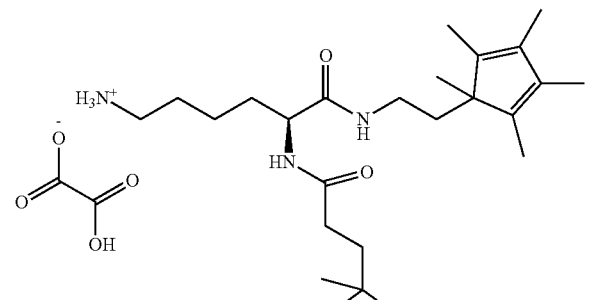

22

23

Step 1. To a solution of sodium 1,2,3,4,5-pentamethylcyclopentodienylylide 5 (9.41 mL of a 0.5 M solution in THF, 4.70 mmol) in THF (7.8 mL), cooled to −78° C. in a dry ice/acetone bath, under Ar, was added 3-bromo-ethylpropionate 17 (0.50 mL, 3.92 mmol) and the mixture was stirred at −78° C. After 1.5 h, the cold bath was removed, and the reaction mixture was stirred for an additional 45 min. The reaction mixture was then quenched by the addition of $H_2O$ (280 mL) and $SiO_2$ (280 mg). After 5 min, the mixture was filtered through a small pad of $SiO_2$, and the filter cake was washed with DCM (20 mL). The filtrate was then concentrated, dissolved in EtOH (3.0 mL) and cooled to 0° C. in an ice/$H_2O$ bath. NaOH (329 mg, 8.23 mmol) in $H_2O$ (3.0 mL) was then added and the mixture was stirred at 0° C. for 19 h, when the reaction was judged complete by LC/MS. The mixture was then poured onto 1N HCl (aq) (10 mL) and extracted with DCM (3×20 mL). Combined organics were washed with brine (20 mL), dried over $MgSO_4$, filtered, and concentrated to afford crude acid 18. LC/MS (Method A): retention time 3.07 min. (ESI) calculated for $C_{13}H_{21}N$: $[M+H]^+$ 209. found 209.

Step 2. Crude acid 18 (3.92 mmol) was dissolved in THF (5.6 mL), then NHS—OH (632 mg, 5.49 mmol), EDC (902 mg, 4.70 mmol) and DCM (5.6 mL) were added. After 15 h, additional NHS—OH (300 mg, 2.61 mmol) was added, and the mixture was stirred until the reaction was judged complete by LC/MS. The mixture was filtered through a pad of $SiO_2$, washed with DCM (50 mL) and the filtrate was then concentrated. The resulting residue was purified by column chromatography (0→50% EtOAc in Hexanes) to afford 893 mg of 19 (2.93 mmol, 75% yield over 2 steps) as an off-white solid. LC/MS (Method A): retention time 3.38 min. (ESI) calculated for $C_{17}H_{24}NO_4$: $[M+H]^+$ 306. found 306.

Step 3. To Fmoc-$N^e$-Lysine 20 (49.4 mg, 0.134 mmol) and NHS ester 19 (45.0 mg, 0.147 mmol) dissolved in DMA (0.50 mL) was added diisopropylethylamine (36 mL, 0.201 mmol). After 15 h, the reaction was judged complete by LC/MS, and purified directly by reverse phase on a $C_{18}$ Aq Isco column (50 g). Eluent: $CH_3CN$ in $H_2O$, each containing 0.05% of AcOH (30% to 95%). The fractions containing product were combined and lyophilized to afford 23.9 mg of compound 21 as a white solid (0.0428 mmol, 32% yield), contaminated with 20% of an unknown impurity. LC/MS (Method A): retention time 3.53 min. (ESI) calculated for $C_{34}H_{43}N_2O_5$: $[M+H]^+$ 559. found 559.

Step 4: Acid 21 (26.5 mg, 0.0474 mmol) and amine 6 (8.5 mg, 0.0474 mmol) were dissolved in DCM (1.0 mL). EDC (13.6 mg, 0.0709 mmol) and HOBt (9.6 mg, 0.0710 mmol) were then added to the reaction mixture. After 1 h, the reaction was judged complete by LC/MS and purified directly by column chromatography (12 g) (0→100% EtOAc in Hexanes) to afford 16.2 mg of compound 22 (0.0225 mmol, 47% yield) as a white solid. LC/MS (Method A): retention time 4.44 min. (ESI) calculated for $C_{46}H_{62}N_3O_4$: $[M+H]^+$ 720. found 720.

Step 5. Compound 22 (16.2 mg, 0.0225 mmol) was dissolved in DCM (0.5 mL), then DBU (3.4 mL, 0.0225 mmol) was added. After 10 min the reaction was judged complete by LC/MS and the reaction mixture was concentrated in vacuo. The resulting residue was dissolved in DMSO (1 mL) and purified by reverse phase on a $C_{18}$ Aq Isco column (15.5 g). Eluent: $CH_3CN$ in $H_2O$, each containing 0.05% of AcOH (10% to 80%). The fractions containing product were combined and lyophilized to afford the acetate of 23 (7.4 mg, 0.0149 mmol) as an off-white solid. The material was dissolved in 1:1 MeCN/$H_2O$ and oxalic acid dihydrate (2.2 mg, 0.0174 mmol) was added. The mixture was lyophilized to afford 7.2 mg of oxalate 23 (0.0122 mmol, 54% yield) as a tan solid. LC/MS (Method A): retention time 2.52 min. (ESI) calculated for free base $C_{31}H_{52}N_3O_2$: $[M+H]^+$ 498. found 498. $^1$H-NMR (500 MHz;

DMSO-$d_6$): δ 7.65-7.61 (m, 3H), 7.56-7.53 (m, 1H), 4.02-3.98 (m, 1H), 2.74-2.70 (m, 2H), 2.25-2.22 (m, 2H), 1.82-1.77 (m, 2H), 1.72 (s, 12H), 1.66 (d, J=13.8 Hz, 12H), 1.58-1.53 (m, 2H), 1.53-1.44 (m, 4H), 1.37-1.32 (m, 2H), 1.27-1.14 (m, 2H), 1.08-1.05 (m, 1H), 0.97-0.89 (m, 1H), 0.84 (s, 3H), 0.81 (s, 3H).

Example 7: Synthesis of (S)-6-amino-N-(2-(furan-3-yl)ethyl)-2-(3-(1,2,3,4,5-pentamethylcyclopenta-2,4-dien-1-yl)propanamido)hexanamidyl Acetate (27)

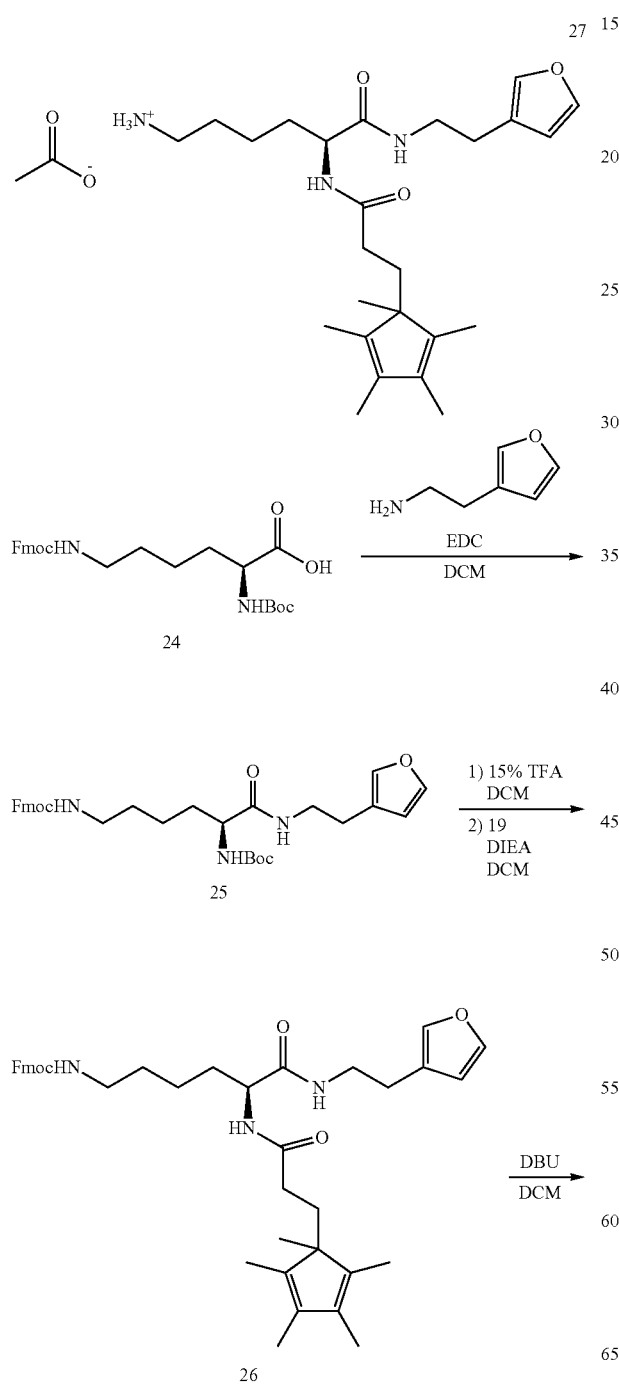

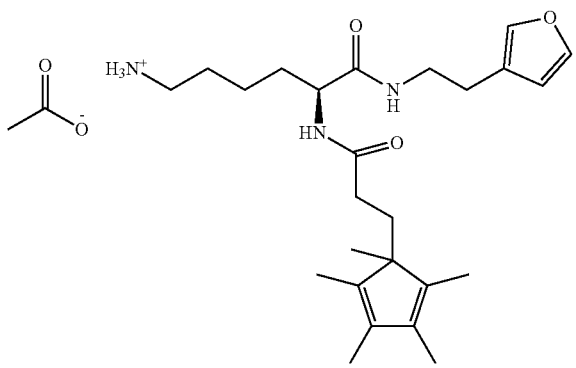

Step 1: To BocNHLys(Fmoc)OH 24 (200 mg, 0.427 mmol) and 2-(furan-3-yl)ethan-1-amine (43 mg, 0.388 mmol) in DCM (2.6 mL), under Ar, added EDC (112 mg, 0.582 mmol). After 16 h, the reaction was judged complete by LC/MS and purified directly by column chromatography (40 g) (10→100% EtOAc in Hexanes) to afford 142.7 mg of compound 25 (0.254 mmol, 66% yield) as a white solid. LC/MS (Method A): retention time 3.19 min. (ESI) calculated for $C_{32}H_{40}N_3O_6$: [M+H]$^+$ 562. found 562.

Step 2: Compound 25 (21.4 mg, 0.0381 mmol) was treated with 15% TFA in DCM (1.0 mL). After 30 min, the reaction was judged complete by LC/MS, concentrated in vacuo, and lyophilized from 1:1 MeCN/$H_2O$ (1 mL) to remove TFA. The crude amine was then dissolved in DCM (1.0 mL) and DIEA was added (20 mL, 0.114 mmol). Once the pH was confirmed to be basic, NHS ester 19 (14.0 mg, 0.0457 mmol) was added. After 5 h, additional NHS ester 19 (18.0 mg, 0.0589 mmol) was added. After an additional 16 h, the reaction mixture was then purified directly by column chromatography (12 g) (10→100% EtOAc in Hexanes) to afford 18.4 mg of compound 26 (0.0282 mmol, 74% yield) as a white solid. LC/MS (Method A): retention time 3.74 min. (ESI) calculated for $C_{40}H_{50}N_3O_5$: [M+H]$^+$ 652. found 652.

Step 3: Compound 26 (28.0 mg, 0.430 mmol) was dissolved in DCM (1.0 mL) then DBU (12.8 mL, 0.0859 mmol) was added. After 5 min, the reaction was judged complete by LC/MS and the mixture was purified directly by reverse phase on a $C_{18}$ Aq Isco column (15.5 g). Eluent: $CH_3CN$ in $H_2O$, each containing 0.05% of AcOH (10% to 100%). The fractions containing product were combined and lyophilized to afford 10.4 mg of compound 27 (0.212 mmol, 49% yield) as a clear film. LC/MS (Method A): retention time 2.65 min. (ESI) calculated for free base $C_{25}H_{40}N_3O_3$: [M+H]$^+$ 430. found 430. $^1$H-NMR (500 MHZ; $CD_3OD$): δ 7.41 (t, J=1.5 Hz, 1H), 7.32 (s, 1H), 6.34 (s, 1H), 4.20 (dd, J=8.5, 5.8 Hz, 1H), 3.42-3.33 (m, 4H), 2.85-2.81 (m, 2H), 2.61 (t, J=7.0 Hz, 2H), 1.90 (s, 3H), 1.77 (s, 6H), 1.73-1.68 (m, 10H), 1.62-1.50 (m, 6H), 1.37-1.28 (m, 2H), 0.91 (s, 3H).

Example 8: (S)-6-amino-N-(2-(2-(2-(1,2,3,4,5-pentamethylcyclopenta-2,4-dien-1-yl)ethoxy)ethoxy)ethyl)-2-(3-(1,2,3,4,5-pentamethylcyclopenta-2,4-dien-1-yl)propanamido)hexanamide Acetate (29)
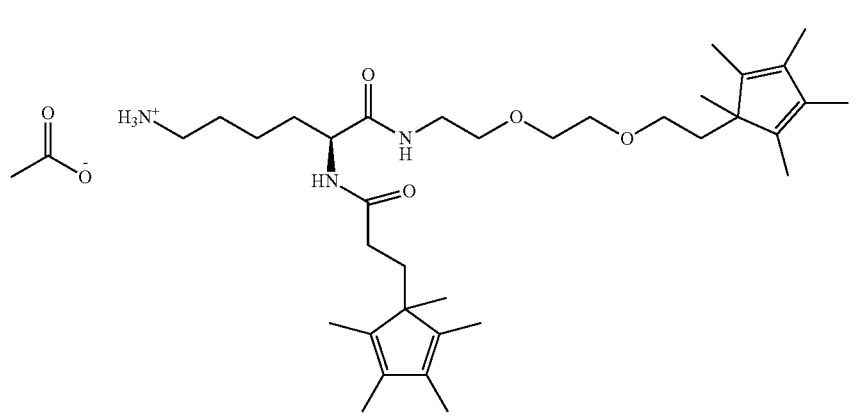
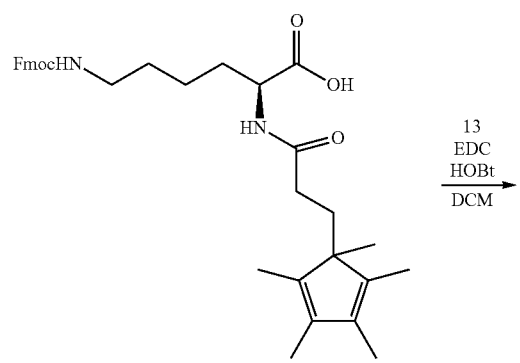
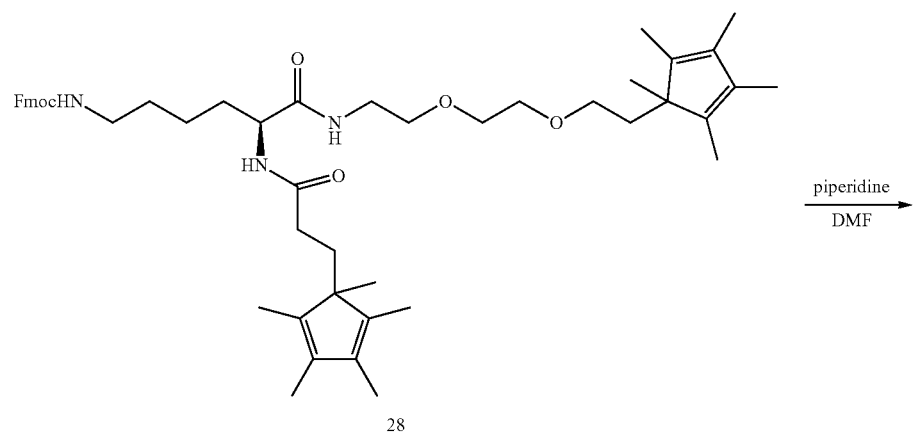

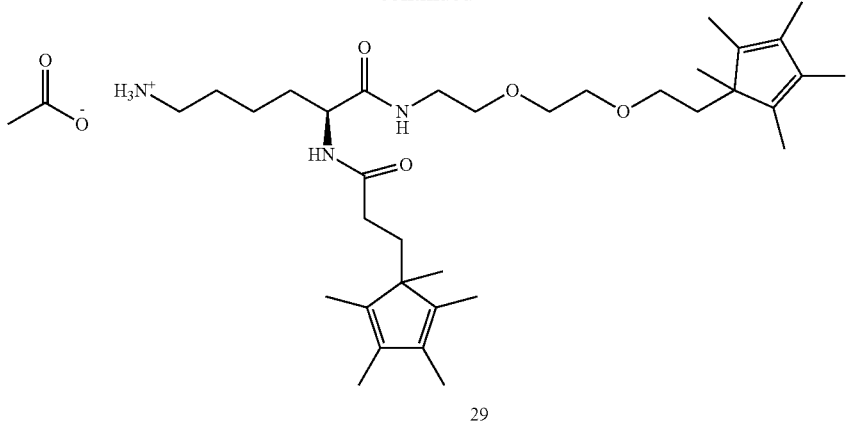

29

Step 1: Acid 21 (50 mg, 0.0896 mmol) and amine 6 (26.3 mg, 0.0985 mmol) were dissolved in DMF (1.6 mL). EDC (32.6 mg, 0.0170 mmol) and HOBt (10.9 mg, 0.0806 mmol) were then added to the reaction mixture. After 3 h, the reaction was judged complete by LC/MS and purified directly by chromatography using $C_{18}$Aq Isco column (50 g). Eluent: $CH_3CN$ in $H_2O$, each containing 0.05% of AcOH (0% to 100%). The fractions containing product were combined and lyophilized to afford 55 mg of compound 28 (0.0681 mmol, 76% yield) as a white solid. LC/MS (Method A): retention time 4.55 min. (ESI) calculated for $C_{50}H_{70}N_3O_6$: $[M+H]^+$ 808.5. found 808.5.

Step 2: Compound 28 (55.0 mg, 0.0681 mmol) was dissolved in DMF (1.4 mL) and then 5% piperidine in DMF (0.8 mL, 0.4087 mmol) was added. After 30 min, the reaction was judged complete by LC/MS and the mixture was purified directly by reverse phase on a $C_{18}$Aq Isco column (50 g). Eluent: $CH_3CN$ in $H_2O$, each containing 0.05% of AcOH (0% to 100%). The fractions containing product were combined and lyophilized to afford 24.0 mg of compound 29 (0.0372 mmol, 55% yield) as a white solid. LC/MS (Method A): retention time 2.59 min. (ESI) calculated for free base $C_{35}H_{60}N_3O_4$: $[M+H]^+$ 586.5. found 586.4. $^1$H-NMR (500 MHZ; $CD_3OD$): δ 4.23 (dd, J=8.5, 5.6 Hz, 1H) 3.45-3.55 (m, 4H) 3.37-3.43 (m, 2H) 3.33-3.36 (m, 2H) 2.73-2.86 (m, 3H) 1.90 (s, 2H) 1.73-1.80 (m, 15H) 1.66-1.73 (m, 15H) 1.47-1.63 (m, 6H) 1.29-1.44 (m, 2H) 0.90 (d, J=2.93 Hz, 6H).

Example 9: Synthesis of 3-(cyclopenta-1,3-dien-1-yl)propan-1-aminium Oxalate and 3-(cyclopenta-1,4-dien-1-yl)propan-1-aminium Oxalate (30)

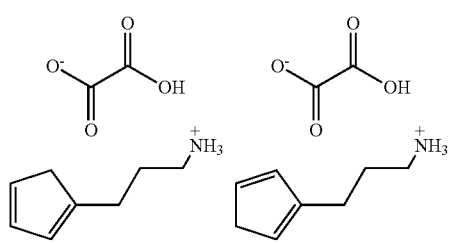

30

Compound 30 was synthesized using 3-bromopropylamine hydrobromide according to Example 1. Oxalate salt was formed according to Step 4 of Example 2 to afford 150.7 mg of compound 30 (0.707 mmol, 31% yield) as a tan solid. LC/MS (Method A): retention time 0.24 min. (ESI) calculated for free base $C_8H_{14}N$: $[M+H]^+$ 124. found 124. $^1$H-NMR (500 MHz; DMSO-$d_6$): δ 7.86-7.53 (bs, 2H), 6.45 (s, 1H), 6.41 (dt, J=2.5, 1.2 Hz, 0.5H), 6.28-6.27 (m, 0.5H), 6.19 (s, 0.5H), 6.06 (s, 0.5H), 2.94 (s, 1H), 2.89 (s, 1H), 2.80-2.76 (m, 2H), 2.45-2.42 (m, 1H), 2.39-2.36 (m, 1H), 1.79-1.73 (m, 2H).

Example 10: Synthesis of 4-(cyclopenta-1,3-dien-1-yl)butan-1-aminium Oxalate and 4-(cyclopenta-1,4-dien-1-yl)butan-1-aminium Oxalate (31)

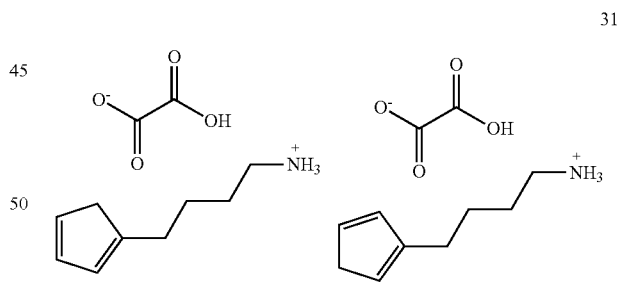

31

Compound 31 was synthesized using 4-bromobutylamine hydrobromide according to Example 1. Oxalate salt was formed according to Step 4 of Example 2 to afford 20.1 mg of compound 31 (0.0884 mmol, 6.2% yield) as a tan solid. LC/MS (Method C): retention time 2.68 min. (ESI) calculated for free base $C_9H_{16}N$: $[M+H]^+$ 138. found 138. $^1$H-NMR (500 MHz; $CD_3OD$): δ 6.54-6.04 (m, 3H), 3.00-2.75 (m, 4H), 2.50-2.47 (m, 1H), 2.45-2.42 (m, 1H), 1.89-1.77 (m, 1H), 1.69-1.64 (m, 4H), 1.21 (d, J=6.9 Hz, 1H).

Example 11: Synthesis of 2-(2-(2-(2-(cyclopenta-1,4-dien-1-yl)ethoxy)ethoxy)ethoxy)ethan-1-aminium Acetate and 2-(2-(2-(2-(cyclopenta-1,3-dien-1-yl)ethoxy)ethoxy)ethoxy)ethan-1-aminium Acetate (34)

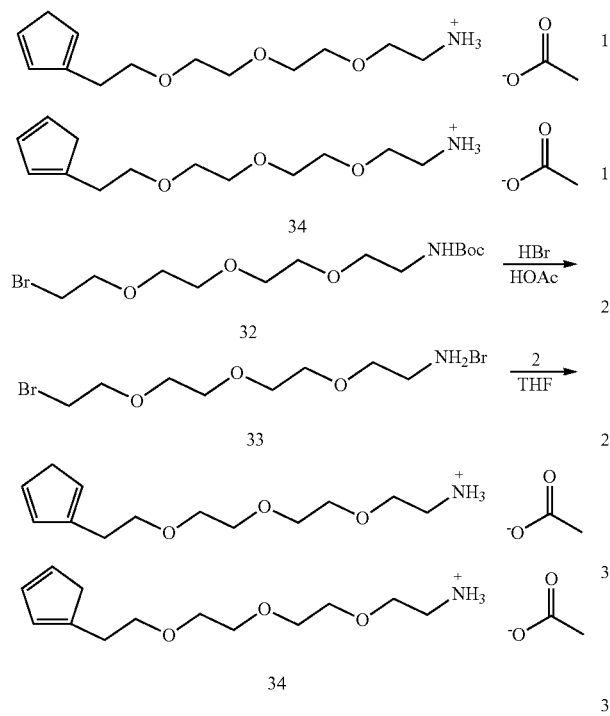

Step 1. Boc-amino-PEG$_3$-bromide 32 (157 mg, 0.441 mmol) was dissolved in AcOH (2.0 mL), purged with Ar, then treated with 33% HBr in acetic acid (1.0 mL). After 1 h, the reaction was concentrated in vacuo, then dried on high vacuum for 1 h. The resulting residue was triturated with anhydrous Et$_2$O (2×) then azeotroped with CHCl$_3$ and dried under high vacuum to afford 142 mg of crude compound 33 (0.421 mmol, 95% yield) as a gold oil.

Step 2. Crude 33 was suspended in anhydrous DME (3.0 mL) and sonicated till complete dissolution. The solution was then cooled to 0° C., under Ar, and treated with sodium cyclopentadienylide 2 (0.50 mL of 2.4 M solution in THF, 1.20 mmol). After 1 h, the reaction was quenched with 10% HOAc (aq) (1.0 mL), concentrated and the resulting residue was diluted with MeCN (1.5 mL) and purified directly by reverse phase on a C$_{18}$ Aq Isco column (50 g). Eluent: CH$_3$CN in H$_2$O, each containing 0.05% of AcOH (10% to 50%). The fractions containing product were combined and lyophilized to afford impure compound 33. A second reverse phase purification on a C$_{18}$ Aq Isco column (50 g) Eluent: CH$_3$CN in H$_2$O, each containing 0.05% of AcOH (10% to 35%)) was performed. The fractions containing product were combined and lyophilized to afford 24 mg of compound 34 (0.0796 mmol, 19% yield) as a gold oil. LC/MS (Method A): retention time 0.74 min. (ESI) calculated for free base C$_{13}$H$_{24}$NO$_3$: [M+H]$^+$ 242. found 242. $^1$H-NMR (500 MHZ; CDCl$_3$): δ 6.50-6.12 (m, 3H), 3.91-3.86 (m, 1H), 3.71-3.63 (m, 12H), 3.24-3.20 (m, 1H), 3.02-2.96 (m, 4H), 2.76-2.73 (m, 1H), 2.71-2.68 (m, 1H).

Example 12: Synthesis of 6-oxo-6-((2-(2,3,4,5-tetramethylcyclopenta-2,4-dien-1-yl)ethyl)amino)hexan-1-aminium Acetate, 6-oxo-6-((2-(1,2,3,4-tetramethylcyclopenta-2,4-dien-1-yl)ethyl)amino)hexan-1-aminium acetate (minor component), and 6-oxo-6-((2-(1,2,3,5-tetramethylcyclopenta-2,4-dien-1-yl)ethyl)amino)hexan-1-aminium Acetate (Minor Component) (38)

Diels Alder linkers 36 and 38 were synthesized from compound 35 as described below.

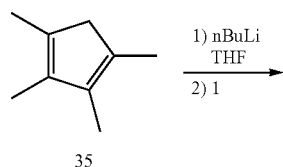

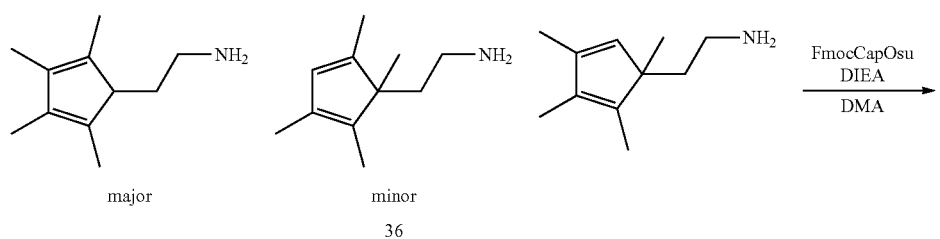

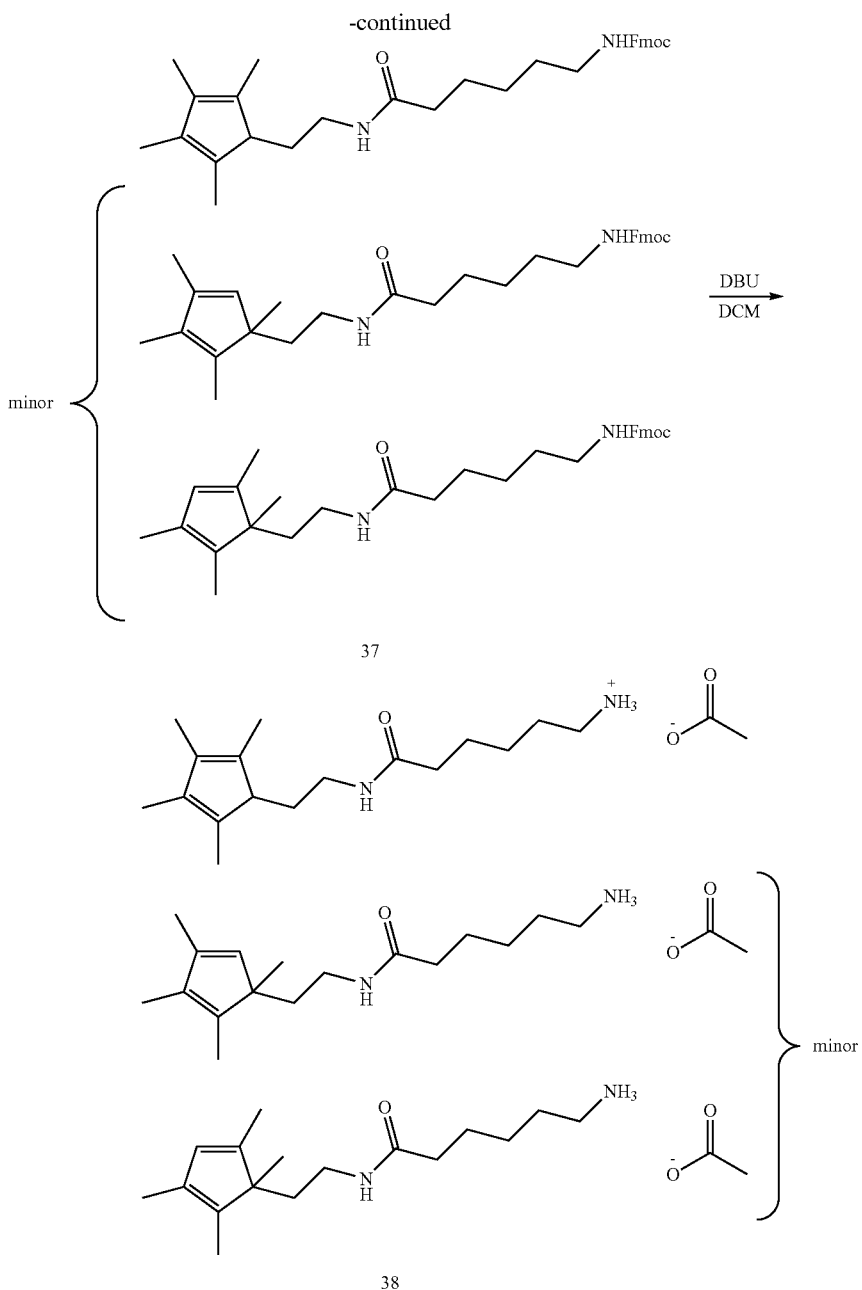

Step 1. To 2,3,4,5-tetramethylcyclopentadiene 35 (1.00 g, 8.18 mmol) in anhydrous THF (20 mL), was added nBuLi (6.6 mL of a 1.6 M solution in Hexanes, 10.6 mmol). The resulting suspension was stirred for 2 h at ambient temperature. In a separate vessel, bromoethylamine hydrobromide 1 (419 mg, 2.05 mmol) was suspended in anhydrous THF (2.0 mL) and cooled to 0° C. in an ice/$H_2O$ bath, under Ar. The preformed lithium salt of 35 was then added to the cold mixture over 5 min. Additional anhydrous THF (2×5 ml) was used to transfer any remaining lithium salt to the reaction mixture. The reaction mixture was stirred while warming to 22° C. After 20 h, the reaction mixture was quenched with $H_2O$, transferred to a separatory funnel and extracted with EtOAc (3×). The combined organics were washed with $H_2O$, then brine, dried over $MgSO_4$, filtered and concentrated. The resulting residue was purified by column chromatography (0→70% [0.1N $NH_3$ in MeOH] in DCM) to afford 101 mg of compound 36 (0.611 mmol, 30% yield) as a light tan semi-solid. LC/MS (Method B): retention time 2.05 min. (ESI) calculated for $C_{11}H_{20}N$: $[M+H]^+$ 166. found 166. $^1$H-NMR (500 MHZ; $CDCl_3$): δ 5.78 (s, 0.8H), 5.75 (s, 0.2H), 5.29 (t, J=0.7 Hz, 0.1H), 2.64 (bs, 0.2H), 2.34-2.29 (m, 1H), 2.12-2.08 (m, 2H), 1.87-1.82 (m, 3H), 1.79 (s, 3H), 1.77 (d, J=0.7 Hz, 3H), 1.75 (dd, J=6.3, 0.6 Hz, 2H), 1.68 (s, 3H), 1.66 (s, 1H), 1.64-1.60 (m, 2H), 0.96 (d, J=0.9 Hz, 1H), 0.90 (s, 3H).

Step 2. Compound 37 was synthesized according to Step 2 in Example 2 in DMA to afford 95.4 mg of compound 37 (0.191 mmol, 85% yield) as an off-white solid. LC/MS (Method A): retention time 3.73 min. (ESI) calculated for $C_{32}H_{41}N_2O_3$: $[M+H]^+$ 501. found 501.

Step 3. Compound 38 was synthesized according to Step 3 in Example 2. Once the reaction was judged complete by LC/MS, the reaction was concentrated, the resulting residue was diluted with DMSO (0.5 mL) and purified directly by reverse phase on a $C_{18}$ Aq Isco column (50 g). Eluent: $CH_3CN$ in $H_2O$, each containing 0.05% of AcOH (10% to 70%). The fractions containing product were combined and lyophilized to afford 20.5 mg of compound 38 (0.0606 mmol, 62% yield) as a yellow film. LC/MS (Method B): retention time 2.32 min. (ESI) calculated for the free amine $C_{17}H_{31}N_2O$: $[M+H]^+$ 279. found 279. $^1$H-NMR (500 MHZ; $CD_3OD$): δ 5.81 (d, J=1.6 Hz, 0.8H), 5.74 (d, J=1.2 Hz, 0.2H), 2.87 (t, J=7.6 Hz, 3H), 2.77 (ddd, J=13.3, 10.7, 5.4 Hz, 0.2H), 2.72-2.66 (m, 0.2H), 2.51-2.48 (m, 2H), 2.14 (td, J=7.4, 2.8 Hz, 2H), 1.89 (s, 3H), 1.85-1.84 (m, 0.8H), 1.81 (d, J=7.7 Hz, 3H), 1.77 (dd, J=7.4, 1.0 Hz, 4H), 1.72-1.69 (m, 4H), 1.66-1.57 (m, 8H), 1.40-1.35 (m, 2H), 1.01-1.00 (m, 0.2H), 0.97 (s, 0.7H), 0.91 (s, 3H).

Example 13: Synthesis of (S)-6-((6-((2-(cyclohexa-1,5-dien-1-yl)ethyl)amino)-6-oxohexyl)amino)-6-oxo-5-(3-(1,2,3,4,5-pentamethylcyclopenta-2,4-dien-1-yl)propanamido)hexan-1-aminium Acetate (Major) and (S)-6-((6-((2-(cyclohexa-1,3-dien-1-yl)ethyl)amino)-6-oxohexyl)amino)-6-oxo-5-(3-(1,2,3,4,5-pentamethylcyclopenta-2,4-dien-1-yl)propanamido)hexan-1-aminium Acetate (Minor) (46)

Diels Alder linkers 42, 44, and 46 were synthesized from compound 39 as described below.

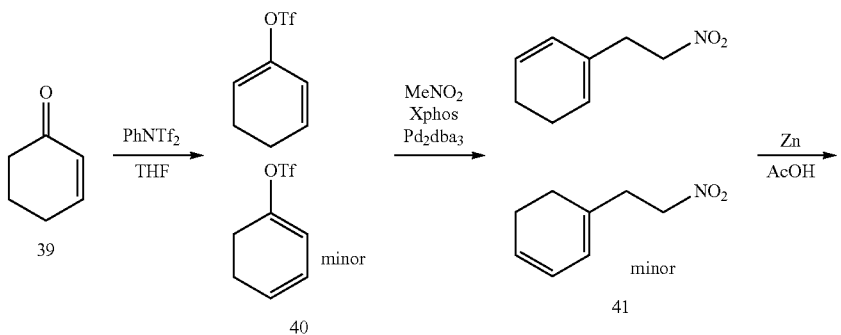

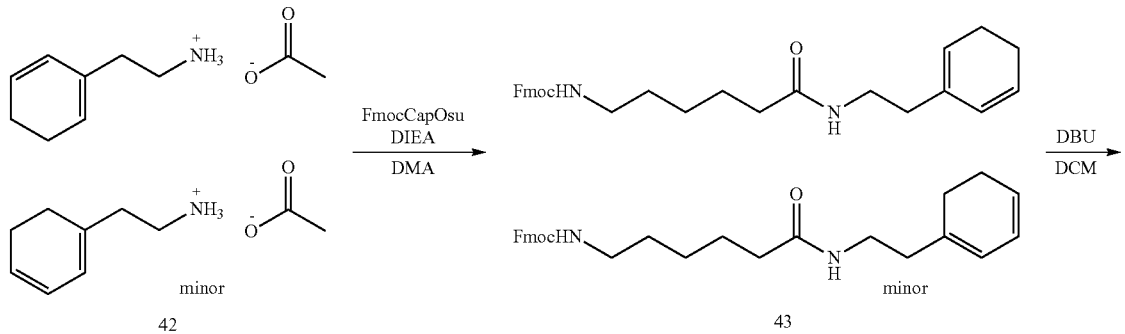

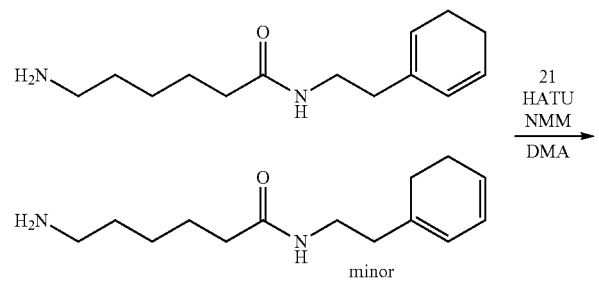

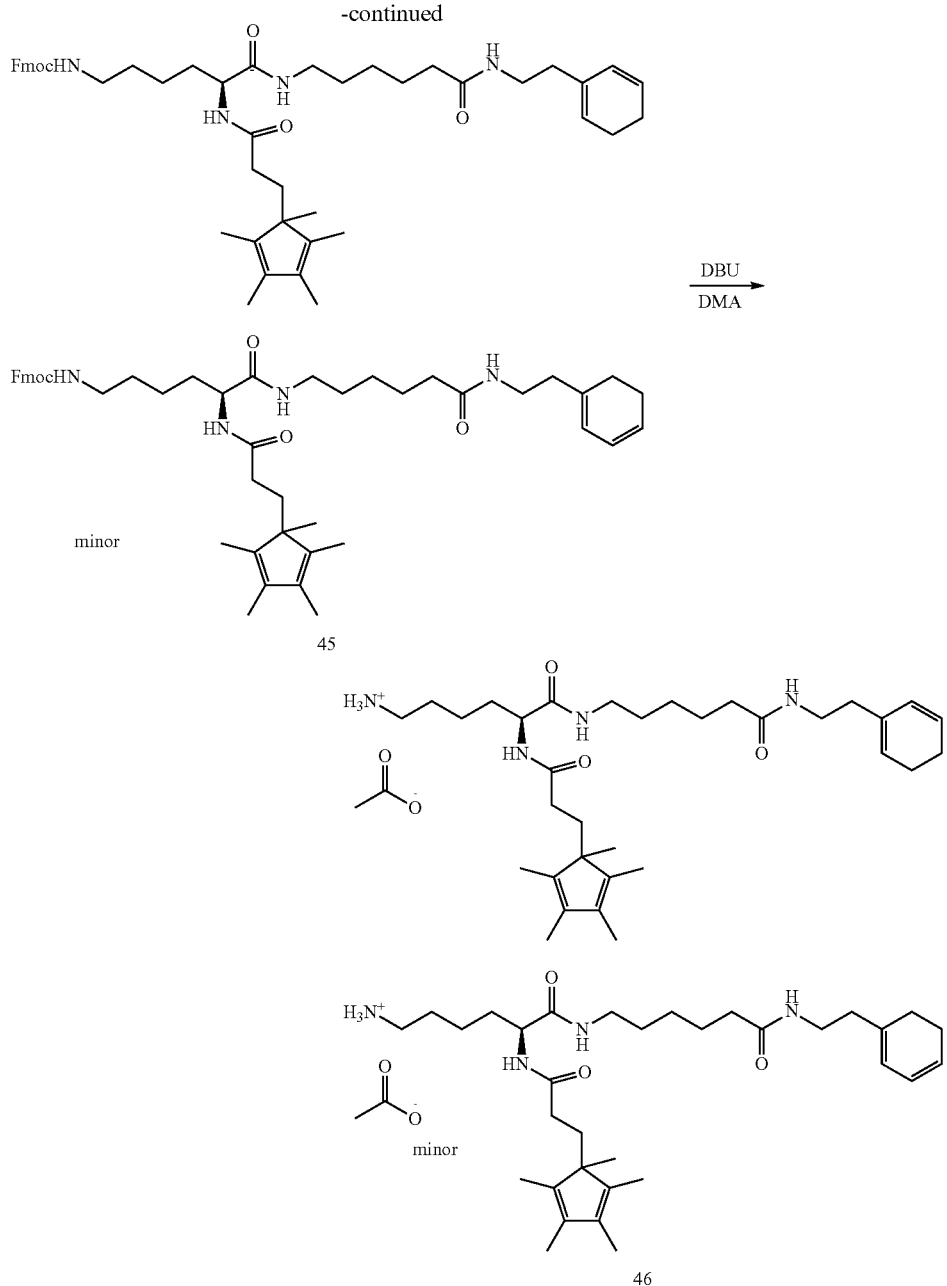

Step 1. LDA (7.2 mL, 14.4 mmol, 2.0 M solution) was added to 10 mL of anhydrous THF at −78° C. under Ar, followed by the addition of a solution of cyclohexanone 39 (1.26 g, 13.1 mmol) in 10 mL of anhydrous THF. The mixture was stirred for 30 min at −78° C., then added dropwise a solution of PhN(Tf)$_2$ (5.1 g, 14.4 mmol) in 10 mL of anhydrous THF. After 15 min, the cold bath was removed, and the resulting mixture was stirred at room temperature for 2 h. The resulting mixture was quenched with 10% NH$_4$Cl solution and extracted with ether (50 mL×2). The combined organics were washed with brine, dried over Na$_2$SO$_4$, and concentrated in vacuo to afford a dark brown oil. The resulting residue was purified by column chromatography (0 to 5% EtOAc in Hexanes) to afford 1.57 g of compound 40 (6.88 mmol, 53% yield) as a colorless oil. LC (Method A): retention time 3.03 min. MS (FID) calculated for C$_7$H$_7$F$_3$O$_3$S [M] 228. found 228.

Step 2. Compound 41 was prepared according to a known procedure reported in Org. Lett. 2013, 15, 3966-3969. A solution of cyclohexa-1,5-dien-1-yl trifluoromethane-sulfonate 40 (410 mg, 0.18 mmol), Pd$_2$(dba)$_3$ (82 mg, 0.009 mmol), XPhos (103 mg, 0.12 mmol), Cs$_2$CO$_3$ (1.4 g, 4.32 mmol), and nitromethane (20 mL) was heated at 65° C. in an oil bath to afford compound 41 (134 mg, 49%) as a clear oil after purification on Isco column chromatography (0 to 2% EtOAc in Hexanes). LC (Method A): retention time 2.9 min. MS (FID) calculated for C$_8$H$_{11}$NO$_2$ [M] 153. found 153.

Step 3. To a solution of compound 41 (50 mg, 0.326 mmol) in AcOH (2.5 mL), Zn dust (213 mmol, 3.26 mmol) was added at room temperature. After 2 h, the reaction was judged complete by LC/MS. The resulting mixture was filtered through celite and concentrated to afford 60 mg of crude compound 42 contaminated with acetate salts, which was used for the next step without further purification. LC/MS (Method A): retention time 0.18 min and 0.25 min. (ESI) calculated for free base $C_8H_{14}N$ [M+H]$^+$ 124.1. found 124.2.

Step 4. Compound 43 was synthesized according to Step 2 in Example 2 in DMA to afford 35.2 mg of compound 43 (0.0768 mmol, 28% yield) as an off-white solid. LC/MS (Method A): retention time 3.33 min. (ESI) calculated for $C_{29}H_{35}N_2O_3$: [M+H]$^+$ 459. found 459.

Step 5. Compound 44 was synthesized according to Step 3 in Example 2. Once the reaction was judged complete by LC/MS, the reaction was concentrated, and the resulting residue was diluted with DMSO (0.5 mL) and purified directly by reverse phase on a $C_{18}$ Aq Isco column (15.5 g). Eluent: $CH_3CN$ in $H_2O$, each containing 0.05% of AcOH (0% to 70%). The fractions containing product were combined and lyophilized to afford impure compound 44. A second reverse phase purification on a EZ Prep (Gemini, 30×150 mm) was performed. Eluent: $CH_3CN$ in $H_2O$, each containing 0.05% of AcOH (5% to 70%). The fractions containing product were combined and lyophilized to afford 7.3 mg of compound 44 (0.0309 mmol, 40% yield) as a clear film. LC/MS (Method B): retention time 1.82 min. (ESI) calculated for free base $C_{14}H_{25}N_2O$: [M+H]$^+$ 237. found 237. $^1$H-NMR (500 MHz; $CD_3OD$): δ 6.11-6.09 (m, 0.1H), 5.85 (s, 2H), 5.81-5.78 (m, 0.2H), 5.55 (s, 1H), 5.49 (s, 0.2H), 3.23 (t, J=7.3 Hz, 2H), 2.85 (t, J=7.5 Hz, 2H), 2.66 (s, 0.1H), 2.58-2.54 (m, 0.2H), 2.24-2.18 (m, 4H), 2.13-2.05 (m, 3H), 1.90 (s, 1H), 1.75-1.69 (m, 0.4H), 1.68-1.59 (m, 4H), 1.42-1.36 (m, 2H).

Step 6. To a solution of compound 44 (9.9 mg, 0.0421 mmol) in DMA (1.1 mL) was added a solution of compound 21 (35.3 mg, 0.0631 mmol), HATU (32.0 mg, 0.0842 mmol), and NMM (14 µL, 0.126 mmol) in DMA (0.40 mL). After 2 hours, the reaction was quenched with AcOH and purified directly by reverse phase on a $C_{18}$ Aq Isco column (50 g). Eluent: $CH_3CN$ in $H_2O$, each containing 0.05% of AcOH (30% to 95%). The fractions containing product were combined and lyophilized to afford 19.8 mg of compound 45 (0.0255 mmol, 61% yield) as a white solid. UPLC/MS (Method D): retention time 2.29 min. (ESI) calculated for $C_{48}H_{65}N_4O_5$: [M+H]$^+$ 778. found 778.

Step 7. To a solution of compound 45 (19.8 mg, 0.0255 mmol) in DMA (0.85 mL) was added a solution of DBU (4.1 mg, 0.0268 mmol) in DMA (30 µL). After 25 minutes, the reaction was quenched with AcOH and purified directly by reverse phase on a $C_{18}$ Aq Isco column (30 g). Eluent: $CH_3CN$ in $H_2O$, each containing 0.05% of AcOH (30% to 95%). The fractions containing product were combined and lyophilized to afford 5.7 mg of compound 46 (0.0103 mmol, 40% yield) as a white solid. LC/MS (Method B): retention time 2.16 min. (ESI) calculated for free base $C_3H_{55}N_4O_3$: [M+H]$^+$ 555. found 555. $^1$H-NMR (300 MHz; $CDCl_3$): δ 7.52 (d, J=3.8 Hz, 1H), 6.35 (d, J=7.5 Hz, 1H), 6.09 (d, J=9.6 Hz, 0.2H), 5.83 (q, J=10.0 Hz, 3H), 5.52 (s, 1H), 5.31 (d, J=7.0 Hz, 3H), 4.84 (d, J=26.1 Hz, 0.5H), 4.36 (q, J=7.1 Hz, 1H), 3.48 (s, 1H), 3.29 (q, J=6.4 Hz, 2H), 3.18 (dt, J=13.6, 6.8 Hz, 2H), 2.86 (t, J=6.8 Hz, 2H), 2.51 (s, 0.2H), 2.18 (dd, J=16.8, 7.2 Hz, 3H), 2.11 (s, 3H), 1.94 (s, 3H), 1.75-1.59 (m, 20H), 1.54-1.25 (m, 10H), 0.88 (s, 3H).

Example 14: Synthesis of (S)-6-((2-(furan-3-yl)ethyl)amino)-5-(3-(furan-3-yl)propanamido)-6-oxo-hexan-1-aminium Acetate (48)

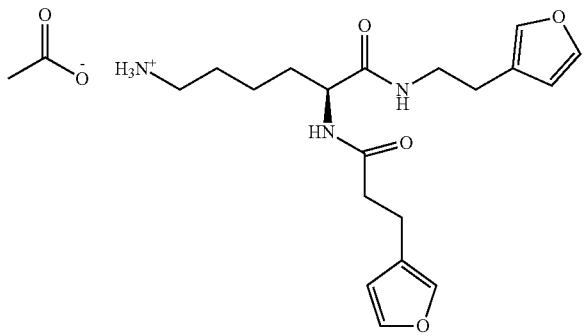

48

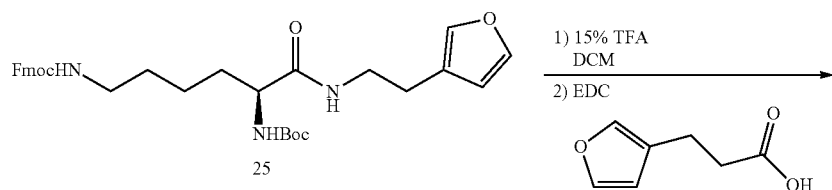

25

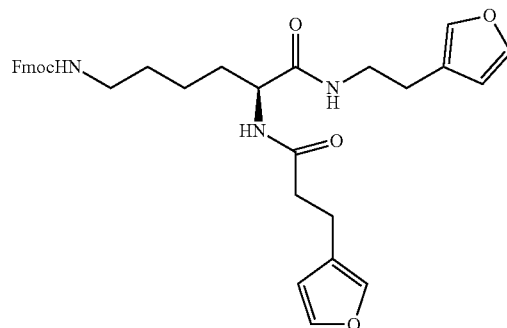

47

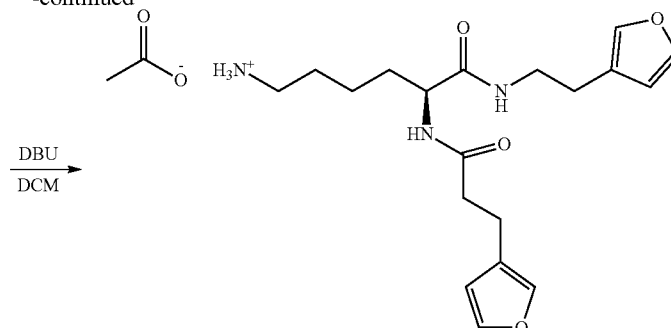

48

-continued

Step 1: Compound 47 was synthesized according to Step 2 in Example 7 using crude deprotected amine 25 (27 mg, 0.0584 mmol), 3-(furan-3-yl)propanoic acid (9.8 mg, 0.070 mmol), and EDCl (20 mg, 0.105 mmol) and TEA (16 mL, 0.117 mmol) in DMF (1.0 mL). After 15 h, the reaction was judged complete by LC/MS. The crude reaction mixture was then purified directly by EZ Prep (Gemini, 30×150 mm). Eluent: $CH_3CN$ in $H_2O$, each containing 0.05% of AcOH (10% to 95%). The fractions containing product were combined and lyophilized to afford 13.5 mg of compound 47 (0.0231 mmol, 40% yield) as a white solid. LC/MS (Method A): retention time 3.2 min. (ESI) calculated for $C_{34}H_{38}N_3O_6$: $[M+H]^+$ 584.3. found 584.3.

Step 2. Compound 47 (10 mg, 0.0171 mmol) was dissolved in DCM (1.2 mL) and 5% piperidine in DMF was dropwise added (200 mL) at room temperature. After 16 h, the reaction was judged complete by LC/MS. The mixture was concentrated to remove all volatiles and dissolved in 0.5 mL of DMSO. The crude residue was purified by EZ Prep (Gemini, 30×150 mm). Eluent: $CH_3CN$ in $H_2O$, each containing 0.05% of AcOH (10% to 95%). The fractions containing product were combined and lyophilized to afford 6.1 mg of compound 48 (0.0145 mmol, 85% yield) as a white solid. LC/MS (Method A): retention time 1.4 min. (ESI) calculated for free base $C_{19}H_{28}N_3O_4$: $[M+H]^+$ 362.2. found 362.2. $^1$H-NMR (500 MHZ; $CD_3OD$): δ 7.41 (dt, J=5.6, 1.7 Hz, 2H), 7.33 (dd, J=1.5, 0.8 Hz, 1H), 7.30 (dd, J=1.5, 0.9 Hz, 1H), 6.35 (ddd, J=4.4, 1.7, 0.8 Hz, 2H), 4.26 (dd, J=8.8, 5.5 Hz, 1H), 3.40-3.34 (m, 3H), 2.85-2.79 (m, 2H), 2.74 (td, J=7.2, 4.5 Hz, 2H), 2.62 (t, J=7.1 Hz, 2H), 2.51-2.48 (m, 2H), 1.90 (s, 2H), 1.78-1.71 (m, 1H), 1.60-1.54 (m, 3H), 1.32-1.22 (m, 2H).

Example 15: Synthesis of 5-(3-methoxyfuran-2-yl)pentan-1-aminium Acetate (53)

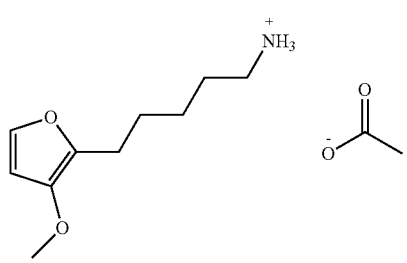

53

-continued

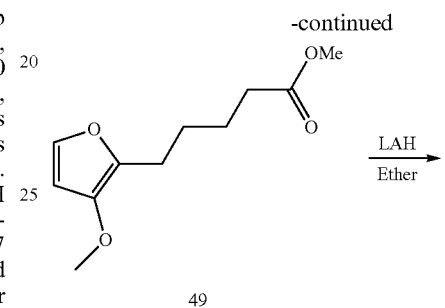

49

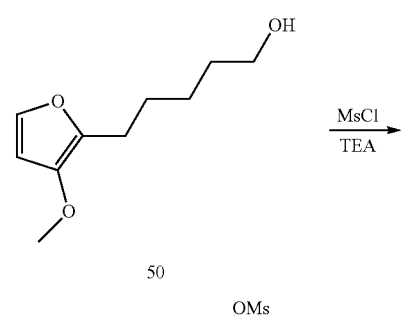

50

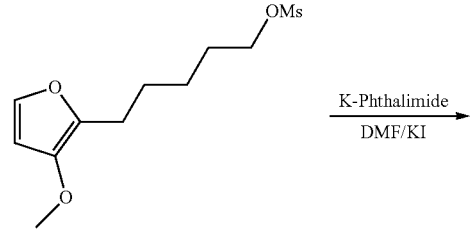

51

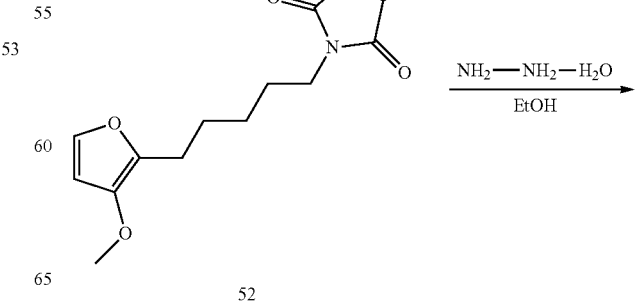

52

-continued

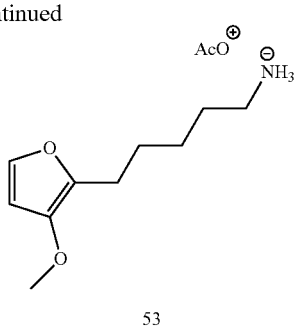

53

Step 1: Compound 49 was prepared as reported in the literature (*Bioconjugate Chem.* 2018, 29, 2046-2414). Reduction of compound 49 (150 mg, 0.706 mmol) by LAH (1.1 mL, 1.5 eq. of 1.0 M solution in THF) followed by treatment of aqueous sodium potassium tartrate (0.5 mL) afforded the corresponding alcohol 50 (136 mg, quant. yield). LC/MS (Method A): retention time 1.9 min. (ESI) calculated for $C_{10}H_{17}O_3$: [M+H]$^+$ 185.1. found 185.1.

Step 2: To compound 50 (130 mg, 0.705 mmol) in anhydrous DCM (2.5 mL) in an ice/$H_2O$ bath, under Ar, was added TEA (150 μL, 1.5 eq.) followed by dropwise addition of methanesulfonyl chloride (71 μL, 1.3 eq.). The resulting mixture was stirred at 0° C. for 30 min then at room temperature for 2 h. The reaction was quenched by the addition of $H_2O$ and extracted with DCM (3×). The combined organics were washed with brine and dried over $Na_2SO_4$ to give 143 mg of crude compound 51 (0.545 mmol, 78% yield), which was used in the next step without further purification. UPLC/MS (Method D): retention time 1.4 min. (ESI) calculated for $C_{11}H_{19}O_5S$: [M+H]$^+$ 263.1. found 262.9.

Step 3: The mixture of compound 51 (143 mg, 0.545 mmol) and K-phthalimide (110 mg, 0.599 mmol) in DMF (1 mL) in the presence of KI (9 mg, 0.1 eq.) was stirred at room temperature for 3 days, until the reaction judged complete by LC/MS, then the volatiles were concentrated in vacuo. The resulting residue was purified by column chromatography (0 to 60% EtOAc in Hexanes) to afford 64 mg of compound 52 (0.204 mmol, 38% yield). LC/MS (Method A): retention time 3.1 min. (ESI) calculated for $C_{18}H_{20}NO_4$: [M+H]$^+$ 314.1. found 314.1.

Step 4: Compound 52 (30 mg, 0.0957 mmol) was dissolved in EtOH (0.5 mL) and added $NH_2$—$NH_2 \cdot H_2O$ (10 μL, 0.143 mmol, 1.5 equiv) at ambient temperature. After 16 h, the reaction was heated slightly to 40° C. to complete the reaction. The crude mixture was concentrated in vacuo and the resulting residue was dissolved in DMSO (1 mL) and purified by EZ Prep (Gemini, 30×150 mm). Eluent: $CH_3CN$ in $H_2O$, each containing 0.05% of AcOH (10% to 95%). The fractions containing product were combined and lyophilized to afford 8.5 mg of compound 53 (0.0464 mmol, 48% yield). UPLC/MS (Method D): retention time 0.83 min. (ESI) calculated for free base $C_{10}H_{18}NO_2$: [M+H]$^+$ 184.1. found 183.9. $^1$H-NMR (500 MHZ; $CDCl_3$): δ 7.10 (t, J=2.4 Hz, 1H), 6.26 (d, J=0.8 Hz, 1H), 3.71 (s, 3H), 3.15 (bs, 2H), 2.72-2.70 (m, 2H), 2.60-2.57 (m, 2H), 2.00 (s, 3H), 1.64-1.58 (m, 2H), 1.51-1.48 (m, 2H), 1.36-1.32 (m, 2H).

Example 16: Synthesis of 3-(3-methoxyfuran-2-yl)propan-1-aminium Acetate (57)

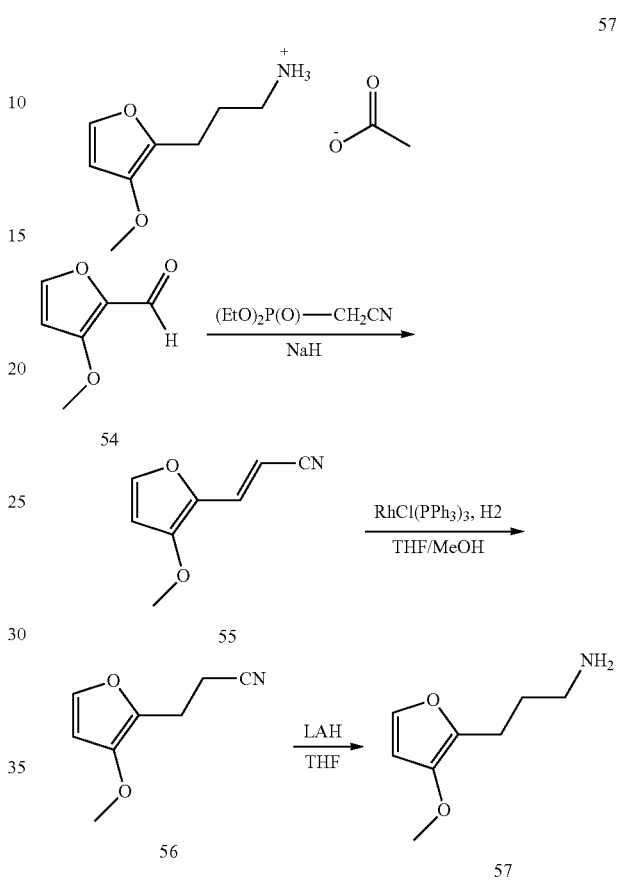

Step 1: To a suspension of NaH (95.4 mg, 2.39 mmol, 1.5 eq.) in anhydrous THF (3 mL), in an ice-bath under Ar, was added dropwise diethyl (cyanomethyl)phosphonate (295 L, 1.82 mmol, 1.15 eq.). The resulting mixture was stirred for 30 min, then to this cold solution was added dropwise a solution of compound 54 (200 mg, 1.59 mmol) in THF (1 mL). After 5 mins, the ice bath was removed. The reaction mixture was stirred for 1 h at room temperature. The reaction was quenched with $H_2O$, and extracted with EtOAc. The crude residue was purified by column chromatography (0 to 90% EtOAc in Hexanes) to afford 220 mg of compound 54 (1.48 mmol, 93% yield) as an off-white solid. UPLC/MS (Method D): retention time 1.09 min and 1.19 min. (Z/E=1:9). (ESI) calculated for $C_8H_8NO_2$: [M+H]$^+$ 150.1. found 149.9.

Step 2: Compound 55 (110 mg, 0.737 mmol) was treated with Wilkinson's catalyst RdCl (PPh$_3$)$_3$ (68 mg, 0.1 eq.) in a mixture of THF/MeOH (4 mL, 1:1, v/v) under $H_2$ pressure. The reaction was complete after 48 h to afford crude, selectively reduced product 56. The crude residue was purified by column chromatography (0 to 90% EtOAc in Hexanes) to yield 44 mg of compound 56 (0.291 mmol, 40% yield). UPLC/MS (Method D): retention time 1.01 min. (ESI) calculated for $C_8H_{10}NO_2$: [M+H]$^+$ 152.1. found 151.9.

Step 3: Compound 56 (8.5 mg, 0.0562 mmol) was treated with LAH (84 μL, 0.0843 mmol, 1.5 eq) in an ice bath. After 2 h, the cold mixture was carefully quenched with H$_2$O (0.5 mL) and 1.0 M NaOH solution (0.5 mL). The desired product was extracted with Et$_2$O and concentrated in vacuo to afford 2.5 mg of compound 56 (0.0161 mmol, 29% yield). UPLC/MS (Method D): retention time 0.53 min. (ESI) calculated for C$_8$H$_{14}$NO$_2$: [M+H]$^+$ 156.1. found 155.9. $^1$H-NMR (500 MHz; CDCl$_3$): δ 7.12 (s, 1H), 6.27 (s, 1H), 3.73 (s, 3H), 2.75 (bs, 2H), 2.66 (t, J=7.3 Hz, 2H), 2.06-2.05 (m, 2H), 1.81-1.78 (m, 2H).

Antibodies and Deglycosylation

In the following examples, two antibodies, an anti-HER2 antibody having variable regions derived from humAb4D5-8 from Carter et al, PNAS 1992 89 4285, also known as trastuzumab, and a non-binding isotype control derived from an immunological antigen having no relation to oncology or infectious diseases, were deglycosylated using 400 U/mg mAb of PNGaseF (NEB P0704L) in PBS pH 7.4 at 37° C. overnight. The reaction mixture was buffer exchanged to PBS pH 7.4 using spin filters (Amicon, 30 kDa cut-off). This allowed the 295Q residue to be accessed by the transglutaminase enzyme to conjugate the antibodies to a maximum loading of 2.

An anti-MSR1 antibody H1H21234N containing a N297Q mutation, which eliminates N-linked glycosylation of the Fc at this site, was also used in the following examples. The mutation allowed the antibodies to be conjugated to a maximum loading of 4 at 295Q and 297Q of the heavy chains. A non-binding antibody containing the same N297Q mutation was used as a non-binding isotype control.

Example 17—Bacterial Transglutaminase Conjugation of Compound 3 Linker mAb-3 Intermediates—Glutaminyl Modified mAbs

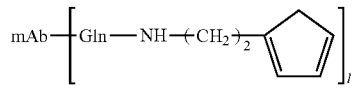

Deglycosylated control, HER2, and MSR1 antibodies were conjugated at 1 mg/mL in PBS pH 7.4. Linker 3 was added in a 50-150 fold molar excess over antibody and the enzymatic reaction was initiated by addition of 12 units of bacterial transglutaminase (Zedira, T1001) per mg antibody and incubated at 37° C. for 4-16 hours. Excess of linker 3 was removed by spin filters (Amicon, 30 kDa cut-off) or size exclusion chromatography using Superdex 200 Increase 10/300 GL column. The conjugates were analyzed by ESI-MS for the determination of the linker antibody ratio (LAR) using a Waters Acquity UPLC interfaced to Xevo G2-S QT of Mass Spectrometer. The chromatographic separation was achieved on a C4 column (2.1×50 mm ACQUITY UPLC BEH protein C4, 1.7 um, 300 A) in a 10 min gradient (minute: percentage of mobile phase B; 0:10%, 1:10%, 5:90%, 7:90%, 7.2:10%, 10:10%). The mobile phase A was 0.1% formic acid in water and mobile phase B was 0.1% formic acid in acetonitrile. The flow rate was set at 0.3 mL/min. The detector TOF scan was set from m/z 500-4500 with major parameters as listed (Capillary voltage 3.0 kV; Sampling Cone 80V; Source Offset at 100V; Source temperatures 150° C.; Desolvation temperature 450° C.; Cone gas 0 L/hr; Desolvation gas 800 L/hr). The spectra were deconvoluted with MaxEnt function within MassLynx software. The resulting molecular ions which when weighted according to intensities corresponded to the loadings listed in Table 3. Size-exclusion HPLC established that all conjugates were >95% monomeric.

Example 18—Diels-Alder Conjugation with Glutaminyl Modified mAbs at pH=7.2: Method A The mAb-3 intermediates were conjugated at 3-5 mg/ml in PBS pH 7.2-7.4 and 10% DMSO. Linker-payloads mc-VC-PABC-MMAE, Doronina, S. O. et al., Nat. Biotechnol. 2003 21 778; mc-VA-PBD, Jeffrey, S. C. et al., Protein Conjugate Chem. 2013 24 1256; mal-PEG8-VC-PABQ-Rifanalog and mal-VC-PABQ-Rifalogue, Lehar, S. M. et al., Nature 2015 527 323-328 (each of which are illustrated below) were added in a 3.5-10-fold molar excess over antibody and incubated at room temperature for 45-120 minutes. The conjugates were purified by Protein A chromatography (Pierce Protein A Columns, ThermoScientific, product no 20356) or size exclusion chromatography using Superdex 200 Increase 10/300 GL column. Drug to antibody ratio was determined by LC-MS (according to the method described in Example 17). The resulting molecular ions which when weighted according to intensities corresponded to the loadings listed in Table 3. Size-exclusion HPLC established that all conjugates were >95% monomeric.

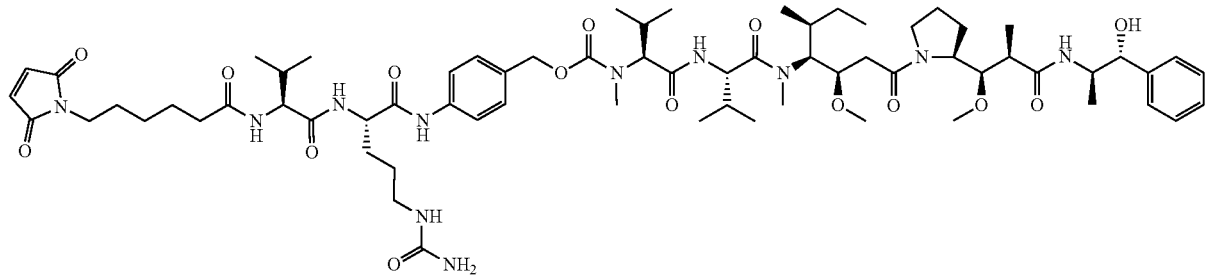

mc-VC-PABC-MMAE

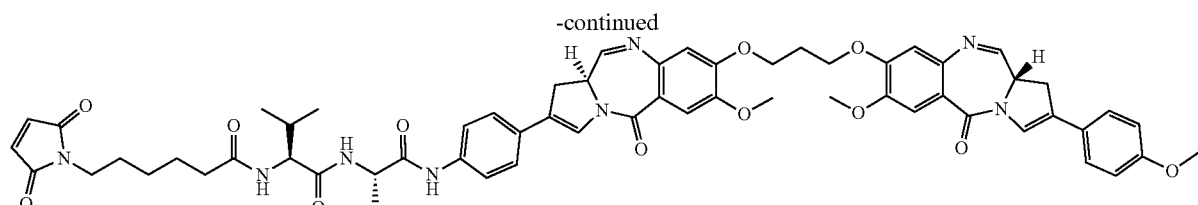

mc-VC-PBD

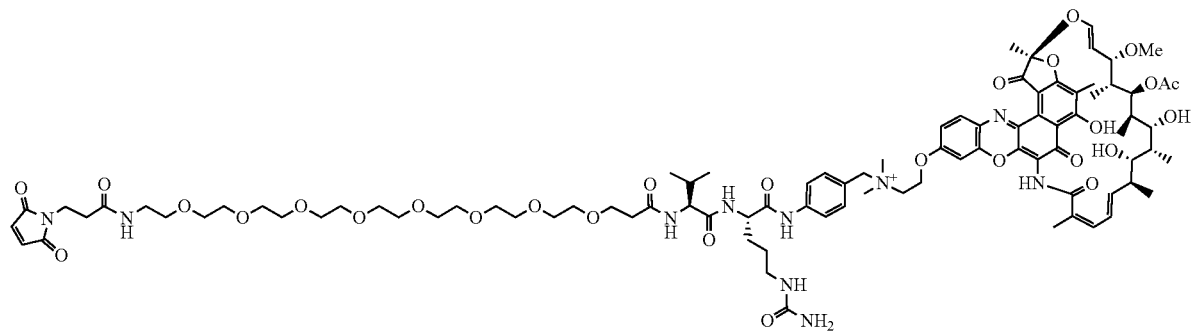

mal-PEG8-VC-PABQ-Rifanalog

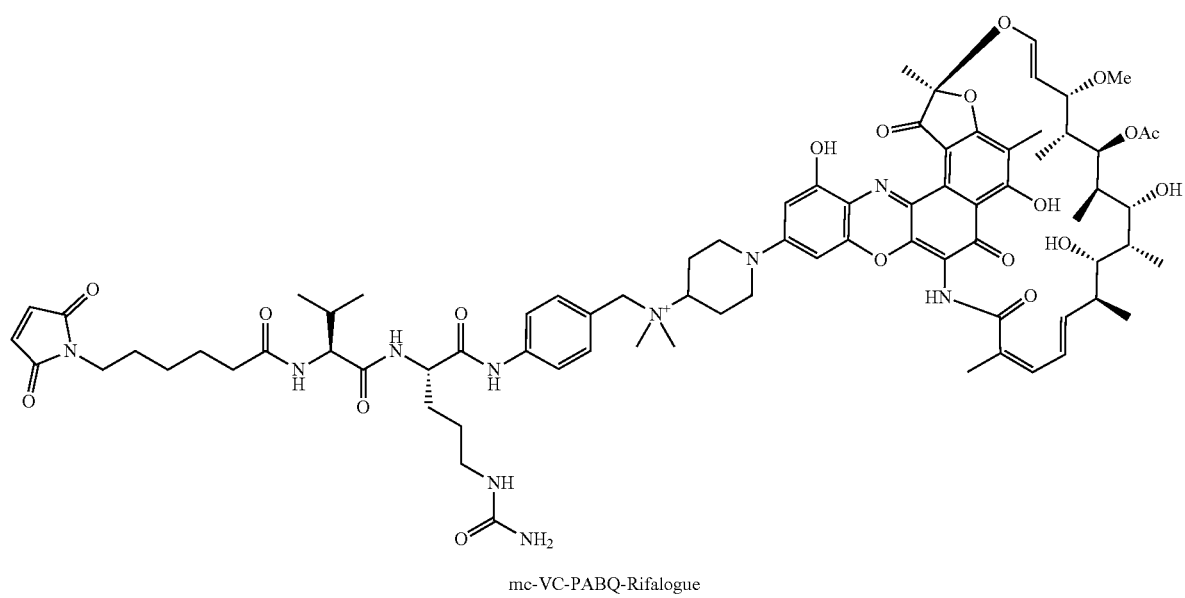

mc-VC-PABQ-Rifalogue

Example 19—Diels-Alder Conjugation with Glutaminyl Modified mAbs at pH=5.5: Method B The mAb-3 intermediates were conjugated at 4 mg/mL in 50 mM Histidine buffer pH 5.5. 10% DMSO was used for mc-VC-PABC-MMAE. Linker-payloads mc-VC-PABC-MMAE or Alexa Fluor™ 647 C2 Maleimide (Invitrogen) were added in an 10-20-fold molar excess over antibody and incubated at room temperature for 24-40 hours. The conjugates were purified by size exclusion chromatography using Superdex 200 Increase 10/300 GL column. Drug to antibody ratio was determined by LC-MS (according to the method described in Example 2). The resulting molecular ions which when weighted according to intensities corresponded to the loadings listed in Table 3. Size-exclusion HPLC established that all conjugates were >95% monomeric.

Example 20—Lysine Conjugation of Compound 4 Linker mAb-4 Intermediates—Stochastic Modified mAbs

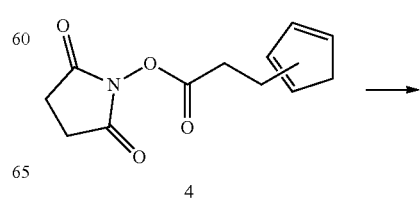

4

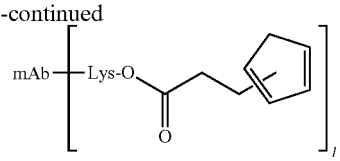

Control and HER2 antibodies were conjugated at 5 mg/mL in 50 mM Phosphate buffer pH 8.0. Linker 4 (St. Amant, A. H. et al., *Protein Conjugate Chem.* 2018 29 2406) was added in a 2-3-fold molar excess over antibody and incubated at room temperature for 2 hours. The reaction mixture was buffer exchanged to PBS, pH 7.4 using spin filters (Amicon, 30 kDa cut-off). The conjugates were analyzed by ESI-MS for the determination of the linker antibody ratio (LAR) using the method described in Example 17. The resulting molecular ions which when weighted according to intensities corresponded to the loadings listed in Table 3.

Example 21—Diels-Alder Conjugation with Stochastic mAb Intermediates

The mAb-4 intermediates were conjugated at 3-5 mg/mL in PBS pH 7.4 and 10% DMSO. Payload (mc-VA-PBD), as illustrated above, was added in a 4-fold molar excess over antibody and incubated at room temperature for 2 hours. Excess linker-payload was removed by treatment with activated charcoal followed by desalting using a Sephadex PD10 column (GE healthcare, product no 17085101). The conjugates were analyzed by ESI-MS for the determination of the drug antibody ratio (DAR) using the method described in Example 2. The resulting molecular ions which when weighted according to intensities corresponded to the loadings listed in Table 3. Size-exclusion HPLC established that all conjugates were >95% monomeric.

Table 3 has listed the loadings (LAR and DAR) for each conjugate. The transglutaminase conjugated 3 produced LARs approaching the theoretical value of 2. Reacting the antibody-3 diene intermediate with the Diels-Alder maleimide partner mc-VC-PABC-MMAE, mal-PEG8-VC-PABQ-Rifanalog, or the interchain disulfide aggregation prone mc-VA-PBD (Jeffrey, S. C. et al., *Protein Conjugate Chem.* 2013 24 1256) produced DARs of similar value. The lysine conjugated diene 4 produced LARs of 1.2 and 1.8, however, the Diels-Alder reaction with the same maleimides yielded conjugates of lower relative DAR. These results indicate that the combined transglutaminase and Diels-Alder conjugations can accommodate a variety of maleimide linker-payloads, improve the overall efficiency, and position them site selectively on the antibody with low levels of aggregate.

TABLE 3

| Antibody Drug Conjugate | Linker to Antibody Ratio (LAR) | Drug to Antibody Ratio (DAR) |
|---|---|---|
| HER2-3-mc-VC-PABC-MMAE | 1.8 | 1.8 |
| Isotype Cntl-3-mc-VC-PABC-MMAE | 1.8 | 1.6 |
| HER2-3-mc-VA-PBD | 1.6 | 1.6 |
| Isotype Cntl-3-mc-VA-PBD | 1.7 | 1.5 |
| HER2-4-mc-VA-PBD | 1.2 | 0.8 |
| Isotype Cntl-4-mc-VA-PBD | 1.8 | 1.0 |
| MSR1-3-mal-PEG8-VC-PABQ-Rifanalog | 4.0 | 2.8 |
| Isotype Cntl-3-mal-PEG8-VC-PABQ-Rifanalog | 4.0 | 3.9 |
| MSR1-3-mc-VC-PABQ-Rifalogue | 4.0 | 3.7 |
| Isotype Cntl-3-mc-VC-PABQ-Rifalogue | 4.0 | 2.9 |
| HER2-9-mc-VC-PABC-MMAE | 1.9 | 1.8 |
| Isotype Cntl-9-mc-VC-PABC-MMAE | 1.9 | 1.7 |
| HER2-13-mc-VC-PABC-MMAE | 1.8 | 1.8 |
| Isotype Cntl-13-mc-VC-PABC-MMAE | 1.8 | 1.6 |
| HER2-16-mc-VC-PABC-MMAE | 1.9 | 1.7 |
| Isotype Cntl-16-mc-VC-PABC-MMAE | 1.97 | 1.7 |
| HER2-10-mc-VC-PABC-MMAE | 0.8 | 0.9 |
| Isotype Cntl-10-mc-VC-PABC-MMAE | 0.9 | 0.9 |
| HER2-38-mc-VC-PABC-MMAE | 1.9 | 1.9 |
| Isotype Cntl-38-mc-VC-PABC-MMAE | 1.9 | 1.8 |
| HER2-44-mc-VC-PABC-MMAE | 1.9 | 1.7 |
| Isotype Cntl-44-mc-VC-PABC-MMAE | 1.9 | 1.6 |
| HER2-48-mc-VC-PABC-MMAE | 2.0 | 3.7 |
| Isotype Cntl-48-mc-VC-PABC-MMAE | 2.0 | 3.6 |
| HER2-46-mc-VC-PABC-MMAE | 1.8 | 3.3 |
| Isotype Cntl-46-mc-VC-PABC-MMAE | 1.8 | 3.0 |
| HER2-27-mc-VC-PABC-MMAE | 1.9 | 1.9 |
| HER2-27-Alexa Fluor™ 647 C2 Maleimide |  | 1.7* |
| Isotype Cntl-27-mc-VC-PABC-MMAE | 1.9 | 1.8 |
| Isotype Cntl-27-Alexa Fluor™ 647 C2 Maleimide |  | 1.7* |

*Alexa Fluor™ 647 C2 Maleimide per antibody ratio

Example 22—Stepwise Diels-Alder Conjugation

In certain embodiments, Method A and Method B may be performed consecutively on the same antibody-linker-payload intermediate bearing two dienes. This strategy can be used to produce antibody-payload conjugates bearing the same payloads or two different payload moieties. For example, an antibody with the compound 27 linker was conjugated to mc-vc-PAB-MMAE via Method A of Example 18, and subsequently further conjugated to Alexa Fluor™ 647 via Method B of Example 19. A buffer exchange step was done between method A and B by spin filters (Amicon, 30 kDa cut-off) to remove the extra payload by PBS pH=7.2 followed by 50 mM Histidine pH=5.5 buffer to change the pH for method B).

TABLE 4

| Compound | 1st Diels-Alder method | Equivalent of 1st Payload | 2nd Diels-Alder method | Equivalent of 2nd Payload |
|---|---|---|---|---|
| 3 | Method A | 8 eq of mc-vc-PAB-MMAE | — | — |
| 9 | Method A | 8 eq of mc-vc-PAB-MMAE | — | — |
| 13 | Method A | 7 eq of mc-vc-PAB-MMAE | — | — |

TABLE 4-continued

| Compound | 1st Diels-Alder method | Equivalent of 1st Payload | 2nd Diels-Alder method | Equivalent of 2nd Payload |
|---|---|---|---|---|
| 16 | Method A | 6 eq of mc-vc-PAB-MMAE | — | — |
| 10 | Method A | 3.5 eq of mc-vc-PAB-MMAE | — | — |
| 38 | Method A | 10 eq of mc-vc-PAB-MMAE | — | — |
| 44 | Method B | 12 eq of mc-vc-PAB-MMAE | — | — |
| 48 | Method B | 20 eq of mc-vc-PAB-MMAE | — | — |
| 46 | Method A | 5.5 eq of mc-vc-PAB-MMAE | Method B | 12 eq of mc-vc-PAB-MMAE |
| 27 | Method A | 6 eq of mc-vc-PAB-MMAE | Method B | 10 eq of Alexa Fluor ™ 647 C2 Maleimide |

Example 23—In Vitro Cytotoxicity Assays

In this Example, the ability of various antibody-drug conjugates and naked payloads to kill antigen-expressing tumor cells in vitro was assessed.

SKBR3 (Her2+) cells were seeded in 96 well plates at 8000 cells per well in complete growth media and grown overnight. For cell viability curves, serially diluted conjugates or naked payloads were added to the cells at final concentrations ranging from 100 nM to 5 pM and incubated for 3 days. NCI H929 and NCI H1975 (Her2−) cells were run as negative controls using similar conditions. To measure viability, cells were incubated with CCK8 (Dojindo) for the final 2 hours and the absorbance at 450 nm ($OD_{450}$) was determined on a Victor (Perkin Elmer). Background $OD_{450}$ levels determined from digitonin (40 nM) treated cells were subtracted from all wells and viability was expressed as a percentage of the untreated controls. $IC_{50}$ values were determined from a four-parameter logistic equation over a 10-point response curve (GraphPad Prism). The $IC_{50}$ for the HER2-3-mc-VC-PAB-MMAE ADCs and Isotype Cntl-3-mc-VC-PAB-MMAE ADCs were 0.096 and >100 nM, respectively. The interchain disulfide conjugates had similar $IC_{50}$ values as the transglutaminase site-specific Diels-Alder conjugates. This indicates that the Diels-Alder conjugations had no effect on the function of the antibody drug conjugate. $IC_{50}$ values are corrected for payload equivalents and the results of other transglutaminase site-specific Diels-Alder conjugates' cell viability are shown in Table 5. For comparison, the mc-VC-PABC-MMAE interchain disulfide conjugated molecules were produced according to Doronina, S. O. et al., *Nat. Biotechnol.* 2003 21 778. All attempts to conjugate mc-VA-PBD were not successful in accordance with results from Jeffrey, S. C. et al., *Protein Conjugate Chem.* 2013 24 1256 and further demonstrate the utility of the site-specific transglutaminase reaction in combination with the Diels-Alder coupling methodology.

TABLE 5

| Cell Type | ADC or Payload | IC50 (nM) | % Kill |
|---|---|---|---|
| SK-BR-3 | MMAE (payload) | 0.031 | 97.3 |
| SK-BR-3 | HER2-mc-VC-PABC-MMAE | 0.080 | 95.9 |
| SK-BR-3 | HER2-3-mc-VC-PABC-MMAE | 0.096 | 95.3 |
| SK-BR-3 | Isotype Cntl-3-mc-VC-PABC-MMAE | >100 | 13.0 |
| SK-BR-3 | HER2-9-mc-VC-PABC-MMAE | 0.046 | 97.2 |
| SK-BR-3 | Isotype Cntl-9-mc-VC-PABC-MMAE | 41 | 66.1 |
| SK-BR-3 | HER2-13-mc-VC-PABC-MMAE | 0.008 | 93.8 |
| SK-BR-3 | Isotype Cntl-13-mc-VC-PABC-MMAE | 32.49 | 79.2 |
| SK-BR-3 | HER2-16-mc-VC-PABC-MMAE | 0.027 | 91.3 |
| SK-BR-3 | Isotype Cntl-16-mc-VC-PABC-MMAE | 21.4 | 90.6 |
| SK-BR-3 | HER2-10-mc-VC-PABC-MMAE | 0.421 | 89.3 |
| SK-BR-3 | Isotype Cntl-10-mc-VC-PABC-MMAE | >100 | PNR* |
| SK-BR-3 | HER2-38-mc-VC-PABC-MMAE | 0.009 | 93.3 |
| SK-BR-3 | Isotype Cntl-38-mc-VC-PABC-MMAE | >100 | PNR* |
| SK-BR-3 | HER2-44-mc-VC-PABC-MMAE | 0.026 | 93.4 |
| SK-BR-3 | Isotype Cntl-44-mc-VC-PABC-MMAE | >100 | PNR* |
| SK-BR-3 | HER2-48-mc-VC-PABC-MMAE | 0.004 | 94.0 |
| SK-BR-3 | Isotype Cntl-48-mc-VC-PABC-MMAE | 25.08 | 94.0 |
| SK-BR-3 | HER2-46-mc-VC-PABC-MMAE | 0.019 | 94.4 |
| SK-BR-3 | Isotype Cntl-46-mc-VC-PABC-MMAE | >100 | PNR* |
| SK-BR-3 | HER2-27-mc-VC-PABC-MMAE HER2-27-Alexa Fluor ™ 647 C2 Maleimide | 0.024 | 94.2 |
| SK-BR-3 | Isotype Cntl-27-mc-VC-PABC-MMAE Isotype Cntl-27-Alexa Fluor ™ 647 C2 Maleimide | 25.94 | 94.0 |
| HER2− | | | |
| NCI H929 | MMAE (payload) | 0.209 | 99.7 |
| NCI H929 | HER2-mc-VC-PABC-MMAE | >100 | 9.1 |
| NCI H929 | HER2-3-mc-VC-PABC-MMAE | >100 | 2.4 |
| NCI H929 | Isotype Cntl-3-mc-VC-PABC-MMAE | >100 | 0.0 |
| NCI H929 | HER2-9-mc-VC-PABC-MMAE | >100 | 2.5 |
| NCI H929 | Isotype Cntl-9-mc-VC-PABC-MMAE | >100 | 5.9 |
| NCI-H1975 | HER2-13-mc-VC-PABC-MMAE | >100 | 16.8 |
| NCI-H1975 | Isotype Cntl-13-mc-VC-PABC-MMAE | >100 | 22.1 |
| NCI-H1975 | HER2-16-mc-VC-PABC-MMAE | >100 | 9.6 |
| NCI-H1975 | Isotype Cntl-16-mc-VC-PABC-MMAE | >100 | 4.4 |
| NCI-H1975 | HER2-10-mc-VC-PABC-MMAE | >100 | 2.3 |
| NCI-H1975 | Isotype Cntl-10-mc-VC-PABC-MMAE | >100 | 1.5 |
| NCI-H1975 | HER2-38-mc-VC-PABC-MMAE | >100 | 9.8 |
| NCI-H1975 | Isotype Cntl-38-mc-VC-PABC-MMAE | >100 | 1.9 |

TABLE 5-continued

| Cell Type | ADC or Payload | IC50 (nM) | % Kill |
|---|---|---|---|
| NCI-H1975 | HER2-44-mc-VC-PABC-MMAE | >100 | 6.2 |
| NCI-H1975 | Isotype Cntl-44-mc-VC-PABC-MMAE | >100 | 1.0 |
| NCI-H1975 | HER2-48-mc-VC-PABC-MMAE | >100 | 25.2 |
| NCI-H1975 | Isotype Cntl-48-mc-VC-PABC-MMAE | >100 | 23.7 |
| NCI-H1975 | HER2-46-mc-VC-PABC-MMAE | >100 | 15.5 |
| NCI-H1975 | Isotype Cntl-46-mc-VC-PABC-MMAE | >100 | 5.3 |
| NCI-H1975 | HER2-27-mc-VC-PABC-MMAE HER2-27-Alexa Fluor ™ 647 C2 Maleimide | >100 | 10.8 |
| NCI-H1975 | Isotype Cntl-27-mc-VC-PABC-MMAE Isotype Cntl-27-Alexa Fluor ™ 647 C2 Maleimide | >100 | 0.0 |

*PNR = Plateau not reached

Example 24—Intracellular *S. aureus* Antibody-Drug Conjugate Killing Assay

Rifamycin analogs according to the present disclosure were conjugated to either an anti-MSR1 antibody as identified in Example 1, or an isotype control antibody also identified in Example 1, in order to test the ability of the ADCs to reduce intracellular *S. aureus*.

THP-1 monocytic cell line was grown in media (RMPI+10% FBS+1% Penicillin/Streptomycin), then seeded at a density of 1e5 cells/well in a 24 well plate and differentiated into macrophages for three days prior to infection using 200 nM PMA. Prior to the experiment, THP-1 were washed with warm media (RMPI without FBS) to remove the Penicillin/Streptomycin. An overnight culture of *S. aureus* NRS384 was grown in RPMI, washed twice with PBS and resuspended at 1e7 cfu/mL in PBS. THP-1s were infected at 1e6 cfu/well with the *S. aureus* suspension in RMPI+10% FBS, a multiplicity of infection of 10:1 (*S. aureus*: macrophages). Plates were spun at 300×g for 5 minutes to synchronize adhesion of the bacteria, then incubated at 37° C. for 2 hours. Free-floating bacteria were removed by washing twice with warm media (RMPI without FBS) and remaining extracellular *S. aureus* were killed by addition of media (RMPI+10% FBS) containing 50 µg/mL of gentamicin. After 1 hour, media was aspirated and the indicated mAbs and ADCs were added in triplicate in a dilution series to infected macrophages in media (RMPI+10% FBS) containing 50 µg/mL gentamicin to prevent extracellular growth of *S. aureus*. The dilution series started at 10 µg/mL, with 1:3 dilutions for 5 points (10, 3.3, 1.1, 0.37, and 0.12 µg/mL final concentrations) for the MSR1 ADCs: MSR1-mc-VC-PABQ-Rifalogue (Interchain CYS), MSR1-mal-PEG8-VC-PABQ-Rifanalog (Interchain CYS), MSR1-3-mc-VC-PABQ-Rifalogue (TG-DA). The MSR1 mAb, isotype control mAb, and isotype control ADCs: Isotype Cntl-mc-VC-PABQ-Rifalogue (Interchain CYS), Isotype Cntl-mal-PEG8-VC-PABQ-Rifanalog (Interchain CYS), and Isotype Cntl-3-mc-VC-PABQ-Rifalogue (TG-DA) were tested at the highest concentration only. Untreated wells were also included as a baseline for infection. After 24 hours, plates were washed twice with warm RPMI without FBS, and then 50 µL of 0.1% Triton X-100 in PBS was added to lyse the THP-1; following lysis, 450 µL of PBS were added to each well. *S. aureus* survival was enumerated by colony forming units through serial dilution in PBS and plating onto trypticase soy agar plates. The results are summarized in Table 6.

TABLE 6

Average colony forming units of anti-MSR1 Ab-Antibiotic

| | mAb or ADC dose (µg/mL) | Median cfu/mL | Standard Deviation |
|---|---|---|---|
| *S. aureus* control | none | 1,270,000 | 138,000 |
| Isotype Cntl-mc-VC-PABQ-Rifalogue (Interchain CYS) | 10 | 1,125,000 | 312,583 |
| MSR1-mc-VC-PABQ-Rifalogue (Interchain CYS) | 10 | 50 (limit of detection) | 0 |
| | 3.3 | 50 (limit of detection) | 0 |
| | 1.1 | 50 (limit of detection) | 0 |
| | 0.4 | 675 | 66 |
| | 0.1 | 95,000 | 6,614 |
| Isotype Cntl-mal-PEG8-VC-PABQ-Rifalogue (Interchain CYS) | 10 | 1,275,000 | 180,277 |
| MSR1-mal-PEG8-VC-PABQ-Rifanalog (Interchain CYS) | 10 | 50 (limit of detection) | 0 |
| | 3.3 | 50 (limit of detection) | 0 |
| | 1.1 | 50 (limit of detection) | 0 |
| | 0.4 | 900 | 173 |
| | 0.1 | 97,500 | 10,897 |
| Isotype Cntl-3-mc-VC-PABQ-Rifalogue (TG-DA) | 10 | 700,000 | 80,364 |
| MSR1-3-mc-VC-PABQ-Rifalogue (TG-DA) | 10 | 50 (limit of detection) | 0 |
| | 3.3 | 50 (limit of detection) | 0 |
| | 1.1 | 50 (limit of detection) | 0 |
| | 0.4 | 350 | 76 |
| | 0.1 | 22,500 | 34,732 |
| Anti-MSR1 mAb | 10 | 900,000 | 212,623 |
| Isotype Cntl mAb | 10 | 1,050,000 | 166,458 |

As shown in Table 6, the MSR1 mc-VC-PABQ-Rifalogue ADC, MSR1 3-mc-VC-PABQ-Rifalogue (Interchain CYS and TG-DA) and MSR1-mal-PEG8-VC-PABQ-Rifanalog (Interchain CYS) at concentrations of 10, 3.3 and 1.1 µg/mL demonstrated the ability to eradicate intracellular *S. aureus* from infected macrophages in vitro, with a dose dependent decrease in activity at lower concentrations. Macrophages treated with unconjugated antibodies (Isotype control mAb, Anti-MSR1 mAb) and Isotype control ADC (Interchain CYS and TG-DA) at 10 µg/mL harbored intracellular *S. aureus* at a similar level to the untreated control. These data demonstrate that an MSR1-3-mc-VC-PABQ-Rifalogue (Interchain CYS and TG-DA) can be used to effectively kill pathogens residing within a macrophage reservoir.

Example 25—Intracellular *S. aureus*
Antibody-Drug Conjugate Killing Assay

Rifamycin analogs of the present disclosure were conjugated to an anti-MSR1 antibody H1H21234N containing a N297Q mutation, which eliminates N-linked glycosylation of the Fc at this site, also used in Example 1, in order to test the ability of the ADCs to reduce intracellular *S. aureus*. The mutation allowed the antibodies to be conjugated to a maximum loading of 4 at 295Q and 297Q of the heavy chains. A non-binding antibody containing the same N297Q mutation was used as a non-binding isotype control antibody, also used in Example 1.

THP-1 monocytic cell line was grown in media (RMPI+ 10% FBS+1% Penicillin/Streptomycin), then seeded at a density of 1e5 cells/well in a 48 well plate and differentiated into macrophages for three days prior to infection using 200 nM PMA. Prior to the experiment, THP-1 were washed with warm media (RMPI without FBS) to remove the Penicillin/ Streptomycin. An overnight culture of *S. aureus* NRS384 was grown in RPMI, washed twice with PBS and resuspended at 1e7 cfu/mL in PBS. THP-1s were infected at 1e6 cfu/well with the *S. aureus* suspension in RMPI+10% FBS, a multiplicity of infection of 10:1 (*S. aureus*: macrophages). Plates were spun at 300×g for 5 minutes to synchronize adhesion of the bacteria, then incubated at 37° C. for 2 hours. Free-floating bacteria were removed by washing twice with warm media (RMPI without FBS) and remaining extracellular *S. aureus* were killed by addition of media (RMPI+10% FBS) containing 50 µg/mL of gentamicin. After 1 hour, media was aspirated and the indicated mAbs and ncADCs were added in at least in duplicate in a dilution series to infected macrophages in media (RMPI+10% FBS) containing 50 µg/mL gentamicin to prevent extracellular growth of *S. aureus*. The dilution series started at 30 µg/mL, with 1:3 dilutions for 6 points (30, 10, 3.3, 1.1, 0.37, and 0.12 µg/mL final concentrations) for the MSR1 ADCs (TG-DA): MSR1-3-mal-PEG8-VC-PABQ-Rifanalog and MSR1-3-mc-VC-PABQ-Rifalogue. The control ADCs (prepared by the transglutaminase-Diels-Alder ("TG-DA") methods of the present disclosure): Isotype Cntl-3-mc-PEG8-VC-PABQ-Rifanalog, Isotype Cntrl-3-mc-VC-PABQ-Rifalogue and unconjugated antibodies were tested at the highest concentration only. Untreated wells were also included as a baseline for infection. After 24 hours, plates were washed twice with warm RPMI without FBS, and then 50 µL of 0.1% Triton X-100 in PBS was added to lyse the THP-1; following lysis, 200 µL of PBS were added to each well. *S. aureus* survival was enumerated by colony forming units through serial dilution in PBS and plating onto trypticase soy agar plates. The results are summarized in Table 7.

TABLE 7

Average colony forming units of anti-MSR1 Ab-Antibiotic

| | mAb or ADC dose (µg/mL) | Median cfu/mL | Standard Deviation |
|---|---|---|---|
| *S. aureus* control | none | 850000 | 110,868 |
| Isotype Cntl-3-mc-VC-PABQ-Rifalogue (TG-DA) | 30 | 70,000 | 6,292 |
| MSR1-3-mc-VC-PABQ-Rifalogue (TG-DA) | 30 | 100 | 35 |
| | 10 | 850 | 141 |
| | 3.3 | 9,250 | 2,828 |
| | 1.1 | 91,250 | 12,374 |
| | 0.4 | 100,000 | 28,284 |
| | 0.1 | 350,000 | 70,711 |
| Isotype Cntl-3- mal-PEG8-VC-PABQ-Rifanalog (TG-DA) | 30 | 92,500 | 5,774 |
| MSR1-3-mc-PEG8-VC-PABQ-Rifanalog (TG-DA) | 30 | 150 | 100 |
| | 10 | 4000 | 2021 |
| | 3.3 | 8,750 | 520 |
| | 1.1 | 82,500 | 19,094 |
| | 0.4 | 135,000 | 11,456 |
| | 0.1 | 350,000 | 187,639 |
| Anti-MSR1 mAb | 30 | 975,000 | 129,904 |
| Isotype Cntl mAb | 30 | 900,000 | 0 |

As shown in Table 7, the MSR1-3-mc-VC-PABQ-Rifalogue (TG-DA) and MSR1-3-mc-PEG8-VC-PABQ-Rifanalog (TG-DA) demonstrated the ability to reduce intracellular *S. aureus* from infected macrophages in vitro, with a dose dependent decrease in activity at lower concentrations and a 3-4 log reduction in bacterial burden at the highest concentrations. Macrophages treated with the control mAbs at 30 µg/mL harbored intracellular *S. aureus* at a similar level to the untreated control and the ADC Isotype Cntl-3-mc-VC-PABQ-Rifalogue (TG-DA) and Isotype Cntl-3-mal-PEG8-VC-PABQ-Rifanalog at 30 µg/mL reduced intracellular *S. aureus* by about one log compared to the untreated control. These data demonstrate that an anti-MSR1 ADCs, MSR1-3-mc-VC-PABQ-Rifalogue (TG-DA) and MSR1-3-mc-PEG8-VC-PABQ-Rifanalog (TG-DA) can be used to effectively kill pathogens residing within a macrophage reservoir.

As various changes can be made in the above-described subject matter without departing from the scope and spirit of the present disclosure, it is intended that all subject matter contained in the above description, or defined in the appended claims, be interpreted as descriptive and illustrative of the present disclosure. Many modifications and variations of the present disclosure are possible in light of the above teachings. Accordingly, the present description is intended to embrace all such alternatives, modifications, and variances which fall within the scope of the appended claims.

All patents, applications, publications, test methods, literature, and other materials cited herein are hereby incorporated by reference in their entirety as if physically present in this specification.

What is claimed is:

1. A method of producing the compound of Formula (1B):

$$BA \text{---} [SP \overset{Gln}{\text{---}} (Z \text{---} L \text{---} D)_2]_d, \quad (1B)$$

wherein

BA is an antibody;

Gln is a glutamine residue of said BA;

SP is

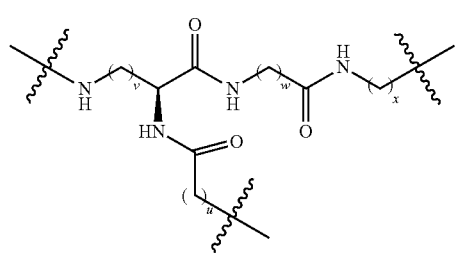

or

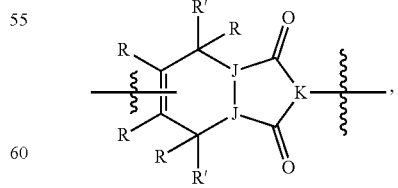

wherein subscripts u, w, x, and v are independently an integer from 1 to 20;

Z is

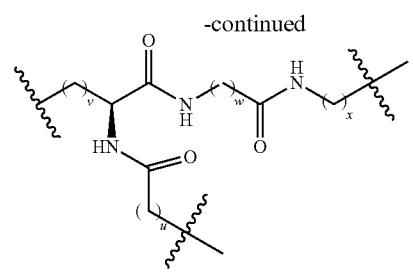

wherein R' is independently H, $C_{1-3}$ alkyl, or two R' together constitute a CHR, CHR—CHR, or O bridge;

R is independently at each occurrence H, $C_{1-3}$ alkyl, —$OC_{1-3}$ alkyl, or —$NHC_{1-3}$ alkyl;

J is CH;
K is N;
L is

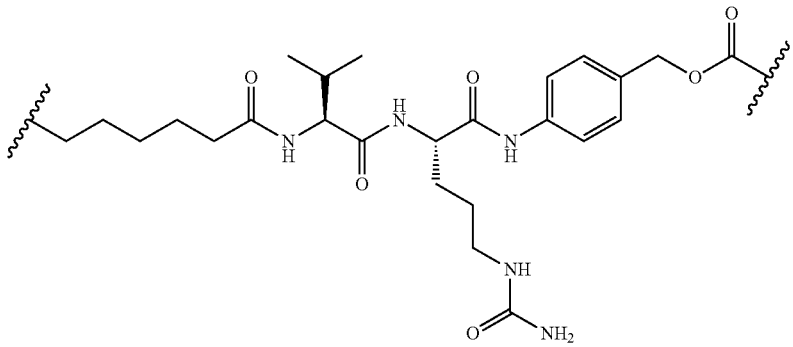 [SMILES: *CCCCCC(=O)N[C@H](C(=O)N[C@@H](CCCNC(N)=O)C(=O)Nc1ccc(COC(*)=O)cc1)C(C)C]

D is a therapeutic moiety, wherein the therapeutic moiety is a maytansinoid, a tubulysin, an auristatin, a dolastatin, a camptothesin, a pyrrolobenzodiazepine, an antibiotic, an antiviral agent, an anti-inflammatory agent, an immunomodulator, an antifungal agent, a steroid, or D is an imaging agent moiety;

d is an integer from 1 to 2, the method comprising the steps of:

a.) contacting: i) a compound having a structure according to Formula (V-x):

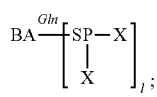
(V-x')

wherein:

X is independently at each occurrence selected from

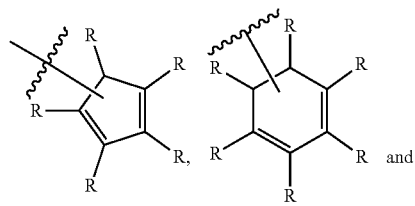
and

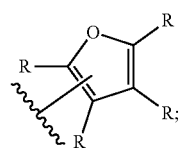

I is an integer from 1 to 2;

with ii) a compound according to Formula (VI-y):

Y-L-D    (VI-y);

wherein:

Y is a moiety according to

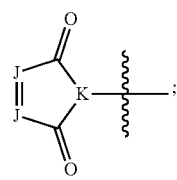

to produce a compound having a structure according to Formula (V-x'z):

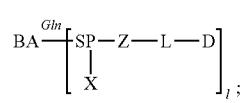
(V-x'z)

b.) contacting the compound according to Formula (V-x'z) with a compound according to Formula (VI-y): Y-L-D (VI-y); and c.) isolating the produced compound of Formula (1B).

2. The method of claim 1, wherein the two X moieties are the same or different.

3. The method of claim 1, wherein the D moiety of step a.) is the same or different from the D moiety of step b.).

4. The method of claim 1, wherein step b.) is performed at a pH of about 5.0 to about 6.0.

5. The method according to claim 1, wherein at least one R is $C_{1-3}$ alkyl, $-OC_{1-3}$ alkyl, or $-NHC_{1-3}$ alkyl.

6. The method according to claim 1, wherein at least one R is $C_{1-3}$ alkyl.

7. The method according to claim 1, wherein X is

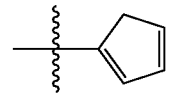 [SMILES: *C1=CC=CC1]

and Y is
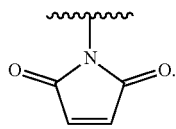
8. The method according to claim 1, wherein SP is
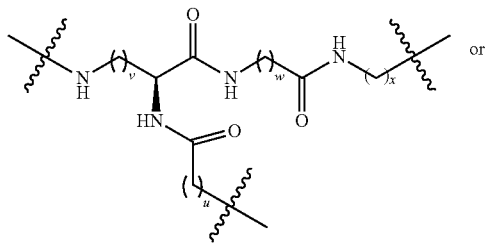 or
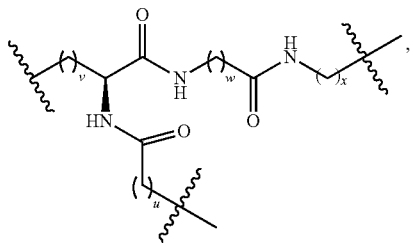
wherein subscripts u, v, w, and x are independently an integer from 1 to 12.
9. The method according to claim 8, wherein SP is
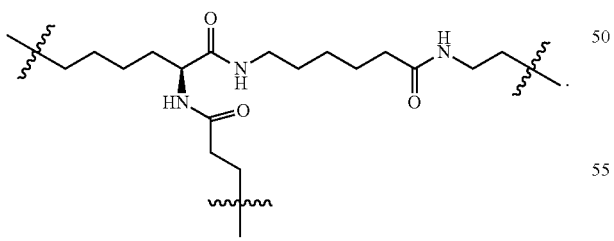
10. The method according to claim 1, wherein
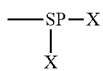
is
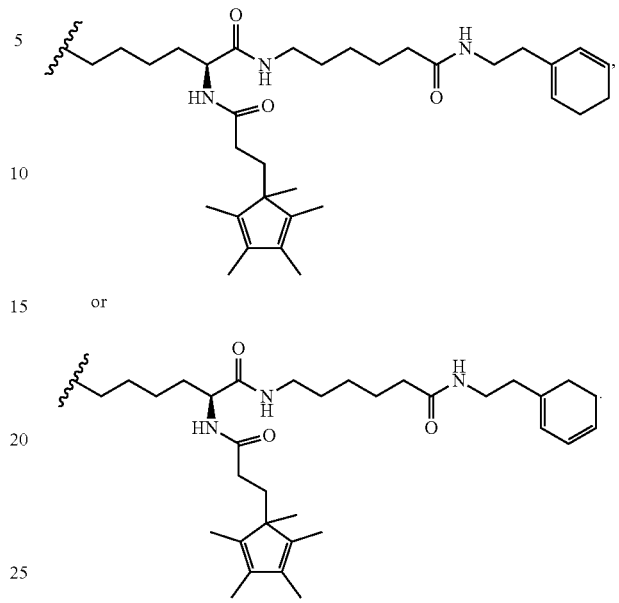
or
11. The method according to claim 1, wherein Z is a moiety according to any one of the following formulas:
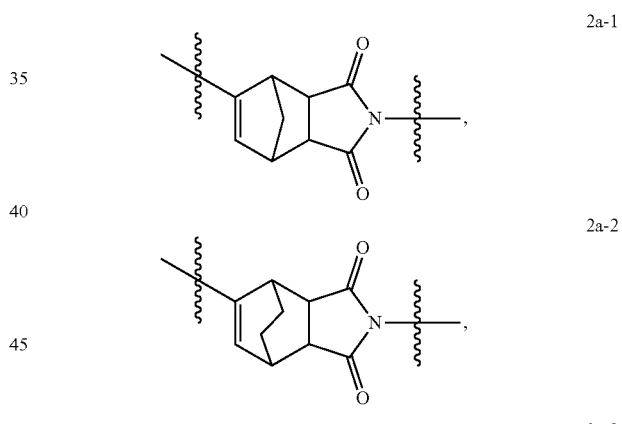
2a-1
2a-2
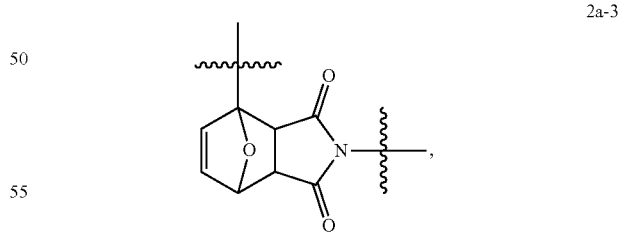
2a-3
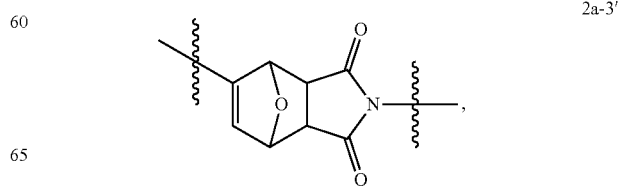
2a-3'

-continued
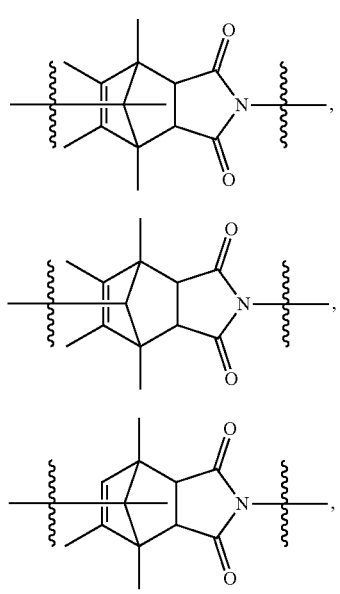
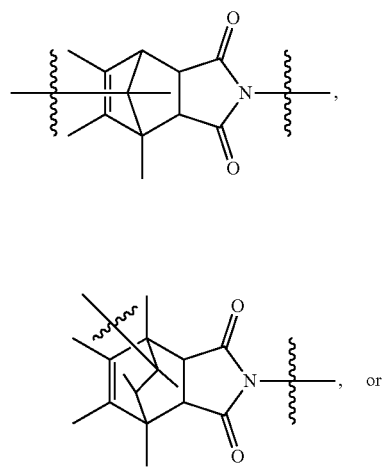
-continued
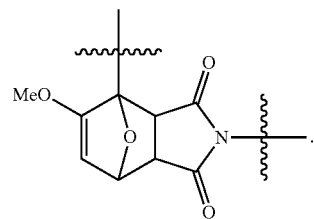
12. The method according to claim 1, wherein Y is a moiety according to
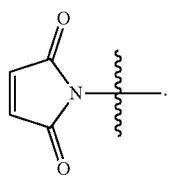 [SMILES: *N1C(=O)C=CC1=O]
13. The method according to claim 1, wherein
is
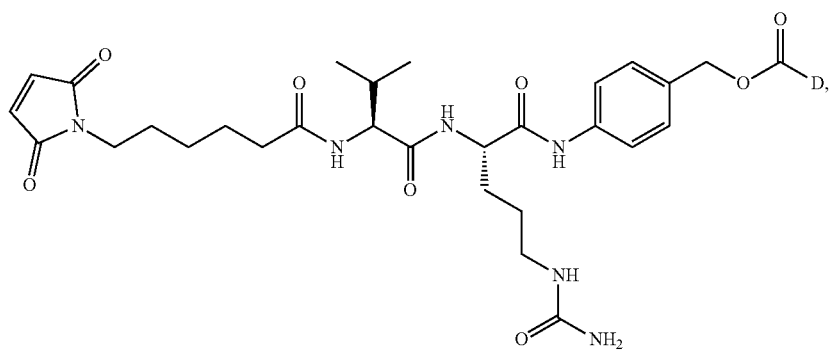
14. The method according to claim 1, wherein the compound Y-L-D (VI-y) is according to wherein D is monomethyl auristatin E (MMAE), wherein D is attached via an amino group.
15. The method according to claim 1, wherein the compound Y-L-D (VI-y) is according to
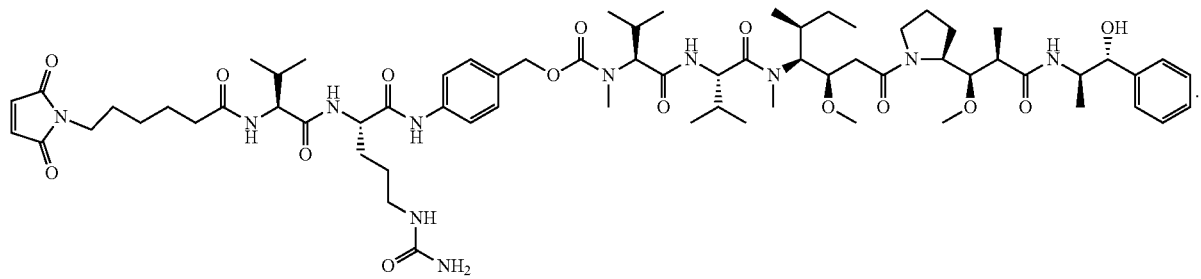 [SMILES: CC[C@H](C)[C@@H]([C@@H](CC(=O)N1CCC[C@H]1[C@H](OC)[C@@H](C)C(=O)N[C@H](C)[C@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCCCCN2C(=O)C=CC2=O)C(C)C)cc1)C(C)C]
16. The method according to claim 1, wherein the compound of Formula (1B) has a structure according to:

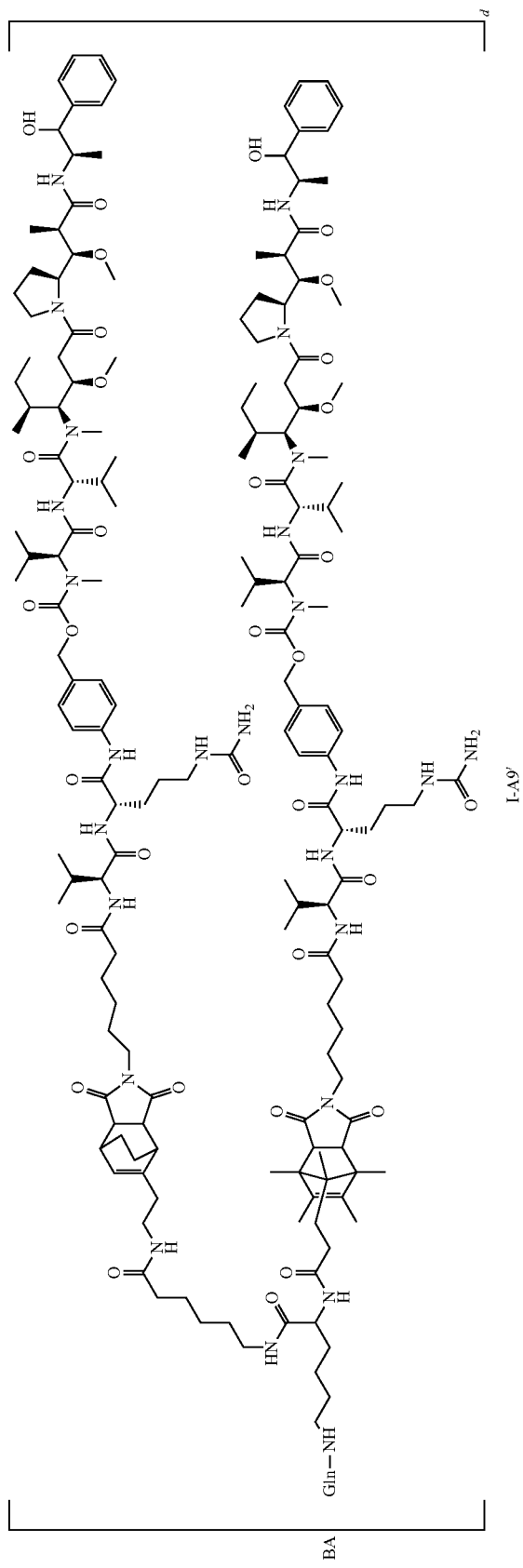

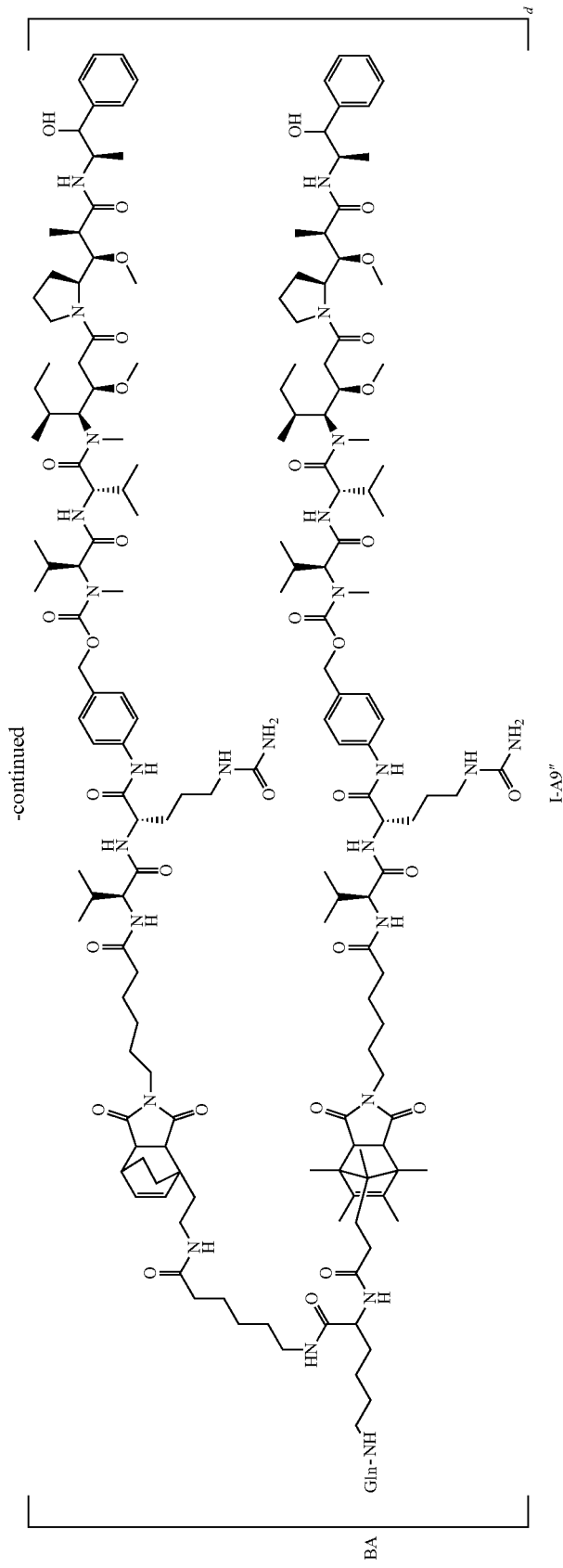
(I-A9' and I-A9")

wherein d is an integer from 1 to 6.

* * * * *